United States Patent
Matsuyama et al.

(10) Patent No.: US 9,512,436 B2
(45) Date of Patent: Dec. 6, 2016

(54) METHOD FOR PRODUCING EXPRESSION PRODUCT OF EXOGENOUS GENE IN YEAST, REGULATOR OF EXPRESSION IN YEAST, AND USE THEREOF

(71) Applicants: Takashi Matsuyama, Nagakute (JP); Mamoru Yamanishi, Nagakute (JP); Chie Imamura, Nagoya (JP); Satoshi Katahira, Nagoya (JP); Akinori Ikeuchi, Nagoya (JP); Yoichiro Ito, Nagoya (JP)

(72) Inventors: Takashi Matsuyama, Nagakute (JP); Mamoru Yamanishi, Nagakute (JP); Chie Imamura, Nagoya (JP); Satoshi Katahira, Nagoya (JP); Akinori Ikeuchi, Nagoya (JP); Yoichiro Ito, Nagoya (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 0 days.

(21) Appl. No.: 15/180,668

(22) Filed: Jun. 13, 2016

(65) Prior Publication Data

US 2016/0281097 A1 Sep. 29, 2016

Related U.S. Application Data

(62) Division of application No. 13/840,918, filed on Mar. 15, 2013, now Pat. No. 9,371,534.

(30) Foreign Application Priority Data

Mar. 15, 2012 (JP) ................. 2012-058423
Jul. 23, 2012 (JP) ................. 2012-163108
Mar. 8, 2013 (JP) ................. 2013-047053

(51) Int. Cl.
*C12N 15/81* (2006.01)
*C12P 21/00* (2006.01)
*C12N 15/67* (2006.01)

(52) U.S. Cl.
CPC ............. *C12N 15/81* (2013.01); *C12P 21/00* (2013.01)

(58) Field of Classification Search
None
See application file for complete search history.

(56) References Cited

U.S. PATENT DOCUMENTS 7,504,493 B2 3/2009 Velculescu et al.

OTHER PUBLICATIONS

Hitzeman et al., "Secretion of Human Interferons by Yeast," Sciene, vol. 219, pp. 620-625, Feb. 11, 1983.
Roberts et al., "Structure, Biosynthesis, and Localization of Dipeptidyl Aminopeptidase B, an Integral Membrane Glycoprotein of the Yeast Vacuole," The Journal of Cell Biology, vol. 108, pp. 1363-1373, Apr. 1989.
Johnston et al. "Complete Nucleotide Sequence of *Saccharomyces cerevisiae* Chromosome VIII," Science, vol. 265, pp. 2077-2082, Sep. 30, 1994.
Carswell et al., "Efficiency of Utilization of the Simian Virus 40 Late Polyadenylation Site: Effects of Upstream Sequences," Molecular and Cellular Biology, Oct. 1989, pp. 4248-4258, vol. 9, No. 10, American Society for Microbiology, USA.
Ingelbrecht et al., "Different 3' End Regions Strongly Influence the Level of Gene Expression in Plant Cells," The Plant Cell, Jul. 1989, pp. 671-680, Vol. 1, American Society of Plant Physiologists, USA.
Kuersten et al., "The Power of the 3' UTR: Translational Control and Development," Nature Reviews: Genetics, Aug. 2003, pp. 626-637, vol. 4.
Zhao et al., "Formation of mRNA 3' Ends in Eukaryotes: Mechanism, Regulation, and Interrelationships with Other Steps in mRNA Synthesis," Microbiology and Molecular Biology Reviews, Jun. 1999, pp. 405-445, vol. 63, No. 2, American Society for Microbiology, USA.
Wang et al., "Precision and functional specificity in mRNA decay," PNAS, Apr. 2002, pp. 5860-5865, vol. 99, No. 9.
Yamanishi et al., "TPS1 Terminator Increases mRNA and Protein Yield in a *Saccharomyces cerevisiae* Expression System," Biosci. Biotechnol. Biochem., 2011, pp. 2234-2236, vol. 75.
Graber et al., "Genomic detection of new yeast pre-mRNA 3'-end-processing signals," Nucleic Acids Research, 1999, pp. 888-894, vol. 27, No. 3, Oxford University Press.
Van Helden et al., "Statistical analysis of yeast genomic downstream sequences reveals putative polyadenylation signals," Nucleic Acids Research, 2000, pp. 1000-1010, vol. 28, No. 4, Oxford University Press.
Graber et al., "Probabilistic prediction of *Saccharomyces cerevisiae* mRNA 3'-processing sites," Nucleic Acids Research, 2002, pp. 1851-1858, vol. 30, No. 8, Oxford University Press.
Gerber et al., "Extensive Association of Functionally and Cytotypically Related mRNAs with Puf Family RNA-Binding Proteins in Yeast," PLOS Biology, 2004, vol. 2, No. 3.
Foat et al., "Profiling condition-specific, genome-wide regulation of mRNA stability in yeast," PNAS, Dec. 2005, pp. 17675-17680, vol. 102, No. 49.
Babiskin et al., "Synthetic RNA modules for fine-tuning gene expression levels in yeast by modulating RNase III activity," Nucleic Acids Research, 2011, pp. 8651-8664, vol. 39, No. 19, Oxford University Press.
Babiskin et al., "A synthetic library of RNA control modules for predictable tuning of gene expression in yeast," Molecular Systems Biology 7, Article 471, 2011, pp. 1-15, EMBO and Macmillan Publishers Limited.
Yamanishi et al., "A Genome-Wide Activity Assessment of Terminator Regions in *Saccharomyces cerevisiae* Provides a 'Terminatome' Toolbox," ACS Synthetic Biology, 2012, pp. A-K, American Chemical Society.
Richard et al., "Transcription termination by nuclear RNA polymerases," Genes & Development, 2009, pp. 1247-1269, vol. 23, Cold Spring Harbor Laboratory Press.

(Continued)

*Primary Examiner* — Nancy J Leith
(74) *Attorney, Agent, or Firm* — Oliff PLC

(57) ABSTRACT

A method for producing an expression product of an exogenous gene in a yeast, including using at least one yeast gene terminator regions selected based on expression intensity data related to the expression intensity of yeast gene terminator regions to cause expression of a gene in a yeast.

3 Claims, 12 Drawing Sheets

(56) References Cited

OTHER PUBLICATIONS

Kuehner et al., "Unravelling the means to an end: RNA polymerase II transcription termination," Nature Reviews: Molecular Cell Biology, May 2011, pp. 1-12, vol. 12, Macmillan Publishers Limited.
Miura et al., "A large-scale full-length cDNA analysis to explore the budding yeast transcriptome," PNAS, Nov. 2006, pp. 17846-17851, vol. 103, No. 47, The National Academy of Sciences of the USA.

Nagalakshmi et al., "The Transcriptional Landscape of the Yeast Genome Defined by RNA Sequencing," Science, Jun. 2008, pp. 1344-1349, vol. 320.

Yamanishi et al., "A Modified Cre-lox Genetic Switch to Dynamically Control Metabolic Flow in *Saccharomyces cerevisiae*," ACS Synthetic Biology, 2012, pp. 172-180, vol. 1, American Chemical Society.

| Rank | Name | Average | S.D. | Average of Screeing |
|---|---|---|---|---|
| 1 | RPL41B | 2.525 | 0.367 | 2.128 |
| 2 | RPL15A | 2.473 | 0.346 | 2.123 |
| 3 | DIT1 | 2.464 | 0.377 | 2.223 |
| 4 | RPL3 | 2.317 | 0.319 | 2.061 |
| 5 | IDP1 | 2.250 | 0.306 | 2.280 |
| 6 | YHI9 | 2.192 | 0.306 | 1.687 |
| 7 | YHL039W | 2.159 | 0.297 | 1.982 |
| 8 | PPA1 | 2.145 | 0.309 | 1.828 |
| 9 | PRC1 | 2.143 | 0.294 | 2.218 |
| 10 | VMA2 | 2.138 | 0.297 | 2.148 |
| 11 | NAT5 | 2.111 | 0.303 | 2.427 |
| 12 | RPS28A | 2.105 | 0.293 | 2.239 |
| 13 | NAT1 | 2.104 | 0.306 | 2.084 |
| 14 | CDC53 | 2.077 | 0.288 | 1.919 |
| 15 | EBS1 | 2.076 | 0.288 | 2.104 |
| 16 | YMR114C | 2.075 | 0.289 | 2.028 |
| 17 | LSC2 | 2.046 | 0.288 | 2.032 |
| 18 | ALY2 | 2.043 | 0.292 | 2.360 |
| 19 | BNA4 | 2.036 | 0.292 | 2.208 |
| 20 | YIP5 | 2.018 | 0.291 | 1.968 |
| 21 | ATG10 | 2.016 | 0.285 | 2.037 |
| 22 | CBR1 | 1.966 | 0.282 | 2.158 |
| 23 | ASP3-1 | 1.964 | 0.286 | 2.275 |
| 24 | SRP54 | 1.925 | 0.271 | 2.042 |
| 25 | YNR021W | 1.915 | 0.271 | 2.094 |
| 26 | YDR119W | 1.901 | 0.288 | 1.928 |
| 27 | YLR361C-A | 1.892 | 0.273 | 2.018 |
| 28 | YPT31 | 1.883 | 0.273 | 1.977 |
| 29 | BUD32 | 1.857 | 0.276 | 2.014 |
| 30 | APL2 | 1.853 | 0.256 | 2.023 |

Fig.5

METHOD FOR PRODUCING EXPRESSION PRODUCT OF EXOGENOUS GENE IN YEAST, REGULATOR OF EXPRESSION IN YEAST, AND USE THEREOF

CROSS-REFERENCE TO RELATED APPLICATION

This is a divisional of application Ser. No. 13/840,918 filed Mar. 15, 2013, and claims the benefit of Japanese Patent Application No. 2013-47053 filed on Mar. 8, 2013, Japanese Patent Application No. 2012-58423 filed on Mar. 15, 2012, and Japanese Patent Application No. 2012-163108 filed on Jul. 23, 2012. The entire disclosures of the prior applications are hereby incorporated by reference in their entirety.

TECHNICAL FIELD

The present teaching relates to a method for producing an expression product of an exogenous gene in a yeast, and to a regulator of expression in a yeast and a use thereof.

DESCRIPTION OF RELATED ART

Genome integration by homologous recombination and genetic recombination using shuttle vectors with *E. coli* is a method that is used to cause expression of arbitrary exogenous genes in *Saccharomyces cerevisiae* and other yeasts and the like. Various vectors are known for gene expression, and these can be obtained commercially. Normally, an expression vector is provided with a cloning site having multiple restriction enzyme sites, so that a desired gene that has been broken into fragments with a suitable restriction enzyme can be inserted into the vector. Promoters, terminator regions and the like for causing expression of the introduced gene are also incorporated in advance. The purpose of a terminator region is to terminate the transcription of the introduced gene into mRNA.

A variety of promoters derived from yeasts and other eukaryotes are used in such expression vectors. Examples include not only the terminator region (CYC1 terminator region) of the yeast cytochrome C1 (CYC1) gene, but also the PGK1 terminator region, TDH3 terminator region, GAP terminator region and the like, which are terminator regions of enzyme genes in yeast glycolytic systems.

Although the only purpose of terminator regions is transcription termination, it is reported that like promoters, they can play a role in regulating the expression levels of gene products (Carswell S. and Alwine J C, *Mol. Cell Biol.*, 9, 4248-4258 (1989), Ingelbrecht I L W, Herman L M F, Dekeyser R A, Van Montagu M C and Depicker A G, *Plant Cell*, 1, 671-680 (1989), Kuersten S and Goodwin E B, *Nature Rev.*, 4, 626-637 (2003), and Zhao J, Hyman L and Moore C, *Microbiol. Mol. Biol. Rev.*, 63, 405-445 (1999)). Moreover, various half-lives have been reported for mRNA (Wang Y, Liu C L, Storey J D, Tibshirani R J, Herschlag D and Brown P O, *Proc. Natl. Acad. Sci. USA*, 99, 5860-5865 (2002)), and specific terminator regions are reportedly involved in mRNA stability (Yamanishi M, Katahira S, Matsuyama T, *Biosci. Biotechnol. Biochem.*, 75, 2234-2236 (2011)). Meanwhile, regions for indicating the transcription termination point (which is the basic function of a terminator), regions for mRNA processing, and regions for PolyA sequence addition have all been reported (Graber J H, Cantor C R, Mohr S C, Smith T F, *Nucleic Acids Res.*, 27, 888-894 (1999), Van Helden J, del Olmo M, Perez-Ortin J E, *Nucleic Acids Res.*, 28, 1000-1010 (2000), and Graber J H, McAllister G D, Smith T F, *Nucleic Acids Res.*, 30, 1851-1858 (2002)). The relationship between the functions of terminator regions and their nucleotide sequences is also being studied (Gerber A P, Herschlag D, Brown P O, PLOS Biol., 2, e79 (2004) and Foat B C, Houshmandi S S, Olivas W M, Bussemaker H J, *Proc. Natl. Acad. Sci. USA*, 102, 17675-17680 (2005)).

BRIEF SUMMARY

For the most part, the nucleotide sequences in yeast terminator regions that contribute to high gene expression and suppression of expression have yet to be identified. To regulate the expression system of an exogenous gene, it is common practice to use a promoter with the desired control function, or to regulate the number of copies of the introduced gene. It is thought that when constructing an expression system, the output of a high-expression system can be further enhanced by combining a high-expression terminator region with a high-expression promoter, while the output of the expression system can be suppressed by using a low-expression terminator region.

It is therefore an object of the disclosures of the present teaching to provide a method for producing an expression product of an exogenous gene in a yeast with excellent output regulation of gene expression, along with a regulator of express in a yeast capable of contributing to output regulation of gene expression, and a use thereof.

The inventors focused on the terminator region as a means of regulating output in gene expression. The inventors then considered the possibility that by selecting a terminator region, it might be possible to either increase or suppress the amount of translation into a protein from a gene transcriptionally regulated by that terminator region, or in other words the expression level of the gene. The inventors found as a result of various researches that a terminator region of a gene from a yeast can contribute to enhancing or suppressing output in gene expression. The disclosures of this Description provide the following means based on these findings.

(1) A method for producing an expression product of an arbitrary gene in a yeast, the method comprising:

using one or two or more kinds of yeast gene terminator regions selected based on expression intensity data about expression intensity of yeast gene terminators to express an arbitrary gene in a yeast.

(2) The production method according to (1), wherein the yeast gene terminators are selected from the group consisting of the yeast genes: ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SLI1, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET6, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RPL24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, POX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJR012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB2, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM4, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP5, SSL2, RPS24B, UTP4, SAW1, DAN2, YPR011C, YER156C, YGL059W, TRM5, SUT1, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1, ECM37, AST1, SMP1, BPL1, UPS1, BAG7, NOG2, RPC10, CYB2, SMD2, RAD1, ATP3, STP2, BUD21, RRN5, YLR352W, FRE4, PAN2, APL3, SEC7, DUS1, CSE1, MAK3, MRPL19, DBP1, FMP48, JAC1, VPS54, FUR1, PUP3, FUN26, SWI1, PWP1, BUD23, ATF1, FMP16, YOL024W, IPK1, RLM1, YNG2, MSS2, FLO8, SHY1, KSP1, KNH1, DON1, KTI11, SMC5, FPS1, SHU1, RAV2, YOR356W, PFA3, ERG8, SEN15, YNL152W, YJL193W, MSH2, CYC1, YLR446W, MRPL13, ISA1, HUA1, YHL010C, NNT1, RMD8, PPR1, ECM9, BSC2, ACO1, MPS2, LEE1, COG5, MCM1, RFC1, TAT2, DML1, KRE9, SPT2, SPC19, QCR8, HXT1, DOA4, MSR1, STU1, ERG10, TFB4, ATG21, GYP6, DAD4, OAF1, YPR013C, GAS1, FAP7, CPA2, RPO31, ATG20, TEP1, YBL081W, SMP3, MCD1, ADK2, SAD1, HUA2, BUD2, YJR136C, RPS14B, MNL1, MDJ1, FLO10, REB1, DSF2, KHA1, MRPL35, YOR283W, PPG1, CIT3, FAA4, SPL2, MET8, HOP2, HFA1, HAP5, ROG1, MAM3, DPH1, RTG3, YNL195C, DCN1, YLR211C, OXA1, YET2, RSC2, MRPL28, CTT1, YAP3, BIG1, UBP8, YOL019W-A, RIB3, NOG1, VID30, MRP17, ZRT1, UAF30, SPO23, YNL122C, SNU71, CDC43, SPC29, DYS1, PRP11, SVF1, BUD20, MEK1, UBP16, PCF11, GRX4, UTP22, HRK1, RPB9, YPL272C, ERG29, DIS3, YFH1, MRM2, RRP5, PTI1, TIF6, FTH1, MPE1, FKS3, ESP1, YDL007C-A, DMC1, JHD2, LEU2, SNF3, SCJ1, YMR317W, CYK3, GPT2, FMP41, SIA1, HXK1, YGL057C, YLR287C, NSR1, YDL241W, RKR1, REX4, TIM17, TES1, RPO21, YNL300W, BSC6, YHR080C, OPI10, RPB8, UBP9, YKR011C, CRP1, RSM24, ARP1, SIK1, GCR2, YLR345W, FET4, MRPL40, THP2, AMD2, YDR524W-C, PSY4, BUD16, HPT1, YDR333C, RHO4, AHC1, YJL206C, SWT1, HEK2, ATP12, XBP1, RMD6, RPL15B, NUP42, PLC1, MAD3, YPS1, MCM16, HXT4, HXK2, ERG12, MMT2, YMR321C, MUM3, HST2, ROG3, DEF1, YLR281C, SSK22, MLH3, YGR131W, CSE4, YCL002C, MRPS18, CAD1, AIF1, SFC1, OYE3, EAF5, RSC9, GYL1, YDL063C, ISA2, GBP2, IMG1, NRP1, DHH1, RHB1, CIK1, PHO89, AGX1, RPB2, MRPL17, GPX2, LYP1, VPS9, BNA3, CKA2, OPI1, YER034W, RSM26, LSM6, THI3, SMC4, SWF1, YAH1, RPF2, HFI1, PLB1, MAM33, YLR413W, PRP8, ENO1, RPC19, YGL007C-A, YMR181C, URA7, YGL108C, SRB7, DAD1, LYS4, ATG18, FMP45, VAM3, SSC1, SNU56, YHR045W, HTA2, YJL213W, RPL20A, ALD4, QCR10, YGR287C, CBP4, PCI8, MCM4, DEM1, ATO3, TPS2, TAF1, KRE6, KGD2, ARB1, NMD5, EFR3, TRP4, HLJ1, ACE2, LDB17, ATG7, OSH6, AFT1, CTF4, YDR286C, AIM44, YLR149C, MRPS9, BET1, YLF2, BOI1, BUD4, CRF1, MLP2, ARX1, RRP12, NAT2, PCL7, ARP7, SFH1, STF1, YML081W, MRP49, FOL3, SAC7, PCS60, TPA1, SSS1, ERO1, NHP2, AIM1, AMD1, VPS38, COG3, YMR244C-A, PYC1, CCC1, TAO3, YDL233W, RPB10, YBR242W, EDC2, YVC1, YDR266C, PMT3, NIS1, YDR128W, ATP15, YML002W, ATG9, IKS1, SUR2, MSD1, SMC3, SPC1, MRPS35, ZIP1, YPR022C, YKL070W, RIM4, YJL127C-B, ARV1, YML6, CYC3, COX9, RMD11, SNU23, PRS2, YNL092W, TIF4632, GBP2, STP4, YIR024C, SHE1, EMG1, NUP192, THI7, NGL1, LDB19, AFG2, ROT1, PIK1, MRPL31, RHO2, MRPL49, FMO1, LRS4, CHS3, SEC8, HXT5, GRX3, YHL042W, AAC3, WSC4, PIN2, PUB1, ERG28, PSR1, ISY1, VPS70, IRC19, DNM1, RPA190, CCR4, SSU72, MRPL7, TBF1, YPR115W, SKP2, CDC73, RPL31B, MAK16, ERB1, DCG1, RNT1, RRP7, GCD7, RAD18, OMS1, YOL048C, PPT2, SCS7, YBL028C, RSC30, TIM23, PRI1, REC102, MCH5, PST1, CLB3, QCR9, MIR1, SSP120, MEF2, RPL14B, YPR003C, RLI1, SWC4, MTM1, SKY1, TOM1, YGL079W, ROM2, TFA2, AIM3, SSQ1, DUG2, MSF1, RPS0B, SCO2, OLE1, SBE2, SAR1, YJR116W, TEF1, AIM13, DFG5, YLR012C, MCM3, RPS7B, DFR1, YBL039W-B, RML2, RSM27, MEC3, YCG1, RFX1, RPL7B, CHS2, PEX5, TIF4631, RPL18B, SMB1, HUL4, NPL6, YOL107W, TRM1, STE6, ASK1, RAD9, YDL012C, RBG2, SEC6, YLR143W, XPT1, HGH1, YIL091C, PRS3, NTC20, YPR196W, MIC17, POA1, NPY1, SNQ2, ADE3, APT2, YGL082W, YHB1, MRPL16, CSH1, GUP1, YJL171C, IDP3, VHT1, PUG1, MPM1, RRP40, DPM1, AFG3, YBP2, YPL183W-A, AIM31, YCR015C, MSN4, YPL038W-A, TSC11, SEC59, ADA2, TPM2, YHR175W-A, POM152, YJR124C, RPL22B, COG7, NEW1, GSM1, UGX2, PRK1, GPD2, LDB16, PAM16, CMC1, TOM6, MBA1, SWC5, PRM10, SAM1, TRS31, YFT2, RGT1, RPL10, KRE33, CDC1, MRPL37, KEX2, VPS13, ACN9, RSC3, PBS2, EPS1, GPI18, ADH4, YTP1, YHM2, ZIM17, LYS5, AIM22, RGM1, ECM10, RDH54, DED1, CSE2, POC4, IPI1, SOL4, YKR075C, RSM10, MAE1, ATF2, SHE4, RSC1, GNT1, MSH4, HSK3, TRS20, NBP35, YBR090C, GLO1, FYV4, AEP2, ARP4, IES3, HYP2, DNF2, GAA1, RPA135, PCL9, SPT5, EDE1, ORC3, YOR304C-A, YCL047C, YER085C, YOL014W, YPL071C, GTS1, RFC2, NDE2, PET127, PLM2, YEA6, RPN7, MDL1, TMA64, NCE103, MCM6, MAS1, TSR1, BAS1, IRC4, TIM21, HCH1, APC5, PMP1, PUF6, YER077C, SNC2, MRP21, YLR036C, YME2, SEC12, YJL062W-A, YMR031C, YAL065C, YNR047W, NHP10, YOL083W, DLS1, IGO2, PAU17, NCS2, TAF7, YDL186W, CMK2, PUS7, TIM9, PMU1, MNP1, SEC16, RIF1, KAR3, MDL2, YLR356W, DCI1, ASP1, NET1, YPL068C, MOT3, NOC3, MRP13, GUT2, ICY1, NTO1, HOS3, TIM54, COX4, UBX2, RVB2, YBL059C-A, RBS1, DCR2, NEM1, MNN9, YNR036C, NOP15, SEC61, RTT106, CCT7, OSM1, SAS5, VPS29, KTI12, POL32, PUS9, SLF1, MUQ1, HSD1, KAR4, STN1, BAT1, THI71, RPL27B, COX5A, AEP1, LPP1, PRM1, YKL222C, TIP41, RPL43B, YCR043C, STP1, AIM8, HXT9, MRP7, YPL216W, SRB6, CTK2, RIT1, NST1, RIB7, MRPL38, SRT1, CBK1, ARL3, DRS2, YLR307C-A, GPI8, SHM2, IPL1, YPL041C, ARR1, GCN20, YPL039W, MNN1, SLX9, SEO1, RMP1, PSA1, CHS6, DAN1, RPB5, SIR3, BCP1, YLL058W, TNA1, TRM13, NOP1, SLP1, PEX31, YIF1, MSA2, ADH3, MNT4, GIS1, SLD2, PIN4, NVJ1, HTS1, RAD7, YKU70, NUF2, YIL001W, ASK10, YBL010C, ATP14, CDC123, MRPL51, YGR127W, YLR392C, APC2, DEP1, APS3, RCL1, DCD1, MIG3, BSP1, YLL014W, TOA1, NBA1, SLC1, IGO1, SDH3, ACS2, YOR093C, MPC54, PFY1, MIA40, YDR034C-A, RDS3, MSC3, TIM50, CSN12, GIN4, SMI1, ADE17, YGR016W, PCP1, SBA1, SRP102, SUM1, ICL1, OAF3, ZRT2, NOP10, BET2, YVH1, SPO75, DNL4, SGV1, IES4, SET4, YCL001W-B, SQT1, REI1, MRPL9, YPL066W, PET191, TEM1, UBX4, DBF20, MSB3, NUP100, RIC1, CUE4, IKI3, YEL043W, MRPL11, MPS1, EAP1, AVT2, GND1, TYW3, POP7, YDR186C, POR2, LSM5, MSH1, TOM22, YBR238C, MEP1, ILV3, YMD8, YJR061W, OSH3, TEF4, SCO1, TDH1, RIM21, YGL185C, NUS1, KTR4, RRP14, TUB4, LEU9, YLR437C, AIM7, ATX2, AI3, OST4, TRA1, MYO5, DAL4, IMG2, LTV1, YGR122W, CFT2, YMR001C-A, CDC16, YAL067W-A, YDR132C, YNL011C, TCP1, CCT3, MKK2, RRI2, ZEO1, RUD3, RTR2, YJL070C, NUP116, ENT1, SLU7, MSC2, SW1, NUP60, AIM28, YOL029C, SHE10, RSB1, SHO1, DLD2, RAX1, LCP5, ATG17, PEX17, GAL4, MET32, YOR223W, STE14, DUG3, SRX1, UFO1, YAT2, NMD3, PRP9, MSN2, PET123, SWD2, SOG2, RRP17, GPB2, YOR293C-A, TEN1, SOV1, PFK27, YIL127C, YNL024C-A, TMT1, SEC39, YER158C, ERP3, YLR257W, PKH3, YNL155W, PSO2, NOP9, GPG1, GIP4, RIB1, CYS4, ZRT3, FMP21, DAK2, ISW1, ACF4, RTT10, RTT109, FMP10, YAP6, APM4, ZAP1, ARO9, SCM4, MIM1, BRR6, SRN2, YOR287C, CLA4, RNR3, ALG8, RAD50, YBR239C, LDB7, ATP17, UGA2, ENA2, YLR408C, SAT4, BOP3, SDH4, YNL045W, RPC40, YNL134C, ARP5, MAD2, GRX6, RSM18, FES1, SGF73, ARH1, MHT1, CNS1, BDH2, YKL063C, GSH1, BOS1, THI72, BSC1, MED8, RAD5, EMP47, SIS2, TEA1, YJL185C, RTF1, CIN4, DIC1, EST2, YNK1, PUS2, PEX13, YNL217W, HOR7, MGS1, YHR009C, YML007C-A, JNM1, YHR078W, YMR155W, STB5, MRP4, STE3, CKS1, TAF13, YNL176C, PCD1, HSP26, DAS1, EDS1, CTR3, PXL1, MRS11, MET3, BDP1, CBF2, DBP6, FAR11, ERI1, MDM10, RPM2, COX13, TOA2, MYO2, PRP5, DRN1, ZDS1, IES2, FAT1, HIS1, MET16, LAS17, ACA1, HIS4, PHO12, EBP2, MRPL6, YLR271W, YBR085C-A, CRR1, SWI3, SWI4, PYK2, BUD7, PEX12, MDV1, IDH2, MRC1, TIM11, SPT15, FBP26, GUP2, NPL4, YCR007C, ABD1, YNL193W, YLR426W, YSP2, SSO2, MRPL23, YHR112C, VPS36, MET7, UTP18, MTW1, DYN1, RNH1, LST4, TAF11, RPL17A, SNA2, YGL041W-A, KAR5, YEH2, YMR118C, CUE2, URA8, YMR034C, YLR152C, YKL088W, HEM13, CAT5, KRE1, IBD2, YOL098C, AIM18, HMG1, TRM7, ADY2, LCD1, YGL194C-A, EFG1, BRX1, HIM1, TCM62, SET6, FIN1, CBF5, ASI1, DUT1, SEC65, YPL067C, RRP43, ASC1, ERG3, RTA1, NFU1, JIP4, YLR419W, YJR011C, YJL045W, ARC18, YBR287W, CAP2, NEO1, TOM5, PEP5, PCC1, PXR1, ALG11, YLR301W, ARG1, RFC4, AIM42, PPA2, DAP1, RTS1, EDC3, IRC23, YBR220C, GPI14, IML1, NIP7, YPT32, MSS18, CHO1, CST26, MOH1, PLP1, MKC7, XYL2, YMR295C, YLR003C, YIL096C, MOT2, RLP7, YSC84, NDL1, PFK1, MRD1, SAC6, REX2, RPA34, AHC2, APC1, YDR222W, VHR1, SUS1, UTH1, IRC8, SNO1, APT1, YOR352W, YMR258C, MRH1, HRP1, SRP21, MRPL22, SEC9, KAR2, YGR054W, HOF1, YDC1, YGR207C, WSC2, SRC1, YAR023C, HAM1, PER1, YKL047W, FLC3, TRM10, PAU15, RFA1, AI2, MPP10, ELC1, PHB1, OST1, LSB1, OKP1, THI22, MRP51, COX20, FCF1, PHO80, FIT1, YPL056C, KIN4, GCD1, FRT1, ACS1, LGE1, YJL136W-A, MLC2, SMF1, ISW2, HIS6, CTR2, GCV2, GAL83, IMP3, GRS1, MRS5, NCE101, BUD17, MKS1, SYF1, ACH1, ARN1, RCN2, UBC12, YER079W, YHL044W, THI20, PML1, IRC10, BMS1, SSA1, DDI2, RPC11, YDR115W, DDC1, IRC21, DUR3, PET100, SKI8, QRI5, QDR1, UBC11, MRT4, POL3, MFB1, TCO89, YDR370C, OYE2, MDM31, SLG1, YOR062C, DNF1, MEH1, AIR2, MSS116, ACB1, ADE12, ELO1, VTA1, MRPL27, YFL054C, SPC34, RGS2, DRS1, GTR1, COX8, KEL2, NUP82, GIR2, FKH2, CLG1, PEX6, HO, YHR003C, NUP84, RRB1, PSY2, BSD2, ESBP6, MED7, RSN1, YKE2, YHL012W, SHE2, RPL2A, DUO1, DST1, PET9, RSA3, GLN4, YKR015C, YJR141W, RIM20, BCK2, SPC42, TRF5, FAA2, TRS130, GUA1, HSL7, PDE2, RRP8, XRS2, SPE1, RFT1, VPS20, SEC20, PAD1, GGC1, ORC1, HMG2, STE2, LSM3, ICS2, TRM2, CDC3, HEM2, SIN4, VIK1, HIS7, RAD54, IQG1, DFG10, TIP1, BRR2, GRX2, HTZ1, BCH2, NRG2, RSC58, TMA16, RAD59, URM1, ADY4, AAP1, ABP1, YGR066C, BRE5, BFR2, LSM1, CHD1, VTI1, AIM11, RFA2, SUR4, YOR228C, DLD3, ISN1, CYC2, SNF5, YMR124W, GIP2, SVL3, SEC13, YEL047C, BEM1, RPL16A, SPR3, ATP4, WAR1, ITR1, FAR3, YOR021C, YBR028C, NOP58, RPN13, YNL035C, YJL049W, YER137C, NOC4, ALG7, MET22, SIL1, TYS1, GLK1, YDR341C, YKR045C, RAD23, BIK1, RPL27A, YOR152C, KNS1, YHR182W, EEB1, RKM1, SNG1, YIL067C, VPS66, TCB1, ADE4, YNL034W, HSP78, HEM15, PKC1, SPP2, MF(ALPHA)1, ARP6, NCS6, RTS3, SPE4, YPL199C, DAL81, SAC1, YOL131W, YHL026C, REC107, YGR174W-A, SGE1, NCB2, YNL320W, CDC20, CSG2, ECM5, NOC2, IES1, SMK1, PHO86, YHR202W, CIN1, PFS1, MCM21, ROT2, GLC7, HRT1, YDR018C, APM1, DPH2, CDH1, HNT3, ATG4, FRE3, ATP2, YMR148W, YAT1, ERG11, PGI1, FKH1, MET30, YGL140C, ARC35, SNX41, SAS2, YHR007C-A, YML083C, ABF1, YLR104W, TOS1, MF(ALPHA)2, FRM2, OPY1, MMF1, DIG1, PMI40, YIL092W, ASI3, FIR1, ERG26, YMR090W, YGL085W, CDC24, YPL113C, YPR010C-A, BIR1, AAH1, EPT1, MSW1, NOP14, CBT1, COX18, COX16, RRD1, BEM4, GEA2, FOB1, ERG7, YLR042C, SEC17, YPR063C, PUT4, MSI1, RPA43, SPE2, DAL1, RPC25, BRO1, AXL1, EAF7, RCR1, YDR338C, RGA1, LOT5, YIH1, RNA1, SKM1, PUT2, HEM4, AIM37, PHO13, YGR015C, AKR2, YKL050C, TCB2, HAC1, ADE1, RTN1, RPL8B, MDM36, JHD1, CCL1, YDR282C, PRE10, PEX14, OMA1, YNR034W-A, NBP2, SPT20, PRP2, YGL041C-B, YBR255W, YOR246C, YFL012W, YLR412W, DUR1,2, RPS4A, YAL037W, ICT1, CTR86, RPN10, RME1, MSB4, SAM35, MAG2, YOL092W, PPZ1, YGL138C, YHR097C, SSZ1, SIS1, CTP1, TAF5, PDC1, YPL150W, GCD10, ENP1, TOM40, ERG6, ECM4, RLF2, RKI1, SAM3, SEC62, CRC1, UME1, TUS1, YNL046W, VTC1, TEL2, YEN1, PEX30, GSG1, NTE1, RBG1, TIM8, YNG1, PMT5, PRP16, SPT6, NIP100, THS1, HMRA1, STE20, AIM10, YGL242C, GTR2, YOL157C, LOT6, KEX1, MET14, UBA2, NUT1, SPO21, PAC10, YND1, DSE3, YJR149W, YOR378W, GSY2, YBR063C, SRV2, YCK1, YKL091C, FMS1, UTP23, YCR090C, SFT2, BNI5, SNX3, FSH2, RGD2, SST2, UNG1, YLR164W, RPS26B, TRE1, MSH5, MYO3, YGL039W, SUP35, AMA1, ATP19, YGL036W, PTK2, PBP2, TRM112, SMC1, NPR1, PFK2, PDE1, RRI1, FRE2, YOR118W, FRE1, ECM38, ALD3, STT3, VMR1, RPC82, URK1, AIX1, REG1, PNT1, YMR279C, RSC8, YJR111C, YLR253W, FSH1, YDR336W, ERD1, VPS41, AYT1, VRG4, YPL009C, VID22, YDR514C, APC11, VPS74, KRE11, RRP6, FOX2, ASM4, MED11, TWF1, GRX5, MYO1, YPL107W, PET54, YLR064W, SPC2, APP1, DBP5, BPH1, YKL151C, NAF1, YKL027W, ARO3, UBX6, TIM18, BNI4, SPC98, PZF1, PIC2, UTP8, YBR235W, SMC6, RLR1, DBF4, RPB11, SHE3, SFB3, SYT1, STU2, NGL2, GDS1, NOP2, SVS1, PRY2, GDA1, BCY1, PUS1, COX7, MRPL15, RER1, SLH1, RPB3, TIF11, YDL173W, YML053C, PEX4, MIG1, CLU1, ECM32, FCY1, HSP32, MAL12, JLP2, DAT1, RMR1, KTR6, OST2, NOP12, IRC3, OPT2, YBL054W, PDX1, AMS1, YBR204C, SLM2, VPS64, PTH2, MRP1, TIF5, AAT2, CPR3, AVT6, CLF1, MDM38, COX12, ESS1, RPG1, SNF11, ERV15, YPR078C, RHO3, SUE1, CLN2, YFL040W, YLR040C, RLA1, YMR272W-B, MND2, EHD3, IMP4, PAH1, HMO1, RPL26A, PIR3, MNN5, FCY22, SMD3, YER186C, QDR2, MHP1, CRH1, LSB3, RMD1, SDA1, AXL2, NOP16, YCL058W-A, ORC6, PRR2, STH1, CCA1, FUS1, MRS6, YBP1, RPL12A, UTR4, MTF2, MAK31, BOP2, UIP5, SSL1, INO4, RPT3, YBR072C-A, YHR159W, ITR2, PUF3, ADD66, GCS1, LYS2, MTR2, TRP1, HXT11, ALG1, SPS18, YOR111W, STI1, SSD1, CRN1, CSN9, RSM22, YIL152W, TOF1, HOM2, MOB1, RAD24, IRC25, RSM23, YLR049C, YBL055C, SPP41, YMR310C, YHC1, YNL040W, AIM41, APL5, ILV2, YIR035C, REC8, MSS51, GAP1, EMP70, HAL1, CDC21, VPS75, YER066W, MCM7, CHZ1, YKL121W, MMS2, BUL2, SEC1, BEM2, YKR018C, NUP2, VPS73, YIL024C, YPL225W, FEN1, YSR3, CST9, YLR241W, MAK10, CUP2, CCP1, ERV14, YJU3, RAP1, IMP1, COA1, TFA1, FAF1, ATP5, ARG3, RVB1, RPA49, NSE4, YKT6, RRN9, APM2, GAT3, SPN1, CKB1, DTD1, TPO2, PRP45, DEG1, PTC5, TSC10, DPB11, YKR005C, RIM15, PNO1, COX15, VPS4, PKH2, MTR4, YLR053C, LEU4, YPK1, PDX3, TIF2, YDL180W, FYV8, BUD13, YBR139W, TPK2, SSH1, YGR102C, YDR348C, RPL28, QCR2, YAR1, SCP1, TIP20, UBC7, SEC11, RPN11, TGL5, HSP60, RPL42B, PRS1, YKL018C-A, TFC6, RNH201, URA1, ALG9, MSG5, AKR1, MNN11, OCA1, YGP1, PPX1, TSC3, PSF3, YAF9, YMR175W-A, LHP1, YMR252C, SLK19, YJR107W, PMC1, HCR1, SKG1, PCT1, LPE10, PGK1, HAS1, SEC23, GPI13, YDR476C, YLR073C, SUI3, RCO1, LYS20, NUP170, RAD27, YLL032C, GDB1, GON7, PRS4, GAL7, RAI1, MLC1, SWD3, REV1, FET3, DAL7, DAL80, COQ5, TRK2, PRP31, SYP1, RPL36A, OSH7, RPL12B, UME6, LCB4, IZH2, MDH3, OGG1, RPL1A, YGL157W, HUB1, TGL4, CAF16, NPP2, URE2, GMH1, AVT3, FAA1, BET5, YPR091C, PET8, STB1, ERG13, UTP10, MMP1, YTH1, EMI2, MES1, PDS1, NPL3, PRD1, YGR235C, PHO8, PEX22, LAP4, LCB2, YLR326W, EMP46, MRPS17, AIM17, NUP57, YER134C, YCR076C, YBL104C, SSM4, YMR187C, YEF3, PIG1, ECM16, SPO20, ILS1, MFT1, RRP46, RPS23A, ECM40, STT4, SOK2, RPL9A, SIR1, SES1, CDC26, SSU1, SAS3, YKL187C, ARG8, RPL16B, LCB3, TVP18, APJ1, GDH1, IPT1, ATP7, YAR029W, PIS1, TRS23, SEC72, CHA4, DMA2, RUP2, DCP2, KAP114, YTA12, PHO87, TPS3, RPS10B, LIP2, PAF1, MEU1, ALK1, RIM11, SLA2, RSC6, CBC2, YBR016W, FIS1, RAS1, SFA1, YOL057W, YOR292C, MCD4, CSM1, MAK32, DAP2, EXG2, DID2, HXT15, DIE2, VAC8, YBR138C, NTH2, YCR099C, RTT107, MAF1, ERG9, PPN1, SRB4, CDC55, YDR248C, YDR003W-A, GLC8, PDR11, SPB4, YSC83, YLR072W, MCH1, RPH1, DAD3, SPT3, YFR057W, IDI1, TDH3, OCA2, PEX18, FUN30, RRP3, ABC1, IWR1, YJR088C, PTR2, SEC26, AQY1, ECM21, BUD27, PFK26, YDR352W, CUP5, ATG3, AGE2, RIX7, HSE1, AGA1, GRX7, AGE1, TUB2, YHR122W, RIB4, VRP1, LAS1, OCA4, YGR277C, BUB3, LPD1, EMI5, CTF18, YOL073C, SIT1, LYS12, FTR1, TUL1, EKI1, LEO1, GAL1, VAC17, REV7, PMP2, TIM13, YMR158C-A, TLG2, YGR106C, YML079W, YFR045W, YBR056W, YLR065C, HSH49, MTF1, LAG1, ATE1, RFM1, RNH203, DBP8, TPS1, YGR205W, PIM1, RAD16, SPI1, SPP1, CHS5, MNR2, PIL1, SMT3, PEF1, SKO1, CDC45, SUC2, RXT3, RPN9, SPO12, RPE1, SEC15, HMI1, RRP4, ERG25, MUC1, TPT1, OPY2, OSH2, VNX1, PXA2, YSW1, SRP14, OST5, CDC4, RPL38, YDR520C, ARO2, DOM34, SWE1, GTO1, RPL37B, RAD3, MEP2, PKH1, ARL1, ROX3, SFT1, SIM1, CIA1, COX5B, CLN1, MNE1, BRE4, UBX5, DSL1, ACK1, YHR140W, ARG82, SCS22, ADH7, HSC82, ARO80, HED1, MAD1, TRP5, RPN3, SEN54, PTM1, ATG23, GIM4, YDR089W, MON2, PEX32, PUS6, YJL038C, SGN1, PRP39, YNR070W, SPO71, SAE3, MGR2, INP53, TUP1, SHP1, INO80, CDC23, GAB1, PTC1, SKI2, DNF3, YOR389W, AIM14, ATP16, VPS51, NSE3, UTP21, MDE1, ALY1, MNI2, BNS1, ILV1, TPO5, THI21, PEX2, YMR194C-B, SFI1, ESF1, YJL068C, GPI1, ISC10, RPL13A, YDR391C, TVP15, YNL108C, YDR051C, SRP101, SAS4, ARG4, PAN5, PTK1, THI6, YOR019W, GCN5, DID4, TRM11, ABZ2, YHR210C, RPL34B, POL31, RPS4B, COG4, RPS16B, LCB1, ARA2, VPH2, YBT1, HSM3, YBL036C, DAL2, VTC4, RPS21B, YOR131C, ADE13, YKL215C, LSM2, FAR10, MCH2, IMD3, USV1, YAR035C-A, RAM1, SNM1, PNG1, RFC3, ARP2, TOR2, ISC1, CTS1, YSH1, AIM4, BIT2, GVP36, SED1, SPG4, KGD1, NMT1, SSY1, LSC1, NRK1, YLR177W, SCD6, YDR210W, LRP1, URA2, PEX21, MCM5, SSE2, PYC2, GFD1, YNL247W, RAD17, BRE2, CDC48, IES5, RPL23A, PTR3, ATP20, PAU3, CPR8, ARO7, YRO2, HRB1, HSP42, RPS18B, FMP23, ADE6, DER1, PPE1, CUE3, ACF2, QNS1, IOC3, NAM9, YDL144C, ENB1, KTR3, PSD1, HOS1, FCY21, CAJ1, ERP4, LRC2, TFB5, PRM3, CPR7, MET17, SAH1, YGR149W, GAC1, TFC7, RHO5, TIF34, YPT1, MSS4, FLC2, PRE2, YCL068C, GAL80, SPG3, URB1, MGE1, STR2, RPL34A, UIP3, NPP1, FMP24, AIM23, BIO3, PRO2, TMN3, EST3, PHO5, YSP1, TUF1, ORM1, OLA1, NMA1, YMR209C, SEC27, SLA1, YCL012C, SLM1, NOP53, YLR162W-A, PAU13, ALA1, YDL133W, CDC37, HCA4, PRB1, GSY1, YIP3, TMA46, RPP1, PRP3, YBL107C, UBP14, VAM10, CBS1, YOR238W, OM14, SEC66, CST6, SSF2, FRS1, NCA2, HMX1, NOP13, RNR2, QDR3, OTU2, SPO13, HUL5, SED4, RRP42, CDC33, MLP1, GOR1, YDL119C, YJR039W, HNT2, SCM3, MET12, VPS33, MGR1, PCM1, YUH1, CDS1, SAP185, CRT10, SNF1, CMP2, APL6, IDH1, YDR428C, SEC21, APL4, PAP2, GPI17, SCH9, HOP1, MUK1, RPS25B, NOB1, STE23, YLR243W, GRE3, CCS1, VEL1, ENO2, COG6, RPL11B, HNT1, LEM3, GPI15, FSF1, SEC8, SOL2, PRS5, VPS71, ACC1, ADE8, GNA1, YNR024W, RSF2, MAL32, PAU21, SPS19, YIL002W-A, SPF1, CCT8, PRM2, PDH1, RBL2, PIF1, VBA1, AFG1, DIN7, IZH1, YPL105C, YCR051W, WWM1, SIP3, SYS1, HPC2, RPL40A, NCR1, YER078C, CAP1, GCN4, AIM38, PTC7, FUN14, COS8, MCH4, PRP24, CWC2, CLC1, SIR4, FUS3, YLR057W, ZRG17, YSA1, PTC3, UBP6, KAP122, EFT2, URA3, ALG2, POL5, RPL1B, LIP1, TMA20, NAS6, IRC5, KIN3, YPL033C, AVT4, YGR266W, CTI6, YNL050C, SDP1, ESF2, NFS1, YER078W-A, IZH4, CWC22, YGR110W, DYN2, SNF4, YMR178W, NSE5, RPL40B, TKL2, HIR1, RPS30A, HSP12, YDR539W, GCV1, NTG1, AZR1, SPO7, YNL022C, DIM1, VAM6, YNR061C, PDA1, YOR032W-A, SPC3, CSR1, COS9, YJR085C, PEX15, TGL2, SGD1, YPL278C, YIL108W, THP1, SCY1, YGR130C, UBC6, END3, UBP15, RPL35B, MSB2, YCT1, SOL3, YDL027C, KIP3, UTP11, SUB1, PRP19, DCW1, TAH18, YER010C, PIN3, GYP1, SCW10, CTK1, ARK1, FYV10, YCR016W, YDJ1, ARF1, BGL2, YHR100C, CBS2, REX3, TSA1, RNA14, RCE1, THR4, SIP18, PMS1, DSK2, CDC50, DPH5, HEM12, SER3, YML119W, ESC1, GAL11, PRE7, RPT5, ERG2, DSE1, SEC22, YFH7, HSF1, GOS1, WRS1, EXO70, TSA2, ALK2, COX6, KRI1, YGL015C, RPS17B, YDR367W, TOM20, RSP5, YBL086C, TRM44, YPR109W, PTP1, AVT7, CYR1, CIS1, FAL1, VPS28, AGA2, QRI1, ATS1, GIT1, THO1, FBP1, YJL016W, UGA3, YBR230W-A, CCE1, NDE1, SET5, HOT1, RPT1, CAR2, PRE4, ECM33, ECM11, RAD33, BUB2, SOP4, SPR1, MOG1, SPO11, YKR070W, YBR246W, YKL071W, AHP1, PRP42, GRC3, KEL3, YMR244W, YMR242W-A, HBN1, VAS1, RTT102, ZUO1, YGR250C, FRQ1, YCL049C, MCR1, UBP11, TIF35, ATG26, YKL107W, HEM14, THR1, LUG1, SPS100, VMA22, YEL020C, RPL2B, GAL10, FKS1, YPL247C, YEL057C, RPS22A, TRK1, VTC2, SNU114, SWD1, UBC8, YPT52, XDJ1, YJR142W, COQ9, ERV25, YKL075C, FPR4, SEN2, GDT1, NOP7, YOR251C, SRL1, YLL023C, IRA2, IES6, MLF3, DIA1, MTG1, FPR1, NCE102, ERG4, SIF2, NUP53, RPL14A, SEC18, SSB2, RAT1, YMR027W, GDI1, VAN1, KAP123, ICL2, LPX1, RPP2A, SCD5, EXO84, CWC21, TRE2, YGR153W, YCR061W, RAD14, CUL3, VPS53, GEA1, GET3, TAD2, POT1, MVP1, PUS4, SMC2, RFC5, TIF3, NTG2, HXT10, CDC60, ENT5, GAT4, PGU1, UFD4, RPL37A, PRE5, PDC6, GCV3, EGD1, MSC7, KEM1, APN1, APE2, YLR456W, MAK5, YPR172W, STE24, RPS9B, CRM1, STP22, DIA2, ECO1, MCX1, YKL065W-A, NTR2, HHO1, RRM3, PRE8, NYV1, RPC53, TMA23, REC104, ZTA1, TEC1, TUB3, YJL123C, AST2, SNX4, ARC1, SOD1, SMA2, RGD1, PHM8, SEM1, GGA2, YAK1, RGA2, SCS3, YTA7, MDM12, AUR1, SKN7, MDG1, RSM7, YOL038C-A, OSW2, TIR3, RSM28, NIF3, FRE6, MDM20, YNR071C, GDH2, VPS8, MVD1, GCD2, TFP3, FMP33, NUG1, CPR6, SCP160, SEC14, YNL181W, PRE6, YLR364W, HOG1, NUP49, RPL21B, RPL42A, GTT2, STR3, ARG5,6, RPS24A, PPM1, AIM46, ILM1, PEX10, PDS5, YDR042C, YDL218W, MGT1, NPC2, YLR194C, PDI1, XKS1, SIW14, KOG1, PDR15, NGR1, SMX3, FIP1, UGA4, EDC1, YDL086W, GGA1, SMM1, AIM39, UBC1, YGR203W, PRP4, YSF3, SNA3, SKI6, CDC12, VPS60, MSC1, SET1, NMA111, SKI7, KRE5, FOL2, DAL3, SAK1, RVS161, YBR141C, LHS1, YFL051C, YGR067C, NOT5, CKB2, ATG2, YJR112W-A, RKM2, RPL36B, CNB1, PRP43, LCB5, PAC1, ARP3, LRC1, RGR1, YDL157C, DPL1, GCY1, YER076C, TFB3, RPS8B, GAT2, GFD2, MRP8, VAC14, YHR138C, PHO90, PSK2, ALT1, ERP5, LAS21, AIM9, SLZ1, SGM1, FMP27, HXT3, YGR273C, RAM2, RET1, YIR007W, RPS2, MTQ2, RPS23B, COS12, RUB1, RGP1, GYP7, YOL138C, PMT2, YMR130W, SPS4, RAD28, YLR099W-A, YOR285W, MBR1, MPH1, NUP159, SEC63, RPS16A, YPL206C, BCD1, HOT13, IVY1, RNA15, YKR104W, STE4, PUP1, SFB2, YCK2, ODC1, FMP42, VPS24, YKL098W, YSY6, RTG2, LYS9, UTR1, HRR25, YBR261C, RPS26A, KTR5, CHL1, MNN10, GLE2, CPD1, SNZ1, PAM17, HIR2, CDC28, YDR061W, ENA5, APM3, YLR118C, AVT1, PEP12, PET18, MAM1, DOA1, FPR2, PIB2, PRP21, TOP2, YBL044W, OST6, AIM24, IRC18, OSW1, COT1, YOR387C, SKP1, STM1, YDL176W, YLR137W, ALE1, PBP1, YNL200C, YBL029C-A, SPE3, RRD2, CNN1, SPR6, PAN3, YRB1, YDL057W, YOR051C, POL4, ORC5, IMP2, ATG19, ARO8, YJL163C, SWI5, LSP1, TMA19, YET3, RAD26, MGA2, IME1, OXR1, GSF2, RPS18A, RUP1, YLR126C, KRE27, TVP23, INO1, ALG14, PUS5, VMA10, SPT16, YLL053C, CHC1, MSH6, SDS24, PTC4, PSP2, VBA2, TSR4, CPR4, DPP1, TFG1, ARN2, YGL230C, NBP1, YKL077W, MOB2, DYN3, UBC13, RFA3, SPG5, GYP5, YPI1, YDR179W-A, CHA1, TOS4, ADH1, SPO1, JJJ2, ADK1, SOK1, GOT1, TIR4, ERP2, SEN1, PHO81, ARF2, YOR227W, TVP38, YDL089W, ZDS2, GCD6, SUI2, VAC7, TAH11, CTR9, YKL100C, NUP188, GRE1, PHB2, BUD3, SMA1, RPL20B, NSP1, PPZ2, STO1, ETR1, SUL1, RPL6B, CPR5, YAL018C, ELP6, ACP1, SHR3, KAP120, YBR137W, IME2, SNF7, YCR023C, GIS2, YIP1, TFC3, CUE1, YLR283W, FUN12, BMH1, RIM1, YMC1, KIC1, NAR1, YBR184W, CAF4, CTK3, NUP157, PRY1, MFA1, POL2, YDL114W, STP3, IRC20, ZPS1, POP1, DUN1, SLY1, UTP6, TAL1, DIB1, PAC2, YNR029C, SPC72, RPC34, KTR7, KRR1, YBR062C, SSA4, VMA9, ATG22, NRD1, INH1, REF2, TSC13, UTP7, AIM15, ARC19, EHT1, YHL017W, NNF2, YPR027C, TGL3, PEX28, TEL1, PGM1, PAN1, HRD3, RPL26B, SDT1, YER128W, PSY3, VPS52, RPB4, AIM2, NUD1, RPS29B, PRO3, RPL32, PXA1, GID8, TRM3, SLX1, PEA2, UBR1, AIP1, RPS10A, CFD1, YOR114W, LEA1, MSN5, RPL6A, PTC2, YER071C, RAS2, ATG14, CDC11, RPS6B, URA6, RPN1, SFH5, YAP1801, FLR1, DDR48, YRA2, APN2, ELF1, YJL217W, YPR089W, GSP2, BUG1, PSE1, SUA5, GPM2, POS5, PRM5, TAF4, GIM5, BNR1, YPS7, HAL5, RPS27B, CAK1, PGA2, SSP2, PMR1, NUP85, LSB6, TMA17, TGL1, ASN2, SEI1, VMA7, MDR1, HBS1, PMT1, PHO2, YHR113W, SSO1, RET2, UBA1, ALD2, SEC28, SEH1, YMR144W, HOC1, PRT1, RPS19B, GCN2, SAP4, YLR179C, COQ6, LYS14, LSM12, YGL117W, RED1, VPS34, VTC3, BRF1, ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, IAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(3) The production method according to (1) or (2), wherein the yeast genes are selected from the group consisting of: YCT1, SOL3, YDL027C, KIP3, UTP11, SUB1, PRP19, DCW1, TAH18, YER010C, PIN3, GYP1, SCW10, CTK1, ARK1, FYV10, YCR016W, YDJ1, ARF1, BGL2, YHR100C, CBS2, REX3, TSA1, RNA14, RCE1, THR4, SIP18, PMS1, DSK2, CDC50, DPH5, HEM12, SER3, YML119W, ESC1, GAL11, PRE7, RPT5, ERG2, DSE1, SEC22, YFH7, HSF1, GOS1, WRS1, EXO70, TSA2, ALK2, COX6, KRI1, YGL015C, RPS17B, YDR367W, TOM20, RSP5, YBL086C, TRM44, YPR109W, PTP1, AVT7, CYR1, CIS1, FAL1, VPS28, AGA2, QRI1, ATS1, GIT1, THO1, FBP1, YJL016W, UGA3, YBR230W-A, CCE1, NDE1, SET5, HOT1, RPT1, CAR2, PRE4, ECM33, ECM11, RAD33, BUB2, SOP4, SPR1, MOG1, SPO11, YKR070W, YBR246W, YKL071W, AHP1, PRP42, GRC3, KEL3, YMR244W, YMR242W-A, HBN1, VAS1, RTT102, ZUO1, YGR250C, FRQ1, YCL049C, MCR1, UBP11, TIF35, ATG26, YKL107W, HEM14, THR1, LUG1, SPS100, VMA22, YEL020C, RPL2B, GAL10, FKS1, YPL247C, YEL057C, RPS22A, TRK1, VTC2, SNU114, SWD1, UBC8, YPT52, YJR142W, COQ9, ERV25, YKL075C, FPR4, SEN2, GDT1, NOP7, YOR251C, SRL1, YLL023C, IRA2, IES6, MLF3, DIA1, MTG1, FPR1, NCE102, ERG4, SIF2, NUP53, RPL14A, SEC18, SSB2, RAT1, YMR027W, GDI1, VAN1, KAP123, ICL2, LPX1, RPP2A, SCD5, EXO84, CWC21, TRE2, YGR153W, YCR061W, RAD14, CUL3, VPS53, GEA1, GET3, TAD2, POT1, MVP1, PUS4, SMC2, RFC5, TIF3, NTG2, HXT10, CDC60, ENT5, GAT4, PGU1, UFD4, RPL37A, PRE5, PDC6, GCV3, EGD1, MSC7, KEM1, APN1, APE2, YLR456W, MAK5, YPR172W, STE24, RPS9B, CRM1, STP22, DIA2, ECO1, MCX1, YKL065W-A, NTR2, HHO1, RRM3, PRE8, NYV1, RPC53, TMA23, REC104, ZTA1, TEC1, TUB3, YIL123C, AST2, SNX4, ARC1, SOD1, SMA2, RGD1, PHM8, SEM1, GGA2, YAK1, RGA2, SCS3, YTA7, MDM12, AUR1, SKN7, MDG1, RSM7, YOL038C-A, OSW2, TIR3, RSM28, NIF3, FRE6, MDM20, YNR071C, GDH2, VPS8, MVD1, GCD2, TFP3, FMP33, NUG1, CPR6, SCP160, SEC14, YNL181W, PRE6, YLR364W, HOG1, NUP49, RPL21B, RPL42A, GTT2, STR3, ARG5,6, RPS24A, PPM1, AIM46, ILM1, PEX10, PDS5, YDR042C, YDL218W, MGT1, NPC2, YLR194C, PDI1, XKS1, SIW14, KOG1, PDR15, NGR1, SMX3, FIP1, UGA4, EDC1, YDL086W, GGA1, SMM1, AIM39, UBC1, YGR203W, PRP4, YSF3, SNA3, SKI6, CDC12, VPS60, MSC1, SET1, NMA111, SKI7, KRE5, FOL2, DAL3, SAK1, RVS161, YBR141C, LHS1, YFL051C, YGR067C, NOT5, CKB2, ATG2, YJR112W-A, RKM2, RPL36B, CNB1, PRP43, LCB5, PAC1, ARP3, LRC1, RGR1, YDL157C, DPL1, GCY1, YER076C, TFB3, RPS8B, GAT2, GFD2, MRP8, VAC14, YHR138C, PHO90, PSK2, ALT1, ERP5, LAS21, AIM9, SLZ1, SGM1, FMP27, HXT3, YGR273C, RAM2, RET1, YIR007W, RPS2, MTQ2, RPS23B, COS12, RUB1, RGP1, GYP7, YOL138C, PMT2, YMR130W, SPS4, RAD28, YLR099W-A, YOR285W, MBR1, MPH1, NUP159, SEC63, RPS16A, YPL206C, BCD1, HOT13, IVY1, RNA15, YKR104W, STE4, PUP1, SFB2, YCK2, ODC1, FMP42, VPS24, YKL098W, YSY6, RTG2, LYS9, UTR1, HRR25, YBR261C, RPS26A, KTR5, CHL1, MNN10, GLE2, CPD1, SNZ1, PAM17, HIR2, CDC28, YDR061W, ENA5, APM3, YLR118C, AVT1, PEP12, PET18, MAM1, DOA1, FPR2, PIB2, PRP21, TOP2, YBL044W, OST6, AIM24, IRC18, OSW1, COT1, YOR387C, SKP1, STM1, YDL176W, YLR137W, ALE1, PBP1, YNL200C, YBL029C-A, SPE3, RRD2, CNN1, SPR6, PAN3, YRB1, YDL057W, YOR051C, POL4, ORC5, IMP2, ATG19, ARO8, YIL163C, SWI5, LSP1, TMA19, YET3, RAD26, MGA2, IME1, OXR1, GSF2, RPS18A, RUP1, YLR126C, KRE27, TVP23, INO1, ALG14, PUS5, VMA10, SPT16, YLL053C, CHC1, MSH6, SDS24, PTC4, PSP2, VBA2, TSR4, CPR4, DPP1, TFG1, ARN2, YGL230C, NBP1, YKL077W, MOB2, DYN3, UBC13, RFA3, SPG5, GYP5, YPI1, YDR179W-A, CHA1, TOS4, ADH1, SPO1, 1112, ADK1, SOK1, GOT1, TIR4, ERP2, SEN1, PHO81, ARF2, YOR227W, TVP38, YDL089W, ZDS2, GCD6, SUI2, VAC7, TAH11, CTR9, YKL100C, NUP188, GRE1, PHB2, BUD3, SMA1, RPL20B, NSP1, PPZ2, STO1, ETR1, SUL1, RPL6B, CPR5, YAL018C, ELP6, ACP1, SHR3, KAP120, YBR137W, IME2, SNF7, YCR023C, GIS2, YIP1, TFC3, CUE1, YLR283W, FUN12, BMH1, RIM1, YMC1, KIC1, NAR1, YBR184W, CAF4, CTK3, NUP157, PRY1, MFA1, POL2, YDL114W, STP3, IRC20, ZPS1, POP1, DUN1, SLY1, UTP6, TAL1, DIB1, PAC2, YNR029C, SPC72, RPC34, KTR7, KRR1, YBR062C, SSA4, VMA9, ATG22, NRD1, INH1, REF2, TSC13, UTP7, AIM15, ARC19, EHT1, YHL017W, NNF2, YPR027C, TGL3, PEX28, TEL1, PGM1, PAN1, HRD3, RPL26B, SDT1, YER128W, PSY3, VPS52, RPB4, AIM2, NUD1, RPS29B, PRO3, RPL32, PXA1, GID8, TRM3, SLX1, PEA2, UBR1, AIP1, RPS10A, CFD1, YOR114W, LEA1, MSN5, RPL6A, PTC2, YER071C, RAS2, ATG14, CDC11, RPS6B, URA6, RPN1, SFH5, YAP1801, FLR1, DDR48, YRA2, APN2, ELF1, YJL217W, YPR089W, GSP2, BUG1, PSE1, SUA5, GPM2, POS5, PRM5, TAF4, GIM5, BNR1, YPS7, HAL5, RPS27B, CAK1, PGA2, SSP2, PMR1, NUP85, LSB6, TMA17, TGL1, ASN2, SEI1, VMA7, MDR1, HBS1, PMT1, PHO2, YHR113W, SSO1, RET2, UBA1, ALD2, SEC28, SEH1, YMR144W, HOC1, PRT1, RPS19B, GCN2, SAP4, YLR179C, COQ6, LYS14, LSM12, YGL117W, RED1, VPS34, VTC3, BRF1, ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, IAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YIL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(4) The production method according to any one of (1) to (3), wherein the yeast genes are selected from the group consisting of: ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, IAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FRS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YIL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(5) The production method according to any one of (1) to (4), wherein the yeast genes are selected from the group consisting of: SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(6) The production method according to any one of (1) to (5), wherein the yeast genes are selected from the group consisting of: FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMU, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(7) The production method according to any one of (1) to (6), wherein the yeast genes are selected from the group consisting of: RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(8) The production method according to any one of (1) to (7), wherein the yeast genes are selected from the group consisting of: YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2 and NAT5.

(9) The production method according to any one of (1) to (8), wherein the yeast genes are selected from the group consisting of: ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SLI1, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET6, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, POX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJR012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB2, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM4, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP5, SSL2, RPS24B, UTP4, SAW1, DAN2, YPR011C, YER156C, YGL059W, TRM5, SUT2, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1, ECM37, AST1, SMP1, BPL1, UPS1, BAG7, NOG2, RPC10, CYB2, SMD2, RAD1, ATP3, STP2, BUD21, RRN5, YLR352W, FRE4, PAN2, APL3, SEC7, DUS1, CSE1, MAK3, MRPL19, DBP1, FMP48, JAC1, VPS54, FUR1, PUP3, FUN26, SWI1, PWP1, BUD23, ATF1, FMP16, YOL024W, IPK1, RLM1, YNG2, MSS2, FLO8, SHY1, KSP1, KNH1, DON1, KTI11, SMC5, FPS1, SHU1, RAV2, YOR356W, PFA3, ERG8, SEN15, YNL152W, YJL193W, MSH2, CYC1, YLR446W, MRPL13, ISA1, HUA1, YHL010C, NNT1, RMD8, PPR1, ECM9, BSC2, ACO1, MPS2, LEE1, COG5, MCM1, RFC1, TAT2, DML1, KRE9, SPT2, SPC19, QCR8, HXT1, DOA4, MSR1, STU1, ERG10, TFB4, ATG21, GYP6, DAD4, OAF1, YPR013C, GAS1, FAP7, CPA2, RPO31, ATG20, TEP1, YBL081W, SMP3, MCD1, ADK2, SAD1, HUA2, BUD2, YJR136C, RPS14B, MNL1, MDJ1, FLO10, REB1, DSF2, KHA1, MRPL35, YOR283W, PPG1, CIT3, FAA4, SPL2, MET8, HOP2, HFA1, HAP5, ROG1, MAM3, DPH1, RTG3, YNL195W, DCN1, YLR211C, OXA1, YET2, RSC2, MRPL28, CTT1, YAP3, BIG1, UBP8, YOL019W-A, RIB3, NOG1, VID30, MRP17, ZRT1, UAF30, SPO23, YNL122C, SNU71, CDC43, SPC29, DYS1, PRP11, SVF1, BUD20, MEK1, UBP16, PCF11, GRX4, UTP22, HRK1, RPB9, YPL272C, ERG29, DIS3, YFH1, MRM2, RRP5, PTI1, TIF6, FTH1, MPE1, FKS3, ESP1, YDL007C-A, DMC1, JHD2, LEU2, SNF3, SCJ1, YMR317W, CYK3, GPT2, FMP41, SIA1, HXK1, YGL057C, YLR287C, NSR1, YDL241W, RKR1, REX4, TIM17, TES1, RPO21, YNL300W, BSC6, YHR080C, OPI10, RPB8, UBP9, YKR011C, CRP1, RSM24, ARP1, SIK1, GCR2, YLR345W, FET4, MRPL40, THP2, AMD2, YDR524W-C, PSY4, BUD16, HPT1, YDR333C, RHO4, AHC1, YJL206C, SWT1, HEK2, ATP12, XBP1, RMD6, RPL15B, NUP42, PLC1, MAD3, YPS1, MCM16, HXT4, HXK2, ERG12, MMT2, YMR321C, MUM3, HST2, ROG3, DEF1, YLR281C, SSK22, MLH3, YGR131W, CSE4, YCL002C, MRPS18, CAD1, AIF1, SFC1, OYE3, EAF5, RSC9, GYL1, YDL063C, ISA2, GBP2, IMG1, NRP1, DHH1, RHB1, CIK1, PHO89, AGX1, RPB2, MRPL17, GPX2, LYP1, VPS9, BNA3, CKA2, OPI1, YER034W, RSM26, LSM6, THI3, SMC4, SWF1, YAH1, RPF2, HFI1, PLB1, MAM33, YLR413W, PRP8, ENO1, RPC19, YGL007C-A, YMR181C, URA7, YGL108C, SRB7, DAD1, LYS4, ATG18, FMP45, VAM3, SSC1, SNU56, YHR045W, HTA2, YJL213W, RPL20A, ALD4, QCR10, YGR287C, CBP4, PCI8, MCM4, DEM1, ATO3, TPS2, TAF1, KRE6, KGD2, ARB1, NMD5, EFR3, TRP4, HLJ1, ACE2, LDB17, ATG7, OSH6, AFT1, CTF4, YDR286C, AIM44, YLR149C, MRPS9, BET1, YLF2, BOI1, BUD4, CRF1, MLP2, ARX1, RRP12, NAT2, PCL7, ARP7, SFH1, STF1, YML081W, MRP49, FOL3, SAC7, PCS60, TPA1, SSS1, ERO1, NHP2, AIM1, AMD1, VPS38, COG3, YMR244C-A, PYC1, CCC1, TAO3 and YDL233W.

(10) The production method according to any one of (1) to (9), wherein the yeast genes are selected from the group consisting of: ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YIL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C, HXT17, YFL052W, ATG1, ECM2, YNR075C-A, YKR041W, ALD5, YHL018W, LUC7 and YPS5.

(11) The production method according to any one of (1) to (10)0, wherein the yeast genes are selected from the group consisting of: ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19 and RAD34.

(12) The production method according to any one of (1) to (11), the method further comprising the step of preparing the yeast gene terminator regions based on nucleotide sequences represented by SEQ ID NOS:10591-15885.

(13) A regulator of gene expression in a yeast, comprising a terminator region of a yeast gene selected from the yeast genes according to (3).

(14) The regulator of gene expression according to (13), wherein the yeast gene is selected from the yeast genes according to (14)

(15) The regulator of gene expression according to (13) or (14), wherein the yeast gene is selected from the yeast genes according to (5).

(16) The regulator of gene expression according to any one of (13) to (15), wherein the yeast gene is selected from the yeast genes according to (9).

(17) A regulator of gene expression in a yeast, selected from the yeast gene terminator regions according to (10).

(18). The regulator of gene expression according to (17), wherein the yeast gene is selected from the yeast genes according to (11).

(19) The regulator of gene expression according to any one of (13) to (18), wherein the terminator region contains one of the following nucleotide sequences, and has activity equivalent to original terminator activity:
  (a) a nucleotide sequence represented by a sequence ID specified by any one of SEQ ID NOS:10590-15885;
  (b) a nucleotide sequence represented by a sequence ID specified by any one of SEQ ID NOS:10590-15885 with 1 or 2 or more nucleotides deleted, substituted, inserted and/or added therein; and
  (c) a nucleotide sequence having 90% or greater identity with a nucleotide sequence represented by a sequence ID specified by any one of SEQ ID NOS:10590-15885.

(20) A cassette for gene expression in a yeast, the cassette comprising:
  a promoter that functions in a yeast; and
  a regulator of gene expression according to any one of embodiments 13 to 18, disposed downstream from the promoter.

(21) A recombinant yeast carrying DNA including a promoter that functions in a yeast, an exogenous gene controlled by the promoter, and a regulator of gene expression according to any one of (13) to (19) disposed downstream from the exogenous gene.

(22) A recombination yeast in which expression intensity of one or two or more kinds of genes selected from endogenous genes and exogenous genes has been modified using a terminator region of a yeast gene selected from the yeast genes according to (3) and (9).

(23) A method for screening regulators of expression in a yeast, the method comprising:
  evaluating an amount of a protein produced by a recombinant yeast carrying DNA including a promoter that functions in a yeast, a coding region encoding an arbitrary protein, and a terminator region from a yeast gene; and
  evaluating expression intensity of the terminator region based on the amount of the protein.

(24) A method for regulating expression intensity of one or two or more kinds of endogenous genes and/or exogenous genes using terminator regions of one or two or more kinds of yeast genes selected from the yeast genes according to (3) and the yeast genes according to (9).

(25) A method for using a yeast to screen drugs, the method comprising:
  using terminator regions of one or two or more kinds of yeast genes selected from the yeast genes according to embodiment 3 and the yeast genes according to embodiment 9 to obtain one or two or more kinds of recombinant yeasts in which expression intensity of one or two or more kinds of genes selected from endogenous genes and exogenous genes associated with the drug has been modified; and
  using the one or two or more kinds of recombinant yeasts to screen the drug.

BRIEF DESCRIPTION OF DRAWINGS

FIG. 5 shows the top 30 terminator regions selected in Example 7.

DETAILED DESCRIPTION

Figure 1:
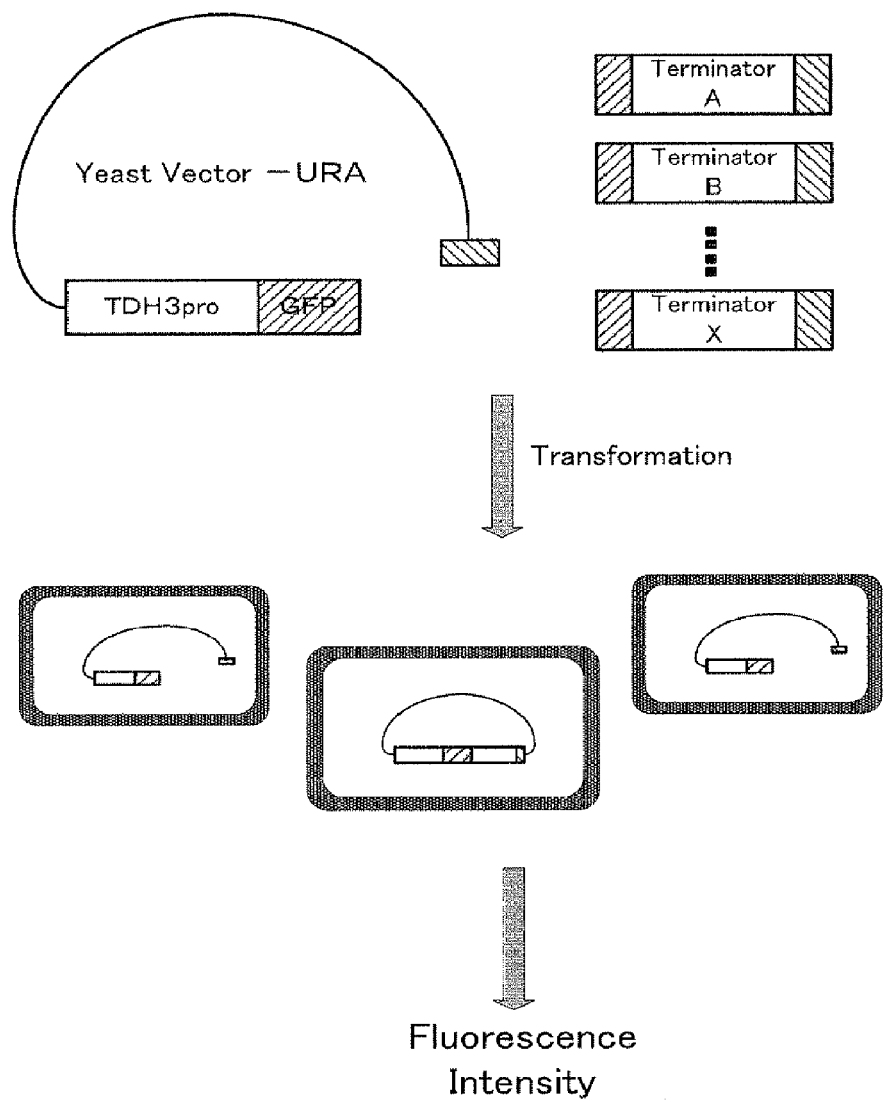
FIG. 1 shows an outline of a vector used in the examples for evaluating terminator regions.

The disclosures of this Description are based on a comprehensive evaluation by the inventors of the effects of yeast gene terminator regions on gene expression levels, focusing on the possibility that a yeast gene terminator region might be used to regulate the expression level of a gene the transcription termination of which is regulated by that terminator region. They are also based on the resulting discovery that yeast gene terminator regions are deeply involved in gene expression levels. The disclosures of this Description allow the expression of exogenous genes in yeasts to be regulated more easily and precisely.

Based on these findings, the disclosures of this Description relate to a method for producing an expression product of a gene in a yeast, to a regulator of gene expression in a yeast, and to a gene expression cassette, recombinant yeast, screening method and the like.

Various embodiments included in the disclosures of this Description are explained in detail below.

(Method for Producing Expression Product of Arbitrary Gene in a Yeast)

The production method of the present teaching comprises a step of causing expression of an arbitrary gene by using a terminator region selected based on expression intensity data about terminator regions of genes from yeasts. Expression intensity data is data about the expression intensity, or in other words the expression level, of a gene that has been attached so that it is transcriptionally controlled by the terminator region. Expression intensity data can be obtained as data about relative expression levels in comparison with expression levels using a known yeast terminator region, such as the yeast PGK1 terminator or the like.

The inventors have shown that when various yeast gene terminator regions are linked under specific conditions (for example, using expression cassettes each comprising the same promoter and exogenous gene), each yeast gene terminator region exhibits its own particular expression intensity.

The terminator region means a region which is arranged downstream of the code region of the gene, codes the sequence of the 3'-UTR region of the mRNA and has a transcript termination function. Transcript termination function comprises functions of terminating transcription from the DNA to the mRNA, processing the 3' end of the mRNA into an appropriate position and adding Poly A to the mRNA (Richard, P. and Manley, J. L. (2009), Genes De. 23. 1247-1269, Kuehner, J. N., Pearson, E. L. and Moore, C. (2011) Nat. Rev. Mol. Cell Biol. 12, 283-294)). Further, the 3'-UTR region coded in the terminator region performs the post-transcriptional control regarding the gene expression. Stability of the mRNA, translation efficiency and localization of the mRNA are founded as major controlling mechanisms.

Expression intensity data is shown below for the terminator regions of 5295 genes obtained from yeasts, particularly the budding yeast *Saccharomyces cerevisiae*. The expression intensity data is shown by the gene name followed (in parentheses) by the relative expression intensity compared to that of the PGK1 terminator region. Although these genes are derived from the model yeast *Saccharomyces cerevisiae*, the teaching is widely applicable to other yeasts including budding yeasts. The gene names are listed below beginning with the gene with the lowest relative expression intensity.

(Expression Intensity Data)

ORC4(0.030), ICY2(0.044), GIC1(0.047), HLR1(0.053), ECM13(0.057), YLR108C(0.060), AQR1(0.064), YHR213W-A(0.065), SUT1(0.068), PLB3(0.070), AIM26(0.072), TPO4(0.073), YPR153W(0.073), GIS3(0.073), WSC3(0.079), FUR4(0.079), DLT1(0.080), MOT1(0.080), YNR063W(0.081), MET13(0.081), YDL156W(0.082), YJL107C(0.082), YJR154W(0.082), YNL042W-B(0.082), VHS1(0.083), GPI19(0.084), YIL057C(0.084), STD1(0.085), CTF19(0.088), RAD34(0.088), YIR021W-A(0.088), FZF1(0.089), YHK8(0.089), YGL188C-A(0.089), HCM1(0.090), CDC6(0.090), YPR157W(0.091), CLB6(0.091), YOX1(0.091), YLR285C-A(0.091), YDR114C(0.092), YHR199C-A(0.092), MPS3(0.092), MUP3(0.093), YIR014W(0.094), AAR2(0.094), YPT35(0.094), AIM33(0.095), SCW11(0.095), BDF1(0.095), YCL042W(0.096), BSC4(0.096), YGL193C(0.096), NUT2(0.097), YJL118W(0.098), YKL069W(0.099), SRB8(0.099), YOR060C(0.099), MDH2(0.099), YPR116W(0.100), YPK2(0.101), GLN3(0.101), YDL211C(0.101), RAD55(0.102), CYM1(0.102), ENT4(0.102), ULA1(0.103), YMR182W-A(0.104), YKR017C(0.104), YOR302W(0.106), YOR072W-B(0.107), VTS1(0.107), FYV12(0.107), YGL235W(0.108), YHR086W-A(0.108), YEL067C(0.109), YPL257W(0.109), UBA3(0.109), YMR105W-A(0.109), YOR316C-A(0.110), TMA10(0.110), YDL159W-A(0.112), ATG29(0.113), YML037C(0.113), NSL1(0.113), YJL077W-B(0.113), POP3(0.113), WHI5(0.113), MIH1(0.114), YGR240C-A(0.115), YRM1(0.115), KAR9(0.115), YJU12(0.116), SPC24(0.116), DPB2(0.117), CHL4(0.117), YMR087W(0.118), CSI1(0.118), YIL134C-A(0.118), BUR2(0.118), PTH1(0.119), SSN8(0.119), AUA1(0.119), YLR154C-G(0.120), YLR342W-A(0.120), YCL001W-A(0.120), FLC1(0.121), YLL006W-A(0.121), VAM7(0.121), YPL077C(0.121), CCZ1(0.123), PRP28(0.123), ACM1(0.123), IME4(0.123), YPR096C(0.123), FRE5(0.124), PDR8(0.125), ILV5(0.125), YIL161W(0.126), PAC11(0.126), UBR2(0.126), YRB2(0.128), YLR125W(0.128), YMR253C(0.128), DSE4(0.128), EPL1(0.128), SNP1(0.128), YMR160W(0.128), SPO77(0.129), BUB1(0.129), YFR016C(0.129), SPC97(0.130), GEM1(0.130), INO2(0.130), SPT10(0.130), YLR132C(0.131), AIM45(0.131), YJR054W(0.132), MBF1(0.132), YAL064C-A(0.132), YML054C-A(0.132), NUP1(0.132), ECM27(0.132), YIL060W(0.133), IRE1(0.133), YHR177W(0.134), YJR079W(0.134), YNL187W(0.136), YML003W(0.136), PIH1(0.136), YDR169C-A(0.136), PET111(0.137), YDL109C(0.137), YOR012W(0.138), YHR050W-A(0.138), TAR1(0.139), RIM9(0.139), YCR095W-A(0.140), RPR2(0.140), COS7(0.140), YDR049W(0.142), CUS1(0.142), JJJ3(0.142), COS10(0.143), MET1(0.144), HXT8(0.145), GLY1(0.146), SUR1(0.146), RTG1(0.147), PHM7(0.147), YJL052C-A(0.147), HXT17(0.147), YFL052W(0.148), ATG1(0.148), ECM2(0.148), YNR075C-A(0.148), YKR041W(0.149), ALD5(0.149), YHL018W(0.149), LUC7(0.149), YPS5(0.149), YLR297W(0.150), SNA4(0.150), BIO4(0.150), YBR298C-A(0.150), ECM12(0.152), SEF1(0.152), YMR247W-A(0.152), EXO1(0.153), CTF13(0.154), HUR1(0.154), SNO3(0.154), BSC5(0.154), YER175W-A(0.155), PGA1(0.155), YLR173W(0.156), YDR119W-A(0.157), IRC15(0.157), MGA1(0.157), YPR174C(0.159), IML3(0.159), YLL054C(0.159), RDS1(0.159), MDM32(0.160), PET494(0.160), YPR036W-A(0.160), GTB1(0.160), ISF1(0.161), KRE29(0.161), SAP190(0.161), YHR214C-E(0.162), GTO3(0.163), YOR365C(0.163), MIP1(0.163), SIP5(0.164), YPL191C(0.164), YPL162C(0.164), YMR291W(0.165), BRN1(0.166), MDM1(0.166), NAT4(0.166), YLR406C-A(0.166), YME1(0.166), CSI2(0.166), YOR008C-A(0.167), CEF1(0.169), BUD25(0.169), DFG16(0.170), GPB1(0.170), KAR1(0.170), PPM2(0.171), DSS1(0.171), RPC37(0.172), VID24(0.172), ERV41(0.172), YGR169C-A(0.172), ECM8(0.173), YHR032W(0.173), ELA1(0.173), PEX29(0.173), LTE1(0.173), HAT2(0.174), SLI1(0.174), MUP1(0.175), ALG13(0.176), FRE7(0.176), YMR147W(0.177), ISU2(0.177), YOR1(0.178), JID1(0.179), ECM3(0.179), ATG5(0.179), MED6(0.180), YPL014W(0.180), YLR030W(0.180), AQY2(0.180), CCT2(0.180), YER067W(0.181), NRG1(0.181), SPT8(0.181), PIR1(0.181), YGR068C(0.182), YER039C-A(0.182), ELM1(0.182), ASE1(0.182), YBL095W(0.183), YNR066C(0.183), MTL1(0.183), CNE1(0.183), CAX4(0.183), NDI1(0.184), FLX1(0.184), YNL130C-A(0.184), CWC25(0.186), YNL254C(0.186), CDC13(0.186), ATP10(0.187), OCT1(0.187), ALF1(0.187), YEF1(0.187), BAP2(0.187), HTL1(0.188), PDC5(0.189), PKP1(0.190), SSK2(0.191), CAF120(0.192), SKN1(0.192), HHF1(0.193), CDC39(0.194), YFR012W(0.194),

YEL048C(0.194), HAP4(0.195), PEX7(0.195), TPO1 (0.196), NFT1(0.196), NGL3(0.198), YMR206W(0.199), DUS3(0.200), YAP7(0.200), CUS2(0.201), YLR415C (0.201), FUI1(0.202), SLM5(0.203), BTT1(0.203), YFR035C(0.203), RRN10(0.203), HAP3(0.204), SSY5 (0.204), SFL1(0.204), KIP1(0.205), CDC15(0.206), GLT1 (0.207), DOC1(0.208), MND1(0.209), AAC1(0.209), CEP3 (0.209), UBC5(0.209), YNL213C(0.209), CLN3(0.210), CSF1(0.210), ECM18(0.210), MRS4(0.210), YIL046W-A (0.211), INP1(0.211), RTT105(0.211), MPT5(0.211), ATG15(0.212), RNH202(0.212), TAX4(0.213), IZH3 (0.213), BDF2(0.214), COX14(0.214), YIP4(0.214), YJR120W(0.214), SAE2(0.215), YMC2(0.216), YGR035C (0.216), NDD1(0.216), HPA2(0.216), STL1(0.216), GPM3 (0.216), ERF2(0.217), MMS21(0.217), YJL133C-A(0.218), YNL024C(0.218), IFH1(0.219), LIN1(0.220), ICS3(0.220), YNR014W(0.220), SPB1(0.220), YNL211C(0.221), SOL1 (0.221), COS111(0.221), HSH155(0.221), NKP2(0.221), NAB3(0.221), FMT1(0.222), YPL152W-A(0.222), BOR1 (0.222), SPC25(0.222), MMS1(0.222), YIL166C(0.223), MAL13(0.223), BFA1(0.223), AEP3(0.224), MTH1(0.225), YGR031W(0.225), BIT61(0.227), YMR230W-A(0.227), SKT5(0.227), YGL258W-A(0.227), PHR1(0.227), HTB2 (0.228), SER1(0.229), BAP3(0.230), YER053C-A(0.230), ATG16(0.231), BIO2(0.231), MEP3(0.232), YNR073C (0.232), PCH2(0.232), APS2(0.232), MDM30(0.233), CLB5(0.233), ISR1(0.234), MRP20(0.234), GUD1(0.235), MED1(0.235), RER2(0.236), MCM10(0.236), YIR018C-A (0.236), SPO14(0.236), NUC1(0.237), MNN4(0.237), IFM1(0.237), YLR412C-A(0.237), ALT2(0.237), NNF1 (0.238), YKL096C-B(0.239), RAD51(0.239), CIT2(0.239), SPT4(0.239), LRC4(0.240), USE1(0.240), YLR455W (0.241), YOL164W-A(0.241), PRP18(0.242), COA2 (0.242), HSP82(0.243), YER184C(0.244), DAD2(0.246), LEU1(0.247), YDL129W(0.247), YPL119C-A(0.248), YOR034C-A(0.249), PRP38(0.249), MSA1(0.250), YBR147W(0.250), BBP1(0.250), MLH1(0.250), SWC3 (0.251), SOH1(0.251), HHF2(0.251), NIP1(0.251), MSL1 (0.251), RIF2(0.252), SPG1(0.252), WHI3(0.253), HTA1 (0.253), ARR3(0.253), YIL077C(0.253), SGF29(0.254), RAD53(0.255), YEL073C(0.257), YNR065C(0.258), NCA3(0.258), YBR296C-A(0.259), ECM23(0.259), YLR225C(0.259), SLD3(0.259), YBR197C(0.259), YBL059W(0.260), YOL075C(0.262), DNA2(0.263), SIZ1 (0.263), REC114(0.263), MSN1(0.264), RGT2(0.264), CBF1(0.264), YGL176C(0.265), PTP2(0.265), GAL3 (0.265), VPS62(0.266), HMS2(0.266), SMF3(0.267), APL1 (0.268), SKI3(0.268), MNS1(0.268), YOR214C(0.268), TID3(0.269), KSS1(0.269), YDR194W-A(0.270), UPC2 (0.270), ARG80(0.270), MRS2(0.271), ATP23(0.272), YML100W-A(0.272), YGL101W(0.272), STE12(0.272), RPI1(0.273), YDR090C(0.273), YEH1(0.273), UTP13 (0.273), AMN1(0.275), YIL089W(0.275), AVL9(0.276), ATO2(0.276), HEM3(0.276), RPA14(0.277), GIP3(0.277), YGR053C(0.278), ALR2(0.278), YAP5(0.278), CDD1 (0.279), SLS1(0.279), MET6(0.279), ABM1(0.279), PET20 (0.280), CBP1(0.280), RAD10(0.280), SPO22(0.281), PIB1 (0.281), EAF3(0.281), YFR032C-B(0.282), ELP2(0.282), YIA6(0.282), PET112(0.282), PAU7(0.283), MEI4(0.283), YEA4(0.283), SGS1(0.284), JEN1(0.284), CLB2(0.284), GIC2(0.284), SWI6(0.284), ULP2(0.286), KIN28(0.286), YKL033W(0.286), CSM4(0.286), YNL095C(0.286), RRN3 (0.286), RNR1(0.286), TPO3(0.286), SUP45(0.287), ABP140(0.288), RPS28B(0.289), MRF1(0.289), GLN1 (0.290), OPT1(0.291), PHO4(0.291), UBP10(0.291), YOL163W(0.291), MDS3(0.292), OTU1(0.292), GAT1 (0.292), HDA3(0.293), MSY1(0.294), GNP1(0.295), YFL041W-A(0.295), YPL141C(0.295), MPH2(0.295), PMA1(0.296), YNL260C(0.296), SKS1(0.296), YDL177C (0.296), SWR1(0.296), RMD5(0.297), RPL9B(0.297), MIC14(0.297), AOS1(0.297), LRG1(0.297), ROX1(0.298), PCL10(0.298), MRPL3(0.298), YER152C(0.298), EAF1 (0.298), HTB1(0.298), SPA2(0.299), SSN2(0.299), YJR129C(0.300), ATG8(0.300), RHR2(0.300), TFG2 (0.300), YBL100W-C(0.301), CSM2(0.301), EXG1(0.301), STE7(0.301), ADH2(0.302), SNT2(0.302), PML39(0.302), SEC2(0.303), ASI2(0.305), MNT3(0.306), BUR6(0.306), BIO5(0.306), YDR506C(0.306), RDR1(0.307), MRPL33 (0.307), YGL159W(0.307), RIM8(0.309), YGR161W-C (0.310), YIG1(0.310), PDR16(0.310), YDR249C(0.311), YDR124W(0.311), HSP30(0.311), SDH2(0.313), YER130C(0.313), FAA3(0.314), BUD22(0.314), TIM22 (0.315), CBP6(0.316), ICE2(0.316), SPC110(0.316), AFT2 (0.316), NAM2(0.316), YPR071W(0.317), DIP5(0.317), SDS3(0.317), POP4(0.317), OCA6(0.317), PTC6(0.317), YBR201C-A(0.318), YPR127W(0.318), SEC10(0.318), ASF2(0.318), SLI15(0.319), RRN7(0.320), ORC2(0.320), GUF1(0.320), GPI2(0.323), RPS9A(0.324), RAD6(0.324), PSR2(0.325), RIP1(0.325), GZF3(0.325), CAR1(0.325), YHR151C(0.325), LEU5(0.325), YBR182C-A(0.326), IRC7(0.326), ASG7(0.327), YOR381W-A(0.327), OCA5 (0.327), YHR035W(0.328), PET117(0.329), ISD11(0.329), HSP150(0.329), CCC2(0.329), YHR131C(0.329), MRK1 (0.330), RXT2(0.330), PPH3(0.330), ODC2(0.331), SHE9 (0.331), YCR075W-A(0.331), CYB5(0.332), YDR415C (0.332), LRO1(0.333), SOF1(0.333), YNL162W-A(0.334), PAU14(0.335), MTO1(0.336), YKL061W(0.336), MSS11 (0.336), SAN1(0.336), SET2(0.336), YMR1(0.336), PHD1 (0.338), YBL071C-B(0.338), MPA43(0.339), SAM37 (0.339), AAT1(0.339), ASH1(0.340), UTR2(0.340), CAT8 (0.341), SLX8(0.341), HXT2(0.342), COY1(0.342), TAF3 (0.342), DSS4(0.342), TOR1(0.342), YMR030W-A(0.343), PAU5(0.343), SFP1(0.343), FHL1(0.344), COX10(0.344), DDR2(0.344), SWM1(0.345), HXT6(0.346), RCR2(0.346), YLR091W(0.346), RMD9(0.346), SHQ1(0.346), YLR346C (0.347), SPT21(0.347), ARE1(0.348), KAP95(0.349), YGR071C(0.349), TRL1(0.350), ECM17(0.350), YML020W(0.350), RPO41(0.351), CFT1(0.351), LRC5 (0.352), THI74(0.352), TPN1(0.352), YOR059C(0.352), PRY3(0.352), YEL1(0.352), CNM67(0.353), STB6(0.354), YOR385W(0.354), RRN6(0.354), COP1(0.354), PDR12 (0.355), ELG1(0.355), SRP40(0.355), SRM1(0.355), YDR109C(0.356), AIM30(0.356), RPC17(0.356), YJL028W(0.356), YBR071W(0.357), APS1(0.357), KIP2 (0.358), ATP22(0.358), PRM6(0.358), BUD31(0.359), IXR1(0.359), NFI1(0.359), YHL015W-A(0.359), VHS3 (0.360), YNL295W(0.361), SML1(0.361), SSK1(0.361), YAE1(0.361), RIM2(0.361), YDR246W-A(0.362), YLR445W(0.362), SPT23(0.362), MTG2(0.363), SGF11 (0.363), BRL1(0.363), YMR315W(0.364), MRPS28 (0.365), ERG5(0.365), UTP30(0.365), MDM35(0.365), ASR1(0.366), YIL102C-A(0.366), USA1(0.366), DOT6 (0.368), COX23(0.369), ADH5(0.370), DAN4(0.370), RMA1(0.370), SCT1(0.370), PHO84(0.371), SFG1(0.371), SLX4(0.372), EST1(0.373), YNL190W(0.373), SNL1 (0.374), RRP15(0.374), YML082W(0.375), DOT1(0.375), PEX1(0.375), YUR1(0.376), YAP1802(0.376), YDR185C (0.376), GET2(0.376), YPL264C(0.377), YDR065W (0.377), YJR115W(0.378), MAK21(0.378), YER064C (0.378), ATR1(0.378), IDP2(0.378), KCS1(0.379), ZPR1 (0.379), ITC1(0.379), OAZ1(0.379), SWC7(0.380), RPL8A (0.380), CAC2(0.380), VTH1(0.382), OCH1(0.382), BUL1 (0.382), YNR004W(0.382), LST7(0.382), MRPS8(0.383), TIS11(0.383), NDC1(0.384), TOS8(0.385), ISM1(0.385),

MSL5(0.385), FMP43(0.386), YJR098C(0.386), COQ3(0.387), TPC1(0.388), RIM101(0.388), ADR1(0.388), ALD6(0.389), YHR087W(0.389), VPS21(0.389), POG1(0.389), YJR005C-A(0.389), SNT1(0.390), YHR022C(0.390), MEF1(0.390), PUP2(0.391), ERP6(0.391), HHT2(0.392), YGR146C(0.392), OAR1(0.392), YOR129C(0.392), YCR045C(0.392), DBP7(0.393), MUB1(0.393), YPL236C(0.393), RIB2(0.394), YPR084W(0.394), AIM5(0.395), UTR5(0.395), HKR1(0.396), YMR010W(0.397), ALR1(0.398), LRE1(0.399), RPN4(0.399), YLR363W-A(0.399), MGM1(0.399), HTD2(0.399), NAM8(0.399), SED5(0.400), YOR161C-C(0.401), YML018C(0.401), NAB2(0.401), YER140W(0.402), PRM4(0.402), RTR1(0.402), YIR042C(0.402), THI80(0.402), FUN19(0.402), DMR1(0.402), SIP1(0.403), CGR1(0.403), MTR3(0.404), YJL144W(0.404), RIM13(0.404), SAL1(0.405), MET28(0.405), INM1(0.405), VID27(0.405), CDC34(0.406), SRO9(0.406), RRP9(0.406), YOL087C(0.406), MCM22(0.406), YMR111C(0.406), NDJ1(0.407), ATG12(0.407), MSM1(0.408), SRS2(0.408), YBR225W(0.409), YLR063W(0.410), AI1(0.410), CDC36(0.410), ASN1(0.410), MET31(0.410), SSP1(0.410), NGG1(0.410), RBA50(0.411), PUT1(0.412), YPT53(0.412), NMA2(0.412), YBR219C(0.413), CDC40(0.413), SGO1(0.414), YJL047C-A(0.414), RPC31(0.414), INP52(0.414), UGO1(0.414), RAD30(0.415), CLB1(0.415), GLO4(0.415), TPK3(0.416), GIM3(0.416), CDC9(0.417), PEX27(0.417), AIM32(0.417), YGL081W(0.418), DJP1(0.418), HMS1(0.419), JSN1(0.419), UBP12(0.420), RSM25(0.420), UBP5(0.420), GIP1(0.420), PUT3(0.421), CKI1(0.421), FAR7(0.421), LAG2(0.421), DAM1(0.422), PSD2(0.423), HMT1(0.423), COR1(0.423), MMR1(0.424), MRPL39(0.424), CTF8(0.424), AGP2(0.425), PRM7(0.425), HIT1(0.425), HAL9(0.426), GPA2(0.426), TIM44(0.426), TFB1(0.426), ECM19(0.428), MRPL32(0.428), YBR284W(0.428), NAS2(0.429), SBE22(0.429), YOR011W-A(0.430), ORT1(0.430), MRPL25(0.430), QNQ1(0.430), APC4(0.430), TYE7(0.431), YPP1(0.431), MMT1(0.431), MRP10(0.431), MRPS5(0.431), LIP5(0.431), CDC27(0.432), ESC2(0.432), CAN1(0.433), MEC1(0.433), TOP1(0.433), SLM3(0.433), SIP4(0.434), URN1(0.434), YCK3(0.434), USO1(0.434), RSM19(0.434), ASG1(0.434), ISU1(0.435), YHL008C(0.435), YNL313C(0.435), KKQ8(0.436), FCY2(0.436), GPD1(0.436), HHT1(0.437), MDJ2(0.437), SDH1(0.437), SSF1(0.437), PIP2(0.438), STE13(0.438), AZF1(0.438), VPS35(0.438), YGL146C(0.439), TAM41(0.440), MIF2(0.441), YDL118W(0.441), HFM1(0.441), PRR1(0.441), MRE11(0.442), FMP37(0.442), MLH2(0.442), BUD5(0.443), YOR342C(0.443), PCL1(0.443), DHR2(0.444), CDC5(0.444), CBP3(0.444), RLP24(0.444), LSG1(0.444), NCL1(0.444), YDR262W(0.445), PGA3(0.445), MID2(0.445), YJL027C(0.446), YOR305W(0.446), QCR6(0.447), MSC6(0.447), RSC4(0.447), PAU18(0.448), POL12(0.448), SME1(0.448), DBF2(0.448), RPS27A(0.448), NHP6A(0.449), YGK3(0.449), SLO1(0.452), AIM36(0.452), UBP13(0.452), TRI1(0.453), CTH1(0.453), PGS1(0.454), NMD4(0.455), YIL064W(0.455), BAR1(0.456), BCS1(0.456), YBL029W(0.456), CTR1(0.456), MRPL20(0.457), AGP3(0.457), YOR338W(0.457), FCF2(0.457), YOR052C(0.457), YJL147C(0.457), RSA1(0.457), PEX8(0.458), YOL159C(0.459), RRP45(0.459), YDL199C(0.459), LIA1(0.459), THI2(0.459), TRZ1(0.459), CYT2(0.460), MGM101(0.460), YNL277W-A(0.460), ARP8(0.460), MRPL36(0.460), YAR028W(0.460), PAU2(0.461), SLD5(0.462), SMD1(0.462), YNL086W(0.463), QCR7(0.463), FMC1(0.463), HOS4(0.463), HEM1(0.463), NAM7(0.464), YPL108W(0.465), BUD14(0.465), BOI2(0.465), HRD1(0.465), YOL114C(0.466), RIS1(0.466), SIC1(0.467), BST1(0.467), KES1(0.467), MET4(0.467), TRS120(0.467), SYC1(0.468), NPA3(0.469), YLH47(0.469), SRL2(0.469), LRC3(0.469), MHR1(0.470), ZIP2(0.470), EAR1(0.470), RSF1(0.470), RIO2(0.471), MET2(0.471), NOP4(0.471), SRD1(0.471), PWP2(0.472), MST1(0.472), PCK1(0.472), CDC7(0.472), TOK1(0.472), PRO1(0.473), RAX2(0.473), LSM7(0.473), SHG1(0.474), TOM7(0.474), DAS2(0.474), SIP2(0.475), RRS1(0.475), EUG1(0.475), PDX1(0.475), RAD61(0.476), SUN4(0.476), HAA1(0.476), YNR048W(0.477), ACO2(0.477), YOL047C(0.477), PMD1(0.477), FZO1(0.477), YEL025C(0.477), GPR1(0.478), BNI1(0.478), RSA4(0.478), YMR185W(0.478), PAU16(0.479), ECM7(0.479), YHP1(0.479), COG8(0.479), LST8(0.479), HST1(0.479), ESA1(0.480), YJL160C(0.480), MER1(0.480), CIN8(0.480), WSS1(0.481), PAT1(0.481), LRC6(0.482), FMP30(0.482), LYS21(0.483), MET18(0.483), MRPL50(0.483), GCR1(0.484), YOR022C(0.484), YJR012C(0.484), PDR3(0.485), YPL229W(0.485), SFK1(0.485), DUS4(0.485), IDS2(0.486), YOL036W(0.486), PHM6(0.486), YPR117W(0.486), RPB7(0.486), MCM2(0.487), MRS1(0.487), GLO2(0.487), YKL105C(0.487), RCK1(0.487), AME1(0.488), DIA3(0.488), HOM3(0.488), YDR541C(0.488), PMT6(0.488), DSE2(0.489), YJL216C(0.489), RIO1(0.489), ALB1(0.490), IBA57(0.490), YOR268C(0.490), CWC24(0.491), ARD1(0.491), UTP15(0.491), MSE1(0.491), UBS1(0.491), YNL234W(0.492), YDL025C(0.492), CAF40(0.492), YBR221 W-A(0.493), ATP18(0.493), MAL33(0.493), YPT6(0.493), OAC1(0.493), YJR151W-A(0.493), YML108W(0.494), COX17(0.494), RAD52(0.495), HST3(0.495), TAZ1(0.495), YNR064C(0.495), YGL010W(0.496), MFA2(0.496), PGM3(0.496), NRM1(0.496), CRS5(0.496), CTM1(0.496), SKG6(0.497), SYF2(0.497), HYM1(0.497), IPI3(0.498), MDH1(0.499), TFB2(0.499), HST4(0.499), MRPL24(0.499), YMR166C(0.500), AVT5(0.501), YGR021W(0.501), SUV3(0.501), YNL146W(0.502), MID1(0.502), AKL1(0.503), MTR10(0.503), LAA1(0.503), HDA1(0.504), SMY2(0.504), MRPL8(0.505), PLB2(0.505), CWP1(0.506), ECM14(0.506), ECM1(0.506), GAL2(0.506), FAS1(0.506), KEL1(0.506), SET7(0.506), TSR2(0.507), FET5(0.507), DRE2(0.507), MMS4(0.508), TGS1(0.508), COQ1(0.508), SUR7(0.508), PCL2(0.508), SER2(0.509), YFL034W(0.509), MKK1(0.509), SSA2(0.510), AVO1(0.510), FMP25(0.511), YRR1(0.511), SLX5(0.511), SAF1(0.511), YPL260W(0.511), YKR096W(0.511), UTP14(0.511), PAM18(0.512), WTM1(0.512), STE18(0.512), AIM20(0.512), SYM1(0.512), SIT4(0.513), SSH4(0.513), MEI5(0.513), CYC8(0.514), DSN1(0.514), STB3(0.514), IMD4(0.514), YPL109C(0.514), ECM25(0.514), YMR102C(0.515), YDR306C(0.516), SUL2(0.516), YOL019W(0.516), PAU10(0.516), HNM1(0.516), MRPL1(0.516), CMK1(0.516), YBR196C-A(0.517), YGL226W(0.517), YPR147C(0.517), PGM2(0.519), SLM4(0.519), MSS1(0.520), YER121W(0.520), YDR381C-A(0.520), VPS72(0.520), YJL043W(0.520), PAN6(0.520), YMR086W(0.521), MDN1(0.521), HEH2(0.521), YKE4(0.521), YKL162C(0.522), ZRG8(0.522), HIP1(0.523), YPR145C-A(0.523), YCL056C(0.523), ERG1(0.523), INP54(0.523), MRPS16(0.524), MOD5(0.524), YJR008W(0.524), RMI1(0.524), YNL146C-A(0.525), RRF1(0.525), CAF130(0.525), BUD9(0.526), GWT1(0.526), BEM3(0.527), STF2(0.527), SSN3(0.527), MAS2(0.527), SLN1(0.528), TLG1(0.528), NOP6(0.528), YOR097C(0.528), HVG1(0.528), GCD11(0.528), TDP1(0.528), ATC1(0.529), CIT1(0.529), GRR1(0.529), RPA12(0.530), ADY3(0.530), CTA1(0.530), SWS2(0.530), SNF8(0.530), CIS3(0.530),

MRPL4(0.531), CLB4(0.531), DBP2(0.532), APQ12 (0.532), UTP5(0.532), MPD1(0.532), MRS3(0.532), AIM43(0.532), ATP11(0.533), SNU66(0.533), ARF3 (0.533), YKU80(0.534), YLR422W(0.534), EGT2(0.534), MSP1(0.535), YLR218C(0.535), MRPL44(0.535), YHR127W(0.536), UBP3(0.536), SOD2(0.536), CYT1 (0.536), POP6(0.536), HSP10(0.536), YHR033W(0.536), YKL161C(0.538), KIN82(0.538), YNL165W(0.538), CYC7(0.538), FYV7(0.538), TAT1(0.539), YNR040W (0.539), DBP3(0.539), SMY1(0.539), TRP3(0.540), SSL2 (0.540), RPS24B(0.540), UTP4(0.540), SAW1(0.540), DAN2(0.541), YPR011C(0.541), YER156C(0.541), YGL059W(0.541), TRM5(0.541), SUT2(0.541), IML2 (0.542), ATP1(0.542), CKA1(0.542), ECM31(0.542), MSK1(0.542), SCC2(0.543), SYG1(0.543), RPO26(0.543), YPR114W(0.544), HIR3(0.544), YIL029C(0.544), MAC1 (0.545), YOR296W(0.545), IST3(0.546), HOR2(0.546), ITT1(0.547), PRP22(0.547), ROD1(0.548), DIA4(0.548), FMP32(0.548), TOM70(0.548), DIP2(0.548), YPR159C-A (0.549), PSP1(0.549), BTS1(0.549), ECM37(0.550), AST1 (0.550), SMP1(0.550), BPL1(0.550), UPS1(0.551), BAG7 (0.551), NOG2(0.551), RPC10(0.552), CYB2(0.552), SMD2(0.552), RAD1(0.552), ATP3(0.553), STP2(0.553), BUD21(0.553), RRN5(0.553), YLR352W(0.553), FRE4 (0.553), PAN2(0.554), APL3(0.555), SEC7(0.555), DUS1 (0.555), CSE1(0.555), MAK3(0.556), MRPL19(0.556), DBP1(0.556), FMP48(0.556), JAC1(0.556), VPS54(0.556), FUR1(0.557), PUP3(0.557), FUN26(0.558), SWI1(0.558), PWP1(0.559), BUD23(0.559), ATF1(0.559), FMP16 (0.559), YOL024W(0.560), IPK1(0.560), RLM1(0.560), YNG2(0.560), MSS2(0.561), FLO8(0.561), SHY1(0.561), KSP1(0.561), KNH1(0.562), DON1(0.562), KTI11(0.562), SMC5(0.562), FPS1(0.562), SHU1(0.563), RAV2(0.563), YOR356W(0.563), PFA3(0.564), ERG8(0.564), SEN15 (0.565), YNL152W(0.565), YJL193W(0.565), MSH2 (0.565), CYC1(0.565), YLR446W(0.566), MRPL13(0.566), ISA1(0.566), HUA1(0.567), YHL010C(0.567), NNT1 (0.567), RMD8(0.567), PPR1(0.568), ECM9(0.568), BSC2 (0.568), ACO1(0.568), MPS2(0.568), LEE1(0.568), COG5 (0.568), MCM1(0.569), RFC1(0.569), TAT2(0.569), DML1 (0.569), KRE9(0.570), SPT2(0.571), SPC19(0.571), QCR8 (0.571), HXT1(0.572), DOA4(0.572), MSR1(0.572), STU1 (0.572), ERG10(0.573), TFB4(0.573), ATG21(0.573), GYP6(0.574), DAD4(0.574), OAF1(0.574), YPR013C (0.574), GAS1(0.574), FAP7(0.575), CPA2(0.575), RPO31 (0.575), ATG20(0.575), TEP1(0.575), YBL081W(0.575), SMP3(0.575), MCD1(0.576), ADK2(0.576), SAD1(0.576), HUA2(0.577), BUD2(0.577), YJR136C(0.577), RPS14B (0.578), MNL1(0.578), MDJ1(0.578), FLO10(0.578), REB1(0.578), DSF2(0.579), KHA1(0.580), MRPL35 (0.580), YOR283W(0.580), PPG1(0.581), CIT3(0.581), FAA4(0.581), SPL2(0.581), MET8(0.581), HOP2(0.582), HFA1(0.582), HAP5(0.583), ROG1(0.584), MAM3(0.584), DPH1(0.584), RTG3(0.584), YNL195C(0.584), DCN1 (0.584), YLR211C(0.585), OXA1(0.585), YET2(0.585), RSC2(0.586), MRPL28(0.586), CTT1(0.586), YAP3 (0.586), BIG1(0.587), UBP8(0.587), YOL019W-A(0.587), RIB5(0.587), NOG1(0.588), VID30(0.588), MRP17(0.588), ZRT1(0.588), UAF30(0.588), SPO23(0.589), YNL122C (0.589), SNU71(0.590), CDC43(0.591), SPC29(0.591), DYS1(0.591), PRP11(0.591), SVF1(0.591), BUD20(0.591), MEK1(0.592), UBP16(0.592), PCF11(0.592), GRX4 (0.593), UTP22(0.593), HRK1(0.593), RPB9(0.593), YPL272C(0.593), ERG29(0.594), DIS3(0.594), YFH1 (0.594), MRM2(0.595), RRP5(0.595), PTI1(0.595), TIF6 (0.595), FTH1(0.595), MPE1(0.595), FKS3(0.595), ESP1 (0.596), YDL007C-A(0.596), DMC1(0.596), JHD2(0.597), LEU2(0.597), SNF3(0.597), SCJ1(0.597), YMR317W (0.598), CYK3(0.598), GPT2(0.598), FMP41(0.598), SIA1 (0.598), HXK1(0.598), YGL057C(0.599), YLR287C (0.599), NSR1(0.599), YDL241W(0.599), RKR1(0.599), REX4(0.600), TIM17(0.600), TES1(0.600), RPO21(0.600), YNL300W(0.601), BSC6(0.601), YHR080C(0.601), OPI10 (0.602), RPB8(0.602), UBP9(0.602), YKR011C(0.602), CRP1(0.602), RSM24(0.602), ARP1(0.603), SIK1(0.603), GCR2(0.603), YLR345W(0.603), FET4(0.603), MRPL40 (0.605), THP2(0.606), AMD2(0.607), YDR524W-C(0.607), PSY4(0.607), BUD16(0.607), HPT1(0.608), YDR333C (0.608), RHO4(0.609), AHC1(0.609), YIL206C(0.609), SWT1(0.610), HEK2(0.610), ATP12(0.610), XBP1(0.610), RMD6(0.611), RPL15B(0.611), NUP42(0.611), PLC1 (0.611), MAD3(0.612), YPS1(0.612), MCM16(0.612), HXT4(0.612), HXK2(0.612), ERG12(0.613), MMT2 (0.613), YMR321C(0.613), MUM3(0.613), HST2(0.613), ROG3(0.613), DEF1(0.615), YLR281C(0.615), SSK22 (0.616), MLH3(0.617), YGR131W(0.617), CSE4(0.617), YCL002C(0.617), MRPS18(0.618), CAD1(0.618), AIF1 (0.618), SFC1(0.618), OYE3(0.619), EAF5(0.619), RSC9 (0.620), GYL1(0.620), YDL063C(0.620), ISA2(0.621), GBP2(0.621), IMG1(0.621), NRP1(0.621), DHH1(0.622), RHB1(0.622), CIK1(0.623), PHO89(0.623), AGX1(0.623), RPB2(0.624), MRPL17(0.624), GPX2(0.625), LYP1 (0.625), VPS9(0.625), BNA3(0.626), CKA2(0.626), OPI1 (0.626), YER034W(0.626), RSM26(0.626), LSM6(0.627), THI3(0.627), SMC4(0.627), SWF1(0.627), YAH1(0.628), RPF2(0.628), HFI1(0.628), PLB1(0.628), MAM33(0.628), YLR413W(0.628), PRP8(0.628), ENO1(0.629), RPC19 (0.629), YGL007C-A(0.629), YMR181C(0.629), URA7 (0.629), YGL108C(0.629), SRB7(0.630), DAD1(0.630), LYS4(0.630), ATG18(0.630), FMP45(0.630), VAM3 (0.630), SSC1(0.631), SNU56(0.631), YHR045W(0.631), HTA2(0.631), YJL213W(0.631), RPL20A(0.632), ALD4 (0.632), QCR10(0.632), YGR287C(0.632), CBP4(0.632), PCI8(0.632), MCM4(0.632), DEM1(0.633), ATO3(0.633), TPS2(0.633), TAF1(0.633), KRE6(0.634), KGD2(0.634), ARB1(0.635), NMD5(0.636), EFR3(0.637), TRP4(0.637), HLJ1(0.638), ACE2(0.638), LDB17(0.638), ATG7(0.639), OSH6(0.639), AFT1(0.639), CTF4(0.639), YDR286C (0.639), AIM44(0.639), YLR149C(0.640), MRPS9(0.640), BET1(0.641), YLF2(0.641), BOI1(0.642), BUD4(0.642), CRF1(0.642), MLP2(0.643), ARX1(0.643), RRP12(0.644), NAT2(0.645), PCL7(0.645), ARP7(0.645), SFH1(0.645), STF1(0.645), YML081W(0.646), MRP49(0.646), FOL3 (0.646), SAC7(0.646), PCS60(0.647), TPA1(0.647), SSS1 (0.647), ERO1(0.647), NHP2(0.648), AIM1(0.648), AMD1 (0.648), VPS38(0.648), COG3(0.648), YMR244C-A (0.648), PYC1(0.648), CCC1(0.648), TAO3(0.649), YDL233W(0.649), RPB10(0.650), YBR242W(0.650), EDC2(0.650), YVC1(0.650), YDR266C(0.651), PMT3 (0.651), NIS1(0.651), YDR128W(0.651), ATP15(0.651), YML002W(0.652), ATG9(0.652), IKS1(0.652), SUR2 (0.652), MSD1(0.652), SMC3(0.653), SPC1(0.653), MRPS35(0.653), ZIP1(0.653), YPR022C(0.654), YKL070W(0.654), RIM4(0.654), YJL127C-B(0.654), ARV1(0.655), YML6(0.655), CYC3(0.656), COX9(0.656), RMD11(0.656), SNU23(0.657), PRS2(0.657), YNL092W (0.657), TIF4632(0.657), CBP2(0.658), STP4(0.658), YIR024C(0.658), SHE1(0.658), EMG1(0.659), NUP192 (0.659), THI7(0.659), NGL1(0.659), LDB19(0.659), AFG2 (0.660), ROT1(0.660), PIK1(0.660), MRPL31(0.660), RHO2(0.660), MRPL49(0.660), FMO1(0.661), LRS4 (0.661), CHS3(0.661), SEC8(0.662), HXT5(0.662), GRX3 (0.663), YHL042W(0.663), AAC3(0.663), WSC4(0.663), PIN2(0.663), PUB1(0.663), ERG28(0.663), PSR1(0.663),

ISY1(0.664), VPS70(0.664), IRC19(0.664), DNM1(0.665), RPA190(0.665), CCR4(0.665), SSU72(0.665), MRPL7(0.665), TBF1(0.666), YPR115W(0.666), SKP2(0.666), CDC73(0.666), RPL31B(0.666), MAK16(0.666), ERB1(0.666), DCG1(0.666), RNT1(0.667), RRP7(0.667), GCD7(0.667), RAD18(0.667), OMS1(0.668), YOL048C(0.668), PPT2(0.668), SCS7(0.668), YBL028C(0.668), RSC30(0.668), TIM23(0.668), PRI1(0.669), REC102(0.669), MCH5(0.669), PST1(0.669), CLB3(0.669), QCR9(0.670), MIR1(0.670), SSP120(0.670), MEF2(0.672), RPL14B(0.672), YPR003C(0.672), RLI1(0.672), SWC4(0.672), MTM1(0.673), SKY1(0.674), TOM1(0.674), YGL079W(0.674), ROM2(0.674), TFA2(0.674), AIM3(0.674), SSQ1(0.675), DUG2(0.675), MSF1(0.675), RPS0B(0.675), SCO2(0.675), OLE1(0.676), SBE2(0.676), SAR1(0.676), YJR116W(0.676), TEF1(0.677), AIM13(0.677), DFG5(0.677), YLR012C(0.677), MCM3(0.677), RPS7B(0.678), DFR1(0.678), YBL039W-B(0.678), RML2(0.679), RSM27(0.679), MEC3(0.679), YCG1(0.679), RFX1(0.680), RPL7B(0.680), CHS2(0.681), PEX5(0.681), TIF4631(0.681), RPL18B(0.681), SMB1(0.682), HUL4(0.682), NPL6(0.682), YOL107W(0.683), TRM1(0.683), STE6(0.683), ASK1(0.684), RAD9(0.684), YDL012C(0.684), RBG2(0.684), SEC6(0.684), YLR143W(0.685), XPT1(0.685), HGH1(0.685), YIL091C(0.685), PRS3(0.686), NTC20(0.686), YPR196W(0.686), MIC17(0.686), POA1(0.687), NPY1(0.687), SNQ2(0.687), ADE3(0.687), APT2(0.688), YGL082W(0.688), YHB1(0.689), MRPL16(0.689), CSH1(0.690), GUP1(0.690), YJL171C(0.690), IDP3(0.690), VHT1(0.691), PUG1(0.691), MPM1(0.691), RRP40(0.691), DPM1(0.691), AFG3(0.691), YBP2(0.691), YPL183W-A(0.692), AIM31(0.692), YCR015C(0.692), MSN4(0.692), YPL038W-A(0.692), TSC11(0.692), SEC59(0.693), ADA2(0.693), TPM2(0.693), YHR175W-A(0.693), POM152(0.694), YJR124C(0.694), RPL22B(0.694), COG7(0.694), NEW1(0.695), GSM1(0.695), UGX2(0.696), PRK1(0.696), GPD2(0.696), LDB16(0.697), PAM16(0.697), CMC1(0.697), TOM6(0.698), MBA1(0.698), SWC5(0.698), PRM10(0.698), SAM1(0.699), TRS31(0.699), YFT2(0.699), RGT1(0.700), RPL10(0.700), KRE33(0.700), CDC1(0.700), MRPL37(0.700), KEX2(0.701), VPS13(0.701), ACN9(0.701), RSC3(0.701), PBS2(0.702), EPS1(0.702), GPI18(0.702), ADH4(0.702), YTP1(0.702), YHM2(0.703), ZIM17(0.703), LYS5(0.703), AIM22(0.703), RGM1(0.703), ECM10(0.703), RDH54(0.703), DED1(0.704), CSE2(0.704), POC4(0.704), IPI1(0.704), SOL4(0.705), YKR075C(0.706), RSM10(0.707), MAE1(0.707), ATF2(0.707), SHE4(0.707), RSC1(0.708), GNT1(0.708), MSH4(0.708), HSK3(0.708), TRS20(0.709), NBP35(0.709), YBR090C(0.709), GLO1(0.709), FYV4(0.709), AEP2(0.709), ARP4(0.710), IES3(0.710), HYP2(0.710), DNF2(0.711), GAA1(0.711), RPA135(0.711), PCL9(0.711), SPT5(0.711), EDE1(0.711), ORC3(0.711), YOR304C-A(0.711), YCL047C(0.711), YER085C(0.711), YOL014W(0.711), YPL071C(0.712), GTS1(0.712), RFC2(0.712), NDE2(0.712), PET127(0.713), PLM2(0.713), YEA6(0.713), RPN7(0.713), MDL1(0.713), TMA64(0.714), NCE103(0.714), MCM6(0.714), MAS1(0.715), TSR1(0.715), BAS1(0.715), IRC4(0.716), TIM21(0.716), HCH1(0.716), APC5(0.716), PMP1(0.716), PUF6(0.716), YER077C(0.716), SNC2(0.716), MRP21(0.716), YLR036C(0.717), YME2(0.717), SEC12(0.717), YJL062W-A(0.718), YMR031(0.718), YAL065C(0.718), YNR047W(0.718), NHP10(0.718), YOL083W(0.719), DLS1(0.719), IGO2(0.719), PAU17(0.719), NCS2(0.720), TAF7(0.720), YDL186W(0.720), CMK2(0.721), PUS7(0.721), TIM9(0.721), PMU1(0.722), MNP1(0.722), SEC16(0.722), RIF1(0.723), KAR3(0.723), MDL2(0.723), YLR356W(0.724), DCI1(0.724), ASP1(0.724), NET1(0.725), YPL068C(0.725), MOT3(0.725), NOC3(0.725), MRP13(0.725), GUT2(0.725), ICY1(0.725), NTO1(0.726), HOS3(0.726), TIM54(0.726), COX4(0.726), UBX2(0.727), RVB2(0.727), YBL059C-A(0.727), RBS1(0.727), DCR2(0.727), NEM1(0.727), MNN9(0.728), YNR036C(0.728), NOP15(0.728), SEC61(0.728), RTT106(0.729), CCT7(0.729), OSM1(0.729), SAS5(0.729), VPS29(0.729), KTI12(0.729), POL32(0.729), PUS9(0.730), SLF1(0.730), MUQ1(0.730), HSD1(0.730), KAR4(0.730), STN1(0.731), BAT1(0.731), THI71(0.731), RPL27B(0.732), COX5A(0.732), AEP1(0.732), LPP1(0.732), PRM1(0.732), YKL222C(0.732), TIP41(0.733), RPL43B(0.733), YCR043C(0.733), STP1(0.734), AIM8(0.734), HXT9(0.734), MRP7(0.734), YPL216W(0.735), SRB6(0.735), CTK2(0.736), RIT1(0.736), NST1(0.737), RIB7(0.737), MRPL38(0.737), SRT1(0.737), CBK1(0.738), ARL3(0.738), DRS2(0.738), YLR307C-A(0.738), GPI8(0.738), SHM2(0.739), IPL1(0.739), YPL041C(0.739), ARR1(0.739), GCN20(0.740), YPL039W(0.740), MNN1(0.740), SLX9(0.740), SEO1(0.741), RMP1(0.741), PSA1(0.741), CHS6(0.741), DAN1(0.742), RPB5(0.742), SIR3(0.742), BCP1(0.742), YLL058W(0.742), TNA1(0.742), TRM13(0.743), NOP1(0.743), SLP1(0.743), PEX31(0.743), YIF1(0.743), MSA2(0.743), ADH3(0.744), MNT4(0.744), GIS1(0.744), SLD2(0.745), PIN4(0.745), NVJ1(0.745), HTS1(0.745), RAD7(0.745), YKU70(0.745), NUF2(0.745), YIL001W(0.745), ASK10(0.745), YBL010C(0.745), ATP14(0.746), CDC123(0.746), MRPL51(0.746), YGR127W(0.747), YLR392C(0.747), APC2(0.747), DEP1(0.747), APS3(0.747), RCL1(0.747), DCD1(0.747), MIG3(0.747), BSP1(0.749), YLL014W(0.750), TOA1(0.750), NBA1(0.750), SLC1(0.750), IGO1(0.752), SDH3(0.752), ACS2(0.752), YOR093C(0.752), MPC54(0.752), PFY1(0.753), MIA40(0.753), YDR034C-A(0.753), RDS3(0.753), MSC3(0.753), TIM50(0.753), CSN12(0.753), GIN4(0.753), SMI1(0.753), ADE17(0.754), YGR016W(0.754), PCP1(0.754), SBA1(0.754), SRP102(0.754), SUM1(0.754), ICL1(0.754), OAF3(0.754), ZRT2(0.754), NOP10(0.755), BET2(0.755), YVH1(0.756), SPO75(0.756), DNL4(0.756), SGV1(0.756), IES4(0.757), SET4(0.757), YCL001W-B(0.757), SQT1(0.757), REI1(0.757), MRPL9(0.757), YPL066W(0.758), PET191(0.758), TEM1(0.758), UBX4(0.759), DBF20(0.760), MSB3(0.760), NUP100(0.760), RIC1(0.760), CUE4(0.761), IKI3(0.761), YEL043W(0.761), MRPL11(0.761), MPS1(0.761), EAP1(0.762), AVT2(0.762), GND1(0.762), TYW3(0.762), POP7(0.762), YDR186C(0.762), POR2(0.762), LSM5(0.763), MSH1(0.763), TOM22(0.763), YBR238C(0.764), MEP1(0.764), ILV3(0.764), YMD8(0.764), YJR061W(0.764), OSH3(0.764), TEF4(0.765), SCO1(0.765), TDH1(0.765), RIM21(0.766), YGL185C(0.766), NUS1(0.766), KTR4(0.767), RRP14(0.767), TUB4(0.767), LEU9(0.767), YLR437C(0.768), AIM7(0.768), ATX2(0.768), AI3(0.769), OST4(0.769), TRA1(0.769), MYO5(0.769), DAL4(0.769), IMG2(0.769), LTV1(0.769), YGR122W(0.770), CFT2(0.770), YMR001C-A(0.771), CDC16(0.771), YAL067W-A(0.771), YDR132C(0.771), YNL011C(0.772), TCP1(0.772), CCT3(0.772), MKK2(0.772), RRI2(0.772), ZEO1(0.772), RUD3(0.772), RTR2(0.772), YIL070C(0.773), NUP116(0.773), ENT1(0.774), SLU7(0.774), MSC2(0.774), STV1(0.774), NUP60(0.775), AIM28(0.776), YOL029C(0.776), SHE10(0.776), RSB1(0.776), SHO1(0.776), DLD2(0.777), RAX1(0.777), LCP5(0.777), ATG17(0.777), PEX17(0.778), GAL4(0.778), MET32(0.778), YOR223W(0.779), STE14(0.779), DUG3(0.780), SRX1(0.780), UFO1(0.780), YAT2

(0.780), NMD3(0.780), PRP9(0.780), MSN2(0.781), PET123(0.781), SWD2(0.781), SOG2(0.781), RRP17(0.781), GPB2(0.781), YOR293C-A(0.781), TEN1(0.781), SOV1(0.782), PFK27(0.782), YIL127C(0.782), YNL024C-A(0.782), TMT1(0.783), SEC39(0.783), YER158C(0.783), ERP3(0.783), YLR257W(0.783), PKH3(0.783), YNL155W(0.783), PSO2(0.783), NOP9(0.783), GPG1(0.784), GIP4(0.784), RIB1(0.784), CYS4(0.784), ZRT3(0.784), FMP21(0.785), DAK2(0.785), ISW1(0.785), ACF4(0.785), RTT10(0.785), RTT109(0.785), FMP10(0.785), YAP6(0.785), APM4(0.785), ZAP1(0.785), ARO9(0.786), SCM4(0.786), MIM1(0.786), BRR6(0.787), SRN2(0.787), YOR287C(0.787), CLA4(0.787), RNR3(0.787), ALG8(0.787), RAD50(0.787), YBR239C(0.788), LDB7(0.788), ATP17(0.788), UGA2(0.788), ENA2(0.788), YLR408C(0.788), SAT4(0.788), BOP3(0.788), SDH4(0.789), YNL045W(0.789), RPC40(0.790), YNL134C(0.790), ARP5(0.790), MAD2(0.790), GRX6(0.790), RSM18(0.790), FES1(0.791), SGF73(0.791), ARH1(0.791), MHT1(0.791), CNS1(0.791), BDH2(0.792), YKL063C(0.792), GSH1(0.792), BOS1(0.792), THI72(0.792), BSC1(0.792), MED8(0.793), RAD5(0.793), EMP47(0.793), SIS2(0.793), TEA1(0.793), YJL185C(0.793), RTF1(0.793), CIN4(0.794), DIC1(0.794), EST2(0.795), YNK1(0.795), PUS2(0.795), PEX13(0.795), YNL217W(0.795), HOR7(0.795), MGS1(0.796), YHR009C(0.796), YML007C-A(0.796), JNM1(0.796), YHR078W(0.796), YMR155W(0.796), STB5(0.796), MRP4(0.796), STE3(0.797), CKS1(0.797), TAF13(0.797), YNL176C(0.797), PCD1(0.797), HSP26(0.797), DAS1(0.798), EDS1(0.798), CTR3(0.798), PXL1(0.798), MRS11(0.799), MET3(0.799), BDP1(0.799), CBF2(0.799), DBP6(0.799), FAR11(0.799), ERI1(0.800), MDM10(0.801), RPM2(0.801), COX13(0.801), TOA2(0.801), MYO2(0.802), PRP5(0.802), DRN1(0.802), ZDS1(0.802), IES2(0.803), FAT1(0.803), HIS1(0.803), MET16(0.803), LAS17(0.803), ACA1(0.803), HIS4(0.803), PHO12(0.804), EBP2(0.804), MRPL6(0.804), YLR271W(0.804), YBR085C-A(0.804), CRR1(0.805), SWI3(0.805), SWI4(0.805), PYK2(0.805), BUD7(0.806), PEX12(0.806), MDV1(0.806), IDH2(0.807), MRC1(0.807), TIM11(0.807), SPT15(0.808), FBP26(0.808), GUP2(0.808), NPL4(0.808), YCR007C(0.809), ABD1(0.809), YNL193W(0.809), YLR426W(0.810), YSP2(0.810), SSO2(0.810), MRPL23(0.810), YHR112C(0.810), VPS36(0.811), MET7(0.811), UTP18(0.811), MTW1(0.811), DYN1(0.812), RNH1(0.812), LST4(0.812), TAF11(0.812), RPL17A(0.812), SNA2(0.812), YGL041W-A(0.813), KAR5(0.813), YEH2(0.814), YMR118C(0.814), CUE2(0.814), URA8(0.814), YMR034C(0.814), YLR152C(0.815), YKL088W(0.815), HEM13(0.815), CAT5(0.815), KRE1(0.815), IBD2(0.817), YOL098C(0.817), AIM18(0.817), HMG1(0.817), TRM7(0.817), ADY2(0.818), LCD1(0.818), YGL194C-A(0.818), EFG1(0.818), BRX1(0.819), HIM1(0.819), TCM62(0.819), SET6(0.819), FIN1(0.819), CBF5(0.820), ASI1(0.820), DUT1(0.820), SEC65(0.820), YPL067C(0.820), RRP43(0.820), ASC1(0.821), ERG3(0.821), RTA1(0.821), NFU1(0.821), JIP4(0.821), YLR419W(0.822), YJR011C(0.822), YJL045W(0.822), ARC18(0.822), YBR287W(0.822), CAP2(0.822), NEO1(0.823), TOM5(0.823), PEP5(0.823), PCC1(0.823), PXR1(0.823), ALG11(0.823), YLR301W(0.824), ARG1(0.824), RFC4(0.824), AIM42(0.824), PPA2(0.824), DAP1(0.824), RTS1(0.825), EDC3(0.825), IRC23(0.825), YBR220C(0.825), GPI14(0.825), IML1(0.825), NIP7(0.826), YPT32(0.826), MSS18(0.826), CHO1(0.826), CST26(0.826), MOH1(0.826), PLP1(0.827), MKC7(0.827), XYL2(0.827), YMR295C(0.828), YLR003C(0.828), YIL096C(0.828), MOT2(0.828), RLP7(0.828), YSC84 (0.828), NDL1(0.828), PFK1(0.828), MRD1(0.829), SAC6(0.829), REX2(0.829), RPA34(0.829), AHC2(0.829), APC1(0.829), YDR222W(0.829), VHR1(0.829), SUS1(0.829), UTH1(0.829), IRC8(0.830), SNO1(0.830), APT1(0.830), YOR352W(0.830), YMR258C(0.831), MRH1(0.831), HRP1(0.831), SRP21(0.831), MRPL22(0.831), SEC9(0.831), KAR2(0.832), YGR054W(0.832), HOF1(0.832), YDC1(0.832), YGR207C(0.833), WSC2(0.833), SRC1(0.833), YAR023C(0.834), HAM1(0.834), PER1(0.834), YKL047W(0.834), FLC3(0.834), TRM10(0.834), PAU15(0.834), RFA1(0.835), AI2(0.835), MPP10(0.835), ELC1(0.835), PHB1(0.836), OST1(0.836), LSB1(0.836), OKP1(0.836), THI22(0.836), MRP51(0.836), COX20(0.837), FCF1(0.837), PHO80(0.837), FIT1(0.837), YPL056C(0.838), KIN4(0.838), GCD1(0.839), FRT1(0.839), ACS1(0.839), LGE1(0.839), YJL136W-A(0.840), MLC2(0.840), SMF1(0.840), ISW2(0.840), HIS6(0.841), CTR2(0.841), GCV2(0.841), GAL83(0.841), IMP3(0.842), GRS1(0.842), MRS5(0.842), NCE101(0.843), BUD17(0.843), MKS1(0.843), SYF1(0.843), ACH1(0.844), ARN1(0.844), RCN2(0.844), UBC12(0.844), YER079W(0.845), YHL044W(0.845), THI20(0.845), PML1(0.845), IRC10(0.846), BMS1(0.846), SSA1(0.846), DDI2(0.846), RPC11(0.846), YDR115W(0.847), DDC1(0.847), IRC21(0.847), DUR3(0.847), PET100(0.847), SKI8(0.847), QRI5(0.847), QDR1(0.847), UBC11(0.848), MRT4(0.848), POL3(0.848), MFB1(0.848), TCO89(0.848), YDR370C(0.848), OYE2(0.848), MDM31(0.849), SLG1(0.849), YOR062C(0.849), DNF1(0.850), MEH1(0.850), AIR2(0.850), MSS116(0.850), ACB1(0.850), ADE12(0.851), ELO1(0.851), VTA1(0.851), MRPL27(0.852), YFL054C(0.852), SPC34(0.852), RGS2(0.853), DRS1(0.853), GTR1(0.853), COX8(0.853), KEL2(0.854), NUP82(0.854), GIR2(0.855), FKH2(0.855), CLG1(0.855), PEX6(0.855), HO(0.855), YHR003C(0.855), NUP84(0.856), RRB1(0.856), PSY2(0.856), BSD2(0.856), ESBP6(0.856), MED7(0.857), RSN1(0.857), YKE2(0.857), YHL012W(0.857), SHE2(0.858), RPL2A(0.858), DUO1(0.858), DST1(0.858), PET9(0.858), RSA3(0.858), GLN4(0.858), YKR015C(0.858), YJR141W(0.858), RIM20(0.858), BCK2(0.859), SPC42(0.859), TRF5(0.859), FAA2(0.859), TRS130(0.859), GUA1(0.860), HSL7(0.860), PDE2(0.860), RRP8(0.860), XRS2(0.860), SPE1(0.860), RFT1(0.860), VPS20(0.860), SEC20(0.860), PAD1(0.861), GGC1(0.861), ORC1(0.861), HMG2(0.861), STE2(0.861), LSM3(0.861), ICS2(0.861), TRM2(0.861), CDC3(0.862), HEM2(0.862), SIN4(0.862), VIK1(0.862), HIS7(0.863), RAD54(0.863), IQG1(0.863), DFG10(0.863), TIP1(0.864), BRR2(0.864), GRX2(0.864), HTZ1(0.864), BCH2(0.864), NRG2(0.865), RSC58(0.865), TMA16(0.865), RAD59(0.866), URM1(0.866), ADY4(0.866), AAP1(0.866), ABP1(0.866), YGR066C(0.867), BRE5(0.868), BFR2(0.868), LSM1(0.868), CHD1(0.868), VTI1(0.868), AIM11(0.868), RFA2(0.869), SUR4(0.869), YOR228C(0.869), DLD3(0.870), ISN1(0.870), CYC2(0.870), SNF5(0.870), YMR124W(0.870), GIP2(0.870), SVL3(0.870), SEC13(0.870), YEL047C(0.870), BEM1(0.871), RPL16A(0.871), SPR3(0.873), ATP4(0.873), WAR1(0.873), ITR1(0.873), FAR3(0.873), YOR021C(0.874), YBR028C(0.874), NOP58(0.875), RPN13(0.877), YNL035C(0.878), YJL049W(0.878), YER137C(0.878), NOC4(0.879), ALG7(0.879), MET22(0.880), SIL1(0.880), TYS1(0.880), GLK1(0.880), YDR341C(0.880), YKR045C(0.880), RAD23(0.880), BIK1(0.881), RPL27A(0.881), YOR152C(0.881), KNS1(0.881), YHR182W(0.881), EEB1(0.881), RKM1(0.881), SNG1(0.882), YIL067C(0.882), VPS66(0.883), TCB1(0.883), ADE4(0.883), YNL034W(0.883), HSP78(0.883), HEM15(0.883), PKC1(0.883), SPP2(0.883), MF(ALPHA)1(0.883),

ARP6(0.884), NCS6(0.884), RTS3(0.884), SPE4(0.884), YPL199C(0.884), DAL81(0.884), SAC1(0.884), YOL131W(0.884), YHL026C(0.884), REC107(0.884), YGR174W-A(0.885), SGE1(0.885), NCB2(0.885), YNL320W(0.885), CDC20(0.885), CSG2(0.886), ECM5(0.886), NOC2(0.886), IES1(0.886), SMK1(0.887), PHO86(0.887), YHR202W(0.887), CIN1(0.887), PFS1(0.887), MCM21(0.887), ROT2(0.888), GLC7(0.888), HRT1(0.888), YDR018C(0.888), APM1(0.888), DPH2(0.888), CDH1(0.889), HNT3(0.889), ATG4(0.889), FRE3(0.889), ATP2(0.889), YMR148W(0.890), YAT1(0.890), ERG11(0.890), PGI1(0.890), FKH1(0.890), MET30(0.890), YGL140C(0.890), ARC35(0.890), SNX41(0.890), SAS2(0.890), YHR007C-A(0.890), YML083C(0.891), ABF1(0.891), YLR104W(0.892), TOS1(0.892), MF(ALPHA)2(0.892), FRM2(0.892), OPY1(0.892), MMF1(0.893), DIG1(0.893), PMI40(0.894), YIL092W(0.894), ASI3(0.895), FIR1(0.895), ERG26(0.895), YMR090W(0.895), YGL085W(0.896), CDC24(0.896), YPL113C(0.896), YPR010C-A(0.896), BIR1(0.896), AAH1(0.896), EPT1(0.896), MSW1(0.896), NOP14(0.897), CBT1(0.897), COX18(0.897), COX16(0.898), RRD1(0.898), BEM4(0.898), GEA2(0.898), FOB1(0.898), ERG7(0.898), YLR042C(0.899), SEC17(0.899), YPR063C(0.899), PUT4(0.900), MSI1(0.900), RPA43(0.900), SPE2(0.900), DAL1(0.901), RPC25(0.901), BRO1(0.901), AXL1(0.901), EAF7(0.901), RCR1(0.901), YDR338C(0.901), RGA1(0.902), LOT5(0.902), YIH1(0.902), RNA1(0.902), SKM1(0.903), PUT2(0.903), HEM4(0.904), AIM37(0.904), PHO13(0.904), YGR015C(0.904), AKR2(0.904), YKL050C(0.904), TCB2(0.904), HAC1(0.904), ADE1(0.905), RTN1(0.905), RPL8B(0.905), MDM36(0.905), JHD1(0.905), CCL1(0.905), YDR282C(0.906), PRE10(0.906), PEX14(0.906), OMA1(0.906), YNR034W-A(0.906), NBP2(0.906), SPT20(0.906), PRP2(0.907), YGL041C-B(0.907), YBR255W(0.907), YOR246C(0.907), YFL012W(0.907), YLR412W(0.908), DUR1,2(0.908), RPS4A(0.908), YAL037W(0.908), ICT1(0.908), CTR86(0.909), RPN10(0.909), RME1(0.909), MSB4(0.909), SAM35(0.909), MAG2(0.909), YOL092W(0.909), PPZ1(0.909), YGL138C(0.910), YHR097C(0.910), SSZ1(0.910), SIS1(0.910), CTP1(0.910), TAF5(0.910), PDC1(0.910), YPL150W(0.910), GCD10(0.911), ENP1(0.911), TOM40(0.911), ERG6(0.912), ECM4(0.912), RLF2(0.913), RKI1(0.913), SAM3(0.913), SEC62(0.913), CRC1(0.914), UME1(0.914), TUS1(0.915), YNL046W(0.916), VTC1(0.916), TEL2(0.916), YEN1(0.916), PEX30(0.917), GSG1(0.917), NTE1(0.918), RBG1(0.918), TIM8(0.918), YNG1(0.918), PMT5(0.918), PRP16(0.918), SPT6(0.918), NIP100(0.919), THS1(0.919), HMRA1(0.920), STE20(0.920), AIM10(0.921), YGL242C(0.921), GTR2(0.921), YOL157C(0.921), LOT6(0.921), KEX1(0.921), MET14(0.922), UBA2(0.922), NUT1(0.922), SPO21(0.923), PAC10(0.923), YND1(0.923), DSE3(0.923), YJR149W(0.923), YOR378W(0.923), GSY2(0.923), YBR063C(0.924), SRV2(0.924), YCK1(0.924), YKL091C(0.925), FMS1(0.925), UTP23(0.925), YCR090C(0.925), SFT2(0.925), BNI5(0.925), SNX3(0.925), FSH2(0.926), RGD2(0.926), SST2(0.926), UNG1(0.927), YLR164W(0.927), RPS26B(0.927), TRE1(0.927), MSH5(0.927), MYO3(0.928), YGL039W(0.928), SUP35(0.929), AMA1(0.929), ATP19(0.929), YGL036W(0.930), PTK2(0.930), PBP2(0.930), TRM112(0.931), SMC1(0.931), NPR1(0.931), PFK2(0.932), PDE1(0.932), RRI1(0.932), FRE2(0.932), YOR118W(0.933), FRE1(0.933), ECM38(0.933), ALD3(0.933), STT3(0.934), VMR1(0.934), RPC82(0.934), URK1(0.934), ATX1(0.934), REG1(0.935), PNT1(0.935), YMR279C(0.935), RSC8(0.935), YJR111C(0.935), YLR253W(0.935), FSH1(0.935), YDR336W(0.935), ERD1(0.935), VPS41(0.936), AYT1(0.936), VRG4(0.936), YPL009C(0.936), VID22(0.936), YDR514C(0.936), APC11(0.937), VPS74(0.937), KRE11(0.937), RRP6(0.938), FOX2(0.938), ASM4(0.938), MED11(0.938), TWF1(0.939), GRX5(0.939), MYO1(0.939), YPL107W(0.939), PET54(0.939), YLR064W(0.940), SPC2(0.940), APP1(0.940), DBP5(0.940), BPH1(0.941), YKL151C(0.941), NAF1(0.941), YKL027W(0.941), ARO3(0.941), UBX6(0.942), TIM18(0.942), BNI4(0.942), SPC98(0.943), PZF1(0.943), PIC2(0.943), UTP8(0.943), YBR235W(0.943), SMC6(0.943), RLR1(0.943), DBF4(0.943), RPB11(0.944), SHE3(0.944), SFB3(0.944), SYT1(0.944), STU2(0.945), NGL2(0.945), GDS1(0.945), NOP2(0.945), SVS1(0.945), PRY2(0.946), GDA1(0.946), BCY1(0.947), PUS1(0.947), COX7(0.947), MRPL15(0.947), RER1(0.948), SLH1(0.948), RPB3(0.948), TIF11(0.948), YDL173W(0.948), YML053C(0.948), PEX4(0.949), MIG1(0.949), CLU1(0.950), ECM32(0.950), FCY1(0.950), HSP32(0.950), MAL12(0.950), JLP2(0.950), DAT1(0.950), RMR1(0.950), KTR6(0.950), OST2(0.951), NOP12(0.951), IRC3(0.951), OPT2(0.952), YBL054W(0.952), PDX1(0.952), AMS1(0.952), YBR204C(0.953), SLM2(0.953), VPS64(0.953), PTH2(0.953), MRP1(0.953), TIF5(0.954), AAT2(0.954), CPR3(0.954), AVT6(0.954), CLF1(0.954), MDM38(0.954), COX12(0.954), ESS1(0.954), RPG1(0.955), SNF11(0.955), ERV15(0.955), YPR078C(0.955), RHO3(0.956), SUE1(0.956), CLN2(0.956), YFL040W(0.956), YLR040C(0.956), RLA1(0.957), YMR272W-B(0.957), MND2(0.957), EHD3(0.957), IMP4(0.957), PAH1(0.958), HMO1(0.958), RPL26A(0.958), PIR3(0.959), MNN5(0.959), FCY22(0.959), SMD3(0.959), YER186C(0.959), QDR2(0.959), MHP1(0.960), CRH1(0.960), LSB3(0.960), RMD1(0.960), SDA1(0.960), AXL2(0.961), NOP16(0.961), YCL058W-A(0.962), ORC6(0.962), PRR2(0.963), STH1(0.963), CCA1(0.963), FUS1(0.963), MRS6(0.963), YBP1(0.963), RPL12A(0.963), UTR4(0.964), MTF2(0.964), MAK31(0.964), BOP2(0.964), UIP5(0.964), SSL1(0.965), INO4(0.965), RPT3(0.965), YBR072C-A(0.966), YHR159W(0.966), ITR2(0.966), PUF3(0.967), ADD66(0.967), GCS1(0.968), LYS2(0.968), MTR2(0.968), TRP1(0.968), HXT11(0.968), ALG1(0.969), SPS18(0.969), YOR111W(0.969), STI1(0.969), SSD1(0.969), CRN1(0.969), CSN9(0.970), RSM22(0.970), YIL152W(0.970), TOF1(0.970), HOM2(0.970), MOB1(0.971), RAD24(0.971), IRC25(0.971), RSM23(0.971), YLR049C(0.971), YBL055C(0.971), SPP41(0.972), YMR310C(0.972), YHC1(0.972), YNL040W(0.973), AIM41(0.973), APL5(0.973), ILV2(0.974), YIR035C(0.974), REC8(0.974), MSS51(0.974), GAP1(0.975), EMP70(0.975), HAL1(0.975), CDC21(0.975), VPS75(0.975), YER066W(0.975), MCM7(0.975), CHZ1(0.976), YKL121W(0.977), MMS2(0.977), BUL2(0.977), SEC1(0.977), BEM2(0.977), YKR018C(0.978), NUP2(0.978), VPS73(0.978), YIL024C(0.978), YPL225W(0.979), FEN1(0.979), YSR3(0.979), CST9(0.979), YLR241W(0.979), MAK10(0.980), CUP2(0.980), CCP1(0.980), ERV14(0.980), YJU3(0.980), RAP1(0.980), IMP1(0.980), COA1(0.981), TFA1(0.981), FAF1(0.981), ATP5(0.981), ARG3(0.982), RVB1(0.982), RPA49(0.982), NSE4(0.982), YKT6(0.982), RRN9(0.983), APM2(0.983), GAT3(0.983), SPN1(0.983), CKB1(0.983), DTD1(0.983), TPO2(0.983), PRP45(0.984), DEG1(0.984), PTC5(0.984), TSC10(0.984), DPB11(0.984), YKR005C(0.985), RIM15(0.985), PNO1(0.985), COX15(0.985), VPS4(0.985), PKH2(0.986), MTR4(0.986), YLR053C(0.986), LEU4(0.986), YPK1(0.987), PDX3(0.987), TIF2(0.988), YDL180W(0.988),

FYV8(0.988), BUD13(0.988), YBR139W(0.988), TPK2(0.988), SSH1(0.989), YGR102C(0.989), YDR348C(0.989), RPL28(0.990), QCR2(0.990), YAR1(0.990), SCP1(0.990), TIP20(0.990), UBC7(0.990), SEC11(0.991), RPN11(0.993), TGL5(0.993), HSP60(0.993), RPL42B(0.994), PRS1(0.994), YKL018C-A(0.994), TFC6(0.994), RNH201(0.994), URA1(0.995), ALG9(0.995), MSG5(0.995), AKR1(0.995), MNN11(0.996), OCA1(0.996), YGP1(0.997), PPX1(0.997), TSC3(0.997), PSF3(0.998), YAF9(0.998), YMR175W-A(0.998), LHP1(0.998), YMR252C(0.999), SLK19(0.999), YJR107W(0.999), PMC1(0.999), HCR1(0.999), SKG1(0.999), PCT1(0.999), LPE10(1.000), PGK1(1.000), HAS1(1.000), SEC23(1.000), GPI13(1.000), YDR476C(1.001), YLR073C(1.001), SUI3(1.001), RCO1(1.001), LYS20(1.002), NUP170(1.002), JJJ1(1.002), RAD27(1.002), YLL032C(1.002), GDB1(1.002), GON7(1.002), PRS4(1.002), GAL7(1.002), RAI1(1.003), MLC1(1.003), SWD3(1.003), REV1(1.003), FET3(1.003), DAL7(1.004), DAL80(1.004), COQ5(1.004), TRK2(1.005), PRP31(1.005), SYP1(1.005), RPL36A(1.005), OSH7(1.005), RPL12B(1.005), UME6(1.006), LCB4(1.006), IZH2(1.006), MDH3(1.006), OGG1(1.006), RPL1A(1.007), YGL157W(1.007), HUB1(1.007), TGL4(1.007), CAF1(1.007), NPP2(1.007), URE2(1.007), GMH1(1.007), AVT3(1.007), FAA1(1.007), BET5(1.008), YPR091C(1.008), PET8(1.009), STB1(1.009), ERG13(1.009), UTP10(1.009), MMP1(1.010), YTH1(1.010), EMI2(1.010), MES1(1.010), PDS1(1.010), NPL3(1.010), PRD1(1.010), YGR235C(1.011), PHO8(1.011), PEX22(1.011), LAP4(1.011), LCB2(1.011), YLR326W(1.011), EMP46(1.011), MRPS17(1.011), AIM17(1.011), NUP57(1.011), YER134C(1.012), YCR076C(1.012), YBL104C(1.012), SSM4(1.012), YMR187C(1.012), YEF3(1.012), PIG1(1.012), ECM16(1.012), SPO20(1.013), ILS1(1.013), MFT1(1.014), RRP46(1.014), RPS23A(1.015), ECM40(1.015), STT4(1.015), SOK2(1.016), RPL9A(1.016), SIR1(1.017), SES1(1.017), CDC26(1.018), SSU1(1.018), SAS3(1.019), YKL187C(1.019), ARG8(1.019), RPL16B(1.019), LCB3(1.020), TVP18(1.020), APJ1(1.021), GDH1(1.021), IPT1(1.021), ATP7(1.021), YAR029W(1.021), PIS1(1.022), TRS23(1.022), SEC72(1.022), CHA4(1.022), DMA2(1.023), RUP2(1.023), DCP2(1.024), KAP114(1.024), YTA12(1.024), PHO87(1.024), TPS3(1.024), RPS10B(1.024), LIP2(1.025), PAF1(1.026), MEU1(1.026), ALK1(1.026), RIM11(1.026), SLA2(1.026), RSC6(1.027), CBC2(1.027), YBR016W(1.027), FIS1(1.027), RAS1(1.027), SFA1(1.028), YOL057W(1.028), YOR292C(1.028), MCD4(1.028), CSM1(1.028), MAK32(1.028), DAP2(1.028), EXG2(1.028), DID2(1.029), HXT15(1.029), DIE2(1.029), VAC8(1.030), YBR138C(1.030), NTH2(1.030), YCR099C(1.031), RTT107(1.031), MAF1(1.031), ERG9(1.031), PPN1(1.031), SRB4(1.032), CDC55(1.032), YDR248C(1.032), YDR003W-A(1.032), GLC8(1.033), PDR11(1.033), SPB4(1.033), YSC83(1.034), YLR072W(1.034), MCH1(1.035), RPH1(1.035), DAD3(1.035), SPT3(1.036), YFR057W(1.036), IDI1(1.036), TDH3(1.036), OCA2(1.036), PEX18(1.036), FUN30(1.037), RRP3(1.037), ABC1(1.037), IWR1(1.037), YJR088C(1.037), PTR2(1.038), SEC26(1.039), AQY1(1.040), ECM21(1.040), BUD27(1.040), PFK26(1.041), YDR352W(1.041), CUP5(1.041), ATG3(1.042), AGE2(1.042), RIX7(1.042), HSE1(1.042), AGA1(1.043), GRX7(1.043), AGE1(1.043), TUB2(1.043), YHR122W(1.043), RIB4(1.043), VRP1(1.043), LAS1(1.043), OCA4(1.044), YGR277C(1.044), BUB3(1.044), LPD1(1.044), EMI5(1.044), CTF18(1.044), YOL073C(1.044), SIT1(1.045), LYS12(1.045), FTR1(1.045), TUL1(1.045), EKI1(1.046), LEO1(1.046), GAL1(1.046), VAC17(1.046), REV7(1.046), PMP2(1.046), TIM13(1.047), YMR158C-A(1.047), TLG2(1.047), YGR106C(1.047), YML079W(1.048), YFR045W(1.048), YBR056W(1.048), YLR065C(1.048), HSH49(1.048), MTF1(1.049), LAG1(1.049), ATE1(1.049), RFM1(1.049), RNH203(1.050), DBP8(1.050), TPS1(1.050), YGR205W(1.050), PIM1(1.050), RAD16(1.050), SPI1(1.051), SPP1(1.051), CHS5(1.051), MNR2(1.051), PIL1(1.052), SMT3(1.052), PEF1(1.052), SKO1(1.052), CDC45(1.052), SUC2(1.052), RXT3(1.052), RPN9(1.053), SPO12(1.053), RPE1(1.053), SEC15(1.053), HMI1(1.054), RRP4(1.054), ERG25(1.054), MUC1(1.055), TPT1(1.055), OPY2(1.055), OSH2(1.055), VNX1(1.055), PXA2(1.055), YSW1(1.057), SRP14(1.057), OST5(1.058), CDC4(1.058), RPL38(1.058), YDR520C(1.058), ARO2(1.059), DOM34(1.059), SWE1(1.059), GTO1(1.059), RPL37B(1.060), RAD3(1.060), MEP2(1.060), PKH1(1.061), ARL1(1.061), ROX3(1.061), SFT1(1.062), SIM1(1.062), CIA1(1.062), COX5B(1.062), CLN1(1.062), MNE1(1.062), BRE4(1.062), UBX5(1.063), DSL1(1.063), ACK1(1.063), YHR140W(1.063), ARG82(1.063), SCS22(1.063), ADH7(1.063), HSC82(1.063), ARO80(1.063), HED1(1.063), MAD1(1.064), TRP5(1.064), RPN3(1.065), SEN54(1.065), PTM1(1.065), ATG23(1.065), GIM4(1.065), YDR089W(1.066), MON2(1.066), PEX32(1.066), PUS6(1.066), YJL038C(1.066), SGN1(1.066), PRP39(1.066), YNR070W(1.067), SPO71(1.067), SAE3(1.067), MGR2(1.068), INP53(1.068), TUP1(1.068), SHP1(1.068), INO80(1.068), CDC23(1.068), GAB1(1.068), PTC1(1.069), SKI2(1.069), DNF3(1.069), YOR389W(1.070), AIM14(1.071), ATP16(1.071), VPS51(1.071), NSE3(1.071), UTP21(1.071), MDE1(1.072), ALY1(1.072), MNI2(1.072), BNS1(1.072), ILV1(1.073), TPO5(1.073), THI21(1.074), PEX2(1.074), YMR194C-B(1.074), SFI1(1.074), ESF1(1.074), YJL068C(1.075), GPI1(1.075), ISC10(1.075), RPL13A(1.076), YDR391C(1.076), TVP15(1.076), YNL108C(1.076), YDR051C(1.076), SRP101(1.076), SAS4(1.076), ARG4(1.077), PAN5(1.077), PTK1(1.077), THI6(1.077), YOR019W(1.077), GCN5(1.077), DID4(1.078), TRM11(1.078), ABZ1(1.079), YHR210C(1.079), RPL34B(1.079), POL31(1.079), RPS4B(1.080), COG4(1.080), RPS16B(1.080), LCB1(1.080), ARA2(1.080), VPH2(1.081), YBT1(1.081), HSM3(1.081), YBL036C(1.081), DAL2(1.081), VTC4(1.081), RPS21B(1.081), YOR131C(1.081), ADE13(1.081), YKL215C(1.081), LSM2(1.082), FAR10(1.082), MCH2(1.082), IMD3(1.082), USV1(1.082), YAR035C-A(1.082), RAM1(1.083), SNM1(1.083), PNG1(1.083), RFC3(1.084), ARP2(1.084), TOR2(1.084), ISC1(1.084), CTS1(1.085), YSH1(1.085), AIM4(1.085), BIT2(1.085), GVP36(1.086), SED1(1.086), SPG4(1.086), KGD1(1.086), NMT1(1.086), SSY1(1.086), LSC1(1.086), NRK1(1.086), YLR177W(1.086), SCD6(1.087), YDR210W(1.087), LRP1(1.087), URA2(1.087), PEX21(1.088), MCM5(1.088), SSE2(1.088), PYC2(1.088), GFD1(1.088), YNL247W(1.088), RAD17(1.089), BRE2(1.089), CDC48(1.089), IES5(1.089), RPL23A(1.089), PTR3(1.089), ATP20(1.089), PAU3(1.089), CPR8(1.090), ARO7(1.090), YRO2(1.090), HRB1(1.091), HSP42(1.091), RPS18B(1.091), FMP23(1.091), ADE6(1.091), DER1(1.092), PPE1(1.092), CUE3(1.092), ACF2(1.092), QNS1(1.092), IOC3(1.093), NAM9(1.093), YDL144C(1.094), ENB1(1.094), KTR3(1.095), PSD1(1.095), HOS1(1.096), FCY21(1.096), CAJ1(1.096), ERP4(1.096), LRC2(1.097), TFB5(1.098), PRM3(1.098), CPR7(1.098), MET17(1.098), SAH1(1.098), YGR149W(1.099), GAC1(1.099), TFC7(1.099), RHO5(1.099), TIF34(1.099), YPT1(1.099), MSS4(1.100), FLC2(1.100), PRE2(1.100), YCL068C(1.101), GAL80(1.101), SPG3(1.101), URB1(1.101),

MGE1(1.102), STR2(1.102), RPL34A(1.102), UIP3(1.102), NPP1(1.102), FMP24(1.102), AIM23(1.102), BIO3(1.103), PRO2(1.103), TMN3(1.103), EST3(1.103), PHO5(1.104), YSP1(1.104), TUF1(1.104), ORM1(1.104), OLA1(1.105), NMA1(1.105), YMR209C(1.105), SEC27(1.105), SLA1 (1.105), YCL012C(1.105), SLM1(1.106), NOP53(1.106), YLR162W-A(1.106), PAU13(1.106), ALA1(1.106), YDL133W(1.107), CDC37(1.107), HCA4(1.107), PRB1 (1.107), GSY1(1.107), YIP3(1.108), TMA46(1.108), RPP1 (1.109), PRP3(1.109), YBL107C(1.109), UBP14(1.110), VAM10(1.110), CBS1(1.110), YOR238W(1.110), OM14 (1.110), SEC66(1.111), CST6(1.111), SSF2(1.111), FRS1 (1.111), NCA2(1.112), HMX1(1.112), NOP13(1.112), RNR2(1.114), QDR3(1.114), OTU2(1.114), SPO13(1.114), HUL5(1.115), SED4(1.115), RRP42(1.115), CDC33 (1.116), MLP1(1.116), GOR1(1.116), YDL119C(1.116), YJR039W(1.116), HNT2(1.116), SCM3(1.116), MET12 (1.117), VPS33(1.117), MGR1(1.117), PCM1(1.117), YUH1(1.117), CDS1(1.117), SAP185(1.118), CRT10 (1.118), SNF1(1.118), CMP2(1.118), APL6(1.118), IDH1 (1.119), YDR428C(1.119), SEC21(1.119), APL4(1.119), PAP2(1.119), GPI17(1.119), SCH9(1.120), HOP1(1.120), MUK1(1.120), RPS25B(1.120), NOB1(1.120), STE23 (1.121), YLR243W(1.122), GRE3(1.122), CCS1(1.122), VEL1(1.122), ENO2(1.123), COG6(1.123), RPL11B (1.123), HNT1(1.123), LEM3(1.123), GPI15(1.124), FSF1 (1.124), SEC3(1.124), SOL2(1.124), PRS5(1.124), VPS71 (1.124), ACC1(1.124), ADE8(1.124), GNA1(1.124), YNR024W(1.126), RSF2(1.126), MAL32(1.126), PAU21 (1.126), SPS19(1.127), YIL002W-A(1.127), SPF1(1.127), CCT8(1.127), PRM2(1.128), PDH1(1.128), RBL2(1.128), PIF1(1.128), VBA1(1.128), AFG1(1.129), DIN7(1.129), IZH1(1.129), YPL105C(1.130), YCR051 W(1.130), WWM1(1.130), SIP3(1.130), SYS1(1.131), HPC2(1.131), RPL40A(1.131), NCR1(1.131), YER078C(1.131), CAP1 (1.131), GCN4(1.131), AIM38(1.131), PTC7(1.132), FUN14(1.132), COS8(1.132), MCH4(1.132), PRP24 (1.132), CWC2(1.132), CLC1(1.132), SIR4(1.133), FUS3 (1.133), YLR057W(1.133), ZRG17(1.133), YSA1(1.133), PTC3(1.134), UBP6(1.134), KAP122(1.134), EFT2(1.134), URA3(1.135), ALG2(1.135), POL5(1.135), RPL1B(1.136), LIP1(1.136), TMA20(1.137), NAS6(1.137), IRC5(1.137), KIN3(1.137), YPL033C(1.137), AVT4(1.137), YGR266W (1.137), CTI6(1.138), YNL050C(1.138), SDP1(1.139), ESF2(1.139), NFS1(1.140), YER078W-A(1.140), IZH4 (1.140), CWC22(1.140), YGR110W(1.140), DYN2(1.140), SNF4(1.141), YMR178W(1.141), NSE5(1.142), RPL40B (1.142), TKL2(1.142), HIR1(1.142), RPS30A(1.142), HSP12(1.142), YDR539W(1.143), GCV1(1.144), NTG1 (1.144), AZR1(1.144), SPO7(1.144), YNL022C(1.144), DIM1(1.145), VAM6(1.145), YNR061C(1.145), PDA1 (1.145), YOR032W-A(1.145), SPC3(1.146), CSR1(1.146), COS9(1.147), YJR085C(1.147), PEX15(1.147), TGL2 (1.147), SGD1(1.147), YPL278C(1.147), YIL108W(1.148), THP1(1.148), SCY1(1.149), YGR130C(1.149), UBC6 (1.149), END3(1.149), UBP15(1.149), RPL35B(1.149), MSB2(1.149), YCT1(1.150), SOL3(1.150), YDL027C (1.151), KIP3(1.151), UTP11(1.151), SUB1(1.152), PRP19 (1.152), DCW1(1.152), TAH18(1.152), YER010C(1.152), PIN3(1.152), GYP1(1.152), SCW10(1.152), CTK1(1.153), ARK1(1.153), FYV10(1.153), YCR016W(1.153), YDJ1 (1.153), ARF1(1.153), BGL2(1.153), YHR100C(1.154), CBS2(1.154), REX3(1.154), TSA1(1.155), RNA14(1.155), RCE1(1.155), THR4(1.155), SIP18(1.156), PMS1(1.156), DSK2(1.156), CDC50(1.156), DPH5(1.156), HEM12 (1.156), SER3(1.157), YML119W(1.157), ESC1(1.157), GAL11(1.158), PRE7(1.158), RPT5(1.158), ERG2(1.158), DSE1(1.158), SEC22(1.159), YFH7(1.159), HSF1(1.159), GOS1(1.160), WRS1(1.161), EXO70(1.161), TSA2(1.162), ALK2(1.162), COX6(1.162), KRI1(1.162), YGL015C (1.163), RPS17B(1.163), YDR367W(1.163), TOM20 (1.163), RSP5(1.163), YBL086C(1.163), TRM44(1.163), YPR109W(1.164), PTP1(1.164), AVT7(1.164), CYR1 (1.164), CIS1(1.164), FAL1(1.164), VPS28(1.165), AGA2 (1.165), QRI1(1.165), ATS1(1.165), GIT1(1.166), THO1 (1.166), FBP1(1.166), YJL016W(1.166), UGA3(1.166), YBR230W-A(1.167), CCE1(1.167), NDE1(1.167), SET5 (1.168), HOT1(1.168), RPT1(1.168), CAR2(1.168), PRE4 (1.169), ECM33(1.169), ECM11(1.169), RAD33(1.169), BUB2(1.169), SOP4(1.169), SPR1(1.170), MOG1(1.170), SPO11(1.171), YKR070W(1.171), YBR246W(1.171), YKL071W(1.172), AHP1(1.172), PRP42(1.172), GRC3 (1.173), KEL3(1.173), YMR244W(1.174), YMR242W-A (1.174), HBN1(1.174), VAS1(1.174), RTT102(1.174), ZUO1(1.175), YGR250C(1.175), FRQ1(1.175), YCL049C (1.175), MCR1(1.175), UBP11(1.175), TIF35(1.176), ATG26(1.176), YKL107W(1.177), HEM14(1.177), THR1 (1.178), LUG1(1.178), SPS100(1.178), VMA22(1.179), YEL020C(1.179), RPL2B(1.179), GAL10(1.180), FKS1 (1.180), YPL247C(1.180), YEL057C(1.180), RPS22A (1.181), TRK1(1.181), VTC2(1.181), SNU114(1.181), SWD1(1.181), UBC8(1.181), YPT52(1.181), XDJ1(1.182), YJR142W(1.182), COQ9(1.183), ERV25(1.184), YKL075C(1.184), FPR4(1.184), SEN2(1.184), GDT1 (1.184), NOP7(1.184), YOR251C(1.184), SRL1(1.184), YLL023C(1.185), IRA2(1.185), IES6(1.185), MLF3 (1.186), DIA1(1.186), MTG1(1.186), FPR1(1.186), NCE102(1.186), ERG4(1.187), SIF2(1.187), NUP53 (1.187), RPL14A(1.187), SEC18(1.187), SSB2(1.188), RAT1(1.188), YMR027W(1.188), GDI1(1.189), VAN1 (1.189), KAP123(1.189), ICL2(1.189), LPX1(1.189), RPP2A(1.190), SCD5(1.190), EXO84(1.190), CWC21 (1.191), TRE2(1.191), YGR153W(1.191), YCR061W (1.191), RAD14(1.192), CUL3(1.192), VPS53(1.192), GEA1(1.192), GET3(1.192), TAD2(1.193), POT1(1.193), MVP1(1.193), PUS4(1.194), SMC2(1.194), RFC5(1.194), TIF3(1.195), NTG2(1.195), HXT10(1.195), CDC60(1.195), ENT5(1.196), GAT4(1.196), PGU1(1.196), UFD4(1.197), RPL37A(1.198), PRE5(1.198), PDC6(1.198), GCV3 (1.198), EGD1(1.199), MSC7(1.200), KEM1(1.200), APN1 (1.200), APE2(1.200), YLR456W(1.200), MAK5(1.201), YPR172W(1.202), STE24(1.202), RPS9B(1.203), CRM1 (1.203), STP22(1.204), DIA2(1.205), ECO1(1.205), MCX1 (1.205), YKL065W-A(1.205), NTR2(1.205), HHO1(1.206), RRM3(1.206), PRE8(1.206), NYV1(1.206), RPC53(1.207), TMA23(1.208), REC104(1.208), ZTA1(1.209), TEC1 (1.209), TUB3(1.209), YJL123C(1.209), AST2(1.209), SNX4(1.210), ARC1(1.210), SOD1(1.210), SMA2(1.211), RGD1(1.211), PHM8(1.211), SEM1(1.211), GGA2(1.211), YAK1(1.211), RGA2(1.211), SCS3(1.212), YTA7(1.213), MDM12(1.213), AUR1(1.213), SKN7(1.213), MDG1 (1.213), RSM7(1.214), YOL038C-A(1.214), OSW2(1.214), TIR3(1.214), RSM28(1.214), NIF3(1.215), FRE6(1.215), MDM20(1.215), YNR071C(1.215), GDH2(1.215), VPS8 (1.216), MVD1(1.216), GCD2(1.216), TFP3(1.216), FMP33(1.216), NUG1(1.217), CPR6(1.219), SCP160 (1.219), SEC14(1.219), YNL181W(1.219), PRE6(1.220), YLR364W(1.220), HOG1(1.221), NUP49(1.221), RPL21B (1.221), RPL42A(1.221), GTT2(1.221), STR3(1.222), ARG5, 6(1.222), RPS24A(1.222), PPM1(1.222), AIM46 (1.222), ILM1(1.222), PEX10(1.222), PDS5(1.223), YDR042C(1.223), YDL218W(1.223), MGT1(1.223), NPC2(1.223), YLR194C(1.223), PDI1(1.223), XKS1 (1.223), SIW14(1.224), KOG1(1.224), PDR15(1.224),

NGR1(1.225), SMX3(1.225), FIP1(1.225), UGA4(1.225), EDC1(1.225), YDL086W(1.225), GGA1(1.226), SMM1(1.227), AIM39(1.227), UBC1(1.227), YGR203W(1.227), PRP4(1.227), YSF3(1.227), SNA3(1.228), SKI6(1.228), CDC12(1.228), VPS60(1.228), MSC1(1.229), SET1(1.229), NMA111(1.229), SKI7(1.229), KRE5(1.229), FOL2(1.229), DAL3(1.230), SAK1(1.230), RVS161(1.230), YBR141C(1.231), LHS1(1.231), YFL051C(1.231), YGR067C(1.231), NOT5(1.231), CKB2(1.231), ATG2(1.232), YJR112W-A(1.232), RKM2(1.232), RPL36B(1.232), CNB1(1.232), PRP43(1.233), LCB5(1.233), PAC1(1.233), ARP3(1.234), LRC1(1.234), RGR1(1.234), YDL157C(1.234), DPL1(1.234), GCY1(1.235), YER076C(1.235), TFB3(1.235), RPS8B(1.235), GAT2(1.235), GFD2(1.235), MRP8(1.236), VAC14(1.236), YHR138C(1.237), PHO90(1.237), PSK2(1.238), ALT1(1.238), ERP5(1.238), LAS21(1.238), AIM9(1.239), SLZ1(1.240), SGM1(1.240), FMP27(1.241), HXT3(1.241), YGR273C(1.241), RAM2(1.241), RET1(1.241), YIR007W(1.241), RPS2(1.242), MTQ2(1.242), RPS23B(1.242), COS12(1.242), RUB1(1.242), RGP1(1.242), GYP7(1.243), YOL138C(1.243), PMT2(1.243), YMR130W(1.243), SPS4(1.244), RAD28(1.244), YLR099W-A(1.245), YOR285W(1.245), MBR1(1.245), MPH1(1.246), NUP159(1.246), SEC63(1.246), RPS16A(1.247), YPL206C(1.247), BCD1(1.247), HOT13(1.248), IVY1(1.248), RNA15(1.248), YKR104W(1.248), STE4(1.249), PUP1(1.250), SFB2(1.251), YCK2(1.251), ODC1(1.251), FMP42(1.251), VPS24(1.251), YKL098W(1.252), YSY6(1.252), RTG2(1.252), LYS9(1.253), UTR1(1.253), HRR25(1.253), YBR261C(1.254), RPS26A(1.254), KTR5(1.254), CHL1(1.255), MNN10(1.255), GLE2(1.255), CPD1(1.255), SNZ1(1.256), PAM17(1.256), HIR2(1.256), CDC28(1.257), YDR061W(1.257), ENA5(1.257), APM3(1.258), YLR118C(1.258), AVT1(1.258), PEP12(1.258), PET18(1.258), MAM1(1.258), DOA1(1.259), FPR2(1.259), PIB2(1.259), PRP21(1.260), TOP2(1.261), YBL044W(1.261), OST6(1.261), AIM24(1.262), IRC18(1.262), OSW1(1.263), COT1(1.263), YOR387C(1.263), SKP1(1.263), STM1(1.263), YDL176W(1.263), YLR137W(1.263), ALE1(1.264), PBP1(1.264), YNL200C(1.264), YBL029C-A(1.265), SPE3(1.265), RRD2(1.265), CNN1(1.266), SPR6(1.266), PAN3(1.267), YRB1(1.268), YDL057W(1.268), YOR051C(1.268), POL4(1.268), ORC5(1.269), IMP2(1.269), ATG19(1.269), ARO8(1.269), YJL163C(1.269), SWI5(1.270), LSP1(1.270), TMA19(1.270), YET3(1.271), RAD26(1.271), MGA2(1.271), IME1(1.272), OXR1(1.272), GSF2(1.273), RPS18A(1.273), RUP1(1.273), YLR126C(1.273), KRE27(1.273), TVP23(1.273), INO1(1.273), ALG14(1.274), PUS5(1.274), VMA10(1.275), SPT16(1.275), YLL053C(1.276), CHC1(1.276), MSH6(1.276), SDS24(1.277), PTC4(1.278), PSP2(1.278), VBA2(1.278), TSR4(1.278), CPR4(1.278), DPP1(1.279), TFG1(1.279), ARN2(1.279), YGL230C(1.279), NBP1(1.280), YKL077W(1.280), MOB2(1.280), DYN3(1.280), UBC13(1.280), RFA3(1.281), SPG5(1.281), GYP5(1.281), YPI1(1.281), YDR179W-A(1.281), CHA1(1.282), TOS4(1.282), ADH1(1.282), SPO1(1.282), JJJ2(1.283), ADK1(1.283), SOK1(1.284), GOT1(1.285), TIR4(1.285), ERP2(1.285), SEN1(1.285), PHO81(1.285), ARF2(1.285), YOR227W(1.285), TVP38(1.286), YDL089W(1.286), ZDS2(1.286), GCD6(1.286), SUI2(1.286), VAC7(1.287), TAH11(1.288), CTR9(1.288), YKL100C(1.289), NUP188(1.289), GRE1(1.289), PHB2(1.289), BUD3(1.290), SMA1(1.290), RPL20B(1.290), NSP1(1.291), PPZ2(1.291), STO1(1.291), ETR1(1.291), SUL1(1.292), RPL6B(1.292), CPR5(1.292), YAL018C(1.292), ELP6(1.292), ACP1(1.293), SHR3(1.293), KAP120(1.293), YBR137W(1.293), IME2(1.293), SNF7(1.293), YCR023C(1.293), GIS2(1.294), YIP1(1.294), TFC3(1.294), CUE1(1.295), YLR283W(1.295), FUN12(1.296), BMH1(1.296), RIM1(1.297), YMC1(1.297), KIC1(1.297), NAR1(1.298), YBR184W(1.298), CAF4(1.298), CTK3(1.298), NUP157(1.299), PRY1(1.299), MFA1(1.300), POL2(1.300), YDL114W(1.300), STP3(1.301), IRC20(1.301), ZPS1(1.302), POP1(1.303), DUN1(1.303), SLY1(1.303), UTP6(1.303), TAL1(1.303), DIB1(1.303), PAC2(1.303), YNR029C(1.304), SPC72(1.305), RPC34(1.305), KTR7(1.305), KRR1(1.305), YBR062C(1.306), SSA4(1.306), VMA9(1.308), ATG22(1.308), NRD1(1.309), INH1(1.309), REF2(1.312), TSC13(1.312), UTP7(1.312), AIM15(1.313), ARC19(1.313), EHT1(1.313), YHL017W(1.313), NNF2(1.313), YPR027C(1.314), TGL3(1.314), PEX28(1.314), TEL1(1.315), PGM1(1.315), PAN1(1.315), HRD3(1.315), RPL26B(1.316), SDT1(1.316), YER128W(1.317), PSY3(1.317), VPS52(1.318), RPB4(1.318), AIM2(1.318), NUD1(1.318), RPS29B(1.320), PRO3(1.320), RPL32(1.321), PXA1(1.321), GID8(1.322), TRM3(1.322), SLX1(1.322), PEA2(1.322), UBR1(1.322), AIP1(1.322), RPS10A(1.323), CFD1(1.324), YOR114W(1.324), LEA1(1.324), MSN5(1.324), RPL6A(1.324), PTC2(1.324), YER071C(1.325), RAS2(1.325), ATG14(1.326), CDC11(1.326), RPS6B(1.326), URA6(1.326), RPN1(1.327), SFH5(1.329), YAP1801(1.329), FLR1(1.329), DDR48(1.329), YRA2(1.329), APN2(1.330), ELF1(1.330), YJL217W(1.331), YPR089W(1.331), GSP2(1.331), BUG1(1.331), PSE1(1.331), SUA5(1.332), GPM2(1.332), POS5(1.332), PRM5(1.334), TAF4(1.334), GIM5(1.336), BNR1(1.336), YPS7(1.337), HAL5(1.337), RPS27B(1.337), CAK1(1.337), PGA2(1.337), SSP2(1.338), PMR1(1.338), NUP85(1.339), LSB6(1.339), TMA17(1.340), TGL1(1.340), ASN2(1.340), SEI1(1.341), VMA7(1.341), MDR1(1.341), HBS1(1.341), PMT1(1.342), PHO2(1.342), YHR113W(1.342), SSO1(1.342), RET2(1.342), UBA1(1.342), ALD2(1.342), SEC28(1.343), SEH1(1.343), YMR144W(1.343), HOC1(1.343), PRT1(1.344), RPS19B(1.344), GCN2(1.345), SAP4(1.345), YLR179C(1.346), COQ6(1.346), LYS14(1.346), LSM12(1.347), YGL117W(1.347), RED1(1.348), VPS34(1.348), VTC3(1.348), BRF1(1.348), ARR2(1.350), VMA21(1.350), PSF1(1.351), SRL3(1.351), YDR379C-A(1.351), ALG12(1.352), RPS25A(1.352), SDS23(1.352), DGA1(1.352), YDR196C(1.353), LOC1(1.354), RPN2(1.355), ANB1(1.355), NAN1(1.355), STB2(1.355), CUE5(1.356), CDC8(1.356), SPH1(1.357), GID7(1.357), UBC4(1.357), RPS22B(1.358), ACT1(1.360), RPS8A(1.360), YNR068C(1.360), FRS2(1.360), TAF8(1.361), THI4(1.361), RBK1(1.362), SET3(1.362), YNL305C(1.362), TPP1(1.362), MSO1(1.363), NSA1(1.364), YMR210W(1.364), ERG24(1.364), YMR31(1.364), MAK11(1.364), URB2(1.364), FAD1(1.365), AGC1(1.366), OM45(1.366), APD1(1.367), GSH2(1.367), SPT14(1.367), YGR210C(1.368), RPS11A(1.368), SWH1(1.369), ANT1(1.369), SAP30(1.369), HRT3(1.369), NSG1(1.370), BAT2(1.370), SOM1(1.371), IPP1(1.372), HIS2(1.372), RSE1(1.372), RTT101(1.372), CRG1(1.373), YJR096W(1.374), IMH1(1.374), SPT7(1.374), MKT1(1.374), GTT3(1.375), PEX11(1.375), YDR374W-A(1.377), YPD1(1.377), DOS2(1.377), YEL023C(1.378), RPF1(1.378), BNA2(1.380), ATG27(1.380), RPL29(1.382), YPS6(1.382), RPL19B(1.382), YDR357C(1.382), ARO4(1.383), YBR096W(1.384), PEP8(1.384), RPL39(1.385), SCC4(1.386), HXT7(1.386), HSV2(1.386), APA2(1.386), TFC1(1.386), SEC53(1.386), PDR5(1.386), MUD2(1.387), RPL19A(1.387), TAF9(1.387), MXR1(1.388), RIX1(1.388), PKR1(1.389), CWC27(1.390), BFR1(1.390), YDR387C(1.390), UIP4(1.390), OST3(1.391), BUD6

Figure 2:
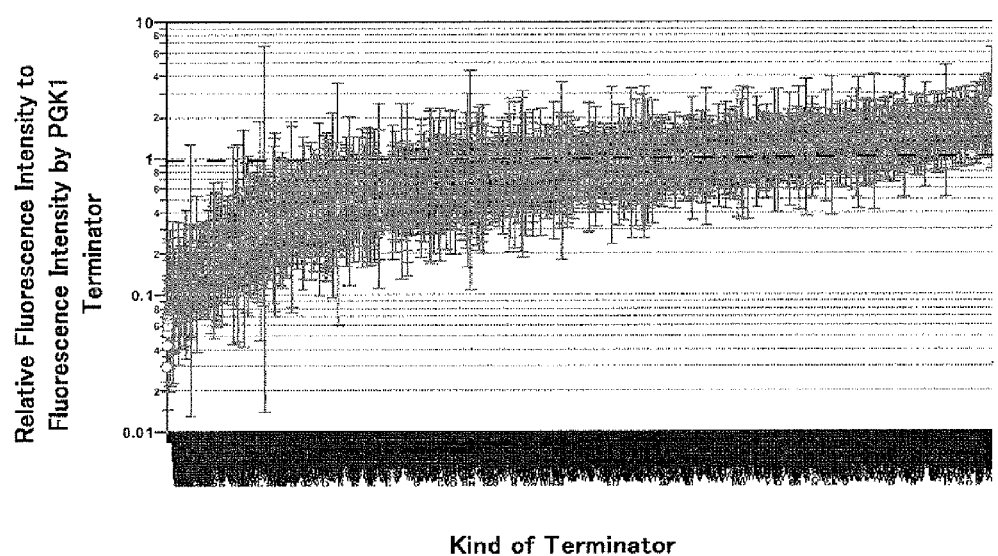
FIG. 2 shows an overview of terminator region evaluation results.

(1.392), GFA1(1.393), RPS8A(1.395), CRZ1(1.396), SLT2 (1.396), SNC1(1.396), SEC5(1.397), PCL6(1.397), DAL5 (1.398), MSB1(1.399), CSL4(1.399), COQ4(1.400), TAH1 (1.400), YPL245W(1.400), PRI2(1.400), LOS1(1.400), SQS1(1.401), PBA1(1.401), YFR017C(1.402), HPA3 (1.402), SCL1(1.403), YGR168C(1.404), SAP155(1.405), MON1(1.405), SGA1(1.405), MNI1(1.406), TFC8(1.407), FAB1(1.407), MED2(1.407), GCN3(1.408), PRE1(1.408), BBC1(1.409), GPA1(1.409), DIG2(1.409), IRS4(1.409), SXM1(1.410), SHU2(1.410), SRO7(1.411), GEF1(1.412), RPL24A(1.413), TMN2(1.413), RIB3(1.414), UBC9 (1.414), MAL11(1.415), ARO10(1.415), LAC1(1.415), RCN1(1.416), MVB12(1.418), TBS1(1.418), CTL1(1.419), NTF2(1.419), BZZ1(1.420), HXT14(1.421), YGR125W (1.421), YNR062C(1.422), STE50(1.422), YLL056C (1.423), HIS3(1.423), CIN2(1.423), TCB3(1.423), NUM1 (1.424), CPA1(1.425), PRP40(1.425), TRR1(1.425), TRP2 (1.426), ADE16(1.427), EFT1(1.427), BET3(1.428), SUA7 (1.430), RPS14A(1.430), FOL1(1.431), DPB4(1.431), VPS16(1.431), ANP1(1.431), YMR099C(1.432), VHS2 (1.432), BMH2(1.432), ADH6(1.432), GSC2(1.433), DBR1 (1.433), ADP1(1.433), CEG1(1.434), MBP1(1.434), FCP1 (1.434), SRY1(1.434), YNL058C(1.435), AVO1(1.435), YMR196W(1.435), RPL35A(1.435), HIF1(1.435), YLR050C(1.436), YER187W(1.436), YOR186W(1.436), RAD57(1.437), ATH1(1.437), PEP7(1.437), YJL055W (1.438), YBR259W(1.439), UBX7(1.439), ILV6(1.439), SAM4(1.441), MRM1(1.441), PHO23(1.441), MYO4 (1.443), BRE1(1.443), YFR032C(1.444), GAS4(1.444), MIP6(1.444), ERV46(1.444), YPR097W(1.444), PET10 (1.445), HDA2(1.445), TRX2(1.445), MED4(1.446), SPO16(1.446), NSG2(1.446), GND2(1.447), PDB1(1.448), BDH1(1.448), NIT3(1.449), MUD1(1.449), ERG20(1.450), RPL18A(1.451), PAI3(1.452), TMA108(1.452), SAM50 (1.452), SLY41(1.452), YDR461C-A(1.454), YMR265C (1.454), YJL132W(1.454), BLM10(1.454), SPO73(1.454), CWC15(1.455), ALO1(1.456), MAP1(1.456), YKR023W (1.456), PET130(1.456), YCS4(1.458), CWH41(1.458), ARP9(1.458), CHK1(1.459), PAM1(1.459), TAF10(1.459), ARA1(1.461), CGI121(1.461), YIL014C-A(1.461), CHS7 (1.461), RPS21A(1.463), VMA13(1.463), NAT3(1.464), ARG2(1.464), DOG1(1.465), TMS1(1.465), PSF2(1.465), YHR126C(1.465), KAP104(1.466), DPS1(1.466), IRR1 (1.466), YAL044W-A(1.466), RPL23B(1.467), YDR307W (1.467), RPL33A(1.468), NAB6(1.468), APA1(1.469), ALG6(1.469), MEX67(1.470), DAK1(1.471), ARC15 (1.471), YOS1(1.472), GAD1(1.472), ECM22(1.473), CYS3(1.473), PBI2(1.474), YBR271W(1.474), GPI10 (1.474), WBP1(1.477), ZRC1(1.477), FIG2(1.477), YOR262W(1.477), MSH3(1.478), IOC2(1.478), YGR201C (1.479), NAP1(1.479), KAE1(1.479), CHS1(1.480), GDE1 (1.480), YTM1(1.480), YHR162W(1.480), TAD3(1.480), ALP1(1.481), TRM8(1.482), NMD2(1.482), YIM1(1.483), BCH1(1.483), RRP1(1.483), VCX1(1.483), UGA1(1.484), HOL1(1.484), GRX1(1.484), EMP24(1.484), YGR237C (1.485), FAP1(1.485), KTR2(1.486), PBP4(1.486), YER163C(1.486), RFS1(1.486), PTA1(1.487), MPD2 (1.487), SGT2(1.487), IKI1(1.487), ECM29(1.488), REV3 (1.489), TPD3(1.489), YDL124W(1.490), MUM2(1.491), YFR026C(1.491), PHS1(1.491), MLS1(1.493), POR1 (1.494), PFD1(1.494), EGD2(1.494), GYP8(1.495), RPT2 (1.495), TEX1(1.495), RPS5(1.496), TPK1(1.496), DOT5 (1.497), LSB5(1.498), DMA1(1.498), BNA6(1.498), VAB2 (1.499), AML1(1.500), SEC31(1.500), KIN1(1.501), STB4 (1.502), GSP1(1.502), AAD4(1.502), MNN2(1.503), RPP1B(1.503), GUK1(1.506), MCK1(1.506), HSP31 (1.506), SBP1(1.506), ZWF1(1.507), IST2(1.508), GPI16 (1.508), CDC42(1.508), AHA1(1.509), UBP2(1.510), YNL115C(1.510), CCW14(1.510), YDL121C(1.510), MCA1(1.510), RPT4(1.511), ERP1(1.512), TMA7(1.513), WHI4(1.513), YDR131C(1.513), PDR1(1.514), TSR3 (1.516), ATG11(1.516), DDP1(1.516), COQ2(1.516), RPP1A(1.517), PMP3(1.517), CRD1(1.517), PHO85 (1.517), YGR017W(1.517), YIL055C(1.518), LAP3(1.518), YOR291W(1.519), GAS5(1.519), YKR043C(1.520), YIL083C(1.520), CHO2(1.521), ELP4(1.521), BIM1 (1.522), CAM1(1.522), DAL82(1.523), UMP1(1.524), YBR241C(1.524), LTP1(1.524), PHO91(1.525), RPP0 (1.526), YOR164C(1.526), TOM71(1.527), FAS2(1.528), FMP46(1.528), TMA22(1.528), YML131W(1.528), YCF1 (1.530), OPI3(1.530), ROM1(1.530), IRC24(1.530), FYV6 (1.531), ATG13(1.534), TRX3(1.534), ENP2(1.534), CEX1 (1.534), VPS3(1.535), TRX1(1.536), DIT1(1.536), SEC4 (1.536), GDH3(1.537), PRE9(1.537), UBP1(1.537), AYR1 (1.537), NIT2(1.537), PDR17(1.538), TUB1(1.539), KEG1 (1.539), CDC25(1.539), PIG2(1.539), NSE1(1.541), VPS25 (1.541), YLR414C(1.541), CWH43(1.541), COG2(1.545), RCY1(1.545), VPS68(1.546), RPL7A(1.548), TAF14 (1.549), SRB5(1.553), UPF3(1.553), YML096W(1.555), ARG81(1.555), NPR2(1.555), PSH1(1.556), TAF6(1.557), MCT1(1.557), SBH1(1.557), PBN1(1.558), VPS45(1.560), SRP68(1.560), SAY1(1.561), PEP1(1.562), CCT4(1.563), COQ10(1.565), RET3(1.566), SSE1(1.566), YSP3(1.567), ABZ1(1.567), PNS1(1.567), DPB3(1.568), YDL073W (1.568), ATM1(1.568), RBD2(1.568), YFR006W(1.569), DDI1(1.569), DCP1(1.570), SAS10(1.570), RMT2(1.571), FIG1(1.572), MUS81(1.573), UBI4(1.573), YBR285W (1.574), DLD1(1.576), RPS15(1.576), YPR170W-B(1.576), SRP1(1.577), PSK1(1.577), RAD4(1.578), PGD1(1.580), PMT4(1.581), ABF2(1.582), SEC24(1.584), URA10 (1.585), CWC23(1.585), RPS11B(1.586), TPM1(1.586), YLR290C(1.588), TRM9(1.588), YAP1(1.589), UGP1 (1.589), SPS2(1.590), PDR10(1.591), POM34(1.591), PNC1(1.591), STE11(1.593), GRH1(1.596), YMR018W (1.596), TRS33(1.596), HEF3(1.597), LAT1(1.597), BDS1 (1.597), HMF1(1.598), PRP6(1.600), FSH3(1.600), SRB2 (1.601), DUG1(1.601), ERD2(1.602), CDA2(1.602), RPS6A(1.602), HUT1(1.604), SHS1(1.604), IRA1(1.605), SSA3(1.606), ELP3(1.606), PRP46(1.606), CSM3(1.606), PEP4(1.607), YHC3(1.610), MDY2(1.610), RPL43A (1.613), HRQ1(1.613), YKL023W(1.613), DFM1(1.614), PCL8(1.614), SKG3(1.614), GPH1(1.615), NEJ1(1.616), URA4(1.617), GPX1(1.620), HOS2(1.622), YDR531W (1.623), PEP3(1.624), MAL31(1.625), YGR283C(1.626), HFD1(1.627), SPR28(1.627), SWP82(1.628), FUM1 (1.629), CDA1(1.629), HOM6(1.630), NHX1(1.631), SNF6 (1.632), ECI1(1.632), CDC10(1.632), MIS1(1.632), YIL165C(1.632), GTT1(1.636), PLP2(1.636), PFA4 (1.636), RPL30(1.637), PRE3(1.640), MTD1(1.640), MNT2(1.642), ECM30(1.643), YNL208W(1.645), YCR024C-B(1.645), PCA1(1.646), HCS1(1.648), DCC1 (1.650), FAR8(1.652), PPH22(1.654), DED81(1.656), GPM1(1.657), COF1(1.658), YGR042W(1.658), YPR148C (1.659), VPS55(1.659), JLP1(1.660), CAT2(1.661), GCN1 (1.664), YGL231C(1.664), GUS1(1.665), YGR111W (1.667), VMA4(1.671), YDR056C(1.671), SCS2(1.672), NQM1(1.675), UFE1(1.677), COG1(1.677), PAA1(1.677), IRC22(1.682), KTR1(1.682), TYW1(1.683), SSB1(1.683), SVP26(1.686), ESC8(1.687), YNL010W(1.687), TIF1 (1.689), EAF6(1.690), SHC1(1.690), KIN2(1.692), DCS2 (1.692), RPS1B(1.692), URA5(1.692), DSD1(1.693), YJL218W(1.694), NPT1(1.694), SRO77(1.695), FMN1 (1.695), CMD1(1.695), YTA6(1.697), RPL21A(1.699), ALG3(1.699), KRE2(1.703), PCL5(1.704), MDM34

(1.705), PFS2(1.708), SNF12(1.708), BNA1(1.709), AIM29 (1.710), SNU13(1.712), RNR4(1.712), MAP2(1.713), DCS1(1.716), RPN5(1.716), PDC2(1.722), DOP1(1.723), SPO74(1.725), PAP1(1.728), RPL24B(1.732), RPN8 (1.734), FPR3(1.734), ERS1(1.735), CPR1(1.736), FIT3 (1.740), HUG1(1.742), VPS5(1.742), PEX3(1.742), RPS29A(1.743), ERV29(1.743), CAF20(1.743), DOG2 (1.743), RPL4A(1.744), YCP4(1.745), PBY1(1.746), FUS2 (1.750), SNF2(1.752), SUI1(1.752), YMR262W(1.759), BUD8(1.761), TED1(1.763), TAH1(1.765), YCL048W-A (1.769), RPL41A(1.774), YDR374C(1.776), VMA8(1.777), YKR051W(1.777), YFL042C(1.778), ORM2(1.778), TAF12(1.778), APE3(1.781), YDR239C(1.782), ERV2 (1.784), SHR5(1.785), YHR192W(1.787), YRB30(1.791), PHO88(1.791), WHI2(1.792), LYS1(1.793), RHO1(1.795), VPS27(1.797), VMA6(1.797), PAB1(1.806), YJR015W (1.807), SIR2(1.809), FAR1(1.809), CPT1(1.814), ECM15 (1.815), ROK1(1.815), YFR018C(1.820), HYR1(1.821), POL1(1.821), CTS2(1.830), UBA4(1.832), SRP72(1.833), RTN2(1.834), HAP1(1.835), ARE2(1.836), RCK2(1.837), INM2(1.839), AFR1(1.840), YOS9(1.840), RTT103(1.842), RPS12(1.845), RNY1(1.847), PPA1(1.848), LEU3(1.849), ERG27(1.850), TMA29(1.851), UBX3(1.852), VPS15 (1.854), RPT6(1.855), LDB18(1.859), YPL088W(1.862), RPL5(1.863), RVS167(1.870), TIR2(1.871), PHA2(1.873), ERI5(1.873), VPS30(1.876), IMD2(1.878), PES4(1.879), EMI1(1.897), YPR085C(1.901), YBR200W-A(1.903), FMP40(1.909), REH1(1.909), SGT1(1.911), CPS1(1.913), YOP1(1.917), TRR2(1.919), STS1(1.920), VPH1(1.931), SWA2(1.933), YGR026W(1.938), CDC53(1.938), FMP52 (1.941), YDR119W(1.945), RNQ1(1.953), SAG1(1.956), RPS20(1.974), TRM82(1.979), VPS1(1.981), YIP5(1.987), YPR1(1.988), ENT2(1.992), YPT31(1.997), PRX1(2.003), YHL039W(2.003), YHI9(2.022), BUD32(2.035), YLR361C-A(2.037), APL2(2.043), PTP3(2.046), YMR114C(2.049), LSC2(2.054), ATG10(2.056), SRP54 (2.065), ENT3(2.077), RPL3(2.080), TYR1(2.095), NAT1 (2.106), YNR021W(2.114), EBS1(2.126), HBT1(2.132), RPL15A(2.145), RPL41B(2.149), RPP2B(2.166), CBR1 (2.178), BNA4(2.233), PRC1(2.240), DIT1(2.244), RPS28A(2.260), ASP3-1(2.300), IDP1(2.304), SCW4 (2.321), VMA2(2.369), ALY2(2.382), and NAT5(2.449).

In the expression intensity data above, the genes names are based on public genome data available by ftp at ncbi.nih-.govigenomes/Fungi/*Saccharomyces_cerevisiae*_uid128. With this genome data, a gene sequence downstream from the coding region of each gene can be obtained by referencing the gene names listed above. It has been reported that the median value of the length of a 3'-UTR in the mRNA of yeasts is about 100 bp, and that most 3'-UTRs are in the range of about 500 bp (Miura F, Kawaguchi N, Sese J, Toyoda A, Hattori M, Morishita S, Ito T, *Proc. Natl. Acad. Sci. USA,* 103, 17846-17851 (2006); Nagalakshmi U, Wang Z, Waern K, Shou C, Raha D, Gerstein M, Snyder M, *Science,* 320, 1344-1349 (2008)). For such reasons, about 300 bp downstream from the termination codon of the coding region is presumed to be the terminator region of the gene in yeasts. A person skilled in the art can design appropriate primers by known techniques based on the nucleotide sequence of the presumed DNA of the terminator region, and amplify the presumed terminator region of the specific gene to perform terminator cloning, and the activity of this as a terminator region can also be evaluated.

An example of the nucleotide sequences of the terminator regions of the aforementioned genes is given by SEQ ID NOS:10591-15885, in the same order as the list of genes above. The nucleotide sequences of the terminator regions of the genes for which expression intensity data is given above are based on results obtained with unique primer sets designed for obtaining the terminator region of each gene, and include roughly 300 bp to 700 bp downstream from the coding region of each gene. The nucleotide sequences of the 5' primers are represented by SEQ ID NOS:1-5295, and the nucleotide sequences of the 3' primers by SEQ ID NOS: 5296-10590.

A terminator region used in this production method may be identical to a specified nucleotide sequence, but it is also possible to use one that has been modified as necessary. For example, this may be a nucleotide sequence of DNA comprising a nucleotide sequence represented by a sequence ID specified by any of SEQ ID NOS:10591-15885 with 1 or 2 or more nucleotides deleted, substituted, inserted and/or added therein, and having terminator activity equivalent to that of the original terminator region. It may also be a nucleotide sequence of DNA that hybridizes under stringent conditions with DNA complementary to all or part of a nucleotide sequence represented by a sequence ID specified by any of SEQ ID NOS:10591-15885, and that has terminator activity equivalent to that of the original terminator region. Moreover, it may be a nucleotide sequence of DNA having at least 80% or preferably at least 85% or more preferably at least 90% or still more preferably at least 95% or most preferably at least 98% or ideally at least 99% identity with a nucleotide sequence represented by a sequence ID specified by any of SEQ ID NOS:10591-15885, and having terminator activity equivalent to that of the original terminator region. Equivalent terminator activity here means for example that the relative expression intensity is within the range of ±20% of the relative expression intensity given by the expression intensity data for the original terminator region. More preferably, it is within the range of ±10%, or still more preferably ±5%.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

Stringent condition refers to conditions, for example in which so-called specific hybrid is formed, a non-specific hybrid is not formed. For example, a condition such that the complementary strand of the DNA or the part thereof having high identity such as at least 80% identical, preferably at least 85% identity, more preferably at least 90%, or still more preferably at least 95%, further more preferably at least 98%, or most preferably at least 99% identity with the predetermined sequence hybridizes with the DNA while the complementary strand or the part thereof having the lower identity does not hybridize with the DNA is included. Typically, sodium salt concentration is 15 to 750 mM, preferably 50 to 750 mM, more preferably 300 to 750 mM, temperature is 25 to 70° C., preferably 50 to 70° C., more preferably 55° to 65° C., and formamide concentration is 0 to 50%, preferably 20 to 50%, more preferably 35 to 45%. Further, stringent condition includes filter washing condition after hybridization which sodium salt concentration is 15 to 600 mM, preferably 50 to 600 mM, more preferably 300 to 600 mM and temperature is 50 to 70° C., preferably 55 to 70° C., more preferably 60° to 65° C., typically. Accordingly, further embodiments of the terminator region include terminator region having high identity such as at least 80% identical, preferably at least 85% identity, more preferably at least 90%, or still more preferably at least 95%, further more preferably at least 98%, or most preferably at least 99% identity with the predetermined terminator region.

The terminator region may be arranged down stream of the code region of the gene of an interest whose expression is to be controlled. The terminator region may effect the expression level of the gene in spite of the code region which is arranged upstream thereof. The terminator region may provide its intrinsic expression controlling ability without the effect of the expression controlling ability of the promoter arranged upstream of the terminator region.

For example, to enhance the expression output of an arbitrary gene (which may be an exogenous gene or an endogenous gene in a yeast), a terminator region exhibiting high expression intensity can be used based on the expression intensity data for the terminator regions of each gene. A relative expression intensity of at least 1.2, or preferably at least 1.3, or more preferably at least 1.4, or still more preferably at least 1.5, or yet more preferably at least 1.6 is desirable, and at least 1.7 or preferably at least 1.8 or more preferably at least 1.9 is still more desirable, while at least 2.0 or more is most desirable.

Examples of terminator regions with a relative expression intensity of 1.2 or more include YCT1, SOL3, YDL027C, KIP3, UTP11, SUB1, PRP19, DCW1, TAH18, YER010C, PIN3, GYP1, SCW10, CTK1, ARK1, FYV10, YCR016W, YDJ1, ARF1, BGL2, YHR100C, CBS2, REX3, TSA1, RNA14, RCE1, THR4, SIP18, PMS1, DSK2, CDC50, DPH5, HEM12, SER3, YML119W, ESC1, GAL11, PRE7, RPT5, ERG2, DSE1, SEC22, YFH7, HSF1, GOS1, WRS1, EXO70, TSA2, ALK2, COX6, KRI1, YGL015C, RPS17B, YDR367W, TOM20, RSP5, YBL086C, TRM44, YPR109W, PTP1, AVT7, CYR1, CIS1, FAL1, VPS28, AGA2, QRI1, ATS1, GIT1, THO1, FBP1, YJL016W, UGA3, YBR230W-A, CCE1, NDE1, SET5, HOT1, RPT1, CAR2, PRE4, ECM33, ECM11, RAD33, BUB2, SOP4, SPR1, MOG1, SPO11, YKR070W, YBR246W, YKL071W, AHP1, PRP42, GRC3, KEL3, YMR244W, YMR242W-A, HBN1, VAS1, RTT102, ZUO1, YGR250C, FRQ1, YCL049C, MCR1, UBP11, TIF35, ATG26, YKL107W, HEM14, THR1, LUG1, SPS100, VMA22, YEL020C, RPL2B, GAL10, FKS1, YPL247C, YEL057C, RPS22A, TRK1, VTC2, SNU114, SWD1, UBC8, YPT52, XDJ1, YJR142W, COQ9, ERV25, YKL075C, FPR4, SEN2, GDT1, NOP7, YOR251C, SRL1, YLL023C, IRA2, IES6, MLF3, DIA1, MTG1, FPR1, NCE102, ERG4, SIF2, NUP53, RPL14A, SEC18, SSB2, RAT1, YMR027W, GDI1, VAN1, KAP123, ICL2, LPX1, RPP2A, SCD5, EXO84, CWC21, TRE2, YGR153W, YCR061W, RAD14, CUL3, VPS53, GEA1, GET3, TAD2, POT1, MVP1, PUS4, SMC2, RFC5, TIF3, NTG2, HXT10, CDC60, ENT5, GAT4, PGU1, UFD4, RPL37A, PRE5, PDC6, GCV3, EGD1, MSC1, KEM1, APN1, APE2, YLR456W, MAK5, YPR172W, STE24, RPS9B, CRM1, STP22, DIA2, ECO1, MCX1, YKL065W-A, NTR2, HHO1, RRM3, PRE8, NYV1, RPC53, TMA23, REC104, ZTA1, TEC1, TUB3, YJL123C, AST2, SNX4, ARC1, SOD1, SMA2, RGD1, PHM8, SEM1, GGA2, YAK1, RGA2, SCS3, YTA7, MDM12, AUR1, SKN7, MDG1, RSM7, YOL038C-A, OSW2, TIR3, RSM28, NIF3, FRE6, MDM20, YNR071C, GDH2, VPS8, MVD1, GCD2, TFP3, FMP33, NUG1, CPR6, SCP160, SEC14, YNL181W, PRE6, YLR364W, HOG1, NUP49, RPL21B, RPL42A, GTT2, STR3, ARG5,6, RPS24A, PPM1, AIM46, ILM1, PEX10, PDS5, YDR042C, YDL218W, MGT1, NPC2, YLR194C, PDI1, XKS1, SIW14, KOG1, PDR15, NGR1, SMX3, FIP1, UGA4, EDC1, YDL086W, GGA1, SMM1, AIM39, UBC1, YGR203W, PRP4, YSF3, SNA3, SKI6, CDC12, VPS60, MSC1, SET1, NMA111, SKI7, KRE5, FOL2, DAL3, SAK1, RVS161, YBR141C, LHS1, YFL051C, YGR067C, NOT5, CKB2, ATG2, YJR112W-A, RKM2, RPL36B, CNB1, PRP43, LCB5, PAC1, ARP3, LRC1, RGR1, YDL157C, DPL1, GCY1, YER076C, TFB3, RPS8B, GAT2, GFD2, MRP8, VAC14, YHR138C, PHO90, PSK2, ALT1, ERP5, LAS21, AIM9, SLZ1, SGM1, FMP27, HXT3, YGR273C, RAM2, RET1, YIR007W, RPS2, MTQ2, RPS23B, COS12, RUB1, RGP1, GYP7, YOL138C, PMT2, YMR130W, SPS4, RAD28, YLR099W-A, YOR285W, MBR1, MPH1, NUP159, SEC63, RPS16A, YPL206C, BCD1, HOT13, IVY1, RNA15, YKR104W, STE4, PUP1, SFB2, YCK2, ODC1, FMP42, VPS24, YKL098W, YSY6, RTG2, LYS9, UTR1, HRR25, YBR261C, RPS26A, KTR5, CHL1, MNN10, GLE2, CPD1, SNZ1, PAM17, HIR2, CDC28, YDR061W, ENA5, APM3, YLR118C, AVT1, PEP12, PET18, MAM1, DOA1, FPR2, PIB2, PRP21, TOP2, YBL044W, OST6, AIM24, IRC18, OSW1, COT1, YOR387C, SKP1, STM1, YDL176W, YLR137W, ALE1, PBP1, YNL200C, YBL029C-A, SPE3, RRD2, CNN1, SPR6, PAN3, YRB1, YDL057W, YOR051C, POL4, ORC5, IMP2, ATG19, ARO8, YJL163C, SWI5, LSP1, TMA19, YET3, RAD26, MGA2, IME1, OXR1, GSF2, RPS18A, RUP1, YLR126C, KRE27, TVP23, INO1, ALG14, PUS5, VMA10, SPT16, YLL053C, CHC1, MSH6, SDS24, PTC4, PSP2, VBA2, TSR4, CPR4, DPP1, TFG1, ARN2, YGL230C, NBP1, YKL077W, MOB2, DYN3, UBC13, RFA3, SPG5, GYP5, YPI1, YDR179W-A, CHA1, TOS4, ADH1, SPO1,1112, ADK1, SOK1, GOT1, TIR4, ERP2, SEN1, PHO81, ARF2, YOR227W, TVP38, YDL089W, ZDS2, GCD6, SUI2, VAC7, TAH11, CTR9, YKL100C, NUP188, GRE1, PHB2, BUD3, SMA1, RPL20B, NSP1, PPZ2, STO1, ETR1, SUL1, RPL6B, CPR5, YAL018C, ELP6, ACP1, SHR3, KAP120, YBR137W, IME2, SNF7, YCR023C, GIS2, YIP1, TFC3, CUE1, YLR283W, FUN12, BMH1, RIM1, YMC1, KIC1, NAR1, YBR184W, CAF4, CTK3, NUP157, PRY1, MFA1, POL2, YDL114W, STP3, IRC20, ZPS1, POP1, DUN1, SLY1, UTP6, TAL1, DIB1, PAC2, YNR029C, SPC72, RPC34, KTR7, KRR1, YBR062C, SSA4, VMA9, ATG22, NRD1, INH1, REF2, TSC13, UTP7, AIM15, ARC19, EHT1, YHL017W, NNF2, YPR027C, TGL3, PEX28, TEL1, PGM1, PAN1, HRD3, RPL26B, SDT1, YER128W, PSY3, VPS52, RPB4, AIM2, NUD1, RPS29B, PRO3, RPL32, PXA1, GID8, TRM3, SLX1, PEA2, UBR1, AIP1, RPS10A, CFD1, YOR114W, LEA1, MSN5, RPL6A, PTC2, YER071C, RAS2, ATG14, CDC11, RPS6B, URA6, RPN1, SFH5, YAP1801, FLR1, DDR48, YRA2, APN2, ELF1, YJL217W, YPR089W, GSP2, BUG1, PSE1, SUA5, GPM2, POS5, PRM5, TAF4, GIM5, BNR1, YPS7, HAL5, RPS27B, CAK1, PGA2, SSP2, PMR1, NUP85, LSB6, TMA17, TGL1, ASN2, SEI1, VMA7, MDR1, HBS1, PMT1, PHO2, YHR113W, SSO1, RET2, UBA1, ALD2, SEC28, SEH1, YMR144W, HOC1, PRT1, RPS19B, GCN2, SAP4, YLR179C, COQ6, LYS14, LSM12, YGL117W, RED1, VPS34, VTC3, BRF1, ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, IAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, NAT5.

Examples of terminator regions with a relative expression intensity of 1.3 or more include PUP1, SFB2, YCK2, ODC1, FMP42, VPS24, YKL098W, YSY6, RTG2, LYS9, UTR1, HRR25, YBR261C, RPS26A, KTR5, CHL1, MNN10, GLE2, CPD1, SNZ1, PAM17, HIR2, CDC28, YDR061W, ENA5, APM3, YLR118C, AVT1, PEP12, PET18, MAM1, DOA1, FPR2, PIB2, PRP21, TOP2, YBL044W, OST6, AIM24, IRC18, OSW1, COT1, YOR387C, SKP1, STM1, YDL176W, YLR137W, ALE1, PBP1, YNL200C, YBL029C-A, SPE3, RRD2, CNN1, SPR6, PAN3, YRB1, YDL057W, YOR051C, POL4, ORC5, IMP2, ATG19, ARO8, YIL163C, SWI5, LSP1, TMA19, YET3, RAD26, MGA2, IME1, OXR1, GSF2, RPS18A, RUP1, YLR126C, KRE27, TVP23, INO1, ALG14, PUS5, VMA10, SPT16, YLL053C, CHC1, MSH6, SDS24, PTC4, PSP2, VBA2, TSR4, CPR4, DPP1, TFG1, ARN2, YGL230C, NBP1, YKL077W, MOB2, DYN3, UBC13, RFA3, SPG5, GYP5, YPI1, YDR179W-A, CHA1, TOS4, ADH1, SPO1, JJJ2, ADK1, SOK1, GOT1, TIR4, ERP2, SEN1, PHO81, ARF2, YOR227W, TVP38, YDL089W, ZDS2, GCD6, SUI2, VAC7, TAH11, CTR9, YKL100C, NUP188, GRE1, PHB2, BUD3, SMA1, RPL20B, NSP1, PPZ2, STO1, ETR1, SUL1, RPL6B, CPR5, YAL018C, ELP6, ACP1, SHR3, KAP120, YBR137W, IME2, SNF7, YCR023C, GIS2, YIP1, TFC3, CUE1, YLR283W, FUN12, BMH1, RIM1, YMC1, KIC1, NAR1, YBR184W, CAF4, CTK3, NUP157, PRY1, MFA1, POL2, YDL114W, STP3, IRC20, ZPS1, POP1, DUN1, SLY1, UTP6, TAL1, DIB1, PAC2, YNR029C, SPC72, RPC34, KTR7, KRR1, YBR062C, SSA4, VMA9, ATG22, NRD1, INH1, REF2, TSC13, UTP7, AIM15, ARC19, EHT1, YHL017W, NNF2, YPR027C, TGL3, PEX28, TEL1, PGM1, PAN1, HRD3, RPL26B, SDT1, YER128W, PSY3, VPS52, RPB4, AIM2, NUD1, RPS29B, PRO3, RPL32, PXA1, GID8, TRM3, SLX1, PEA2, UBR1, AIP1, RPS10A, CFD1, YOR114W, LEA1, MSN5, RPL6A, PTC2, YER071C, RAS2, ATG14, CDC11, RPS6B, URA6, RPN1, SFH5, YAP1801, FLR1, DDR48, YRA2, APN2, ELF1, YIL217W, YPR089W, GSP2, BUG1, PSE1, SUA5, GPM2, POS5, PRM5, TAF4, GIM5, BNR1, YPS7, HAL5, RPS27B, CAK1, PGA2, SSP2, PMR1, NUP85, LSB6, TMA17, TGL1, ASN1, SEI1, VMA7, MDR1, HBS1, PMT1, PHO2, YHR113W, SSO1, RET2, UBA1, ALD2, SEC28, SEH1, YMR144W, HOC1, PRT1, RPS19B, GCN2, SAP4, YLR179C, COQ6, LYS14, LSM12, YGL117W, RED1, VPS34, VTC3, BRF1, ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, TAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG3, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMU, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP3, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.4 or more include ARR2, VMA21, PSF1, SRL3, YDR379C-A, ALG12, RPS25A, SDS23, DGA1, YDR196C, LOC1, RPN2, ANB1, NAN1, STB2, CUE3, CDC8, SPH1, GID7, UBC4, RPS22B, ACT1, RPS8A, YNR068C, FRS2, TAF8, THI4, RBK1, SET3, YNL305C, TPP1, MSO1, NSA1, YMR210W, ERG24, YMR31, MAK11, URB2, FAD1, AGC1, OM45, APD1, GSH2, SPT14, YGR210C, RPS11A, SWH1, ANT1, SAP30, HRT3, NSG1, BAT2, SOM1, IPP1, HIS2, RSE1, RTT101, CRG1, YJR096W, IMH1, SPT7, MKT1, GTT3, PEX11, YDR374W-A, YPD1, DOS2, YEL023C, RPF1, BNA2, ATG27, RPL29, YPS6, RPL19B, YDR357C, ARO4, YBR096W, PEP8, RPL39, SCC4, HXT7, HSV2, APA2, TFC1, SEC53, PDR5, MUD2, RPL19A, TAF9, MXR1, RIX1, PKR1, CWC27, BFR1, YDR387C, UIP4, OST3, BUD6, GFA1, RPS8A, CRZ1, SLT2, SNC1, SEC8, PCL6, DAL5, MSB1, CSL4, COQ4, IAH1, YPL245W, PRI2, LOS1, SQS1, PBA1, YFR017C, HPA3, SCL1, YGR168C, SAP155, MON1, SGA1, MNI1, TFC8, FAB1, MED2, GCN3, PRE1, BBC1, GPA1, DIG2, IRS4, SXM1, SHU2, SRO7, GEF1, RPL24A, TMN2, RIB3, UBC9, MAL11, ARO10, LAC1, RCN1, MVB12, TBS1, CTL1, NTF2, BZZ1, HXT14, YGR125W, YNR062C, STE50, YLL056C, HIS3, CIN2, TCB3, NUM1, CPA1, PRP40, TRR1, TRP2, ADE16, EFT1, BET5, SUA7, RPS14A, FOL1, DPB4, VPS16, ANP1, YMR099C, VHS2, BMH2, ADH6, GSC2, DBR1, ADP1, CEG1, MBP1, FCP1, SRY1, YNL058C, AVO2, YMR196W, RPL35A, HIF1, YLR050C, YER187W, YOR186W, RAD57, ATH1, PEP7, YJL055W, YBR259W, UBX7, ILV6, SAM4, MRM1, PHO23, MYO4, BRE1, YFR032C, GAS4, MIP6, ERV46, YPR097W, PET10, HDA2, TRX2, MED4, SPO16, NSG2, GND2, PDB1, BDH1, NIT3, MUD1, ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMU, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP3, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.5 or more include ERG20, RPL18A, PAI3, TMA108, SAM50, SLY41, YDR461C-A, YMR265C, YJL132W, BLM10, SPO73, CWC15, ALO1, MAP1, YKR023W, PET130, YCS4, CWH41, ARP9, CHK1, PAM1, TAF10, ARA1, CGI121, YIL014C-A, CHS7, RPS21A, VMA13, NAT3, ARG2, DOG1, TMS1, PSF2, YHR126C, KAP104, DPS1, IRR1, YAL044W-A, RPL23B, YDR307W, RPL33A, NAB6, APA1, ALG6, MEX67, DAK1, ARC15, YOS1, GAD1, ECM22, CYS3, PBI2, YBR271W, GPI10, WBP1, ZRC1, FIG2, YOR262W, MSH3, IOC2, YGR201C, NAP1, KAE1, CHS1, GDE1, YTM1, YHR162W, TAD3, ALP1, TRM8, NMD2, YIM1, BCH1, RRP1, VCX1, UGA1, HOL1, GRX1, EMP24, YGR237C, FAP1, KTR2, PBP4, YER163C, RFS1, PTA1, MPD2, SGT2, IKI1, ECM29, REV3, TPD3, YDL124W, MUM2, YFR026C, PHS1, MLS1, POR1, PFD1, EGD2, GYP5, RPT2, TEX1, RPS5, TPK1, DOT5, LSB5, DMA1, BNA6, VAB2, AML1, SEC31, KIN1, STB4, GSP1, AAD4, MNN2, RPP1B, GUK1, MCK1, HSP31, SBP1, ZWF1, IST2, GPI16, CDC42, AHA1, UBP2, YNL115C, CCW14, YDL121C, MCA1, RPT4, ERP1, TMA7, WHI4, YDR131C, PDR1, TSR3, ATG11, DDP1, COQ2, RPP1A, PMP3, CRD1, PHO85, YGR017W, YIL055C, LAP3, YOR291W, GAS5, YKR043C, YIL083C, CHO2, ELP4, BIM1, CAM1, DAL82, UMP1, YBR241C, LTP1, PHO91, RPP0, YOR164C, TOM71, FAS2, FMP46, TMA22, YML131W, YCF1, OPI3, ROM1, IRC24, FYV6, ATG13, TRX3, ENP2, CEX1, VPS3, TRX1, DIT2, SEC4, GDH3, PRE9, UBP1, AYR1, NIT2, PDR17, TUB1, KEG1, CDC25, PIG2, NSE1, VPS25, YLR414C, CWH43, COG2, RCY1, VPS68, RPL7A, TAF14, SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMU, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP3, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.6 or more include SRB5, UPF3, YML096W, ARG81, NPR2, PSH1, TAF6, MCT1, SBH1, PBN1, VPS45, SRP68, SAY1, PEP1, CCT4, COQ10, RET3, SSE1, YSP3, ABZ1, PNS1, DPB3, YDL073W, ATM1, RBD2, YFR006W, DDI1, DCP1, SAS10, RMT2, FIG1, MUS81, UBI4, YBR285W, DLD1, RPS15, YPR170W-B, SRP1, PSK1, RAD4, PGD1, PMT4, ABF2, SEC24, URA10, CWC23, RPS11B, TPM1, YLR290C, TRM9, YAP1, UGP1, SPS2, PDR10, POM34, PNC1, STE11, GRH1, YMR018W, TRS33, HEF3, LAT1, BDS1, HMF1, PRP6, FSH3, SRB2, DUG1, ERD2, CDA2, RPS6A, HUT1, SHS1, IRA1, SSA3, ELP3, PRP46, CSM3, PEP4, YHC3, MDY2, RPL43A, HRQ1, YKL023W, DFM1, PCL8, SKG3, GPH1, NEJ1, URA4, GPX1, HOS2, YDR531W, PEP3, MAL31, YGR283C, HFD1, SPR28, SWP82, FUM1, CDA1, HOM6, NHX1, SNF6, ECI1, CDC10, MIS1, YIL165C, GTT1, PLP2, PFA4, RPL30, PRE3, MTD1, MNT2, ECM30, YNL208W, YCR024C-B, PCA1, HCS1, DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YIL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMU, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP3, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.7 or more include DCC1, FAR8, PPH22, DED81, GPM1, COF1, YGR042W, YPR148C, VPS55, JLP1, CAT2, GCN1, YGL231C, GUS1, YGR111W, VMA4, YDR056C, SCS2, NQM1, UFE1, COG1, PAA1, IRC22, KTR1, TYW1, SSB1, SVP26, ESC8, YNL010W, TIF1, EAF6, SHC1, KIN2, DCS2, RPS1B, URA5, DSD1, YJL218W, NPT1, SRO77, FMN1, CMD1, YTA6, RPL21A, ALG3, KRE2, PCL5, MDM34, PFS2, SNF12, BNA1, AIM29, SNU13, RNR4, MAP2, DCS1, RPN5, PDC2, DOP1, SPO74, PAP1, RPL24B, RPN8, FPR3, ERS1, CPR1, FIT3, HUG1, VPS5, PEX3, RPS29A, ERV29, CAF20, DOG2, RPL4A, YCP4, PBY1, FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.8 or more include FUS2, SNF2, SUI1, YMR262W, BUD8, TED1, TAH1, YCL048W-A, RPL41A, YDR374C, VMA8, YKR051W, YFL042C, ORM2, TAF12, APE3, YDR239C, ERV2, SHR5, YHR192W, YRB30, PHO88, WHI2, LYS1, RHO1, VPS27, VMA6, PAB1, YJR015W, SIR2, FAR1, CPT1, ECM15, ROK1, YFR018C, HYR1, POL1, CTS2, UBA4, SRP72, RTN2, HAP1, ARE2, RCK2, INM2, AFR1, YOS9, RTT103, RPS12, RNY1, PPA1, LEU3, ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 1.9 or more include ERG27, TMA29, UBX3, VPS15, RPT6, LDB18, YPL088W, RPL5, RVS167, TIR2, PHA2, ERJ5, VPS30, IMD2, PES4, EMI1, YPR085C, YBR200W-A, FMP40, REH1, SGT1, CPS1, YOP1, TRR2, STS1, VPH1, SWA2, YGR026W, CDC53, FMP52, YDR119W, RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Examples of terminator regions with a relative expression intensity of 2.0 or more include RNQ1, SAG1, RPS20, TRM82, VPS1, YIP5, YPR1, ENT2, YPT31, PRX1, YHL039W, YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Other examples include YHI9, BUD32, YLR361C-A, APL2, PTP3, YMR114C, LSC2, ATG10, SRP54, ENT3, RPL3, TYR1, NAT1, YNR021W, EBS1, HBT1, RPL15A, RPL41B, RPP2B, CBR1, BNA4, PRC1, DIT1, RPS28A, ASP3-1, IDP1, SCW4, VMA2, ALY2, and NAT5.

Moreover, RPL41B, RPL15A, DIT1, RPL3, IDP1, YHI9, YHL039W, PPA1, PRC1, VMA2, NAT5, RPS28A, NAT1, CDC53, EBS1, YMR114C, LSC2, ALY2, BNA4, YIP5, ATG10, CBR1, ASP3-1, SRP54, YNR021W, YDR119W, YLR361C-A, YPT31, BUD32 and APL2 are also desirable. Strong terminator activity can be obtained more reliably with these 30 terminator regions. RPL41B, RPL115A, DIT1, RPL3 and IDP1 are especially desirable. Strong terminator activity can be obtained even more reliably with these terminator regions. That is, strong terminator activity can be obtained with a high degree of reliability under different culture conditions, under salt stress and osmotic stress, and in different hosts. Of these, terminator regions of DIT1, RPL41B and RPL3 can provide strong terminator activity even under different culture conditions for example. Moreover, terminator regions of RPL41B and IDP1 can provide strong terminator activity even under salt stress because they are resistant to salt stress from the medium. In addition, terminator regions of DIT1 and RPL41B can provide strong terminator activity even under osmotic stress because they are resistant to osmotic stress. DIT1 terminator region in particular can provide strong terminator activity regardless of the host for example.

When the aim is to suppress the expression activity of an arbitrary gene (which may be an endogenous gene or an exogenous gene in a yeast), on the other hand, a terminator region exhibiting low expression intensity can be used based on the aforementioned expression intensity data. A relative intensity of no more than 0.8 or preferably no more than 0.7 or more preferably no more than 0.6 or still more preferably no more than 0.5 or yet more preferably no more than 0.4 is desirable, and no more than 0.3 or preferably no more than 0.2 is more desirable, while no more than 0.1 is most desirable.

Examples of terminator regions with a relative expression intensity of no more than 0.8 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, MB, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PMR6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, POX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJL012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB1, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM4, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP5, SSL2, RPS24B, UTP4, SAW1, DAN2, YPR011C, YER156C, YGL059W, TRM5, SUT2, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1, ECM37, AST1, SMP1, BPL1, UPS1, BAG7, NOG2, RPC10, CYB2, SMD2, RAD1, ATP3, STP2, BUD21, RRN5, YLR352W, FRE4, PAN2, APL3, SEC7, DUS1, CSE1, MAK3, MRPL19, DBP1, FMP48, JAC1, VPS54, FUR1, PUP3, FUN26, SWI1, PWP1, BUD23, ATF1, FMP16, YOL024W, IPK1, RLM1, YNG2, MSS2, FLO8, SHY1, KSP1, KNH1, DON1, KTI11, SMC5, FPS1, SHU1, RAV2, YOR356W, PFA3, ERG8, SEN15, YNL152W, YJL193W, MSH2, CYC1, YLR446W, MRPL13, ISA1, HUA1, YHL010C, NNT1, RMD8, PPR1, ECM9, BSC2, ACO1, MPS2, LEE1, COG5, MCM1, RFC1, TAT2, DML1, KRE9, SPT2, SPC19, QCR8, HXT1, DOA4, MSR1, STU1, ERG10, TFB4, ATG21, GYP6, DAD4, OAF1, YPR013C, GAS1, FAP7, CPA2, RPO31, ATG20, TEP1, YBL081W, SMP3, MCD1, ADK2, SAD1, HUA2, BUD2, YJR136C, RPS14B, MNL1, MDJ1, FLO10, REB1, DSF2, KHA1, MRPL35, YOR283W, PPG1, CIT3, FAA4, SPL2, MET8, HOP2, HFA1, HAP5, ROG1, MAM3, DPH1, RTG3, YNL195C, DCN1, YLR211C, OXA1, YET2, RSC2, MRPL28, CTT1, YAP3, BIG1, UBP8, YOL019W-A, RIB3, NOG1, VID30, MRP17, ZRT1, UAF30, SPO23, YNL122C, SNU71, CDC43, SPC29, DYS1, PRP11, SVF1, BUD20, MEK1, UBP16, PCF11, GRX4, UTP22, HRK1, RPB9, YPL272C, ERG29, DIS3, YFH1, MRM2, RRP5, PTI1, TIF6, FTH1, MPE1, FKS3, ESP1, YDL007C-A, DMC1, JHD2, LEU2, SNF3, SCJ1, YMR317W, CYK3, GPT2, FMP41, SIA1, HXK1, YGL057C, YLR287C, NSR1, YDL241W, RKR1, REX4, TIM17, TES1, RPO21, YNL300W, BSC6, YHR080C, OPI10, RPB8, UBP9, YKR011C, CRP1, RSM24, ARP1, SIK1, GCR2, YLR345W, FET4, MRPL40, THP2, AMD2, YDR524W-C, PSY4, BUD16, HPT1, YDR333C, RHO4, AHC1, YJL206C, SWT1, HEK2, ATP12, XBP1, RMD6, RPL15B, NUP42, PLC1, MAD3, YPS1, MCM16, HXT4, HXK2, ERG12, MMT2, YMR321C, MUM3, HST2, ROG3, DEF1, YLR281C, SSK22, MLH3, YGR131W, CSE4, YCL002C, MRPS18, CAD1, AIF1, SFC1, OYE3, EAF5, RSC9, GYL1, YDL063C, ISA2, GBP2, IMG1, NRP1, DHH1, RHB1, CIK1, PHO89, AGX1, RPB2, MRPL17, GPX2, LYP1, VPS9, BNA3, CKA2, OPI1, YER034W, RSM26, LSM6, THI3, SMC4, SWF1, YAH1, RPF2, HFI1, PLB1, MAM33, YLR413W, PRP8, ENO1, RPC19, YGL007C-A, YMR181C, URA7, YGL108C, SRB7, DAD1, LYS4, ATG18, FMP45, VAM3, SSC1, SNU56, YHR045W, HTA2, YJL213W, RPL20A, ALD4, QCR10, YGR287C, CBP4, PCI8, MCM4, DEM1, ATO3, TPS2, TAF1, KRE6, KGD2, ARB1, NMD5, EFR3, TRP4, HLJ1, ACE2, LDB17, ATG7, OSH6, AFT1, CTF4, YDR286C, AIM44, YLR149C, MRPS9, BET1, YLF2, BOI1, BUD4, CRF1, MLP2, ARX1, RRP12, NAT2, PCL7, ARP7, SFH1, STF1, YML081W, MRP49, FOL3, SAC7, PCS60, TPA1, SSS1, ERO1, NHP2, AIM1, AMD1, VPS38, COG3, YMR244C-A, PYC1, CCC1, TAO3, YDL233W, RPB10, YBR242W, EDC2, YVC1, YDR266C, PMT3, NIS1, YDR128W, ATP15, YML002W, ATG9, IKS1, SUR2, MSD1, SMC3, SPC1, MRPS35, ZIP1, YPR022C, YKL070W, RIM4, YJL127C-B, ARV1, YML6, CYC3, COX9, RMD11, SNU23, PRS2, YNL092W, TIF4632, GBP2, STP4, YIR024C, SHE1, EMG1, NUP192, THI7, NGL1, LDB19, AFG2, ROT1, PIK1, MRPL31, RHO2, MRPL49, FMO1, LRS4, CHS3, SEC8, HXT5, GRX3, YHL042W, AAC3, WSC4, PIN2, PUB1, ERG28, PSR1, ISY1, VPS70, IRC19, DNM1, RPA190, CCR4, SSU72, MRPL7, TBF1, YPR115W, SKP2, CDC73, RPL31B, MAK16, ERB1, DCG1, RNT1, RRP7, GCD7, RAD18, OMS1, YOL048C, PPT2, SCS7, YBL028C, RSC30, TIM23, PRI1, REC102, MCH5, PST1, CLB3, QCR9, MIR1, SSP120, MEF2, RPL14B, YPR003C, RLI1, SWC4, MTM1, SKY1, TOM1, YGL079W, ROM2, TFA2, AIM3, SSQ1, DUG2, MSF1, RPS0B, SCO2, OLE1, SBE2, SAR1, YJR116W, TEF1, AIM13, DFG5, YLR012C, MCM3, RPS7B, DFR1, YBL039W-B, RML2, RSM27, MEC3, YCG1, RFX1, RPL7B, CHS2, PEX5, TIF4631, RPL18B, SMB1, HUL4, NPL6, YOL107W, TRM1, STE6, ASK1, RAD9, YDL012C, RBG2, SEC6, YLR143W, XPT1, HGH1, YIL091C, PRS3, NTC20, YPR196W, MIC17, POA1, NPY1, SNQ2, ADE3, APT2, YGL082W, YHB1, MRPL16, CSH1, GUP1, YJL171C, IDP3, VHT1, PUG1, MPM1, RRP40, DPM1, AFG3, YBP2, YPL183W-A, AIM31, YCR015C, MSN4, YPL038W-A, TSC11, SEC59, ADA2, TPM2, YHR175W-A, POM152, YJR124C, RPL22B, COG7, NEW1, GSM1, UGX2, PRK1, GPD2, LDB16, PAM16, CMC1, TOM6, MBA1, SWC5, PRM10, SAM1, TRS31, YFT2, RGT1, RPL10, KRE33, CDC1, MRPL37, KEX2, VPS13, ACN9, RSC3, PBS2, EPS1, GPI18, ADH4, YTP1, YHM2, ZIM17, LYS5, AIM22, RGM1, ECM10, RDH54, DED1, CSE2, POC4, IPI1, SOL4, YKR075C, RSM10, MAE1, ATF2, SHE4, RSC1, GNT1, MSH4, HSK3, TRS20, NBP35, YBR090C, GLO1, FYV4, AEP2, ARP4, IES3, HYP2, DNF2, GAA1, RPA135, PCL9, SPT5, EDE1, ORC3, YOR304C-A, YCL047C, YER085C, YOL014W, YPL071C, GTS1, RFC2, NDE2, PET127, PLM2, YEA6, RPN7, MDL1, TMA64, NCE103, MCM6, MAS1, TSR1, BAS1, IRC4, TIM21, HCH1, APC5, PMP1, PUF6, YER077C, SNC2, MRP21, YLR036C, YME2, SEC12, YJL062W-A, YMR031C, YAL065C, YNR047W, NHP10, YOL083W, DLS1, IGO2, PAU17, NCS2, TAF7, YDL186W, CMK2, PUS7, TIM9, PMU1, MNP1, SEC16, RIF1, KAR3, MDL2, YLR356W, DCI1, ASP1, NET1, YPL068C, MOT3, NOC3, MRP13, GUT2, ICY1, NTO1, HOS3, TIM54, COX4, UBX2, RVB2, YBL059C-A, RBS1, DCR2, NEM1, MNN9, YNR036C, NOP15, SEC61, RTT106, CCT7, OSM1, SAS5, VPS29, KTI12, POL32, PUS9, SLF1, MUQ1, HSD1, KAR4, STN1, BAT1, THI71, RPL27B, COX5A, AEP1, LPP1, PRM1, YKL222C, TIP41, RPL43B, YCR043C, STP1, AIM8, HXT9, MRP7, YPL216W, SRB6, CTK2, RIT1, NST1, RIB7, MRPL38, SRT1, CBK1, ARL3, DRS2, YLR307C-A, GPI8, SHM2, IPL1, YPL041C, ARR1, GCN20, YPL039W, MNN1, SLX9, SEO1, RMP1, PSA1, CHS6, DAN1, RPB5, SIR3, BCP1, YLL058W, TNA1, TRM13, NOP1, SLP1, PEX31, YIF1, MSA2, ADH3, MNT4, GIS1, SLD2, PIN4, NVJ1, HTS1, RAD7, YKU70, NUF2, YIL001W, ASK10, YBL010C, ATP14, CDC123, MRPL51, YGR127W, YLR392C, APC2, DEP1, APS3, RCL1, DCD1, MIG3, BSP1, YLL014W, TOA1, NBA1, SLC1, IGO1, SDH3, ACS2, YOR093C, MPC54, PFY1, MIA40, YDR034C-A, RDS3, MSC3, TIM50, CSN12, GIN4, SMI1, ADE17, YGR016W, PCP1, SBA1, SRP102, SUM1, ICL1, OAF3, ZRT2, NOP10, BET2, YVH1, SPO75, DNL4, SGV1, IES4, SET4, YCL001W-B, SQT1, REI1, MRPL9, YPL066W, PET191, TEM1, UBX4, DBF20, MSB3, NUP100, RIC1, CUE4, IKI3, YEL043W, MRPL11, MPS1, EAP1, AVT2, GND1, TYW3, POP7, YDR186C, POR2, LSM5, MSH1, TOM22, YBR238C, MEP1, ILV3, YMD8, YJR061W, OSH3, TEF4, SCO1, TDH1, RIM21, YGL185C, NUS1, KTR4, RRP14, TUB4, LEU9, YLR437C, AIM7, ATX2, AI3, OST4, TRA1, MYO5, DAL4, IMG2, LTV1, YGR122W, CFT2, YMR001C-A, CDC16, YAL067W-A, YDR132C, YNL011C, TCP1, CCT3, MKK2, RRI2, ZEO1, RUD3, RTR2, YJL070C, NUP116, ENT1, SLU7, MSC2, SW1, NUP60, AIM28, YOL029C, SHE10, RSB1, SHO1, DLD2, RAX1, LCP5, ATG17, PEX17, GAL4, MET32, YOR223W, STE14, DUG3, SRX1, UFO1, YAT2, NMD3, PRP9, MSN2, PET123, SWD2, SOG2, RRP17, GPB2, YOR293C-A, TEN1, SOV1, PFK27, YIL127C, YNL024C-A, TMT1, SEC39, YER158C, ERP3, YLR257W, PKH3, YNL155W, PSO2, NOP9, GPG1, GIP4, RIB1, CYS4, ZRT3, FMP21, DAK2, ISW1, ACF4, RTT10, RTT109, FMP10, YAP6, APM4, ZAP1, ARO9, SCM4, MIM1, BRR6, SRN2, YOR287C, CLA4, RNR3, ALG8, RAD50, YBR239C, LDB7, ATP17, UGA2, ENA2, YLR408C, SAT4, BOP3, SDH4, YNL045W, RPC40, YNL134C, ARP5, MAD2, GRX6, RSM18, FES1, SGF73, ARH1, MHT1, CNS1, BDH2, YKL063C, GSH1, BOS1, THI72, BSC1, MED8, RAD5, EMP47, SIS2, TEA1, YJL185C, RTF1, CIN4, DIC1, EST2, YNK1, PUS2, PEX13, YNL217W, HOR7, MGS1, YHR009C, YML007C-A, JNM1, YHR078W, YMR155W, STB5, MRP4, STE3, CKS1, TAF13, YNL176C, PCD1, HSP26, DAS1, EDS1, CTR3, PXL1, MRS11, MET3, BDP1, CBF2, DBP6, FAR11, ERI1, MDM10, RPM2, COX13, TOA2, MYO2, PRP5, DRN1, ZDS1, IES2, FAT1, HIS1, MET16, LAS17, ACA1, HIS4, PHO12, EBP2, MRPL6, YLR271W, YBR085C-A, CRR1, SWI3, SWI4, PYK2, BUD7, PEX12, MDV1, IDH2, MRC1, TIM11, SPT15, FBP26, GUP2, NPL4, YCR007C, ABD1, YNL193W, YLR426W, YSP2, SSO2, MRPL23, YHR112C, VPS36, MET7, UTP18, MTW1, DYN1, RNH1, LST4, TAF11, RPL17A, SNA2, YGL041W-A, KAR5, YEH2, YMR118C, CUE2, URA8, YMR034C, YLR152C, YKL088W, HEM13, CAT5, KRE1, IBD2, YOL098C, AIM18, HMG1, TRM7, ADY2, LCD1, YGL194C-A, EFG1, BRX1, HIM1, TCM62, SET6, FIN1, CBF5, ASI1, DUT1, SEC65, YPL067C, RRP43, ASC1, ERG3, RTA1, NFU1, JIP4, YLR419W, YJR011C, YJL045W, ARC18, YBR287W, CAP2, NEO1, TOM5, PEP5, PCC1, PXR1, ALG11, YLR301W, ARG1, RFC4, AIM42, PPA2, DAP1, RTS1, EDC3, IRC23, YBR220C, GPI14, IML1, NIP7, YPT32, MSS18, CHO1, CST26, MOH1, PLP1, MKC7, XYL2, YMR295C, YLR003C, YIL096C, MOT2, RLP7, YSC84, NDL1, PFK1, MRD1, SAC6, REX2, RPA34, AHC2, APC1, YDR222W, VHR1, SUS1, UTH1, IRC8, SNO1, APT1, YOR352W, YMR258C, MRH1, HRP1, SRP21, MRPL22, SEC9, KAR2, YGR054W, HOF1, YDC1, YGR207C, WSC2, SRC1, YAR023C, HAM1, PER1, YKL047W, FLC3, TRM10, PAU15, RFA1, AI2, MPP10, ELC1, PHB1, OST1, LSB1, OKP1, THI22, MRP51, COX20, FCF1, PHO80, FIT1, YPL056C, KIN4, GCD1, FRT1, ACS1, LGE1, YJL136W-A, MLC2, SMF1, ISW2, HIS6, CTR2, GCV2, GAL83, IMP3, GRS1, MRS5, NCE101, BUD17, MKS1, SYF1, ACH1, ARN1, RCN2, UBC12, YER079W, YHL044W, THI20, PML1, IRC10, BMS1, SSA1, DDI2, RPC11, YDR115W, DDC1, IRC21, DUR3, PET100, SKI8, QRI5, QDR1, UBC11, MRT4, POL3, MFB1, TCO89, YDR370C, OYE2, MDM31, SLG1, YOR062C.

Examples of terminator regions with a relative expression intensity of no more than 0.7 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YIL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELM, PEX29, LTE1, HAT2, SLI1, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, INP2, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, PDX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJR012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB2, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM5, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP3, SSL2, RPS24B, UTP4, SAW1, DAN2, YPR011C, YER156C, YGL059W, TRM5, SUT2, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1, ECM37, AST1, SMP1, BPL1, UPS1, BAG7, NOG2, RPC10, CYB2, SMD2, RAD1, ATP3, STP2, BUD21, RRN5, YLR352W, FRE4, PAN2, APL3, SEC7, DUS1, CSE1, MAK3, MRPL19, DBP1, FMP48, JAC1, VPS54, FUR1, PUP3, FUN26, SWI1, PWP1, BUD23, ATF1, FMP16, YOL024W, IPK1, RLM1, YNG2, MSS2, FLO8, SHY1, KSP1, KNH1, DON1, KTI11, SMC5, FPS1, SHU1, RAV2, YOR356W, PFA3, ERG8, SEN15, YNL152W, YJL193W, MSH2, CYC1, YLR446W, MRPL13, ISA1, HUA1, YHL010C, NNT1, RMD8, PPR1, ECM9, BSC2, ACO1, MPS2, LEE1, COG5, MCM1, RFC1, TAT2, DML1, KRE9, SPT2, SPC19, QCR8, HXT1, DOA4, MSR1, STU1, ERG10, TFB4, ATG21, GYP6, DAD4, OAF1, YPR013C, GAS1, FAP7, CPA2, RPO31, ATG20, TEP1, YBL081W, SMP3, MCD1, ADK2, SAD1, HUA2, BUD2, YJR136C, RPS14B, MNL1, MDJ1, FLO10, REB1, DSF2, KHA1, MRPL35, YOR283W, PPG1, CIT3, FAA4, SPL2, MET8, HOP2, HFA1, HAP5, ROG1, MAM3, DPH1, RTG3, YNL195C, DCN1, YLR211C, OXA1, YET2, RSC2, MRPL28, CTT1, YAP3, BIG1, UBP8, YOL019W-A, RIB3, NOG1, VID30, MRP17, ZRT1, UAF30, SPO23, YNL122C, SNU71, CDC43, SPC29, DYS1, PRP11, SVF1, BUD20, MEK1, UBP16, PCF11, GRX4, UTP22, HRK1, RPB9, YPL272C, ERG29, DIS3, YFH1, MRM2, RRP5, PTI1, TIF6, FTH1, MPE1, FKS3, ESP1, YDL007C-A, DMC1, JHD2, LEU2, SNF3, SCJ1, YMR317W, CYK3, GPT2, FMP41, SIA1, HXK1, YGL057C, YLR287C, NSR1, YDL241W, RKR1, REX4, TIM17, TES1, RPO21, YNL300W, BSC6, YHR080C, OPI10, RPB8, UBP9, YKR011C, CRP1, RSM24, ARP1, SIK1, GCR2, YLR345W, FET4, MRPL40, THP2, AMD2, YDR524W-C, PSY4, BUD16, HPT1, YDR333C, RHO4, AHC1, YJL206C, SWT1, HEK2, ATP12, XBP1, RMD6, RPL15B, NUP42, PLC1, MAD3, YPS1, MCM16, HXT4, HXK2, ERG12, MMT2, YMR321C, MUM3, HST2, ROG3, DEF1, YLR281C, SSK22, MLH3, YGR131W, CSE4, YCL002C, MRPS18, CAD1, AIF1, SFC1, OYE3, EAF5, RSC9, GYL1, YDL063C, ISA2, GBP2, IMG1, NRP1, DHH1, RHB1, CIK1, PHO89, AGX1, RPB2, MRPL17, GPX2, LYP1, VPS9, BNA3, CKA2, OPI1, YER034W, RSM26, LSM6, THI3, SMC4, SWF1, YAH1, RPF2, HFI1, PLB1, MAM33, YLR413W, PRP8, ENO1, RPC19, YGL007C-A, YMR181C, URA7, YGL108C, SRB7, DAD1, LYS4, ATG18, FMP45, VAM3, SSC1, SNU56, YHR045W, HTA2, YJL213W, RPL20A, ALD4, QCR10, YGR287C, CBP4, PCI8, MCM4, DEM1, ATO3, TPS2, TAF1, KRE6, KGD2, ARB1, NMD5, EFR3, TRP4, HLJ1, ACE2, LDB17, ATG7, OSH6, AFT1, CTF4, YDR286C, AIM44, YLR149C, MRPS9, BET1, YLF2, BOI1, BUD4, CRF1, MLP2, ARX1, RRP12, NAT2, PCL7, ARP7, SFH1, STF1, YML081W, MRP49, FOL3, SAC7, PCS60, TPA1, SSS1, ERO1, NHP2, AIM1, AMD1, VPS38, COG3, YMR244C-A, PYC1, CCC1, TAO3, YDL233W, RPB10, YBR242W, EDC2, YVC1, YDR266C, PMT3, NIS1, YDR128W, ATP15, YML002W, ATG9, IKS1, SUR2, MSD1, SMC3, SPC1, MRPS35, ZIP1, YPR022C, YKL070W, RIM4, YJL127C-B, ARV1, YML6, CYC3, COX9, RMD11, SNU23, PRS2, YNL092W, TIF4632, CBP2, STP4, YIR024C, SHE1, EMG1, NUP192, THI7, NGL1, LDB19, AFG2, ROT1, PIK1, MRPL31, RHO2, MRPL49, FMO1, LRS4, CHS3, SEC8, HXT5, GRX3, YHL042W, AAC3, WSC4, PIN2, PUB1, ERG28, PSR1, ISY1, VPS70, IRC19, DNM1, RPA190, CCR4, SSU72, MRPL7, TBF1, YPR115W, SKP2, CDC73, RPL31B, MAK16, ERB1, DCG1, RNT1, RRP7, GCD7, RAD18, OMS1, YOL048C, PPT2, SCS7, YBL028C, RSC30, TIM23, PRI1, REC102, MCH5, PST1, CLB3, QCR9, MIR1, SSP120, MEF2, RPL14B, YPR003C, RID, SWC4, MTM1, SKY1, TOM1, YGL079W, ROM2, TFA2, AIM3, SSQ1, DUG2, MSF1, RPS0B, SCO2, OLE1, SBE2, SAR1, YJR116W, TEF1, AIM13, DFG5, YLR012C, MCM3, RPS7B, DFR1, YBL039W-B, RML2, RSM27, MEC3, YCG1, RFX1, RPL7B, CHS2, PEX5, TIF4631, RPL18B, SMB1, HUL4, NPL6, YOL107W, TRM1, STE6, ASK1, RAD9, YDL012C, RBG2, SEC6, YLR143W, XPT1, HGH1, YIL091C, PRS3, NTC20, YPR196W, MIC17, POA1, NPY1, SNQ2, ADE3, APT2, YGL082W, YHB1, MRPL16, CSH1, GUP1, YJL171C, IDP3, VHT1, PUG1, MPM1, RRP40, DPM1, AFG3, YBP2, YPL183W-A, AIM31, YCR015C, MSN4, YPL038W-A, TSC11, SEC59, ADA2, TPM2, YHR175W-A, POM152, YJR124C, RPL22B, COG7, NEW1, GSM1, UGX2, PRK1, GPD2, LDB16, PAM16, CMC1, TOM6, MBA1, SWC5, PRM10, SAM1, TRS31, YFT2, RGT1, RPL10, KRE33, CDC1, MRPL37, KEX2, VPS13, ACN9, RSC3, PBS2, EPS1, GPI18, ADH4, YTP1, YHM2, ZIM17, LYS5, AIM22, RGM1, ECM10, RDH54, DED1, CSE2, POC4, IPI1, SOL4, YKR075C, RSM10, MAE1, ATF2, SHE4, RSC1, GNT1, MSH4, HSK3, TRS20, NBP35, YBR090C, GLO1, FYV4, AEP2, ARP4, IES3, HYP2, DNF2, GAA1, RPA135, PCL9, SPT5, EDE1, ORC3, YOR304C-A, YCL047C, YER085C, YOL014W, YPL071C, GTS1, RFC2, NDE2, PET127, PLM2, YEA6, RPN7, MDL1, TMA64, NCE103, MCM6, MAS1, TSR1, BAS1, IRC4, TIM21, HCH1, APC5, PMP1, PUF6, YER077C, SNC2, MRP21, YLR036C, YME2, SEC12, YJL062W-A, YMR031C, YAL065C, YNR047W, NHP10, YOL083W, DLS1, IGO2, PAU17, NCS2, TAF7, YDL186W, CMK2, PUS7, TIM9, PMU1, MNP1, SEC16, RIF1, KAR3, MDL2, YLR356W, DCI1, ASP1, NET1, YPL068C, MOT3, NOC3, MRP13, GUT2, ICY1, NTO1, HOS3, TIM54, COX4, UBX2, RVB2, YBL059C-A, RBS1, DCR2, NEM1, MNN9, YNR036C, NOP15, SEC61, RTT106, CCT7, OSM1, SAS5, VPS29, KTI12, POL32, PUS9, SLF1, MUQ1, HSD1, KAR4, STN1, BAT1, THI71, RPL27B, COX5A, AEP1, LPP1, PRM1, YKL222C, TIP41, RPL43B, YCR043C, STP1, AIM8, HXT9, MRP7, YPL216W, SRB6, CTK2, RIT1, NST1, RIB7, MRPL38, SRT1, CBK1, ARL3, DRS2, YLR307C-A, GPI8, SHM2, IPL1, YPL041C, ARR1, GCN20, YPL039W, MNN1, SLX9, SEO1, RMP1, PSA1, CHS6, DAN1, RPB5, SIR3, BCP1, YLL058W, TNA1, TRM13, NOP1, SLP1, PEX31, YIF1, MSA2, ADH3, MNT4, GIS1, SLD2, PIN4, NVJ1, HTS1, RAD7, YKU70, NUF2, YIL001W, ASK10, YBL010C, ATP14, CDC123, MRPL51, YGR127W, YLR392C, APC2, DEP1, APS3, RCL1, DCD1, MIG3.

Examples of terminator regions with a relative expression intensity of no more than 0.6 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJL098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, POX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJR012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB2, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM4, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP5, SSL2, RPS24B, UTP4, SAW1, DAN2, YPR011C, YER156C, YGL059W, TRM5, SUT2, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1, ECM37, AST1, SMP1, BPL1, UPS1, BAG7, NOG2, RPC10, CYB2, SMD2, RAD1, ATP3, STP2, BUD21, RRN5, YLR352W, FRE4, PAN2, APL3, SEC7, DUS1, CSE1, MAK3, MRPL19, DBP1, FMP48, JAC1, VPS54, FUR1, PUP3, FUN26, SWI1, PWP1, BUD23, ATF1, FMP16, YOL024W, IPK1, RLM1, YNG3, MSS2, FLO8, SHY1, KSP1, KNH1, DON1, KTI11, SMC5, FPS1, SHU1, RAV2, YOR356W, PFA3, ERG8, SEN15, YNL152W, YJL193W, MSH2, CYC1, YLR446W, MRPL13, ISA1, HUA1, YHL010C, NNT1, RMD8, PPR1, ECM9, BSC2, ACO1, MPS2, LEE1, COG5, MCM1, RFC1, TAT2, DML1, KRE9, SPT2, SPC19, QCR8, HXT1, DOA4, MSR1, STU1, ERG10, TFB4, ATG21, GYP6, DAD4, OAF1, YPR013C, GAS1, FAP7, CPA2, RPO31, ATG20, TEP1, YBL081W, SMP3, MCD1, ADK2, SAD1, HUA2, BUD2, YJR136C, RPS14B, MNL1, MDJ1, FLO10, REB1, DSF2, KHA1, MRPL35, YOR283W, PPG1, CIT3, FAA4, SPL2, MET8, HOP2, HFA1, HAP5, ROG1, MAM3, DPH1, RTG3, YNL195C, DCN1, YLR211C, OXA1, YET2, RSC2, MRPL28, CTT1, YAP3, BIG1, UBP8, YOL019W-A, RIB3, NOG1, VID30, MRP17, ZRT1, UAF30, SPO23, YNL122C, SNU71, CDC43, SPC29, DYS1, PRP11, SVF1, BUD20, MEK1, UBP16, PCF11, GRX4, UTP22, HRK1, RPB9, YPL272C, ERG29, DIS3, YFH1, MRM2, RRP5, PTI1, TIF6, FTH1, MPE1, FKS3, ESP1, YDL007C-A, DMC1, JHD2, LEU2, SNF3, SCJ1, YMR317W, CYK3, GPT2, FMP41, SIA1, HXK1, YGL057C, YLR287C, NSR1, YDL241W, RKR1, REX4, TIM17, TES1, RPO21, YNL300W, BSC6, YHR080C, OPI10, RPB8, UBP9, YKR011C, CRP1, RSM24, ARP1, SIK1, GCR2, YLR345W, FET4, MRPL40, THP2, AMD2, YDR524W-C, PSY4, BUD16, HPT1, YDR333C, RHO4, AHC1, YJL206C, SWT1, HEK2, ATP12, XBP1, RMD6, RPL15B, NUP42, PLC1, MAD3, YPS1, MCM16, HXT4, HXK2, ERG12, MMT2, YMR321C, MUM3, HST2, ROG3, DEF1, YLR281C, SSK22, MLH3, YGR131W, CSE4, YCL002C, MRPS18, CAD1, AIF1, SFC1, OYE3, EAF5, RSC9, GYL1, YDL063C, ISA2, GBP2, IMG1, NRP1, DHH1, RHB1, CIK1, PHO89, AGX1, RPB2, MRPL17, GPX2, LYP1, VPS9, BNA3, CKA2, OPI1, YER034W, RSM26, LSM6, THI3, SMC4, SWF1, YAH1, RPF2, HFI1, PLB1, MAM33, YLR413W, PRP8, ENO1, RPC19, YGL007C-A, YMR181C, URA7, YGL108C, SRB7, DAD1, LYS4, ATG18, FMP45, VAM3, SSC1, SNU56, YHR045W, HTA2, YJL213W, RPL20A, ALD4, QCR10, YGR287C, CBP4, PCI8, MCM4, DEM1, ATO3, TPS2, TAF1, KRE6, KGD2, ARB1, NMD5, EFR3, TRP4, HLJ1, ACE2, LDB17, ATG7, OSH6, AFT1, CTF4, YDR286C, AIM44, YLR149C, MRPS9, BET1, YLF2, BOI1, BUD4, CRF1, MLP2, ARX1, RRP12, NAT2, PCL7, ARP7, SFH1, STF1, YML081W, MRP49, FOL3, SAC7, PCS60, TPA1, SSS1, ERO1, NHP2, AIM1, AMD1, VPS38, COG3, YMR244C-A, PYC1, CCC1, TAO3, YDL233W.

Examples of terminator regions with a relative expression intensity of no more than 0.5 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-

A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP1, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJL129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NDJ1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1,

MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3, SLO1, AIM36, UBP13, TRI1, CTH1, PGS1, NMD4, YIL064W, BAR1, BCS1, YBL029W, CTR1, MRPL20, AGP3, YOR338W, FCF2, YOR052C, YJL147C, RSA1, PEX8, YOL159C, RRP45, YDL199C, LIA1, THI2, TRZ1, CYT2, MGM101, YNL277W-A, ARP8, MRPL36, YAR028W, PAU2, SLD5, SMD1, YNL086W, QCR7, FMC1, HOS4, HEM1, NAM7, YPL108W, BUD14, BOI2, HRD1, YOL114C, RIS1, SIC1, BST1, KES1, MET4, TRS120, SYC1, NPA3, YLH47, SRL2, LRC3, MHR1, ZIP2, EAR1, RSF1, RIO2, MET2, NOP4, SRD1, PWP2, MST1, PCK1, CDC7, TOK1, PRO1, RAX2, LSM7, SHG1, TOM7, DAS2, SIP2, RRS1, EUG1, PDX1, RAD61, SUN4, HAA1, YNR048W, ACO2, YOL047C, PMD1, FZO1, YEL025C, GPR1, BNI1, RSA4, YMR185W, PAU16, ECM7, YHP1, COG8, LST8, HST1, ESA1, YJL160C, MER1, CIN8, WSS1, PAT1, LRC6, FMP30, LYS21, MET18, MRPL50, GCR1, YOR022C, YJR012C, PDR3, YPL229W, SFK1, DUS4, IDS2, YOL036W, PHM6, YPR117W, RPB7, MCM2, MRS1, GLO2, YKL105C, RCK1, AME1, DIA3, HOM3, YDR541C, PMT6, DSE2, YJL216C, RIO1, ALB1, IBA57, YOR268C, CWC24, ARD1, UTP15, MSE1, UBS1, YNL234W, YDL025C, CAF40, YBR221W-A, ATP18, MAL33, YPT6, OAC1, YJR151W-A, YML108W, COX17, RAD52, HST3, TAZ1, YNR064C, YGL010W, MFA2, PGM3, NRM1, CRS5, CTM1, SKG6, SYF2, HYM1, IPI3, MDH1, TFB2, HST4, MRPL24, YMR166C, AVT5, YGR021W, SUV3, YNL146W, MID1, AKL1, MTR10, LAA1, HDA1, SMY2, MRPL8, PLB2, CWP1, ECM14, ECM1, GAL2, FAS1, KEL1, SET7, TSR2, FET5, DRE2, MMS4, TGS1, COQ1, SUR7, PCL2, SER2, YFL034W, MKK1, SSA2, AVO1, FMP25, YRR1, SLX5, SAF1, YPL260W, YKR096W, UTP14, PAM18, WTM1, STE18, AIM20, SYM1, SIT4, SSH4, MEI5, CYC8, DSN1, STB3, IMD4, YPL109C, ECM25, YMR102C, YDR306C, SUL2, YOL019W, PAU10, HNM1, MRPL1, CMK1, YBR196C-A, YGL226W, YPR147C, PGM2, SLM4, MSS1, YER121W, YDR381C-A, VPS72, YJL043W, PAN6, YMR086W, MDN1, HEH2, YKE4, YKL162C, ZRG8, HIP1, YPR145C-A, YCL056C, ERG1, INP54, MRPS16, MOD5, YJR008W, RMI1, YNL146C-A, RRF1, CAF130, BUD9, GWT1, BEM3, STF2, SSN3, MAS2, SLN1, TLG1, NOP6, YOR097C, HVG1, GCD11, TDP1, ATC1, CIT1, GRR1, RPA12, ADY3, CTA1, SWS2, SNF8, CIS3, MRPL4, CLB4, DBP2, APQ12, UTP5, MPD1, MRS3, AIM43, ATP11, SNU66, ARF3, YKU80, YLR422W, EGT2, MSP1, YLR218C, MRPL44, YHR127W, UBP3, SOD2, CYT1, POP6, HSP10, YHR033W, YKL161C, KIN82, YNL165W, CYC7, FYV7, TAT1, YNR040W, DBP3, SMY1, TRP3, SSL2, RPS24B, UTP4, SAW1, DAN2, YPR011C, YER156C, YGL059W, TRM5, SUT2, IML2, ATP1, CKA1, ECM31, MSK1, SCC2, SYG1, RPO26, YPR114W, HIR3, YIL029C, MAC1, YOR296W, IST3, HOR2, ITT1, PRP22, ROD1, DIA4, FMP32, TOM70, DIP2, YPR159C-A, PSP1, BTS1.

Examples of terminator regions with a relative expression intensity of no more than 0.4 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, MB, COS10, MET1, HXT8, GLY1, SUR1, RTG1, PHM7, YIL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, YGR071C, TRL1, ECM17, YML020W, RPO41, CFT1, LRC5, THI74, TPN1, YOR059C, PRY3, YEL1, CNM67, STB6, YOR385W, RRN6, COP1, PDR12, ELG1, SRP40, SRM1, YDR109C, AIM30, RPC17, YJL028W, YBR071W, APS1, KIP2, ATP22, PRM6, BUD31, IXR1, NFI1, YHL015W-A, VHS3, YNL295W, SML1, SSK1, YAE1, RIM2, YDR246W-A, YLR445W, SPT23, MTG2, SGF11, BRL1, YMR315W, MRPS28, ERG5, UTP30, MDM35, ASR1, YIL102C-A, USA1, DOT6, COX23, ADH5, DAN4, RMA1, SCT1, PHO84, SFG1, SLX4, EST1, YNL190W, SNL1, RRP15, YML082W, DOT1, PEX1, YUR1, YAP1802, YDR185C, GET2, YPL264C, YDR065W, YJR115W, MAK21, YER064C, ATR1, IDP2, KCS1, ZPR1, ITC1, OAZ1, SWC7, RPL8A, CAC2, VTH1, OCH1, BUL1, YNR004W, LST7, MRPS8, TIS11, NDC1, TOS8, ISM1, MSL5, FMP43, YJR098C, COQ3, TPC1, RIM101, ADR1, ALD6, YHR087W, VPS21, POG1, YJR005C-A, SNT1, YHR022C, MEF1, PUP2, ERP6, HHT2, YGR146C, OAR1, YOR129C, YCR045C, DBP7, MUB1, YPL236C, RIB2, YPR084W, AIM5, UTR5, HKR1, YMR010W, ALR1, LRE1, RPN4, YLR363W-A, MGM1, HTD2, NAM8, SED5, YOR161C-C, YML018C, NAB2, YER140W, PRM4, RTR1, YIR042C, THI80, FUN19, DMR1, SIP1, CGR1, MTR3, YJL144W, RIM13, SAL1, MET28, INM1, VID27, CDC34, SRO9, RRP9, YOL087C, MCM22, YMR111C, NAT1, ATG12, MSM1, SRS2, YBR225W, YLR063W, AI1, CDC36, ASN1, MET31, SSP1, NGG1, RBA50, PUT1, YPT53, NMA2, YBR219C, CDC40, SGO1, YJL047C-A, RPC31, INP52, UGO1, RAD30, CLB1, GLO4, TPK3, GIM3, CDC9, PEX27, AIM32, YGL081W, DJP1, HMS1, JSN1, UBP12, RSM25, UBP5, GIP1, PUT3, CKI1, FAR7, LAG2, DAM1, PSD2, HMT1, COR1, MMR1, MRPL39, CTF8, AGP2, PRM7, HIT1, HAL9, GPA2, TIM44, TFB1, ECM19, MRPL32, YBR284W, NAS2, SBE22, YOR011W-A, ORT1, MRPL25, QNQ1, APC4, TYE7, YPP1, MMT1, MRP10, MRPS5, LIP5, CDC27, ESC2, CAN1, MEC1, TOP1, SLM3, SIP4, URN1, YCK3, USO1, RSM19, ASG1, ISU1, YHL008C, YNL313C, KKQ8, FCY2, GPD1, HHT1, MDJ2, SDH1, SSF1, PIP2, STE13, AZF1, VPS35, YGL146C, TAM41, MIF2, YDL118W, HFM1, PRR1, MRE11, FMP37, MLH2, BUD5, YOR342C, PCL1, DHR2, CDC5, CBP3, RLP24, LSG1, NCL1, YDR262W, PGA3, MID2, YJL027C, YOR305W, QCR6, MSC6, RSC4, PAU18, POL12, SME1, DBF2, RPS27A, NHP6A, YGK3.

Examples of terminator regions with a relative expression intensity of no more than 0.3 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, PRP38, MSA1, YBR147W, BBP1, MLH1, SWC3, SOH1, HHF2, NIP1, MSL1, RIF2, SPG1, WHI3, HTA1, ARR3, YIL077C, SGF29, RAD53, YEL073C, YNR065C, NCA3, YBR296C-A, ECM23, YLR225C, SLD3, YBR197C, YBL059W, YOL075C, DNA2, SIZ1, REC114, MSN1, RGT2, CBF1, YGL176C, PTP2, GAL3, VPS62, HMS2, SMF3, APL1, SKI3, MNS1, YOR214C, TID3, KSS1, YDR194W-A, UPC2, ARG80, MRS2, ATP23, YML100W-A, YGL101W, STE12, RPI1, YDR090C, YEH1, UTP13, AMN1, YIL089W, AVL9, ATO2, HEM3, RPA14, GIP3, YGR053C, ALR2, YAP5, CDD1, SLS1, MET8, ABM1, PET20, CBP1, RAD10, SPO22, PIB1, EAF3, YFR032C-B, ELP2, YIA6, PET112, PAU7, MEI4, YEA4, SGS1, JEN1, CLB2, GIC2, SWI6, ULP2, KIN28, YKL033W, CSM4, YNL095C, RRN3, RNR1, TPO3, SUP45, ABP140, RPS28B, MRF1, GLN1, OPT1, PHO4, UBP10, YOL163W, MDS3, OTU1, GAT1, HDA3, MSY1, GNP1, YFL041W-A, YPL141C, MPH2, PMA1, YNL260C, SKS1, YDL177C, SWR1, RMD5, RPL9B, MIC14, AOS1, LRG1, ROX1, PCL10, MRPL3, YER152C, EAF1, HTB1, SPA2, SSN2, YJR129C, ATG8, RHR2, TFG2, YBL100W-C, CSM2, EXG1, STE7, ADH2, SNT2, PML39, SEC2, ASI2, MNT3, BUR6, BIO5, YDR506C, RDR1, MRPL33, YGL159W, RIM8, YGR161W-C, YIG1, PDR16, YDR249C, YDR124W, HSP30, SDH2, YER130C, FAA3, BUD22, TIM22, CBP6, ICE2, SPC110, AFT2, NAM2, YPR071W, DIP5, SDS3, POP4, OCA6, PTC6, YBR201C-A, YPR127W, SEC10, ASF2, SLI15, RRN7, ORC2, GUF1, GPI2, RPS9A, RAD6, PSR2, RIP1, GZF3, CAR1, YHR151C, LEU5, YBR182C-A, IRC7, ASG7, YOR381W-A, OCA5, YHR035W, PET117, ISD11, HSP150, CCC2, YHR131C, MRK1, RXT2, PPH3, ODC2, SHE9, YCR075W-A, CYB5, YDR415C, LRO1, SOF1, YNL162W-A, PAU14, MTO1, YKL061W, MSS11, SAN1, SET2, YMR1, PHD1, YBL071C-B, MPA43, SAM37, AAT1, ASH1, UTR2, CAT8, SLX8, HXT2, COY1, TAF3, DSS4, TOR1, YMR030W-A, PAU5, SFP1, FHL1, COX10, DDR2, SWM1, HXT6, RCR2, YLR091W, RMD9, SHQ1, YLR346C, SPT21, ARE1, KAP95, and YGR071C.

Examples of terminator regions with a relative expression intensity of no more than 0.2 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU2, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, YPS5, YLR297W, SNA4, BIO4, YBR298C-A, ECM12, SEF1, YMR247W-A, EXO1, CTF13, HUR1, SNO3, BSC5, YER175W-A, PGA1, YLR173W, YDR119W-A, IRC15, MGA1, YPR174C, IML3, YLL054C, RDS1, MDM32, PET494, YPR036W-A, GTB1, ISF1, KRE29, SAP190, YHR214C-E, GTO3, YOR365C, MIP1, SIP5, YPL191C, YPL162C, YMR291W, BRN1, MDM1, NAT4, YLR406C-A, YME1, CSI2, YOR008C-A, CEF1, BUD25, DFG16, GPB1, KAR1, PPM2, DSS1, RPC37, VID24, ERV41, YGR169C-A, ECM8, YHR032W, ELA1, PEX29, LTE1, HAT2, SW, MUP1, ALG13, FRE7, YMR147W, ISU2, YOR1, JID1, ECM3, ATG5, MED6, YPL014W, YLR030W, AQY2, CCT2, YER067W, NRG1, SPT8, PIR1, YGR068C, YER039C-A, ELM1, ASE1, YBL095W, YNR066C, MTL1, CNE1, CAX4, NDI1, FLX1, YNL130C-A, CWC25, YNL254C, CDC13, ATP10, OCT1, ALF1, YEF1, BAP2, HTL1, PDC5, PKP1, SSK2, CAF120, SKN1, HHF1, CDC39, YFR012W, YEL048C, HAP4, PEX7, TPO1, NFT1, NGL3, YMR206W, DUS3, YAP7, CUS2, YLR415C, FUI1, SLM5, BTT1, YFR035C, RRN10, HAP3, SSY5, SFL1, KIP1, CDC15, GLT1, DOC1, MND1, AAC1, CEP3, UBC5, YNL213C, CLN3, CSF1, ECM18, MRS4, YIL046W-A, INP1, RTT105, MPT5, ATG15, RNH202, TAX4, IZH3, BDF2, COX14, YIP4, YJR120W, SAE2, YMC2, YGR035C, NDD1, HPA2, STL1, GPM3, ERF2, MMS21, YJL133C-A, YNL024C, IFH1, LIN1, ICS3, YNR014W, SPB1, YNL211C, SOL1, COS111, HSH155, NKP2, NAB3, FMT1, YPL152W-A, BOR1, SPC25, MMS1, YIL166C, MAL13, BFA1, AEP3, MTH1, YGR031W, BIT61, YMR230W-A, SKT5, YGL258W-A, PHR1, HTB2, SER1, BAP3, YER053C-A, ATG16, BIO2, MEP3, YNR073C, PCH2, APS2, MDM30, CLB5, ISR1, MRP20, GUD1, MED1, RER2, MCM10, YIR018C-A, SPO14, NUC1, MNN4, IFM1, YLR412C-A, ALT2, NNF1, YKL096C-B, RAD51, CIT2, SPT4, LRC4, USE1, YLR455W, YOL164W-A, PRP18, COA2, HSP82, YER184C, DAD2, LEU1, YDL129W, YPL119C-A, YOR034C-A, and PRP38.

Examples of terminator regions with a relative expression intensity of no more than 0.1 include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, RAD34, YIR021W-A, FZF1, YHK8, YGL188C-A, HCM1, CDC6, YPR157W, CLB6, YOX1, YLR285C-A, YDR114C, YHR199C-A, MPS3, MUP3, YIR014W, AAR2, YPT35, AIM33, SCW11, BDF1, YCL042W, BSC4, YGL193C, NUT2, YJL118W, YKL069W, SRB8, YOR060C, MDH2, YPR116W, YPK2, GLN3, YDL211C, RAD55, CYM1, ENT4, ULA1, YMR182W-A, YKR017C, YOR302W, YOR072W-B, VTS1, FYV12, YGL235W, YHR086W-A, YEL067C, YPL257W, UBA3, YMR105W-A, YOR316C-A, TMA10, YDL159W-A, ATG29, YML037C, NSL1, YJL077W-B, POP3, WHI5, MIH1, YGR240C-A, YRM1, KAR9, YJU1(12, SPC24, DPB2, CHL4, YMR087W, CSI1, YIL134C-A, BUR2, PTH1, SSN8, AUA1, YLR154C-G, YLR342W-A, YCL001W-A, FLC1, YLL006W-A, VAM7, YPL077C, CCZ1, PRP28, ACM1, IME4, YPR096C, FRE5, PDR8, ILV5, YIL161W, PAC11, UBR2, YRB2, YLR125W, YMR253C, DSE4, EPL1, SNP1, YMR160W, SPO77, BUB1, YFR016C, SPC97, GEM1, INO2, SPT10, YLR132C, AIM45, YJR054W, MBF1, YAL064C-A, YML054C-A, NUP1, ECM27, YIL060W, IRE1, YHR177W, YJR079W, YNL187W, YML003W, PIH1, YDR169C-A, PET111, YDL109C, YOR012W, YHR050W-A, TAR1, RIM9, YCR095W-A, RPR2, COS7, YDR049W, CUS1, JJJ3, COS10, MET1, HXT8, GLY1, SUR1, RTG1, PHM7, YJL052C-A, HXT17, YFL052W, ATG1, ECM2, YNR075C-A, YKR041W, ALD5, YHL018W, LUC7, and YPS5.

Other examples include ORC4, ICY2, GIC1, HLR1, ECM13, YLR108C, AQR1, YHR213W-A, SUT1, PLB3, AIM26, TPO4, YPR153W, GIS3, WSC3, FUR4, DLT1, MOT1, YNR063W, MET13, YDL156W, YJL107C, YJR154W, YNL042W-B, VHS1, GPI19, YIL057C, STD1, CTF19, and RAD34.

When the aim is to make the expression output of an arbitrary gene equivalent to that obtained in the past (with a widely-used terminator region for example), or when a known terminator region is used as a benchmark, a terminator region exhibiting moderate expression intensity can be selected based on the aforementioned expression intensity data. The relative intensity in this case is preferably more than 0.8 but less than 1.2, or more preferably 0.9 to 1.1, or still more preferably 0.95 to 1.05.

Examples of terminator regions with a relative expression intensity of more than 0.8 but less than 1.2 include YLL014W, TOA1, NBA1, SLC1, IGO1, SDH3, ACS2, YOR093C, MPC54, PFY1, MIA40, YDR034C-A, RDS3, MSC3, TIM50, CSN12, GIN4, SMI1, ADE17, YGR016W, PCP1, SBA1, SRP102, SUM1, ICL1, OAF3, ZRT2, NOP10, BET2, YVH1, SPO75, DNL4, SGV1, IES4, SET4, YCL001W-B, SQT1, REI1, MRPL9, YPL066W, PET191, TEM1, UBX4, DBF20, MSB3, NUP100, RIC1, CUE4, IKI3, YEL043W, MRPL11, MPS1, EAP1, AVT2, GND1, TYW3, POP7, YDR186C, POR2, LSM5, MSH1, TOM22, YBR238G, MEP1, ILV3, YMD8, YJR061W, OSH3, TEF4, SCO1, TDH1, RIM21, YGL185C, NUS1, KTR4, RRP14, TUB4, LEU9, YLR437C, AIM7, ATX2, AI3, OST4, TRA1, MYO5, DAL4, IMG2, LTV1, YGR122W, CFT2, YMR001C-A, CDC16, YAL067W-A, YDR132C, YNL011C, TCP1, CCT3, MKK2, RRI2, ZEO1, RUD3, RTR2, YJL070C, NUP116, ENT1, SLU7, MSC2, SW1, NUP60, AIM28, YOL029C, SHE10, RSB1, SHO1, DLD2, RAX1, LCP5, ATG17, PEX17, GAL4, MET32, YOR223W, STE14, DUG3, SRX1, UFO1, YAT2, NMD3, PRP9, MSN2, PET123, SWD2, SOG2, RRP17, GPB2, YOR293C-A, TEN1, SOV1, PFK27, YIL127C, YNL024C-A, TMT1, SEC39, YER158C, ERP3, YLR257W, PKH3, YNL155W, PSO2, NOP9, GPG1, GIP4, RIB1, CYS4, ZRT3, FMP21, DAK2, ISW1, ACF4, RTT10, RTT109, FMP10, YAP6, APM4, ZAP1, ARO9, SCM4, MIM1, BRR6, SRN2, YOR287C, CLA4, RNR3, ALG8, RAD50, YBR239C, LDB7, ATP17, UGA2, ENA2, YLR408C, SAT4, BOP3, SDH4, YNL045W, RPC40, YNL134C, ARP5, MAD2, GRX6, RSM18, FES1, SGF73, ARH1, MHT1, CNS1, BDH2, YKL063C, GSH1, BOS1, THI72, BSC1, MED8, RAD5, EMP47, SIS2, TEA1, YJL185C, RTF1, CIN4, DIC1, EST2, YNK1, PUS2, PEX13, YNL217W, HOR7, MGS1, YHR009C, YML007C-A, JNM1, YHR078W, YMR155W, STB5, MRP4, STE3, CKS1, TAF13, YNL176C, PCD1, HSP26, DAS1, EDS1, CTR3, PXL1, MRS11, MET3, BDP1, CBF2, DBP6, FAR11, ERI1, MDM10, RPM2, COX13, TOA2, MYO2, PRP5, DRN1, ZDS1, IES2, FAT1, HIS1, MET16, LAS17, ACA1, HIS4, PHO12, EBP2, MRPL6, YLR271W, YBR085C-A, CRR1, SWI3, SWI4, PYK2, BUD7, PEX12, MDV1, IDH2, MRC1, TIM11, SPT15, FBP26, GUP2, NPL4, YCR007C, ABD1, YNL193W, YLR426W, YSP2, SSO2, MRPL23, YHR112C, VPS36, MET7, UTP18, MTW1, DYN1, RNH1, LST4, TAF11, RPL17A, SNA2, YGL041W-A, KAR5, YEH2, YMR118C, CUE2, URA8, YMR034C, YLR152C, YKL088W, HEM13, CAT5, KRE1, IBD2, YOL098C, AIM18, HMG1, TRM7, ADY2, LCD1, YGL194C-A, EFG1, BRX1, HIM1, TCM62, SET6, FIN1, CBF5, ASI1, DUT1, SEC65, YPL067C, RRP43, ASC1, ERG3, RTA1, NFU1, JIP4, YLR419W, YJR011C, YJL045W, ARC18, YBR287W, CAP2, NEO1, TOM5, PEP5, PCC1, PXR1, ALG11, YLR301W, ARG1, RFC4, AIM42, PPA2, DAP1, RTS1, EDC3, IRC23, YBR220C, GPI14, IML1, NIP7, YPT32, MSS18, CHO1, CST26, MOH1, PLP1, MKC7, XYL2, YMR295C, YLR003C, YIL096C, MOT2, RLP7, YSC84, NDL1, PFK1, MRD1, SAC6, REX2, RPA34, AHC2, APC1, YDR222W, VHR1, SUS1, UTH1, IRC8, SNO1, APT1, YOR352W, YMR258C, MRH1, HRP1, SRP21, MRPL22, SEC9, KAR2, YGR054W, HOF1, YDC1, YGR207C, WSC2, SRC1, YAR023C, HAM1, PER1, YKL047W, FLC3, TRM10, PAU15, RFA1, AI2, MPP10, ELC1, PHB1, OST1, LSB1, OKP1, THI22, MRP51, COX20, FCF1, PHO80, FIT1, YPL056C, KIN4, GCD1, FRT1, ACS1, LGE1, YJL136W-A, MLC2, SMF1, ISW2, HIS6, CTR2, GCV2, GAL83, IMP3, GRS1, MRS5, NCE101, BUD17, MKS1, SYF1, ACH1, ARN1, RCN2, UBC12, YER079W, YHL044W, THI20, PML1, IRC10, BMS1, SSA1, DDI2, RPC11, YDR115W, DDC1, IRC21, DUR3, PET100, SKI8, QRI5, QDR1, UBC11, MRT4, POL3, MFB1, TCO89, YDR370C, OYE2, MDM31, SLG1, YOR062C, DNF1, MEH1, AIR2, MSS116, ACB1, ADE12, ELO1, VTA1, MRPL27, YFL054C, SPC34, RGS2, DRS1, GTR1, COX8, KEL2, NUP82, GIR2, FKH2, CLG1, PEX6, HO, YHR003C, NUP84, RRB1, PSY2, BSD2, ESBP6, MED7, RSN1, YKE2, YHL012W, SHE2, RPL2A, DUO1, DST1, PET9, RSA3, GLN4, YKR015C, YJR141W, RIM20, BCK2, SPC42, TRF5, FAA2, TRS130, GUA1, HSL7, PDE2, RRP8, XRS2, SPE1, RFT1, VPS20, SEC20, PAD1, GGC1, ORC1, HMG2, STE2, LSM3, ICS2, TRM2, CDC3, HEM2, SIN4, VIK1, HIS7, RAD54, IQG1, DFG10, TIP1, BRR2, GRX2, HTZ1, BCH2, NRG2, RSC58, TMA16, RAD59, URM1, ADY4, AAP1, ABP1, YGR066C, BRE5, BFR2, LSM1, CHD1, VTI1, AIM11, RFA2, SUR4, YOR228C, DLD3, ISN1, CYC2, SNF5, YMR124W, GIP2, SVL3, SEC13, YEL047C, BEM1, RPL16A, SPR3, ATP4, WAR1, ITR1, FAR3, YOR021C, YBR028C, NOP58, RPN13, YNL035C, YJL049W, YER137C, NOC4, ALG7, MET22, SIL1, TYS1, GLK1, YDR341C, YKR045C, RAD23, BIK1, RPL27A, YOR152C, KNS1, YHR182W, EEB1, RKM1, SNG1, YIL067C, VPS66, TCB1, ADE4, YNL034W, HSP78, HEM15, PKC1, SPP2, MF(ALPHA)1, ARP6, NCS6, RTS3, SPE4, YPL199C, DAL81, SAC1, YOL131W, YHL026C, REC107, YGR174W-A, SGE1, NCB2, YNL320W, CDC20, CSG2, ECM5, NOC2, IES1, SMK1, PHO86, YHR202W, CIN1, PFS1, MCM21, ROT2, GLC7, HRT1, YDR018C, APM1, DPH2, CDH1, HNT3, ATG4, FRE3, ATP2, YMR148W, YAT1, ERG11, PGI1, FKH1, MET30, YGL140C, ARC35, SNX41, SAS2, YHR007C-A, YML083C, ABF1, YLR104W, TOS1, MF(ALPHA)2, FRM2, OPY1, MMF1, DIG1, PMI40, YIL092W, ASI3, FIR1, ERG26, YMR090W, YGL085W, CDC24, YPL113C, YPR010C-A, BIR1, AAH1, EPT1, MSW1, NOP14, CBT1, COX18, COX16, RRD1, BEM4, GEA2, FOB1, ERG7, YLR042C, SEC17, YPR063C, PUT4, MSI1, RPA43, SPE2, DAL1, RPC25, BRO1, AXL1, EAF7, RCR1, YDR338C, RGA1, LOT5, YIH1, RNA1, SKM1, PUT2, HEM4, AIM37, PHO13, YGR015C, AKR2, YKL050C, TCB2, HAC1, ADE1, RTN1, RPL8B, MDM36, JHD1, CCL1, YDR282G, PRE10, PEX14, OMA1, YNR034W-A, NBP2, SPT20, PRP2, YGL041C-B, YBR255W, YOR246C, YFL012W, YLR412W, DUR1,2, RPS4A, YAL037W, ICT1, CTR86, RPN10, RME1, MSB4, SAM35, MAG2, YOL092W, PPZ1, YGL138C, YHR097C, SSZ1, SIS1, CTP1, TAF5, PDC1, YPL150W, GCD10, ENP1, TOM40, ERG6, ECM4, RLF2, RKI1, SAM3, SEC62, CRC1, UME1, TUS1, YNL046W, VTC1, TEL2, YEN1, PEX30, GSG1, NTE1, RBG1, TIM8, YNG1, PMT5, PRP16, SPT6, NIP100, THS1, HMRA1, STE20, AIM10, YGL242C, GTR2, YOL157C, LOT6, KEX1, MET14, UBA2, NUT1, SPO21, PAC10, YND1, DSE3, YJR149W, YOR378W, GSY2, YBR063C, SRV2, YCK1, YKL091C, FMS1, UTP23, YCR090C, SFT2, BNI5, SNX3, FSH2, RGD2, SST2, UNG1, YLR164W, RPS26B, TRE1, MSH5, MYO3, YGL039W, SUP35, AMA1, ATP19, YGL036W, PTK2, PBP2, TRM112, SMC1, NPR1, PFK2, PDE1, RRI1, FRE2, YOR118W, FRE1, ECM38, ALD3, STT3, VMR1, RPC82, URK1, ATX1, REG1, PNT1, YMR279G, RSC8, YJR111C, YLR253W, FSH1, YDR336W, ERD1, VPS41, AYT1, VRG4, YPL009C, VID22, YDR514C, APC11, VPS74, KRE11, RRP6, FOX2, ASM4, MED11, TWF1, GRX5, MYO1, YPL107W, PET54, YLR064W, SPC2, APP1, DBP5, BPH1, YKL151C, NAF1, YKL027W, ARO3, UBX6, TIM18, BNI4, SPC98, PZF1, PIC2, UTP8, YBR235W, SMC6, RLR1, DBF4, RPB11, SHE3, SFB3, SYT1, STU2, NGL2, GDS1, NOP2, SVS1, PRY2, GDA1, BCY1, PUS1, COX7, MRPL15, RER1, SLH1, RPB3, TIF11, YDL173W, YML053C, PEX4, MIG1, CLU1, ECM32, FCY1, HSP32, MAL12, JLP2, DAT1, RMR1, KTR6, OST2, NOP12, IRC3, OPT2, YBL054W, PDX1, AMS1, YBR204C, SLM2, VPS64, PTH2, MRP1, TIF5, AAT2, CPR3, AVT6, CLF1, MDM38, COX12, ESS1, RPG1, SNF11, ERV15, YPR078C, RHO3, SUE1, CLN2, YFL040W, YLR040C, RLA1, YMR272W-B, MND2, EHD3, IMP4, PAH1, HMO1, RPL26A, PIR3, MNN5, FCY22, SMD3, YER186C, QDR2, MHP1, CRH1, LSB3, RMD1, SDA1, AXL2, NOP16, YCL058W-A, ORC6, PRR2, STH1, CCA1, FUS1, MRS6, YBP1, RPL12A, UTR4, MTF2, MAK31, BOP2, UIP5, SSL1, INO4, RPT3, YBR072C-A, YHR159W, ITR2, PUF3, ADD66, GCS1, LYS2, MTR2, TRP1, HXT11, ALG1, SPS18, YOR111W, STI1, SSD1, CRN1, CSN9, RSM22, YIL152W, TOF1, HOM2, MOB1, RAD24, IRC25, RSM23, YLR049C, YBL055C, SPP41, YMR310C, YHC1, YNL040W, AIM41, APL5, ILV2, YIR035C, REC8, MSS51, GAP1, EMP70, HAL1, CDC21, VPS75, YER066W, MCM7, CHZ1, YKL121W, MMS2, BUL2, SEC1, BEM2, YKR018C, NUP2, VPS73, YIL024C, YPL225W, FEN1, YSR3, CST9, YLR241W, MAK10, CUP2, CCP1, ERV14, YJU3, RAP1, IMP1, COA1, TFA1, ATP5, ARG3, RVB1, RPA49, NSE4, YKT6, RRN9, APM2, GAT3, SPN1, CKB1, DTD1, TPO2, PRP45, DEG1, PTC5, TSC10, DPB11, YKR005C, RIM15, PNO1, COX15, VPS4, PKH2, MTR4, YLR053C, LEU4, YPK1, PDX3, TIF2, YDL180W, FYV8, BUD13, YBR139W, TPK2, SSH1, YGR102C, YDR348C, RPL28, QCR2, YAR1, SCP1, TIP20, UBC7, SEC11, RPN11, TGL5, HSP60, RPL42B, PRS1, YKL018C-A, TFC6, RNH201, URA1, ALG9, MSG5, AKR1, MNN11, OCA1, YGP1, PPX1, TSC3, PSF3, YAF9, YMR175W-A, LHP1, YMR252C, SLK19, YJL107W, PMC1, HCR1, SKG1, PCT1, LPE10, PGK1, HAS1, SEC23, GPI13, YDR476C, YLR073C, SUI3, RCO1, LYS20, NUP170, JJJ1, RAD27, YLL032C, GDB1, GON7, PRS4, GAL7, RAI1, MLC1, SWD3, REV1, FET3, DAL7, DAL80, COQ5, TRK2, PRP31, SYP1, RPL36A, OSH7, RPL12B, UME6, LCB4, IZH2, MDH3, OGG1, RPL1A, YGL157W, HUB1, TGL4, CAF16, NPP2, URE2, GMH1, AVT3, FAA1, BET5, YPR091C, PET8, STB1, ERG13, UTP10, MMP1, YTH1, EMI2, MES1, PDS1, NPL3, PRD1, YGR235C, PHO8, PEX22, LAP4, LCB2, YLR326W, EMP46, MRPS17, AIM17, NUP57, YER134C, YCR076C, YBL104C, SSM4, YMR187C, YEF3, PIG1, ECM16, SPO20, ILS1, MFT1, RRP46, RPS23A, ECM40, STT4, SOK2, RPL9A, SIR1, SES1, CDC26, SSU1, SAS3, YKL187C, ARG8, RPL16B, LCB3, TVP18, APJ1, GDH1, IPT1, ATP7, YAR029W, PIS1, TRS23, SEC72, CHA4, DMA2, RUP2, DCP2, KAP114, YTA12, PHO87, TPS3, RPS10B, LIP2, PAF1, MEU1, ALK1, RIM11, SLA2, RSC6, CBC2, YBR016W, FIS1, RAS1, SFA1, YOL057W, YOR292C, MCD4, CSM1, MAK32, DAP2, EXG2, DID2, HXT15, DIE2, VAC8, YBR138C, NTH2, YCR099C, RTT107, MAF1, ERG9, PPN1, SRB4, CDC55, YDR248C, YDR003W-A, GLC8, PDR11, SPB4, YSC83, YLR072W, MCH1, RPH1, DAD3, SPT3, YFR057W, IDI1, TDH3, OCA2, PEX18, FUN30, RRP3, ABC1, IWR1, YJR088C, PTR2, SEC26, AQY1, ECM21, BUD27, PFK26, YDR352W, CUP5, ATG3, AGE2, RIX7, HSE1, AGA1, GRX7, AGE1, TUB2, YHR122W, RIB4, VRP1, LAS1, OCA4, YGR277C, BUB3, LPD1, EMI5, CTF18, YOL073C, SIT1, LYS12, FTR1, TUL1, EKI1, LEO1, GAL1, VAC17, REV7, PMP2, TIM13, YMR158C-A, TLG2, YGR106C, YML079W, YFR045W, YBR056W, YLR065C, HSH49, MTF1, LAG1, ATE1, RFM1, RNH203, DBP8, TPS1, YGR205W, PIM1, RAD16, SPI1, SPP1, CHS5, MNR2, PIL1, SMT3, PEF1, SKO1, CDC45, SUC2, RXT3, RPN9, SPO12, RPE1, SEC15, HMI1, RRP4, ERG25, MUC1, TPT1, OPY2, OSH2, VNX1, PXA2, YSW1, SPR14, OST5, CDC4, RPL38, YDR520C, ARO2, DOM34, SWE1, GTO1, RPL37B, RAD3, MEP2, PKH1, ARL1, ROX3, SFT1, SIM1, CIA1, COX5B, CLN1, MNE1, BRE4, UBX5, DSL1, ACK1, YHR140W, ARG82, SCS22, ADH7, HSC82, ARO80, HED1, MAD1, TRP5, RPN3, SEN54, PTM1, ATG23, GIM4, YDR089W, MON2, PEX32, PUS6, YJL038C, SGN1, PRP39, YNR070W, SPO71, SAE3, MGR2, INP53, TUP1, SHP1, INO80, CDC23, GAB1, PTC1, SKI2, DNF3, YOR389W, AIM14, ATP16, VPS51, NSE3, UTP21, MDE1, ALY1, MNI2, BNS1, ILV1, TPO5, THI21, PEX2, YMR194C-B, SFI1, ESF1, YJL068C, GPI1, ISC10, RPL13A, YDR391C, TVP15, YNL108C, YDR051C, SRP101, SAS4, ARG4, PAN5, PTK1, THI6, YOR019W, GCN5, DID4, TRM11, ABZ2, YHR210C, RPL34B, POL31, RPS4B, COG4, RPS16B, LCB1, ARA2, VPH2, YBT1, HSM3, YBL036C, DAL2, VTC4, RPS21B, YOR131C, ADE13, YKL215C, LSM2, FAR10, MCH2, IMD3, USV1, YAR035C-A, RAM1, SNM1, PNG1, RFC3, ARP2, TOR2, ISC1, CTS1, YSH1, AIM4, BIT2, GVP36, SED1, SPG4, KGD1, NMT1, SSY1, LSC1, NRK1, YLR177W, SCD6, YDR210W, LRP1, URA2, PEX21, MCM5, SSE2, PYC1, GFD1, YNL247W, RAD17, BRE2, CDC48, IES5, RPL23A, PTR3, ATP20, PAU3, CPR6, ARO7, YRO2, HRB1, HSP42, RPS18B, FMP23, ADE6, DER1, PPE1, CUE3, ACF2, QNS1, IOC3, NAM9, YDL144C, ENB1, KTR3, PSD1, HOS1, FCY21, CAJ1, ERP4, LRC2, TFB5, PRM3, CPR7, MET17, SAH1, YGR149W, GAC1, TFC7, RHO5, TIF34, YPT1, MSS4, FLC2, PRE2, YCL068C, GAL80, SPG3, URB1, MGE1, STR2, RPL34A, UIP3, NPP1, FMP24, AIM23, BIO3, PRO2, TMN3, EST3, PHO5, YSP1, TUF1, ORM1, OLA1, NMA1, YMR209C, SEC27, SLA1, YCL012C, SLM1, NOP53, YLR162W-A, PAU13, ALA1, YDL133W, CDC37, HCA4, PRB1, GSY1, YIP3, TMA46, RPP1, PRP3, YBL107C, UBP14, VAM10, CBS1, YOR238W, OM14, SEC66, CST6, SSF2, FRS1, NCA2, HMX1, NOP13, RNR2, QDR3, OTU2, SPO13, HUL5, SED4, RRP42, CDC33, MLP1, GOR1, YDL119C, YJR039W, HNT2, SCM3, MET12, VPS33, MGR1, PCM1, YUH1, CDS1, SAP185, CRT10, SNF1, CMP2, APL6, IDH1, YDR428C, SEC21, APL4, PAP2, GPI17, SCH9, HOP1, MUK1, RPS25B, NOB1, STE23, YLR243W, GRE3, CCS1, VEL1, ENO2, COG6, RPL11B, HNT1, LEM3, GPI15, FSF1, SEC8, SOL2, PRS5, VPS71, ACC1, ADE8, GNA1, YNR024W, RSF2, MAL32, PAU21, SPS19, YIL002W-A, SPF1, CCT8, PRM2, PDH1, RBL2, PIF1, VBA1, AFG1, DIN7, IZH1, YPL105C, YCR051W, WWM1, SIP3, SYS1, HPC2, RPL40A, NCR1, YER078C, CAP1, GCN4, AIM38, PTC7, FUN14, COS8, MCH4, PRP24, CWC2, CLC1, SIR4, FUS3, YLR057W, ZRG17, YSA1, PTC3, UBP6, KAP122, EFT2, URA3, ALG2, POL5, RPL1B, LIP1, TMA20, NAS6, IRC5, KIN3, YPL033C, AVT4, YGR266W, CTI6, YNL050C, SDP1, ESF2, NFS1, YER078W-A, IZH4, CWC22, YGR110W, DYN2, SNF4, YMR178W, NSE5, RPL40B, TKL2, HIR1, RPS30A, HSP12, YDR539W, GCV1, NTG1, AZR1, SPO7, YNL022C, DIM1, VAM6, YNR061C, PDA1, YOR032W-A, SPC3, CSR1, COS9, YJR085C, PEX15, TGL2, SGD1, YPL278C, YIL108W, THP1, SCY1, YGR130C, UBC6, END3, UBP15, RPL35B, MSB2, YCT1, SOL3, YDL027C, KIP3, UTP11, SUB1, PRP19, DCW1, TAH18, YER010C, PIN3, GYP1, SCW10, CTK1, ARK1, FYV10, YCR016W, YDJ1, ARF1, BGL2, YHR100C, CBS2, REX3, TSA1, RNA14, RCE1, THR4, SIP18, PMS1, DSK2, CDC50, DPH5, HEM12, SER3, YML119W, ESC1, GAL11, PRE7, RPT5, ERG2, DSE1, SEC22, YFH7, HSF1, GOS1, WRS1, EXO70, TSA2, ALK2, COX6, KRI1, YGL015C, RPS17B, YDR367W, TOM20, RSP5, YBL086C, TRM44, YPR109W, PTP1, AVT7, CYR1, CIS1, FAL1, VPS28, AGA2, QRI1, ATS1, GIT1, THO1, FBP1, YJL016W, UGA3, YBR230W-A, CCE1, NDE1, SET5, HOT1, RPT1, CAR2, PRE4, ECM33, ECM11, RAD33, BUB2, SOP4, SPR1, MOG1, SPO11, YKR070W, YBR246W, YKL071W, AHP1, PRP42, GRC3, KEL3, YMR244W, YMR242W-A, HBN1, VAS1, RTT102, ZUO1, YGR250C, FRQ1, YCL049C, MCR1, UBP11, TIF35, ATG26, YKL107W, HEM14, THR1, LUG1, SPS100, VMA22, YEL020C, RPL2B, GAL10, FKS1, YPL247C, YEL057C, RPS22A, TRK1, VTC2, SNU114, SWD1, UBC8, YPT52, XDJ1, YJR142W, COQ9, ERV25, YKL075C, FPR4, SEN2, GDT1, NOP7, YOR251C, SRL1, YLL023C, IRA2, IES6, MLF3, DIA1, MTG1, FPR1, NCE102, ERG4, SIF2, NUP53, RPL14A, SEC18, SSB2, RAT1, YMR027W, GDI1, VAN1, KAP123, ICL2, LPX1, RPP2A, SCD5, EXO84, CWC21, TRE2, YGR153W, YCR061W, RAD14, CUL3, VPS53, GEA1, GET3, TAD2, POT1, MVP1, PUS4, SMC2, RFC5, TIF3, NTG2, HXT10, CDC60, ENT5, GAT4, PGU1, UFD4, RPL37A, PRE5, PDC6, GCV3, EGD1, MSC7, KEM1, APN1, APE2, YLR456W, MAK5, YPR172W, STE24, RPS9B, CRM1, STP22, DIA2, ECO1, MCX1, YKL065W-A, NTR2, HHO1, RRM3, PRE8, NYV1, RPC53, TMA23, REC104, ZTA1, TEC1, TUB3, YJL123C, AST2, SNX4, ARC1, SOD1, SMA2, RGD1, PHM8, SEM1, GGA2, YAK1, RGA2, SCS3, YTA7, MDM12, AUR1, SKN7, MDG1, RSM7, YOL038C-A, OSW2, TIR3, RSM28, NIF3, FRE6, MDM20, YNR071C, GDH2, VPS8, MVD1, GCD2, TFP3, FMP33, NUG1, CPR6, SCP160, SEC14, YNL181W, PRE6, YLR364W, HOG1, NUP49, RPL21B, RPL42A, GTT2, STR3, ARG5,6, RPS24A, PPM1, AIM46, ILM1, PEX10, PDS5, YDR042C, YDL218W, MGT1, NPC2, YLR194C, PDI1, XKS1, SIW14, KOG1, PDR15, NGR1, SMX3, FIP1, UGA4, EDC1, YDL086W, GGA1, SMM1, AIM39, UBC1, YGR203W, PRP4, YSF3, SNA3, SKI6, CDC12, VPS60, MSC1, SET1, NMA111, SKI7, KRE5, FOL2, DAL3, SAK1, RVS161, YBR141C, LHS1, YFL051C, YGR067C, NOT5, CKB2, ATG2, YJR112W-A, RKM2, RPL36B, CNB1, PRP43, LCB5, PAC1, ARP3, LRC1, RGR1, YDL157C, DPL1, GCY1, YER076C, TFB3, RPS8B, GAT2, GFD2, MRP8, VAC14, YHR138C, PHO90, PSK2, ALT1, ERP5, LAS21, AIM9, SLZ1, SGM1, FMP27, HXT3, YGR273C, RAM2, RET1, YIR007W, RPS2, MTQ2, RPS23B, COS12, RUB1, RGP1, GYP7, YOL138C, PMT2, YMR130W, SPS4, RAD28, YLR099W-A, YOR285W, MBR1, MPH1, NUP159, SEC63, RPS16A, YPL206C, BCD1, HOT13, IVY1, RNA15, YKR104W, and STE4.

Examples of terminator regions with a relative expression intensity of 0.9 to 1.1 include DNF1, MEH1, AIR2, MSS116, ACB1, ADE12, ELO1, VTA1, MRPL27, YFL054C, SPC34, RGS2, DRS1, GTR1, COX8, KEL2, NUP82, GIR2, FKH2, CLG1, PEX6, HO, YHR003C, NUP84, RRB1, PSY2, BSD2, ESBP6, MED7, RSN1, YKE2, YHL012W, SHE2, RPL2A, DUO1, DST1, PET9, RSA3, GLN4, YKR015C, YJR141W, RIM20, BCK2, SPC42, TRF5, FAA2, TRS130, GUA1, HSL7, PDE2, RRP8, XRS2, SPE1, RFT1, VPS20, SEC20, PAD1, GGC1, ORC1, HMG2, STE2, LSM3, ICS2, TRM2, CDC3, HEM2, SIN4, VIK1, HIS7, RAD54, IQG1, DFG10, TIP1, BRR2, GRX2, HTZ1, BCH2, NRG2, RSC58, TMA16, RAD59, URM1, ADY4, AAP1, ABP1, YGR066C, BRE5, BFR2, LSM1, CHD1, VTI1, AIM11, RFA2, SUR4, YOR228C, DLD3, ISN1, CYC2, SNF5, YMR124W, GIP2, SVL3, SEC13, YEL047C, BEM1, RPL16A, SPR3, ATP4, WAR1, ITR1, FAR3, YOR021C, YBR028C, NOP58, RPN13, YNL035C, YJL049W, YER137C, NOC4, ALG7, MET22, SIL1, TYS1, GLK1, YDR341C, YKR045C, RAD23, BIK1, RPL27A, YOR152C, KNS1, YHR182W, EEB1, RKM1, SNG1, YIL067C, VPS66, TCB1, ADE4, YNL034W, HSP78, HEM15, PKC1, SPP2, MF(ALPHA)1, ARP6, NCS6, RTS3, SPE4, YPL199C, DAL81, SAC1, YOL131W, YHL026C, REC107, YGR174W-A, SGE1, NCB2, YNL320W, CDC20, CSG2, ECM5, NOC2, IES1, SMK1, PHO86, YHR202W, CIN1, PFS1, MCM21, ROT2, GLC7, HRT1, YDR018C, APM1, DPH2, CDH1, HNT3, ATG4, FRE3, ATP2, YMR148W, YAT1, ERG11, PGI1, FKH1, MET30, YGL140C, ARC35, SNX41, SAS2, YHR007C-A, YML083C, ABF1, YLR104W, TOS1, MF(ALPHA)2, FRM2, OPY1, MMF1, DIG1, PMI40, YIL092W, ASI3, FIR1, ERG26, YMR090W, YGL085W, CDC24, YPL113C, YPR010C-A, BIR1, AAH1, EPT1, MSW1, NOP14, CBT1, COX18, COX16, RRD1, BEM4, GEA2, FOB1, ERG7, YLR042C, SEC17, YPR063C, PUT4, MSI1, RPA43, SPE2, DAL1, RPC25, BRO1, AXL1, EAF7, RCR1, YDR338C, RGA1, LOT5, YIH1, RNA1, SKM1, PUT2, HEM4, AIM37, PHO13, YGR015C, AKR2, YKL050C, TCB2, HAC1, ADE1, RTN1, RPL8B, MDM36, JHD1, CCL1, YDR282C, PRE10, PEX14, OMA1, YNR034W-A, NBP2, SPT20, PRP2, YGL041C-B, YBR255W, YOR246C, YFL012W, YLR412W, DUR1,2, RPS4A, YAL037W, ICT1, CTR86, RPN10, RME1, MSB4, SAM35, MAG2, YOL092W, PPZ1, YGL138C, YHR097C, SSZ1, SIS1, CTP1, TAF5, PDC1, YPL150W, GCD10, ENP1, TOM40, ERG6, ECM4, RLF2, RKI1, SAM3, SEC62, CRC1, UME1, TUS1, YNL046W, VTC1, TEL2, YEN1, PEX30, GSG1, NTE1, RBG1, TIM8, YNG1, PMT5, PRP16, SPT6, NIP100, THS1, HMRA1, STE20, AIM10, YGL242C, GTR2, YOL157C, LOT6, KEX1, MET14, UBA2, NUT1, SPO21, PAC10, YND1, DSE3, YJR149W, YOR378W, GSY2, YBR063C, SRV2, YCK1, YKL091C, FMS1, UTP23, YCR090C, SFT2, BNI5, SNX3, FSH2, RGD2, SST2, UNG1, YLR164W, RPS26B, TRE1, MSH5, MYO3, YGL039W, SUP35, AMA1, ATP19, YGL036W, PTK2, PBP2, TRM112, SMC1, NPR1, PFK2, PDE1, RRI1, FRE2, YOR118W, FRE1, ECM38, ALD3, STT3, VMR1, RPC82, URK1, AIX1, REG1, PNT1, YMR279C, RSC8, YJR111C, YLR253W, FSH1, YDR336W, ERD1, VPS41, AYT1, VRG4, YPL009C, VID22, YDR514C, APC11, VPS74, KRE11, RRP6, FOX2, ASM4, MED11, TWF1, GRX5, MYO1, YPL107W, PET54, YLR064W, SPC2, APP1, DBP5, BPH1, YKL151C, NAF1, YKL027W, ARO3, UBX6, TIM18, BNI4, SPC98, PZF1, PIC2, UTP8, YBR235W, SMC6, RLR1, DBF4, RPB11, SHE3, SFB3, SYT1, STU2, NGL2, GDS1, NOP2, SVS1, PRY2, GDA1, BCY1, PUS1, COX7, MRPL15, RER1, SLH1, RPB3, TIF11, YDL173W, YML053W, PEX4, MIG1, CLU1, ECM32, FCY1, HSP32, MAL12, JLP2, DAT1, RMR1, KTR6, OST2, NOP12, IRC3, OPT2, YBL054W, PDX1, AMS1, YBR204C, SLM2, VPS64, PTH2, MRP1, TIF5, AAT2, CPR3, AVT6, CLF1, MDM38, COX12, ESS1, RPG1, SNF11, ERV15, YPR078C, RHO3, SUE1, CLN2, YFL040W, YLR040C, RLA1, YMR272W-B, MND2, EHD3, IMP4, PAH1, HMO1, RPL26A, PIR3, MNN5, FCY22, SMD3, YER186C, QDR2, MHP1, CRH1, LSB3, RMD1, SDA1, AXL2, NOP16, YCL058W-A, ORC6, PRR2, STH1, CCA1, FUS1, MRS6, YBP1, RPL12A, UTR4, MTF2, MAK31, BOP2, UIP5, SSL1, INO4, RPT3, YBR072C-A, YHR159W, ITR2, PUF3, ADD66, GCS1, LYS2, MTR2, TRP1, HXT11, ALG1, SPS18, YOR111W, STI1, SSD1, CRN1, CSN9, RSM22, YIL152W, TOF1, HOM2, MOB1, RAD24, IRC25, RSM23, YLR049C, YBL055C, SPP41, YMR310C, YHC1, YNL040W, AIM41, APL5, ILV2, YIR035C, REC8, MSS51, GAP1, EMP70, HAL1, CDC21, VPS75, YER066W, MCM7, CHZ1, YKL121W, MMS2, BUL2, SEC1, BEM2, YKR018C, NUP2, VPS73, YIL024C, YPL225W, FEN1, YSR3, CST9, YLR241W, MAK10, CUP2, CCP1, ERV14, YJU3, RAP1, IMP1, COA1, TFA1, FAF1, ATP5, ARG3, RVB1, RPA49, NSE4, YKT6, RRN9, APM2, GAT3, SPN1, CKB1, DTD1, TPO2, PRP45, DEG1, PTC5, TSC10, DPB11, YKR005C, RIM15, PNO1, COX15, VPS4, PKH2, MTR4, YLR053C, LEU4, YPK1, PDX3, TIF2, YDL180W, FYV8, BUD13, YBR139W, TPK2, SSH1, YGR102C, YDR348C, RPL28, QCR2, YAR1, SCP1, TIP20, UBC7, SEC11, RPN11, TGL5, HSP60, RPL42B, PRS1, YKL018C-A, TFC6, RNH201, URA1, ALG9, MSG5, AKR1, MNN11, OCA1, YGP1, PPX1, TSC3, PSF3, YAF9, YMR175W-A, LHP1, YMR252C, SLK19, YJR107W, PMC1, HCR1, SKG1, PCT1, LPE10, PGK1, HAS1, SEC23, GPI13, YDR476C, YLR073C, SUI3, RCO1, LYS20, NUP170, JJJ1, RAD27, YLL032C, GDB1, GON7, PRS4, GAL7, RAI1, MLC1, SWD3, REV1, FET3, DAL7, DAL80, COQ5, TRK2, PRP31, SYP1, RPL36A, OSH7, RPL12B, UME6, LCB4, IZH2, MDH3, OGG1, RPL1A, YGL157W, HUB1, TGL4, CAF16, NPP2, URE2, GMH1, AVT3, FAA1, BET5, YPR091C, PET8, STB1, ERG13, UTP10, MMP1, YTH1, EMI2, MES1, PDS1, NPL3, PRD1, YGR235C, PHO8, PEX22, LAP4, LCB2, YLR326W, EMP46, MRPS17, AIM17, NUP57, YER134C, YCR076C, YBL104C, SSM4, YMR187C, YEF3, PIG1, ECM16, SPO20, ILS1, MFT1, RRP46, RPS23A, ECM40, STT4, SOK2, RPL9A, SIR1, SES1, CDC26, SSU1, SAS3, YKL187C, ARG8, RPL16B, LCB3, TVP18, APJ1, GDH1, IPT1, ATP7, YAR029W, PIS1, TRS23, SEC72, CHA4, DMA2, RUP2, DCP2, KAP114, YTA12, PHO87, TPS3, RPS10B, LIP2, PAF1, MEU1, ALK1, RIM11, SLA2, RSC6, CBC2, YBR016W, FIS1, RAS1, SFA1, YOL057W, YOR292C, MCD4, CSM1, MAK32, DAP2, EXG2, DID2, HXT15, DIE2, VAC8, YBR138C, NTH2, YCR099C, RTT107, MAF1, ERG9, PPN1, SRB4, CDC55, YDR248C, YDR003W-A, GLC8, PDR11, SPB4, YSC83, YLR072W, MCH1, RPH1, DAD3, SPT3, YFR057W, IDI1, TDH3, OCA2, PEX18, FUN30, RRP3, ABC1, IWR1, YJR088C, PTR2, SEC26, AQY1, ECM21, BUD27, PFK26, YDR352W, CUP5, ATG3, AGE2, RIX7, HSE1, AGA1, GRX7, AGE1, TUB2, YHR122W, RIB4, VRP1, LAS1, OCA4, YGR277C, BUB3, LPD1, EMI5, CTF18, YOL073C, SIT1, LYS12, FTR1, TUL1, EKI1, LEO1, GAL1, VAC17, REV7, PMP2, TIM13, YMR158C-A, TLG2, YGR106C, YML079W, YFR045W, YBR056W, YLR065C, HSH49, MTF1, LAG1, ATE1, RFM1, RNH203, DBP8, TPS1, YGR205W, PIM1, RAD16, SPI1, SPP1, CHS5, MNR2, PIL1, SMT3, PEF1, SKO1, CDC45, SUC2, RXT3, RPN9, SPO12, RPE1, SEC15, HMI1, RRP4, ERG25, MUC1, TPT1, OPY2, OSH2, VNX1, PXA2, YSW1, SRP14, OST5, CDC4, RPL38, YDR520C, ARO2, DOM34, SWE1, GTO1, RPL37B, RAD3, MEP2, PKH1, ARL1, ROX3, SFT1, SIM1, CIA1, COX5B, CLN1, MNE1, BRE4, UBX5, DSL1, ACK1, YHR140W, ARG82, SCS22, ADH7, HSC82, ARO80, HED1, MAD1, TRP5, RPN3, SEN54, PTM1, ATG23, GIM4, YDR089W, MON2, PEX32, PUS6, YJL038C, SGN1, PRP39, YNR070W, SPO71, SAE3, MGR2, INP53, TUP1, SHP1, INO80, CDC23, GAB1, PTC1, SKI2, DNF3, YOR389W, AIM14, ATP16, VPS51, NSE3, UTP21, MDE1, ALY1, MNI2, BNS1, ILV1, TPO5, THI21, PEX2, YMR194C-B, SFI1, ESF1, YJL068C, GPI1, ISC10, RPL13A, YDR391C, TVP15, YNL108C, YDR051C, SRP101, SAS4, ARG4, PAN5, PTK1, THI6, YOR019W, GCN5, DID4, TRM11, ABZ2, YHR210C, RPL34B, POL31, RPS4B, COG4, RPS16B, LCB1, ARA2, VPH2, YBT1, HSM3, YBL036C, DAL2, VTC4, RPS21B, YOR131C, ADE13, YKL215C, LSM2, FAR10, MCH2, IMD3, USV1, YAR035C-A, RAM1, SNM1, PNG1, RFC3, ARP2, TOR2, ISC1, CTS1, YSH1, AIM4, BIT2, GVP36, SED1, SPG4, KGD1, NMT1, SSY1, LSC1, NRK1, YLR177W, SCD6, YDR210W, LRP1, URA2, PEX21, MCM5, SSE2, PYC2, GFD1, YNL247W, RAD17, BRE2, CDC48, IES5, RPL23A, PTR3, ATP20, PAU3, CPR6, ARO7, YRO2, HRB1, HSP42, RPS18B, FMP23, ADE6, DER1, PPE1, CUE3, ACF2, QNS1, IOC3, NAM9, YDL144C, ENB1, KTR3, PSD1, HOS1, FCY21, CAJ1, ERP4, LRC2, TFB5, PRM3, CPR7, MET17, SAH1, YGR149W, GAC1, TFC7, RHO5, TIF34, YPT1, MSS4, FLC2, PRE2, YCL068C, GAL80, SPG3, URB1, MGE1, STR2, RPL34A, UIP3, NPP1, FMP24, AIM23, BIO3, PRO2, TMN3, EST3, PHO5, YSP1, TUF1, ORM1, OLA1, NMA1, YMR209C, SEC27, SLA1, YCL012C, SLM1, NOP53, YLR162W-A, PAU13, ALA1, YDL133W, CDC37, HCA4, PRB1, GSY1, YIP3, TMA46, RPP1, PRP3, YBL107C, UBP14, VAM10, CBS1, YOR238W, OM14, SEC66, CST6, SSF2, FRS1, NCA2, HMX1, NOP13, RNR2, QDR3, OTU2, SPO13, HUL5, SED4, RRP42, CDC33, MLP1, GOR1, YDL119C, YJR039W, HNT2, SCM3, MET12, VPS33, MGR1, PCM1, YUH1, CDS1, SAP185, CRT10, SNF1, CMP2, APL6, IDH1, YDR428C, SEC21, APL4, PAP2, GPI17, SCH9, HOP1, MUK1, RPS25B, NOB1, STE23, YLR243W, GRE3, CCS1, VEL1, ENO2, COG6, RPL11B, HNT1, LEM3, GPI15, FSF1, SEC8, SOL2, PRS5, VPS71, ACC1, ADE8, GNA1, YNR024W, RSF2, MAL32, PAU21, SPS19, YIL002W-A, SPF1, CCT8, PRM2, PDH1, RBL2, PIF1, VBA1, AFG1, DIN7, IZH1, YPL105C, YCR051W, WWM1, SIP3, SYS1, HPC2, RPL40A, NCR1, YER078C, CAP1, GCN4, AIM38, PTC7, FUN14, COS8, MCH4, PRP24, CWC2, CLC1, SIR4, FUS3, YLR057W, ZRG17, YSA1, PTC3, UBP6, KAP122, EFT2, URA3, ALG2, POL5, RPL1B, LIP1, TMA20, NAS6, IRC5, KIN3, YPL033C, AVT4, YGR266W, CTI6, YNL050C, SDP1, ESF2, NFS1, YER078W-A, IZH4, CWC22, YGR110W, DYN2, SNF4, YMR178W, NSE5, RPL40B, TKL2, HIR1, RPS30A, HSP12, YDR539W, GCV1, NTG1, AZR1, SPO7, YNL022C, DIM1, VAM6, YNR061C, PDA1, YOR032W-A, SPC3, CSR1, COS9, YJR085C, PEX15, TGL2, SGD1, YPL278C, YIL108W, THP1, SCY1, YGR130C, UBC6, END3, UBP15, RPL35B, and MSB2.

In this production method, the expression levels of two or more arbitrary genes can be regulated individually by using two or more corresponding terminator regions for expressing the two or more arbitrary genes. In the case of exogenous genes for example, the expression levels of multiple exogenous genes can be controlled easily and precisely by using promoters with the same or different outputs.

To cause expression of arbitrary genes with such terminator regions, a vector can be constructed having DNA (a gene) coding for an arbitrary protein under the control of a promoter that functions in a yeast, and also having DNA comprising a terminator region disposed so as to transcriptionally control the gene, known yeast transformation techniques can then be used to obtain a recombinant yeast carrying this DNA, and this yeast can then be cultured.

The type of gene is not specified, and any gene may be used. For example, in the case of biomass including cellulose decomposition to produce a decomposition product that is used as is by a yeast for fermentation, the gene may be a cellobiohydrolase, endoglucanase or other cellulase gene, or a gene for a hemicellulase that decomposes hemicellulose. Other examples include genes for beta-glucosidase, xylose isomerase, and various other enzymes suited to using biomass including cellulose decomposition products. Other examples include enzymes for producing useful substances that may be industrial raw materials and the like by yeast fermentation. Scaffolding proteins for presenting such cellulases and the like on the yeast surface are also possible. Scaffolding proteins of various cellulose-producing microorganisms are known as scaffolding proteins.

A gene introduced from the outside into a host yeast is considered an exogenous gene even if it was originally intrinsic to the yeast. An exogenous gene may be expressed within a yeast, or may secretorily expressed outside the yeast. The mode of production may be selected as necessary. In the case of secretory expression, necessary gene modifications may be performed by known methods.

Methods of preparing and culturing (fermenting) such recombinant yeasts are well-known to those skilled in the art, and the present production method can be implemented by a person skilled in the art with reference to known techniques. Promoters that function in yeasts can be selected appropriately according to the desired expression intensity. When strong expression intensity is desired, a known high-output promoter such as a TEF1 promoter, ADH1 promoter, TPI1 promoter, HXT7 promoter, TDH3 promoter, PGK1 promoter, PYK1 promoter or the like can be selected appropriately. For induced expression, a GAL1 promoter, GAL10 promoter or other known inducible promoter can be used.

Various known yeasts can be used as host yeasts. For purposes of ethanol fermentation and the like, examples include *Saccharomyces cerevisiae* and other *Saccharomyces* yeasts, *Schizosaccharomyces pombe* and other *Schizosaccharomyces* yeasts, *Candida shehatae* and other *Candida* yeasts, *Pichia stipites* and other *Pichia* yeasts, *Hansenula* yeasts, *Trichosporon* yeasts, *Brettanomyces* yeasts, *Pachysolen* yeasts, *Yamadazyma* yeasts, and *Kluyveromyces marxianus*, *Kluyveromyces lactis* and other *Kluyveromyces* yeasts and the like. Of these, a *Saccharomyces* yeast is preferred from the standpoint of industrial utility and the like, and *Saccharomyces cerevisiae* is especially desirable.

The recombination techniques and recombinant yeasts disclosed in the present Description as explained above can be achieved in accordance with the methods described in Molecular Cloning, 3rd Edition and Current Protocols in Molecular Biology and the like. Various well-known conventional methods can also be used for transformation, such as transformation methods, transfection methods, conjugation methods, protoplast methods, electroporation methods, lipofection methods, lithium acetate methods and the like, which are similarly well-known to those skilled in the art.

(Regulator of Expression in a Yeast)

The regulator of expression in a yeast of the present teaching may include a yeast gene terminator region having the aforementioned expression intensity data. This expression regulator can enhance or suppress the expression output of an arbitrary gene when incorporated and used in an expression cassette, expression vector or the like. Suitable terminator regions for use in this expression regulator were explained above, and can be selected based on the aforementioned expression intensity data.

(Cassette for Gene Expression in Yeast)

The yeast expression cassette of the present teaching is provided with a promoter that functions in a yeast and the expression regulator of the present teaching, disposed downstream from this promoter. The expression cassette may also be provided with a multicloning site or other insertion site for introducing an exogenous gene that can be controlled by a promoter and the expression regulator of the present teaching. Moreover, this gene expression cassette may also be provided in advance with a suitable exogenous gene. Promoters and exogenous genes that can be used in this gene expression cassette were described above, and can be selected appropriately based on known techniques.

(Recombinant Yeast)

The recombinant yeast of the present teaching may be provided with a promoter that functions in the yeast, an exogenous gene controlled by this promoter, and the expression regulator of the present teaching disposed downstream from the exogenous gene. The exogenous gene is provided in such a way that it can be transcriptionally controlled by the expression regulator of the present teaching. Promoters and genes that can be used in the recombinant yeast are described above, and can be selected appropriately based on known techniques.

A recombinant yeast in which the expression intensity of one or two or more kinds of genes selected from the endogenous genes and exogenous genes has been modified using the terminator regions of one or two or more kinds of yeast genes each selected from the previously-described yeast genes with high expression intensity and yeast genes with low expression intensity is also provided as a recombinant yeast. The expression of another gene can also be regulated using the terminator region of a yeast gene with moderate expression intensity as described above.

(Method for Screening Regulators of Expression in Yeast)

The method of screening regulators of expression in a yeast of the present teaching comprises a step of evaluating the amount of an arbitrary protein produced by a recombinant yeast carrying DNA comprising a promoter that functions in the yeast, a coding region coding for the protein and a terminator region from a yeast gene, and a step of evaluating the expression intensity of the terminator region based on the amount of the protein.

Terminator regions suitable for regulating the expression of an arbitrary gene in a yeast can be screened by this method. Conventionally, it was not clear that terminator regions had this kind of expression regulating ability. With this screening method it is possible to provide a new means for regulating expression systems in a yeast, thereby facilitating more precise expression regulation of genes in a yeasts.

In the screening process, terminator regions in yeasts are obtained, recombinant yeasts are obtained each having introduced DNA comprising a promoter that functions in the yeast, one of the obtained terminator regions and a coding region encoding an arbitrary protein, which is disposed so that it can be expressed, and the amount of the protein obtained by the operation of the promoter and terminator region under fixed conditions is evaluated. The promoter is preferably one that is common to the terminator regions being evaluated. The arbitrary protein is also preferably one that is common to the terminator regions being evaluated. A protein the amount of which can be easily evaluated, such as GFP or another fluorescent protein, is preferably adopted as the arbitrary protein. The recombinant yeast is prepared and the terminator regions are obtained as explained above. Known conditions may be adopted for culturing the recombinant yeast when evaluating the amount of the protein.

Next, the expression intensity of the terminator regions is evaluated based on the amounts of the proteins produced by the recombinant yeasts. In the evaluation, the amount of the protein can be compared with the amount of protein produced under the same conditions using a terminator region for comparison, such as a known terminator region for example. When the protein is a fluorescent protein, relative intensity in comparison with a known terminator region or the like can be obtained by an evaluation using fluorescence intensity obtained with a fluorescence measurement device. The expression intensity of multiple terminator regions can also be compared by evaluating the amounts of proteins produced under identical conditions.

Expression of an exogenous gene with the desired intensity can be achieved by obtaining such terminator regions with various expression intensities. More precise expression regulation is facilitated by providing terminator regions as a new means for regulating output in an expression system.

(Method for Regulating Expression Intensity of Gene in a Yeast)

The disclosures of this Description provide a method for regulating the expression intensity of a gene in a yeast, whereby the expression intensity of one or two or more kinds of genes selected from the endogenous genes and exogenous genes is regulated by using the terminator regions of one or two or more kinds of yeast genes selected from yeast genes with high expression intensity and yeast genes with low expression intensity. This regulation method facilitates regulation of an arbitrary gene, such as raising or lowering the expression intensity of the gene. The expression intensity of an arbitrary gene can be regulated more easily and precisely by applying a new means of regulating gene expression, in addition to the type of promoter, the number of gene copies and the like. Yeast genes with high expression intensity and yeast genes with low expression intensity were explained above.

Moreover, the expression intensity of other endogenous genes and exogenous genes can also be regulated by using the terminator region of a yeast gene with moderate expression intensity as described above.

(Drug Screening Method Using Yeast)

The disclosures of this Description provide a method comprising a step of using the terminator regions of one or two or more kinds of yeast genes selected from yeast genes with high expression intensity and yeast genes with low expression intensity to obtain one or two or more kinds of recombinant yeasts in which the expression intensity of one or two or more kinds of genes selected from the endogenous genes and exogenous genes associated with a drug has been modified, and a step of using the one or two or more kinds of recombinant genes to screen that drug. With this screening method, drugs can be screened efficiently because it is possible to use a yeast in which the expression intensity of an arbitrary gene is regulated. Moreover, because the expression intensity of the arbitrary gene is regulated, it is possible to evaluate the relationship between the expression intensity or expression product quantity of this gene and the effect of the drug or the like.

EXAMPLE

The present teachings is not limited by these examples. The genetic recombination operations discussed below were performed in accordance with the published Molecular Cloning or the like.

Example 1

Preparation of Transformation Vector

In this example, a vector was prepared for causing expression of an exogenous gene using an arbitrary terminator in a yeast as shown in FIG. 1.

The vector prepared in this example was a CEN-type shuttle vector having at least one selection marker, one or two copies of which are carried in the yeast cell. That is, a TDH3 promoter having SacI sites added to both ends and a yeast codon-optimized GFP gene having KpnI sites added to both ends were cloned in that order between the SacI site and KpnI site of Takara Bio pAUR112.

Example 2

Design of Primers for Terminator Sequence Amplification

In this example, PCR primers were designed capable of amplifying the respective terminator regions of about 5295 genes selected from a yeast, and these primers were used to amplify terminator sequences from a genome. Using the public PCR primer design software Primer3 (primer3.sourceforge.net), forward primers and reverse primers for amplifying roughly 300 to 700 bp terminator regions downstream from the ORF of each gene were designed based on published yeast genome data available by ftp at ncbi/nih.gov/genomes/Fungi/*Saccharomyces_cerevisiae*_uid128. The nucleotide sequences of the designed primers are shown by SEQ ID NOS:1-10590.

In each terminator-specific primer, 5'-GAATTG-TATAACTGAGGTACC-3' (SEQ ID NO:15886) was added to the 5' end of the forward primer and 5'-ATCAGTTAT-TACCCGGGTACC-3' (SEQ ID NO:15887) to the 5' end of the reverse primer as sequences for annealing with the 2nd PCR primers used in amplification, to ultimately synthesize 1st PCR primers. (Operon Biotechnologies, Inc.).

Example 3

Amplification of Terminator Sites from Yeast Genome

In this example, the respective terminator sites were amplified by a gene amplification reaction from a yeast genome using the primers prepared in Example 2. That is, genome DNA was extracted from the wild yeast W303-1a strain, and used as the template in a PCR reaction using PRIMESTAR®HS DNA Polymerase (Takara Bio Inc.).

The PCR reaction was performed under the following conditions using the terminator-specific 1st PCR primers on a 96-well plate with 10 μl per well. 10 seconds at 98° C. was followed by 35 cycles of a cycle of 10 seconds at 98° C., 15 seconds at 55° C. and 15 seconds at 72° C. The samples at the four corner of the 96-well plate were electrophoresed to confirm amplification.

Using 1 μl of the 1st PCR reaction solution diluted to 1/200 as the template, 2nd PCR was performed with 10 μl per well. DNA with the following nucleotide sequences was used as the forward primer and reverse primer for 2nd PCR.

```
Forward primer:
                                      (SEQ ID NO: 15888)
5'-CCGCTGCTGGCATTACCCATGGTATGGATGAATTGTATAACTG
AGGTAC-3'

Reverse primer:
                                      (SEQ ID NO: 15889)
5'-CTCACAAATTAGAGCTTCAATTTAATTATATCAGTTATTACCC
GGGTAC-3'
```

The PCR reaction was performed under the following conditions. 15 seconds at 98° C. was followed by 30 cycles of a cycle of 10 seconds at 98° C., 15 seconds at 61° C. and 15 seconds at 72° C. The samples at the four corner of the 96-well plate were electrophoresed to confirm amplification. The 96-well plate was dried with a vacuum pump, and stored at 4° C.

Example 4

In this example, each terminator site was cloned to a yeast by the gap repair cloning method.

Because homologous recombination occurs and DNA fragments can be linked in the cells of budding yeasts if there are homologous regions of roughly tens of bp, (Ma H, Kunes S, Schatz P J, Botstein D, *Gene,* 58, 201-216 (1987)), the PCR amplified vector fragments were cleaved with a restriction enzyme, mixed, and transformed into a yeast using the aforementioned vector homologous parts of the 2nd PCR primers, and the terminator sites were cloned downstream from the GFP gene.

A wild strain of yeast (W303-1a) was cultured in YPD liquid medium, and then treated with a FROZEN-EZ YEAST TRANSFORMATION II KIT™ (Zymo Research) to prepare competent cells. The aforementioned transformation vector was cleaved with KpnI, and 40 ng of the cleaved vector and 10 μl of competent cells per sample were added to the 2nd PCR product dried on the 96-well plate, and mixed well at room temperature.

Transformation was performed for 45 minutes at room temperature, and the transformation solution was added to 1 ml of uracil-deficient medium (2% glucose, 0.67% Yeast Nitrogen base w/o amino acids (Difco Laboratories, Inc.), 0.082% Complete Supplement Mixture (CSM)+40Ade (For-Medium Ltd.)), and then added to a 96 deep well plate and shaking cultured for 60 hours at 30° C., 160 rpm with a Bioshaker (TAITEC CORPORATION).

Example 5

In this example, terminator activity was evaluated by evaluating the GFP protein produced by the yeasts prepared in Example 4 by flow cytometry (FCM).

The fluorescence of the GFP protein inside the yeast cells was excited with a 488 nm laser using a 510/10 filter set in a CELL LAB QUANTA™ SC MPL flow cytometer (Beckman-Coulter Inc.). About 5300 individual fluorescence intensities were measured in transformed yeasts each having a different terminator.

The average value of fluorescence intensity was determined with IgorPro ver. 6.1 (WaveMetrics) based on the measured values of fluorescence intensity, and standardized using 1 as the value for the commonly-used PGK1 terminator. The standard deviation was determined for the 5295 terminators for which activity could be measured, as shown in FIG. 2. The average values for fluorescence activity were converted to relative expression intensity, and given as follows.

ORC4(0.030), ICY2(0.044), GIC1(0.047), HLR1(0.053), ECM13(0.057), YLR108C(0.060), AQR1(0.064), YHR213W-A(0.065), SUT1(0.068), PLB3(0.070), AIM26 (0.072), TPO4(0.073), YPR153W(0.073), GIS3(0.073), WSC3(0.079), FUR4(0.079), DLT1(0.080), MOT1(0.080), YNR063W(0.081), MET13(0.081), YDL156W(0.082), YJL107C(0.082), YJR154W(0.082), YNL042W-B(0.082), VHS1(0.083), GPI19(0.084), YIL057C(0.084), STD1 (0.085), CTF19(0.088), RAD34(0.088), YIR021W-A (0.088), FZF1(0.089), YHK8(0.089), YGL188C-A(0.089), HCM1(0.090), CDC6(0.090), YPR157W(0.091), CLB6 (0.091), YOX1(0.091), YLR285C-A(0.091), YDR114C (0.092), YHR199C-A(0.092), MPS3(0.092), MUP3(0.093), YIR014W(0.094), AAR2(0.094), YPT35(0.094), AIM33 (0.095), SCW11(0.095), BDF1(0.095), YCL042W(0.096), BSC4(0.096), YGL193C(0.096), NUT2(0.097), YJL118W (0.098), YKL069W(0.099), SRB8(0.099), YOR060C (0.099), MDH2(0.099), YPR116W(0.100), YPK2(0.101), GLN3(0.101), YDL211C(0.101), RAD55(0.102), CYM1 (0.102), ENT4(0.102), ULA1(0.103), YMR182W-A(0.104), YKR017C(0.104), YOR302W(0.106), YOR072W-B (0.107), VTS1(0.107), FYV12(0.107), YGL235W(0.108), YHR086W-A(0.108), YEL067C(0.109), YPL257W(0.109), UBA3(0.109), YMR105W-A(0.109), YOR316C-A(0.110), TMA10(0.110), YDL159W-A(0.112), ATG29(0.113), YML037C(0.113), NSL1(0.113), YJL077W-B(0.113), POP3(0.113), WHI5(0.113), MIH1(0.114), YGR240C-A (0.115), YRM1(0.115), KAR9(0.115), YJU2(0.116), SPC24 (0.116), DPB2(0.117), CHL4(0.117), YMR087W(0.118), CSI1(0.118), YIL134C-A(0.118), BUR2(0.118), PTH1 (0.119), SSN8(0.119), AUA1(0.119), YLR154C-G(0.120), YLR342W-A(0.120), YCL001W-A(0.120), FLC1(0.121), YLL006W-A(0.121), VAM7(0.121), YPL077C(0.121), CCZ1(0.123), PRP28(0.123), ACM1(0.123), IME4(0.123), YPR096C(0.123), FRE5(0.124), PDR8(0.125), ILV5 (0.125), YIL161W(0.126), PAC11(0.126), UBR2(0.126),

YRB2(0.128), YLR125W(0.128), YMR253C(0.128), DSE4(0.128), EPL1(0.128), SNP1(0.128), YMR160W(0.128), SPO77(0.129), BUB1(0.129), YFR016C(0.129), SPC97(0.130), GEM1(0.130), INO2(0.130), SPT10(0.130), YLR132C(0.131), AIM45(0.131), YJR054W(0.132), MBF1(0.132), YAL064C-A(0.132), YML054C-A(0.132), NUP1(0.132), ECM27(0.132), YIL060W(0.133), IRE1(0.133), YHR177W(0.134), YJR079W(0.134), YNL187W(0.136), YML003W(0.136), PIH1(0.136), YDR169C-A(0.136), PET111(0.137), YDL109C(0.137), YOR012W(0.138), YHR050W-A(0.138), TAR1(0.139), RIM9(0.139), YCR095W-A(0.140), RPR2(0.140), COS7(0.140), YDR049W(0.142), CUS1(0.142), JJJ3(0.142), COS10(0.143), MET1(0.144), HXT8(0.145), GLY1(0.146), SUR1(0.146), RTG1(0.147), PHM7(0.147), YJL052C-A(0.147), HXT17(0.147), YFL052W(0.148), ATG1(0.148), ECM2(0.148), YNR075C-A(0.148), YKR041W(0.149), ALD5(0.149), YHL018W(0.149), LUC7(0.149), YPS5(0.149), YLR297W(0.150), SNA4(0.150), BIO4(0.150), YBR298C-A(0.150), ECM12(0.152), SEF1(0.152), YMR247W-A(0.152), EXO1(0.153), CTF13(0.154), HUR1(0.154), SNO3(0.154), BSC5(0.154), YER175W-A(0.155), PGA1(0.155), YLR173W(0.156), YDR119W-A(0.157), IRC15(0.157), MGA1(0.157), YPR174C(0.159), IML3(0.159), YLL054C(0.159), RDS1(0.159), MDM32(0.160), PET494(0.160), YPR036W-A(0.160), GTB1(0.160), ISF1(0.161), KRE29(0.161), SAP190(0.161), YHR214C-E(0.162), GTO3(0.163), YOR365C(0.163), MIP1(0.163), SIP5(0.164), YPL191C(0.164), YPL162C(0.164), YMR291W(0.165), BRN1(0.166), MDM1(0.166), NAT4(0.166), YLR406C-A(0.166), YME1(0.166), CSI2(0.166), YOR008C-A(0.167), CEF1(0.169), BUD25(0.169), DFG16(0.170), GPB1(0.170), KAR1(0.170), PPM2(0.171), DSS1(0.171), RPC37(0.172), VID24(0.172), ERV41(0.172), YGR169C-A(0.172), ECM8(0.173), YHR032W(0.173), ELA1(0.173), PEX29(0.173), LTE1(0.173), HAT2(0.174), SLI1(0.174), MUP1(0.175), ALG13(0.176), FRE7(0.176), YMR147W(0.177), ISU2(0.177), YOR1(0.178), JID1(0.179), ECM3(0.179), ATG5(0.179), MED6(0.180), YPL014W(0.180), YLR030W(0.180), AQY2(0.180), CCT2(0.180), YER067W(0.181), NRG1(0.181), SPT8(0.181), PIR1(0.181), YGR068C(0.182), YER039C-A(0.182), ELM1(0.182), ASE1(0.182), YBL095W(0.183), YNR066C(0.183), MTL1(0.183), CNE1(0.183), CAX4(0.183), NDI1(0.184), FLX1(0.184), YNL130C-A(0.184), CWC25(0.186), YNL254C(0.186), CDC13(0.186), ATP10(0.187), OCT1(0.187), ALF1(0.187), YEF1(0.187), BAP2(0.187), HTL1(0.188), PDC5(0.189), PKP1(0.190), SSK2(0.191), CAF120(0.192), SKN1(0.192), HHF1(0.193), CDC39(0.194), YFR012W(0.194), YEL048C(0.194), HAP4(0.195), PEX7(0.195), TPO1(0.196), NFT1(0.196), NGL3(0.198), YMR206W(0.199), DUS3(0.200), YAP7(0.200), CUS2(0.201), YLR415C(0.201), FUI1(0.202), SLM5(0.203), BTT1(0.203), YFR035C(0.203), RRN10(0.203), HAP3(0.204), SSY5(0.204), SFL1(0.204), KIP1(0.205), CDC15(0.206), GLT1(0.207), DOC1(0.208), MND1(0.209), AAC1(0.209), CEP3(0.209), UBC5(0.209), YNL213C(0.209), CLN3(0.210), CSF1(0.210), ECM18(0.210), MRS4(0.210), YIL046W-A(0.211), INP1(0.211), RTT105(0.211), MPT5(0.211), ATG15(0.212), RNH202(0.212), TAX4(0.213), IZH3(0.213), BDF2(0.214), COX14(0.214), YIP4(0.214), YJR120W(0.214), SAE2(0.215), YMC2(0.216), YGR035C(0.216), NDD1(0.216), HPA2(0.216), STL1(0.216), GPM3(0.216), ERF2(0.217), MMS21(0.217), YJL133C-A(0.218), YNL024C(0.218), IFH1(0.219), LIN1(0.220), ICS3(0.220), YNR014W(0.220), SPB1(0.220), YNL211C(0.221), SOL1(0.221), COS111(0.221), HSH155(0.221), NKP2(0.221), NAB3(0.221), FMT1(0.222), YPL152W-A(0.222), BOR1(0.222), SPC25(0.222), MMS1(0.222), YIL166C(0.223), MAL13(0.223), BFA1(0.223), AEP3(0.224), MTH1(0.225), YGR031W(0.225), BIT61(0.227), YMR230W-A(0.227), SKT5(0.227), YGL258W-A(0.227), PHR1(0.227), HTB2(0.228), SER1(0.229), BAP3(0.230), YER053C-A(0.230), ATG16(0.231), BIO2(0.231), MEP3(0.232), YNR073C(0.232), PCH2(0.232), APS2(0.232), MDM30(0.233), CLB5(0.233), ISR1(0.234), MRP20(0.234), GUD1(0.235), MED1(0.235), RER2(0.236), MCM10(0.236), YIR018C-A(0.236), SPO14(0.236), NUC1(0.237), MNN4(0.237), IFM1(0.237), YLR412C-A(0.237), ALT2(0.237), NNF1(0.238), YKL096C-B(0.239), RAD51(0.239), CIT2(0.239), SPT4(0.239), LRC4(0.240), USE1(0.240), YLR455W(0.241), YOL164W-A(0.241), PRP18(0.242), COA2(0.242), HSP82(0.243), YER184C(0.244), DAD2(0.246), LEU1(0.247), YDL129W(0.247), YPL119C-A(0.248), YOR034C-A(0.249), PRP38(0.249), MSA1(0.250), YBR147W(0.250), BBP1(0.250), MLH1(0.250), SWC3(0.251), SOH1(0.251), HHF2(0.251), NIP1(0.251), MSL1(0.251), RIF2(0.252), SPG1(0.252), WHI3(0.253), HTA1(0.253), ARR3(0.253), YIL077C(0.253), SGF29(0.254), RAD53(0.255), YEL073C(0.257), YNR065C(0.258), NCA3(0.258), YBR296C-A(0.259), ECM23(0.259), YLR225C(0.259), SLD3(0.259), YBR197C(0.259), YBL059W(0.260), YOL075C(0.262), DNA2(0.263), SIZ1(0.263), REC114(0.263), MSN1(0.264), RGT2(0.264), CBF1(0.264), YGL176C(0.265), PTP2(0.265), GAL3(0.265), VPS62(0.266), HMS2(0.266), SMF3(0.267), APL1(0.268), SKI3(0.268), MNS1(0.268), YOR214C(0.268), TID3(0.269), KSS1(0.269), YDR194W-A(0.270), UPC2(0.270), ARG80(0.270), MRS2(0.271), ATP23(0.272), YML100W-A(0.272), YGL101W(0.272), STE12(0.272), RPI1(0.273), YDR090C(0.273), YEH1(0.273), UTP13(0.273), AMN1(0.275), YIL089W(0.275), AVL9(0.276), ATO2(0.276), HEM3(0.276), RPA14(0.277), GIP3(0.277), YGR053C(0.278), ALR2(0.278), YAP5(0.278), CDD1(0.279), SLS1(0.279), MET6(0.279), ABM1(0.279), PET20(0.280), CBP1(0.280), RAD10(0.280), SPO22(0.281), PIB1(0.281), EAF3(0.281), YFR032C-B(0.282), ELP2(0.282), YIA6(0.282), PET112(0.282), PAU7(0.283), MEI4(0.283), YEA4(0.283), SGS1(0.284), JEN1(0.284), CLB2(0.284), GIC2(0.284), SWI6(0.284), ULP2(0.286), KIN28(0.286), YKL033W(0.286), CSM4(0.286), YNL095C(0.286), RRN3(0.286), RNR1(0.286), TPO3(0.286), SUP45(0.287), ABP140(0.288), RPS28B(0.289), MRF1(0.289), GLN1(0.290), OPT1(0.291), PHO4(0.291), UBP10(0.291), YOL163W(0.291), MDS3(0.292), OTU1(0.292), GAT1(0.292), HDA3(0.293), MSY1(0.294), GNP1(0.295), YFL041W-A(0.295), YPL141C(0.295), MPH2(0.295), PMA1(0.296), YNL260C(0.296), SKS1(0.296), YDL177C(0.296), SWR1(0.296), RMD5(0.297), RPL9B(0.297), MIC14(0.297), AOS1(0.297), LRG1(0.297), ROX1(0.298), PCL10(0.298), MRPL3(0.298), YER152C(0.298), EAF1(0.298), HTB1(0.298), SPA2(0.299), SSN2(0.299), YJR129C(0.300), ATG8(0.300), RHR2(0.300), TFG2(0.300), YBL100W-C(0.301), CSM2(0.301), EXG1(0.301), STE7(0.301), ADH2(0.302), SNT2(0.302), PML39(0.302), SEC2(0.303), ASI2(0.305), MNT3(0.306), BUR6(0.306), BIO5(0.306), YDR506C(0.306), RDR1(0.307), MRPL33(0.307), YGL159W(0.307), RIM8(0.309), YGR161W-C(0.310), YIG1(0.310), PDR16(0.310), YDR249C(0.311), YDR124W(0.311), HSP30(0.311), SDH2(0.311), YER130C(0.313), FAA3(0.314), BUD22(0.314), TIM22(0.315), CBP6(0.316), ICE2(0.316), SPC110(0.316), AFT2(0.316), NAM2(0.316), YPR071W(0.317), DIP5(0.317),

SDS3(0.317), POP4(0.317), OCA6(0.317), PTC6(0.317), YBR201C-A(0.318), YPR127W(0.318), SEC10(0.318), ASF2(0.318), SLI15(0.319), RRN7(0.320), ORC2(0.320), GUF1(0.320), GPI2(0.323), RPS9A(0.324), RAD6(0.324), PSR2(0.325), RIP1(0.325), GZF3(0.325), CAR1(0.325), YHR151C(0.325), LEU5(0.325), YBR182C-A(0.326), IRC7(0.326), ASG7(0.327), YOR381W-A(0.327), OCA5(0.327), YHR035W(0.328), PET117(0.329), ISD11(0.329), HSP150(0.329), CCC2(0.329), YHR131C(0.329), MRK1(0.330), RXT2(0.330), PPH3(0.330), ODC2(0.331), SHE9(0.331), YCR075W-A(0.331), CYB5(0.332), YDR415C(0.332), LRO1(0.333), SOF1(0.333), YNL162W-A(0.334), PAU14(0.335), MTO1(0.336), YKL061W(0.336), MSS11(0.336), SAN1(0.336), SET2(0.336), YMR1(0.336), PHD1(0.338), YBL071C-B(0.338), MPA43(0.339), SAM37(0.339), AAT1(0.339), ASH1(0.340), UTR2(0.340), CAT8(0.341), SLX8(0.341), HXT2(0.342), COY1(0.342), TAF3(0.342), DSS4(0.342), TOR1(0.342), YMR030W-A(0.343), PAU5(0.343), SFP1(0.343), FHL1(0.344), COX10(0.344), DDR2(0.344), SWM1(0.345), HXT6(0.346), RCR2(0.346), YLR091W(0.346), RMD9(0.346), SHQ1(0.346), YLR346C(0.347), SPT21(0.347), ARE1(0.348), KAP95(0.349), YGR071C(0.349), TRL1(0.350), ECM17(0.350), YML020W(0.350), RPO41(0.351), CFT1(0.351), LRC5(0.352), THI74(0.352), TPN1(0.352), YOR059C(0.352), PRY3(0.352), YEL1(0.352), CNM67(0.353), STB6(0.354), YOR385W(0.354), RRN6(0.354), COP1(0.354), PDR12(0.355), ELG1(0.355), SRP40(0.355), SRM1(0.355), YDR109C(0.356), AIM30(0.356), RPC17(0.356), YJL028W(0.356), YBR071W(0.357), APS1(0.357), KIP2(0.358), ATP22(0.358), PRM6(0.358), BUD31(0.359), IXR1(0.359), NFI1(0.359), YHL015W-A(0.359), VHS3(0.360), YNL295W(0.361), SML1(0.361), SSK1(0.361), YAE1(0.361), RIM2(0.361), YDR246W-A(0.362), YLR445W(0.362), SPT23(0.362), MTG2(0.363), SGF11(0.363), BRL1(0.363), YMR315W(0.364), MRPS28(0.365), ERG5(0.365), UTP30(0.365), MDM35(0.365), ASR1(0.366), YIL102C-A(0.366), USA1(0.366), DOT6(0.368), COX23(0.369), ADH5(0.370), DAN4(0.370), RMA1(0.370), SCT1(0.370), PHO84(0.371), SFG1(0.371), SLX4(0.372), EST1(0.373), YNL190W(0.373), SNL1(0.374), RRP15(0.374), YML082W(0.375), DOT1(0.375), PEX1(0.375), YUR1(0.376), YAP1802(0.376), YDR185C(0.376), GET2(0.376), YPL264C(0.377), YDR065W(0.377), YJL115W(0.378), MAK21(0.378), YER064C(0.378), ATR1(0.378), IDP2(0.378), KCS1(0.379), ZPR1(0.379), ITC1(0.379), OAZ1(0.379), SWC7(0.380), RPL8A(0.380), CAC2(0.380), VTH1(0.382), OCH1(0.382), BUL1(0.382), YNR004W(0.382), LST7(0.382), MRPS8(0.383), TIS11(0.383), NDC1(0.384), TOS8(0.385), ISM1(0.385), MSL5(0.385), FMP43(0.386), YJR098C(0.386), COQ3(0.387), TPC1(0.388), RIM101(0.388), ADR1(0.388), ALD6(0.389), YHR087W(0.389), VPS21(0.389), POG1(0.389), YJR005C-A(0.389), SNT1(0.390), YHR022C(0.390), MEF1(0.390), PUP2(0.391), ERP6(0.391), HHT2(0.392), YGR146C(0.392), OAR1(0.392), YOR129C(0.392), YCR045C(0.392), DBP7(0.393), MUB1(0.393), YPL236C(0.393), RIB2(0.394), YPR084W(0.394), AIM5(0.395), UTR5(0.395), HKR1(0.396), YMR010W(0.397), ALR1(0.398), LRE1(0.399), RPN4(0.399), YLR363W-A(0.399), MGM1(0.399), HTD2(0.399), NAM8(0.399), SED5(0.400), YOR161C-C(0.401), YML018C(0.401), NAB2(0.401), YER140W(0.402), PRM4(0.402), RTR1(0.402), YIR042C(0.402), THI80(0.402), FUN19(0.402), DMR1(0.402), SIP1(0.403), CGR1(0.403), MTR3(0.404), YJL144W(0.404), RIM13(0.404), SAL1(0.405), MET28(0.405), INM1(0.405), VID27(0.405), CDC34(0.406), SRO9(0.406), RRP9(0.406), YOL087C(0.406), MCM22(0.406), YMR111C(0.406), NDJ1(0.407), ATG12(0.407), MSM1(0.408), SRS2(0.408), YBR225W(0.409), YLR063W(0.410), AI1(0.410), CDC36(0.410), ASN1(0.410), MET31(0.410), SSP1(0.410), NGG1(0.410), RBA50(0.411), PUT1(0.412), YPT53(0.412), NMA2(0.412), YBR219C(0.413), CDC40(0.413), SGO1(0.414), YJL047C-A(0.414), RPC31(0.414), INP52(0.414), UGO1(0.414), RAD30(0.415), CLB1(0.415), GLO4(0.415), TPK3(0.416), GIM3(0.416), CDC9(0.417), PEX27(0.417), AIM32(0.417), YGL081W(0.418), DJP1(0.418), HMS1(0.419), JSN1(0.419), UBP12(0.420), RSM25(0.420), UBP5(0.420), GIP1(0.420), PUT3(0.421), CKI1(0.421), FAR7(0.421), LAG2(0.421), DAM1(0.422), PSD2(0.423), HMT1(0.423), COR1(0.423), MMR1(0.424), MRPL39(0.424), CTF8(0.424), AGP2(0.425), PRM7(0.425), HIT1(0.425), HAL9(0.426), GPA2(0.426), TIM44(0.426), TFB1(0.426), ECM19(0.428), MRPL32(0.428), YBR284W(0.428), NAS2(0.429), SBE22(0.429), YOR011W-A(0.430), ORT1(0.430), MRPL25(0.430), QNQ1(0.430), APC4(0.430), TYE7(0.431), YPP1(0.431), MMT1(0.431), MRP10(0.431), MRPS5(0.431), LIP5(0.431), CDC27(0.432), ESC2(0.432), CAN1(0.433), MEC1(0.433), TOP1(0.433), SLM3(0.433), SIP4(0.434), URN1(0.434), YCK3(0.434), USO1(0.434), RSM19(0.434), ASG1(0.434), ISU1(0.435), YHL008C(0.435), YNL313C(0.435), KKQ8(0.436), FCY2(0.436), GPD1(0.436), HHT1(0.437), MDJ2(0.437), SDH1(0.437), SSF1(0.437), PIP2(0.438), STE13(0.438), AZF1(0.438), VPS35(0.438), YGL146C(0.439), TAM41(0.440), MIF2(0.441), YDL118W(0.441), HFM1(0.441), PRR1(0.441), MRE11(0.442), FMP37(0.442), MLH2(0.442), BUD5(0.443), YOR342C(0.443), PCL1(0.443), DHR2(0.444), CDC5(0.444), CBP3(0.444), RLP24(0.444), LSG1(0.444), NCL1(0.444), YDR262W(0.445), PGA3(0.445), MID2(0.445), YJL027C(0.446), YOR305W(0.446), QCR6(0.447), MSC6(0.447), RSC4(0.447), PAU18(0.448), POL12(0.448), SME1(0.448), DBF2(0.448), RPS27A(0.448), NHP6A(0.449), YGK3(0.449), SLO1(0.452), AIM36(0.452), UBP13(0.452), TRI1(0.453), CTH1(0.453), PGS1(0.454), NMD4(0.455), YIL064W(0.455), BAR1(0.456), BCS1(0.456), YBL029W(0.456), CTR1(0.456), MRPL20(0.457), AGP3(0.457), YOR338W(0.457), FCF2(0.457), YOR052C(0.457), YJL147C(0.457), RSA1(0.457), PEX8(0.458), YOL159C(0.459), RRP45(0.459), YDL199C(0.459), LIA1(0.459), THI2(0.459), TRZ1(0.459), CYT2(0.460), MGM101(0.460), YNL277W-A(0.460), ARP8(0.460), MRPL36(0.460), YAR028W(0.460), PAU2(0.461), SLD5(0.462), SMD1(0.462), YNL086W(0.463), QCR7(0.463), FMC1(0.463), HOS4(0.463), HEM1(0.463), NAM7(0.464), YPL108W(0.465), BUD14(0.465), BOI2(0.465), HRD1(0.465), YOL114C(0.466), RIS1(0.466), SIC1(0.467), BST1(0.467), KES1(0.467), MET4(0.467), TRS120(0.467), SYC1(0.468), NPA3(0.469), YLH47(0.469), SRL2(0.469), LRC3(0.469), MHR1(0.470), ZIP2(0.470), EAR1(0.470), RSF1(0.470), RIO2(0.471), MET2(0.471), NOP4(0.471), SRD1(0.471), PWP2(0.472), MST1(0.472), PCK1(0.472), CDC7(0.472), TOK1(0.472), PRO1(0.473), RAX2(0.473), LSM7(0.473), SHG1(0.474), TOM7(0.474), DAS2(0.474), SIP2(0.475), RRS1(0.475), EUG1(0.475), PDX1(0.475), RAD61(0.476), SUN4(0.476), HAA1(0.476), YNR048W(0.477), ACO2(0.477), YOL047C(0.477), PMD1(0.477), FZO1(0.477), YEL025C(0.477), GPR1(0.478), BNI1(0.478), RSA4(0.478), YMR185W(0.478), PAU16(0.479), ECM7(0.479), YHP1(0.479), COG8(0.479), LST8(0.479), HST1(0.479), ESA1(0.480), YJL160C(0.480), MER1(0.480), CIN8(0.480), WSS1(0.481), PAT1(0.481), LRC6(0.482), FMP30(0.482),

LYS21(0.483), MET18(0.483), MRPL50(0.483), GCR1(0.484), YOR022C(0.484), YJR012C(0.484), PDR3(0.485), YPL229W(0.485), SFK1(0.485), DUS4(0.485), IDS2(0.486), YOL036W(0.486), PHM6(0.486), YPR117W(0.486), RPB7(0.486), MCM2(0.487), MRS1(0.487), GLO2(0.487), YKL105C(0.487), RCK1(0.487), AME1(0.488), DIA3(0.488), HOM3(0.488), YDR541C(0.488), PMT6(0.488), DSE2(0.489), YJL216C(0.489), RIO1(0.489), ALB1(0.490), IBA57(0.490), YOR268C(0.490), CWC24(0.491), ARD1(0.491), UTP15(0.491), MSE1(0.491), UBS1(0.491), YNL234W(0.492), YDL025C(0.492), CAF40(0.492), YBR221 W-A(0.493), ATP18(0.493), MAL33(0.493), YPT6(0.493), OAC1(0.493), YJR151W-A(0.493), YML108W(0.494), COX17(0.494), RAD52(0.495), HST3(0.495), TAZ1(0.495), YNR064C(0.495), YGL010W(0.496), MFA2(0.496), PGM3(0.496), NRM1(0.496), CRS5(0.496), CTM1(0.496), SKG6(0.497), SYF2(0.497), HYM1(0.497), IPI3(0.498), MDH1(0.499), TFB2(0.499), HST4(0.499), MRPL24(0.499), YMR166C(0.500), AVT5(0.501), YGR021W(0.501), SUV3(0.501), YNL146W(0.502), MID1(0.502), AKL1(0.503), MTR10(0.503), LAA1(0.503), HDA1(0.504), SMY2(0.504), MRPL8(0.505), PLB2(0.505), CWP1(0.506), ECM14(0.506), ECM1(0.506), GAL2(0.506), FAS1(0.506), KEL1(0.506), SET7(0.506), TSR2(0.507), FET5(0.507), DRE2(0.507), MMS4(0.508), TGS1(0.508), COQ1(0.508), SUR7(0.508), PCL2(0.508), SER2(0.509), YFL034W(0.509), MKK1(0.509), SSA2(0.510), AVO1(0.510), FMP25(0.511), YRR1(0.511), SLX5(0.511), SAF1(0.511), YPL260W(0.511), YKR096W(0.511), UTP14(0.511), PAM18(0.512), WTM1(0.512), STE18(0.512), AIM20(0.512), SYM1(0.512), SIT4(0.513), SSH4(0.513), MEI5(0.513), CYC8(0.514), DSN1(0.514), STB3(0.514), IMD4(0.514), YPL109C(0.514), ECM25(0.514), YMR102C(0.515), YDR306C(0.516), SUL2(0.516), YOL019W(0.516), PAU10(0.516), HNM1(0.516), MRPL1(0.516), CMK1(0.516), YBR196C-A(0.517), YGL226W(0.517), YPR147C(0.517), PGM2(0.519), SLM4(0.519), MSS1(0.520), YER121W(0.520), YDR381C-A(0.520), VPS72(0.520), YJL043W(0.520), PAN6(0.520), YMR086W(0.521), MDN1(0.521), HEH2(0.521), YKE4(0.521), YKL162C(0.522), ZRG8(0.522), HIP1(0.523), YPR145C-A(0.523), YCL056C(0.523), ERG1(0.523), INP54(0.523), MRPS16(0.524), MOD5(0.524), YJL008W(0.524), RMI1(0.524), YNL146C-A(0.525), RRF1(0.525), CAF130(0.525), BUD9(0.526), GWT1(0.526), BEM3(0.527), STF2(0.527), SSN3(0.527), MAS2(0.527), SLN1(0.528), TLG1(0.528), NOP6(0.528), YOR097C(0.528), HVG1(0.528), GCD11(0.528), TDP1(0.528), ATC1(0.529), CIT1(0.529), GRR1(0.529), RPA12(0.530), ADY3(0.530), CTA1(0.530), SWS2(0.530), SNF8(0.530), CIS3(0.530), MRPL4(0.531), CLB4(0.531), DBP2(0.532), APQ12(0.532), UTP5(0.532), MPD1(0.532), MRS3(0.532), AIM43(0.532), ATP11(0.533), SNU66(0.533), ARF3(0.533), YKU80(0.534), YLR422W(0.534), EGT2(0.534), MSP1(0.535), YLR218C(0.535), MRPL44(0.535), YHR127W(0.536), UBP3(0.536), SOD2(0.536), CYT1(0.536), POP6(0.536), HSP10(0.536), YHR033W(0.536), YKL161C(0.538), KIN82(0.538), YNL165W(0.538), CYC7(0.538), FYV7(0.538), TAT1(0.539), YNR040W(0.539), DBP3(0.539), SMY1(0.539), TRP3(0.540), SSL2(0.540), RPS24B(0.540), UTP4(0.540), SAW1(0.540), DAN2(0.541), YPR011C(0.541), YER156C(0.541), YGL059W(0.541), TRM5(0.541), SUT2(0.541), IML2(0.542), ATP1(0.542), CKA1(0.542), ECM31(0.542), MSK1(0.542), SCC2(0.543), SYG1(0.543), RPO26(0.543), YPR114W(0.544), HIR3(0.544), YIL029C(0.544), MAC1(0.545), YOR296W(0.545), IST3(0.546), HOR2(0.546), ITT1(0.547), PRP22(0.547), ROD1(0.548), DIA4(0.548), FMP32(0.548), TOM70(0.548), DIP2(0.548), YPR159C-A(0.549), PSP1(0.549), BTS1(0.549), ECM37(0.550), AST1(0.550), SMP1(0.550), BPL1(0.550), UPS1(0.551), BAG7(0.551), NOG2(0.551), RPC10(0.552), CYB2(0.552), SMD2(0.552), RAD1(0.552), ATP3(0.553), STP2(0.553), BUD21(0.553), RRN5(0.553), YLR352W(0.553), FRE4(0.553), PAN2(0.554), APL3(0.555), SEC7(0.555), DUS1(0.555), CSE1(0.555), MAK3(0.556), MRPL19(0.556), DBP1(0.556), FMP48(0.556), JAC1(0.556), VPS54(0.556), FUR1(0.557), PUP3(0.557), FUN26(0.558), SWI1(0.558), PWP1(0.559), BUD23(0.559), ATF1(0.559), FMP16(0.559), YOL024W(0.560), IPK1(0.560), RLM1(0.560), YNG2(0.560), MSS2(0.561), FLO8(0.561), SHY1(0.561), KSP1(0.561), KNH1(0.562), DON1(0.562), KTI11(0.562), SMC5(0.562), FPS1(0.562), SHU1(0.563), RAV2(0.563), YOR356W(0.563), PFA3(0.564), ERG8(0.564), SEN15(0.565), YNL152W(0.565), YJL193W(0.565), MSH2(0.565), CYC1(0.565), YLR446W(0.566), MRPL13(0.566), ISA1(0.566), HUA1(0.567), YHL010C(0.567), NNT1(0.567), RMD8(0.567), PPR1(0.568), ECM9(0.568), BSC2(0.568), ACO1(0.568), MPS2(0.568), LEE1(0.568), COG5(0.568), MCM1(0.569), RFC1(0.569), TAT2(0.569), DML1(0.569), KRE9(0.570), SPT2(0.571), SPC19(0.571), QCR8(0.571), HXT1(0.572), DOA4(0.572), MSR1(0.572), STU1(0.572), ERG10(0.573), TFB4(0.573), ATG21(0.573), GYP6(0.574), DAD4(0.574), OAF1(0.574), YPR013C(0.574), GAS1(0.574), FAP7(0.575), CPA2(0.575), RPO31(0.575), ATG20(0.575), TEP1(0.575), YBL081W(0.575), SMP3(0.575), MCD1(0.576), ADK2(0.576), SAD1(0.576), HUA2(0.577), BUD2(0.577), YJR136C(0.577), RPS14B(0.578), MNL1(0.578), MDJ1(0.578), FLO10(0.578), REB1(0.578), DSF2(0.579), KHA1(0.580), MRPL35(0.580), YOR283W(0.580), PPG1(0.581), CIT3(0.581), FAA4(0.581), SPL2(0.581), MET8(0.581), HOP2(0.582), HFA1(0.582), HAP5(0.583), ROG1(0.584), MAM3(0.584), DPH1(0.584), RTG3(0.584), YNL195C(0.584), DCN1(0.584), YLR211C(0.585), OXA1(0.585), YET2(0.585), RSC2(0.586), MRPL28(0.586), CTT1(0.586), YAP3(0.586), BIG1(0.587), UBP8(0.587), YOL019W-A(0.587), RIB5(0.587), NOG1(0.588), VID30(0.588), MRP17(0.588), ZRT1(0.588), UAF30(0.588), SPO23(0.589), YNL122C(0.589), SNU71(0.590), CDC43(0.591), SPC29(0.591), DYS1(0.591), PRP11(0.591), SVF1(0.591), BUD20(0.591), MEK1(0.592), UBP16(0.592), PCF11(0.592), GRX4(0.593), UTP22(0.593), HRK1(0.593), RPB9(0.593), YPL272C(0.593), ERG29(0.594), DIS3(0.594), YFH1(0.594), MRM2(0.595), RRP5(0.595), PTI1(0.595), TIF6(0.595), FTH1(0.595), MPE1(0.595), FKS3(0.595), ESP1(0.596), YDL007C-A(0.596), DMC1(0.596), JHD2(0.597), LEU2(0.597), SNF3(0.597), SCJ1(0.597), YMR317W(0.598), CYK3(0.598), GPT2(0.598), FMP41(0.598), SIA1(0.598), HXK1(0.598), YGL057C(0.599), YLR287C(0.599), NSR1(0.599), YDL241W(0.599), RKR1(0.599), REX4(0.600), TIM17(0.600), TES1(0.600), RPO21(0.600), YNL300W(0.601), BSC6(0.601), YHR080C(0.601), OPI10(0.602), RPB8(0.602), UBP9(0.602), YKR011C(0.602), CRP1(0.602), RSM24(0.602), ARP1(0.603), SIK1(0.603), GCR2(0.603), YLR345W(0.603), FET4(0.603), MRPL40(0.605), THP2(0.606), AMD2(0.607), YDR524W-C(0.607), PSY4(0.607), BUD16(0.607), HPT1(0.608), YDR333C(0.608), RHO4(0.609), AHC1(0.609), YIL206C(0.609), SWT1(0.610), HEK2(0.610), ATP12(0.610), XBP1(0.610), RMD6(0.611), RPL15B(0.611), NUP42(0.611), PLC1(0.611), MAD3(0.612), YPS1(0.612), MCM16(0.612), HXT4(0.612), HXK2(0.612), ERG12(0.613), MMT2(0.613), YMR321C(0.613), MUM3(0.613), HST2(0.613),

ROG3(0.613), DEF1(0.615), YLR281C(0.615), SSK22 (0.616), MLH3(0.617), YGR131W(0.617), CSE4(0.617), YCL002C(0.617), MRPS18(0.618), CAD1(0.618), AIF1 (0.618), SFC1(0.618), OYE3(0.619), EAF5(0.619), RSC9 (0.620), GYL1(0.620), YDL063C(0.620), ISA2(0.621), GBP2(0.621), IMG1(0.621), NRP1(0.621), DHH1(0.622), RHB1(0.622), CIK1(0.623), PHO89(0.623), AGX1(0.623), RPB2(0.624), MRPL17(0.624), GPX2(0.625), LYP1 (0.625), VPS9(0.625), BNA3(0.626), CKA2(0.626), OPI1 (0.626), YER034W(0.626), RSM26(0.626), LSM6(0.627), THI3(0.627), SMC4(0.627), SWF1(0.627), YAH1(0.628), RPF2(0.628), HFI1(0.628), PLB1(0.628), MAM33(0.628), YLR413W(0.628), PRP8(0.628), ENO1(0.629), RPC19 (0.629), YGL007C-A(0.629), YMR181C(0.629), URA7 (0.629), YGL108C(0.629), SRB7(0.630), DAD1(0.630), LYS4(0.630), ATG18(0.630), FMP45(0.630), VAM3 (0.630), SSC1(0.631), SNU56(0.631), YHR045W(0.631), HTA2(0.631), YJL213W(0.631), RPL20A(0.632), ALD4 (0.632), QCR10(0.632), YGR287C(0.632), CBP4(0.632), PCI8(0.632), MCM4(0.632), DEM1(0.633), ATO3(0.633), TPS2(0.633), TAF1(0.633), KRE6(0.634), KGD2(0.634), ARB1(0.635), NMD5(0.636), EFR3(0.637), TRP4(0.637), HLJ1(0.638), ACE2(0.638), LDB17(0.638), ATG7(0.639), OSH6(0.639), AFT1(0.639), CTF4(0.639), YDR286C (0.639), AIM44(0.639), YLR149C(0.640), MRPS9(0.640), BET1(0.641), YLF2(0.641), BOI1(0.642), BUD4(0.642), CRF1(0.642), MLP2(0.643), ARX1(0.643), RRP12(0.644), NAT2(0.645), PCL7(0.645), ARP7(0.645), SFH1(0.645), STF1(0.645), YML081W(0.646), MRP49(0.646), FOL3 (0.646), SAC7(0.646), PCS60(0.647), TPA1(0.647), SSS1 (0.647), ERO1(0.647), NHP2(0.648), AIM1(0.648), AMD1 (0.648), VPS38(0.648), COG3(0.648), YMR244C-A (0.648), PYC1(0.648), CCC1(0.648), TAO3(0.649), YDL233W(0.649), RPB10(0.650), YBR242W(0.650), EDC2(0.650), YVC1(0.650), YDR266C(0.651), PMT3 (0.651), NIS1(0.651), YDR128W(0.651), ATP15(0.651), YML002W(0.652), ATG9(0.652), IKS1(0.652), SUR2 (0.652), MSD1(0.652), SMC3(0.653), SPC1(0.653), MRPS35(0.653), ZIP1(0.653), YPR022C(0.654), YKL070W(0.654), RIM4(0.654), YJL127C-B(0.654), ARV1(0.655), YML6(0.655), CYC3(0.656), COX9(0.656), RMD11(0.656), SNU23(0.657), PRS2(0.657), YNL092W (0.657), TIF4632(0.657), CBP2(0.658), STP4(0.658), YIR024C(0.658), SHE1(0.658), EMG1(0.659), NUP192 (0.659), THI7(0.659), NGL1(0.659), LDB19(0.659), AFG2 (0.660), ROT1(0.660), PIK1(0.660), MRPL31(0.660), RHO2(0.660), MRPL49(0.660), FMO1(0.661), LRS4 (0.661), CHS3(0.661), SEC8(0.662), HXT5(0.662), GRX3 (0.663), YHL042W(0.663), AAC3(0.663), WSC4(0.663), PIN2(0.663), PUB1(0.663), ERG28(0.663), PSR1(0.663), ISY1(0.664), VPS70(0.664), IRC19(0.664), DNM1(0.665), RPA190(0.665), CCR4(0.665), SSU72(0.665), MRPL7 (0.665), TBF1(0.666), YPR115W(0.666), SKP2(0.666), CDC73(0.666), RPL31B(0.666), MAK16(0.666), ERB1 (0.666), DCG1(0.666), RNT1(0.667), RRP7(0.667), GCD7 (0.667), RAD18(0.667), OMS1(0.668), YOL048C(0.668), PPT2(0.668), SCS7(0.668), YBL028C(0.668), RSC30 (0.668), TIM23(0.668), PRI1(0.669), REC102(0.669), MCH5(0.669), PST1(0.669), CLB3(0.669), QCR9(0.670), MIR1(0.670), SSP120(0.670), MEF2(0.672), RPL14B (0.672), YPR003C(0.672), RLI1(0.672), SWC4(0.672), MTM1(0.673), SKY1(0.674), TOM1(0.674), YGL079W (0.674), ROM2(0.674), TFA2(0.674), AIM3(0.674), SSQ1 (0.675), DUG1(0.675), MSF1(0.675), RPS0B(0.675), SCO2(0.675), OLE1(0.676), SBE2(0.676), SAR1(0.676), YJR116W(0.676), TEF1(0.677), AIM13(0.677), DFG5 (0.677), YLR012C(0.677), MCM3(0.677), RPS7B(0.678), DFR1(0.678), YBL039W-B(0.678), RML2(0.679), RSM27 (0.679), MEC3(0.679), YCG1(0.679), RFX1(0.680), RPL7B(0.680), CHS2(0.681), PEX5(0.681), TIF4631 (0.681), RPL18B(0.681), SMB1(0.682), HUL4(0.682), NPL6(0.682), YOL107W(0.683), TRM1(0.683), STE6 (0.683), ASK1(0.684), RAD9(0.684), YDL012C(0.684), RBG2(0.684), SEC6(0.684), YLR143W(0.685), XPT1 (0.685), HGH1(0.685), YIL091C(0.685), PRS3(0.686), NTC20(0.686), YPR196W(0.686), MIC17(0.686), POA1 (0.687), NPY1(0.687), SNQ2(0.687), ADE3(0.687), APT2 (0.688), YGL082W(0.688), YHB1(0.689), MRPL16 (0.689), CSH1(0.690), GUP1(0.690), YJL171C(0.690), IDP3(0.690), VHT1(0.691), PUG1(0.691), MPM1(0.691), RRP40(0.691), DPM1(0.691), AFG3(0.691), YBP2(0.691), YPL183W-A(0.692), AIM31(0.692), YCR015C(0.692), MSN4(0.692), YPL038W-A(0.692), TSC11(0.692), SEC59 (0.693), ADA2(0.693), TPM2(0.693), YHR175W-A(0.693), POM152(0.694), YJR124C(0.694), RPL22B(0.694), COG7 (0.694), NEW1(0.695), GSM1(0.695), UGX2(0.696), PRK1(0.696), GPD2(0.696), LDB16(0.697), PAM16 (0.697), CMC1(0.697), TOM6(0.698), MBA1(0.698), SWC5(0.698), PRM10(0.698), SAM1(0.699), TRS31 (0.699), YFT2(0.699), RGT1(0.700), RPL10(0.700), KRE33(0.700), CDC1(0.700), MRPL37(0.700), KEX2 (0.701), VPS13(0.701), ACN9(0.701), RSC3(0.701), PBS2 (0.702), EPS1(0.702), GPI18(0.702), ADH4(0.702), YTP1 (0.702), YHM2(0.703), ZIM17(0.703), LYS5(0.703), AIM22(0.703), RGM1(0.703), ECM10(0.703), RDH54 (0.703), DED1(0.704), CSE2(0.704), POC4(0.704), IPI1 (0.704), SOL4(0.705), YKR075C(0.706), RSM10(0.707), MAE1(0.707), ATF2(0.707), SHE4(0.707), RSC1(0.708), GNT1(0.708), MSH4(0.708), HSK3(0.708), TRS20(0.709), NBP35(0.709), YBR090C(0.709), GLO1(0.709), FYV4 (0.709), AEP2(0.709), ARP4(0.710), IES3(0.710), HYP2 (0.710), DNF2(0.711), GAA1(0.711), RPA135(0.711), PCL9(0.711), SPT5(0.711), EDE1(0.711), ORC3(0.711), YOR304C-A(0.711), YCL047C(0.711), YER085C(0.711), YOL014W(0.711), YPL071C(0.712), GTS1(0.712), RFC2 (0.712), NDE2(0.712), PET127(0.713), PLM2(0.713), YEA6(0.713), RPN7(0.713), MDL1(0.713), TMA64 (0.714), NCE103(0.714), MCM6(0.714), MAS1(0.715), TSR1(0.715), BAS1(0.715), IRC4(0.716), TIM21(0.716), HCH1(0.716), APC5(0.716), PMP1(0.716), PUF6(0.716), YER077C(0.716), SNC2(0.716), MRP21(0.716), YLR036C (0.717), YME2(0.717), SEC12(0.717), YJL062W-A(0.718), YMR031C(0.718), YAL065C(0.718), YNR047W(0.718), NHP10(0.718), YOL083W(0.719), DLS1(0.719), IGO2 (0.719), PAU17(0.719), NCS2(0.720), TAF7(0.720), YDL186W(0.720), CMK2(0.721), PUS7(0.721), TIM9 (0.721), PMU1(0.722), MNP1(0.722), SEC16(0.722), RIF1 (0.723), KAR3(0.723), MDL2(0.723), YLR356W(0.724), DCI1(0.724), ASP1(0.724), NET1(0.725), YPL068C (0.725), MOT3(0.725), NOC3(0.725), MRP13(0.725), GUT2(0.725), ICY1(0.725), NTO1(0.726), HOS3(0.726), TIM54(0.726), COX4(0.726), UBX2(0.727), RVB2(0.727), YBL059C-A(0.727), RBS1(0.727), DCR2(0.727), NEM1 (0.727), MNN9(0.728), YNR036C(0.728), NOP15(0.728), SEC61(0.728), RTT106(0.729), CCT7(0.729), OSM1 (0.729), SAS5(0.729), VPS29(0.729), KTI12(0.729), POL32(0.729), PUS9(0.730), SLF1(0.730), MUQ1(0.730), HSD1(0.730), KAR4(0.730), STN1(0.731), BAT1(0.731), THI71(0.731), RPL27B(0.732), COX5A(0.732), AEP1 (0.732), LPP1(0.732), PRM1(0.732), YKL222C(0.732), TIP41(0.733), RPL43B(0.733), YCR043C(0.733), STP1 (0.734), AIM8(0.734), HXT9(0.734), MRP7(0.734), YPL216W(0.735), SRB6(0.735), CTK2(0.736), RIT1 (0.736), NST1(0.737), RIB7(0.737), MRPL38(0.737),

SRT1(0.737), CBK1(0.738), ARL3(0.738), DRS2(0.738), YLR307C-A(0.738), GPI8(0.738), SHM2(0.739), IPL1(0.739), YPL041C(0.739), ARR1(0.739), GCN20(0.740), YPL039W(0.740), MNN1(0.740), SLX9(0.740), SEO1(0.741), RMP1(0.741), PSA1(0.741), CHS6(0.741), DAN1(0.742), RPB5(0.742), SIR3(0.742), BCP1(0.742), YLL058W(0.742), TNA1(0.742), TRM13(0.743), NOP1(0.743), SLP1(0.743), PEX31(0.743), YIF1(0.743), MSA2(0.743), ADH3(0.744), MNT4(0.744), GIS1(0.744), SLD2(0.745), PIN4(0.745), NVJ1(0.745), HTS1(0.745), RAD7(0.745), YKU70(0.745), NUF2(0.745), YIL001W(0.745), ASK10(0.745), YBL010C(0.745), ATP14(0.746), CDC123(0.746), MRPL51(0.746), YGR127W(0.747), YLR392C(0.747), APC2(0.747), DEP1(0.747), APS3(0.747), RCL1(0.747), DCD1(0.747), MIG3(0.747), BSP1(0.749), YLL014W(0.750), TOA1(0.750), NBA1(0.750), SLC1(0.750), IGO1(0.752), SDH3(0.752), ACS2(0.752), YOR093C(0.752), MPC54(0.752), PFY1(0.753), MIA40(0.753), YDR034C-A(0.753), RDS3(0.753), MSC3(0.753), TIM50(0.753), CSN12(0.753), GIN4(0.753), SMI1(0.753), ADE17(0.754), YGR016W(0.754), PCP1(0.754), SBA1(0.754), SRP102(0.754), SUM1(0.754), ICL1(0.754), OAF3(0.754), ZRT2(0.754), NOP10(0.755), BET2(0.755), YVH1(0.756), SPO75(0.756), DNL4(0.756), SGV1(0.756), IES4(0.757), SET4(0.757), YCL001W-B(0.757), SQT1(0.757), REI1(0.757), MRPL9(0.757), YPL066W(0.758), PET191(0.758), TEM1(0.758), UBX4(0.759), DBF20(0.760), MSB3(0.760), NUP100(0.760), RIC1(0.760), CUE4(0.761), IKI3(0.761), YEL043W(0.761), MRPL11(0.761), MPS1(0.761), EAP1(0.762), AVT2(0.762), GND1(0.762), TYW3(0.762), POP7(0.762), YDR186C(0.762), POR2(0.762), LSM5(0.763), MSH1(0.763), TOM22(0.763), YBR238C(0.764), MEP1(0.764), ILV3(0.764), YMD8(0.764), YJR061W(0.764), OSH3(0.764), TEF4(0.765), SCO1(0.765), TDH1(0.765), RIM21(0.766), YGL185C(0.766), NUS1(0.766), KTR4(0.767), RRP14(0.767), TUB4(0.767), LEU9(0.767), YLR437C(0.768), AIM7(0.768), ATX2(0.768), AI3(0.769), OST4(0.769), TRA1(0.769), MYO5(0.769), DAL4(0.769), IMG2(0.769), LTV1(0.769), YGR122W(0.770), CFT2(0.770), YMR001C-A(0.771), CDC16(0.771), YAL067W-A(0.771), YDR132C(0.771), YNL011C(0.772), TCP1(0.772), CCT3(0.772), MKK2(0.772), RRI2(0.772), ZEO1(0.772), RUD3(0.772), RTR2(0.772), YIL070C(0.773), NUP116(0.773), ENT1(0.774), SLU7(0.774), MSC2(0.774), STV1(0.774), NUP60(0.775), AIM28(0.776), YOL029C(0.776), SHE10(0.776), RSB1(0.776), SHO1(0.776), DLD2(0.777), RAX1(0.777), LCP5(0.777), ATG17(0.777), PEX17(0.778), GAL4(0.778), MET32(0.778), YOR223W(0.779), STE14(0.779), DUG3(0.780), SRX1(0.780), UFO1(0.780), YAT2(0.780), NMD3(0.780), PRP9(0.780), MSN2(0.781), PET123(0.781), SWD2(0.781), SOG2(0.781), RRP17(0.781), GPB2(0.781), YOR293C-A(0.781), TEN1(0.781), SOV1(0.782), PFK27(0.782), YIL127C(0.782), YNL024C-A(0.782), TMT1(0.783), SEC39(0.783), YER158C(0.783), ERP3(0.783), YLR257W(0.783), PKH3(0.783), YNL155W(0.783), PSO2(0.783), NOP9(0.783), GPG1(0.784), GIP4(0.784), RIB1(0.784), CYS4(0.784), ZRT3(0.784), FMP21(0.785), DAK2(0.785), ISW1(0.785), ACF4(0.785), RTT10(0.785), RTT109(0.785), FMP10(0.785), YAP6(0.785), APM4(0.785), ZAP1(0.785), ARO9(0.786), SCM4(0.786), MIM1(0.786), BRR6(0.787), SRN2(0.787), YOR287C(0.787), CLA4(0.787), RNR3(0.787), ALG8(0.787), RAD50(0.787), YBR239C(0.788), LDB7(0.788), ATP17(0.788), UGA2(0.788), ENA2(0.788), YLR408C(0.788), SAT4(0.788), BOP3(0.788), SDH4(0.789), YNL045W(0.789), RPC40(0.790), YNL134C(0.790), ARP5(0.790), MAD2(0.790), GRX6(0.790), RSM18(0.790), FES1(0.791), SGF73(0.791), ARH1(0.791), MHT1(0.791), CNS1(0.791), BDH2(0.792), YKL063C(0.792), GSH1(0.792), BOS1(0.792), THI72(0.792), BSC1(0.792), MED8(0.793), RAD5(0.793), EMP47(0.793), SIS2(0.793), TEA1(0.793), YJL185C(0.793), RTF1(0.793), CIN4(0.794), DIC1(0.794), EST2(0.795), YNK1(0.795), PUS2(0.795), PEX13(0.795), YNL217W(0.795), HOR7(0.795), MGS1(0.796), YHR009C(0.796), YML007C-A(0.796), JNM1(0.796), YHR078W(0.796), YMR155W(0.796), STB5(0.796), MRP4(0.796), STE3(0.797), CKS1(0.797), TAF13(0.797), YNL176C(0.797), PCD1(0.797), HSP26(0.797), DAS1(0.798), EDS1(0.798), CTR3(0.798), PXL1(0.798), MRS11(0.799), MET3(0.799), BDP1(0.799), CBF2(0.799), DBP6(0.799), FAR11(0.799), ERI1(0.800), MDM10(0.801), RPM2(0.801), COX13(0.801), TOA2(0.801), MYO2(0.802), PRP5(0.802), DRN1(0.802), ZDS1(0.802), IES2(0.803), FAT1(0.803), HIS1(0.803), MET16(0.803), LAS17(0.803), ACA1(0.803), HIS4(0.803), PHO12(0.804), EBP2(0.804), MRPL6(0.804), YLR271W(0.804), YBR085C-A(0.804), CRR1(0.805), SWI3(0.805), SWI4(0.805), PYK2(0.805), BUD7(0.806), PEX12(0.806), MDV1(0.806), IDH2(0.807), MRC1(0.807), TIM11(0.807), SPT15(0.808), FBP28(0.808), GUP2(0.808), NPL4(0.808), YCR007C(0.809), ABD1(0.809), YNL193W(0.809), YLR426W(0.810), YSP2(0.810), SSO2(0.810), MRPL23(0.810), YHR112C(0.810), VPS36(0.811), MET7(0.811), UTP18(0.811), MTW1(0.811), DYN1(0.812), RNH1(0.812), LST4(0.812), TAF11(0.812), RPL17A(0.812), SNA2(0.812), YGL041W-A(0.813), KAR5(0.813), YEH2(0.814), YMR118C(0.814), CUE2(0.814), URA8(0.814), YMR034C(0.814), YLR152C(0.815), YKL088W(0.815), HEM13(0.815), CAT5(0.815), KRE1(0.815), IBD2(0.817), YOL098C(0.817), AIM18(0.817), HMG1(0.817), TRM7(0.817), ADY2(0.818), LCD1(0.818), YGL194C-A(0.818), EFG1(0.818), BRX1(0.819), HIM1(0.819), TCM62(0.819), SET6(0.819), FIN1(0.819), CBF5(0.820), ASI1(0.820), DUT1(0.820), SEC65(0.820), YPL067C(0.820), RRP43(0.820), ASC1(0.821), ERG3(0.821), RTA1(0.821), NFU1(0.821), JIP4(0.821), YLR419W(0.822), YJR011C(0.822), YJL045W(0.822), ARC18(0.822), YBR287W(0.822), CAP2(0.822), NEO1(0.823), TOM5(0.823), PEP5(0.823), PCC1(0.823), PXR1(0.823), ALG11(0.823), YLR301W(0.824), ARG1(0.824), RFC4(0.824), AIM42(0.824), PPA2(0.824), DAP1(0.824), RTS1(0.825), EDC3(0.825), IRC23(0.825), YBR220C(0.825), GPI14(0.825), IML1(0.825), NIP7(0.826), YPT32(0.826), MSS18(0.826), CHO1(0.826), CST26(0.826), MOH1(0.826), PLP1(0.827), MKC7(0.827), XYL2(0.827), YMR295C(0.828), YLR003C(0.828), YIL096C(0.828), MOT2(0.828), RLP7(0.828), YSC84(0.828), NDL1(0.828), PFK1(0.828), MRD1(0.829), SAC6(0.829), REX2(0.829), RPA34(0.829), AHC2(0.829), APC1(0.829), YDR222W(0.829), VHR1(0.829), SUS1(0.829), UTH1(0.829), IRC8(0.830), SNO1(0.830), APT1(0.830), YOR352W(0.830), YMR258C(0.831), MRH1(0.831), HRP1(0.831), SRP21(0.831), MRPL22(0.831), SEC9(0.831), KAR2(0.832), YGR054W(0.832), HOF1(0.832), YDC1(0.832), YGR207C(0.833), WSC2(0.833), SRC1(0.833), YAR023C(0.834), HAM1(0.834), PER1(0.834), YKL047W(0.834), FLC3(0.834), TRM10(0.834), PAU15(0.834), RFA1(0.835), AI2(0.835), MPP10(0.835), ELC1(0.835), PHB1(0.836), OST1(0.836), LSB1(0.836), OKP1(0.836), THI22(0.836), MRP51(0.836), COX20(0.837), FCF1(0.837), PHO80(0.837), FIT1(0.837), YPL056C(0.838), KIN4(0.838), GCD1(0.839), FRT1(0.839), ACS1(0.839), LGE1(0.839), YJL136W-A(0.840), MLC2(0.840), SMF1(0.840), ISW2(0.840), HIS6(0.841), CTR2(0.841),

GCV2(0.841), GAL83(0.841), IMP3(0.842), GRS1(0.842), MRS5(0.842), NCE101(0.843), BUD17(0.843), MKS1(0.843), SYF1(0.843), ACH1(0.844), ARN1(0.844), RCN2(0.844), UBC12(0.844), YER079W(0.845), YHL044W(0.845), THI20(0.845), PML1(0.845), IRC10(0.846), BMS1(0.846), SSA1(0.846), DDI2(0.846), RPC11(0.846), YDR115W(0.847), DDC1(0.847), IRC21(0.847), DUR3(0.847), PET100(0.847), SKI8(0.847), QRI5(0.847), QDR1(0.847), UBC11(0.848), MRT4(0.848), POL3(0.848), MFB1(0.848), TCO89(0.848), YDR370C(0.848), OYE2(0.848), MDM31(0.849), SLG1(0.849), YOR062C(0.849), DNF1(0.850), MEH1(0.850), AIR2(0.850), MSS116(0.850), ACB1(0.850), ADE12(0.851), ELO1(0.851), VTA1(0.851), MRPL27(0.852), YFL054C(0.852), SPC34(0.852), RGS2(0.853), DRS1(0.853), GTR1(0.853), COX8(0.853), KEL2(0.854), NUP82(0.854), GIR2(0.855), FKH2(0.855), CLG1(0.855), PEX6(0.855), HO(0.855), YHR003C(0.855), NUP84(0.856), RRB1(0.856), PSY2(0.856), BSD2(0.856), ESBP6(0.856), MED7(0.857), RSN1(0.857), YKE2(0.857), YHL012W(0.857), SHE2(0.858), RPL2A(0.858), DUO1(0.858), DST1(0.858), PET9(0.858), RSA3(0.858), GLN4(0.858), YKR015C(0.858), YJR141W(0.858), RIM20(0.858), BCK2(0.859), SPC42(0.859), TRF5(0.859), FAA2(0.859), TRS130(0.859), GUA1(0.860), HSL7(0.860), PDE2(0.860), RRP8(0.860), XRS2(0.860), SPE1(0.860), RFT1(0.860), VPS20(0.860), SEC20(0.860), PAD1(0.861), GGC1(0.861), ORC1(0.861), HMG2(0.861), STE2(0.861), LSM3(0.861), ICS2(0.861), TRM2(0.861), CDC3(0.862), HEM2(0.862), SIN4(0.862), VIK1(0.862), HIS7(0.863), RAD54(0.863), IQG1(0.863), DFG10(0.863), TIP1(0.864), BRR2(0.864), GRX2(0.864), HTZ1(0.864), BCH2(0.864), NRG2(0.865), RSC58(0.865), TMA16(0.865), RAD59(0.866), URM1(0.866), ADY4(0.866), AAP1(0.866), ABP1(0.866), YGR066C(0.867), BRE5(0.868), BFR2(0.868), LSM1(0.868), CHD1(0.868), VTI1(0.868), AIM11(0.868), RFA2(0.869), SUR4(0.869), YOR228C(0.869), DLD3(0.870), ISN1(0.870), CYC2(0.870), SNF5(0.870), YMR124W(0.870), GIP2(0.870), SVL3(0.870), SEC13(0.870), YEL047C(0.870), BEM1(0.871), RPL16A(0.871), SPR3(0.873), ATP4(0.873), WAR1(0.873), ITR1(0.873), FAR3(0.873), YOR021C(0.874), YBR028C(0.874), NOP58(0.875), RPN13(0.877), YNL035C(0.878), YJL049W(0.878), YER137C(0.878), NOC4(0.879), ALG7(0.879), MET22(0.880), SIL1(0.880), TYS1(0.880), GLK1(0.880), YDR341C(0.880), YKR045C(0.880), RAD23(0.880), BIK1(0.881), RPL27A(0.881), YOR152C(0.881), KNS1(0.881), YHR182W(0.881), EEB1(0.881), RKM1(0.881), SNG1(0.882), YIL067C(0.882), VPS66(0.883), TCB1(0.883), ADE4(0.883), YNL034W(0.883), HSP78(0.883), HEM15(0.883), PKC1(0.883), SPP2(0.883), MF(ALPHA)1(0.883), ARP6(0.884), NCS6(0.884), RTS3(0.884), SPE4(0.884), YPL199C(0.884), DAL81(0.884), SAC1(0.884), YOL131W(0.884), YHL026C(0.884), REC107(0.884), YGR174W-A(0.885), SGE1(0.885), NCB2(0.885), YNL320W(0.885), CDC20(0.885), CSG2(0.886), ECM5(0.886), NOC2(0.886), IES1(0.886), SMK1(0.887), PHO86(0.887), YHR202W(0.887), CIN1(0.887), PFS1(0.887), MCM21(0.887), ROT2(0.888), GLC7(0.888), HRT1(0.888), YDR018C(0.888), APM1(0.888), DPH2(0.888), CDH1(0.889), HNT3(0.889), ATG4(0.889), FRE3(0.889), ATP2(0.889), YMR148W(0.890), YAT1(0.890), ERG11(0.890), PGI1(0.890), FKH1(0.890), MET30(0.890), YGL140C(0.890), ARC35(0.890), SNX41(0.890), SAS2(0.890), YHR007C-A(0.890), YML083C(0.891), ABF1(0.891), YLR104W(0.892), TOS1(0.892), MF(ALPHA)2(0.892), FRM2(0.892), OPY1(0.892), MMF1(0.893), DIG1(0.893), PMI40(0.894), YIL092W(0.894), ASI3(0.895), FIR1(0.895), ERG26(0.895), YMR090W(0.895), YGL085W(0.896), CDC24(0.896), YPL113C(0.896), YPR010C-A(0.896), BIR1(0.896), AAH1(0.896), EPT1(0.896), MSW1(0.896), NOP14(0.897), CBT1(0.897), COX18(0.897), COX16(0.898), RRD1(0.898), BEM4(0.898), GEA2(0.898), FOB1(0.898), ERG7(0.898), YLR042C(0.899), SEC17(0.899), YPR063C(0.899), PUT4(0.900), MSI1(0.900), RPA43(0.900), SPE2(0.900), DAL1(0.901), RPC25(0.901), BRO1(0.901), AXL1(0.901), EAF7(0.901), RCR1(0.901), YDR338C(0.901), RGA1(0.902), LOT5(0.902), YIH1(0.902), RNA1(0.902), SKM1(0.903), PUT2(0.903), HEM4(0.904), AIM37(0.904), PHO13(0.904), YGR015C(0.904), AKR2(0.904), YKL050C(0.904), TCB2(0.904), HAC1(0.904), ADE1(0.905), RTN1(0.905), RPL8B(0.905), MDM36(0.905), JHD1(0.905), CCL1(0.905), YDR282C(0.906), PRE10(0.906), PEX14(0.906), OMA1(0.906), YNR034W-A(0.906), NBP2(0.906), SPT20(0.906), PRP2(0.907), YGL041C-B(0.907), YBR255W(0.907), YOR246C(0.907), YFL012W(0.907), YLR412W(0.908), DUR1,2(0.908), RPS4A(0.908), YAL037W(0.908), ICT1(0.908), CTR86(0.909), RPN10(0.909), RME1(0.909), MSB4(0.909), SAM35(0.909), MAG2(0.909), YOL092W(0.909), PPZ1(0.909), YGL138C(0.910), YHR097C(0.910), SSZ1(0.910), SIS1(0.910), CTP1(0.910), TAF5(0.910), PDC1(0.910), YPL150W(0.910), GCD10(0.911), ENP1(0.911), TOM40(0.911), ERG6(0.912), ECM4(0.912), RLF2(0.913), RKI1(0.913), SAM3(0.913), SEC62(0.913), CRC1(0.914), UME1(0.914), TUS1(0.915), YNL046W(0.916), VTC1(0.916), TEL2(0.916), YEN1(0.916), PEX30(0.917), GSG1(0.917), NTE1(0.918), RBG1(0.918), TIM8(0.918), YNG1(0.918), PMT5(0.918), PRP16(0.918), SPT6(0.918), NIP100(0.919), THS1(0.919), HMRA1(0.920), STE20(0.920), AIM10(0.921), YGL242C(0.921), GTR2(0.921), YOL157C(0.921), LOT6(0.921), KEX1(0.921), MET14(0.922), UBA2(0.922), NUT1(0.922), SPO21(0.923), PAC10(0.923), YND1(0.923), DSE3(0.923), YJR149W(0.923), YOR378W(0.923), GSY2(0.923), YBR063C(0.924), SRV2(0.924), YCK1(0.924), YKL091C(0.925), FMS1(0.925), UTP23(0.925), YCR090C(0.925), SFT2(0.925), BNI5(0.925), SNX3(0.925), FSH2(0.926), RGD2(0.926), SST2(0.926), UNG1(0.927), YLR164W(0.927), RPS26B(0.927), TRE1(0.927), MSH5(0.927), MYO3(0.928), YGL039W(0.928), SUP35(0.929), AMA1(0.929), ATP19(0.929), YGL036W(0.930), PTK2(0.930), PBP2(0.930), TRM112(0.931), SMC1(0.931), NPR1(0.931), PFK2(0.932), PDE1(0.932), RRI1(0.932), FRE2(0.932), YOR118W(0.933), FRE1(0.933), ECM38(0.933), ALD3(0.933), STT3(0.934), VMR1(0.934), RPC82(0.934), URK1(0.934), ATX1(0.934), REG1(0.935), PNT1(0.935), YMR279C(0.935), RSC8(0.935), YJR111C(0.935), YLR253W(0.935), FSH1(0.935), YDR336W(0.935), ERD1(0.935), VPS41(0.936), AYT1(0.936), VRG4(0.936), YPL009C(0.936), VID22(0.936), YDR514C(0.936), APC11(0.937), VPS74(0.937), KRE11(0.937), RRP6(0.938), FOX2(0.938), ASM4(0.938), MED11(0.938), TWF1(0.939), GRX5(0.939), MYO1(0.939), YPL107W(0.939), PET54(0.939), YLR064W(0.940), SPC2(0.940), APP1(0.940), DBP5(0.940), BPH1(0.941), YKL151C(0.941), NAF1(0.941), YKL027W(0.941), ARO3(0.941), UBX6(0.942), TIM18(0.942), BNI4(0.942), SPC98(0.943), PZF1(0.943), PIC2(0.943), UTP8(0.943), YBR235W(0.943), SMC6(0.943), RLR1(0.943), DBF4(0.943), RPB11(0.944), SHE3(0.944), SFB3(0.944), SYT1(0.944), STU2(0.945), NGL2(0.945), GDS1(0.945), NOP2(0.945), SVS1(0.945), PRY2(0.946), GDA1(0.946), BCY1(0.947), PUS1(0.947), COX7(0.947), MRPL15(0.947), RER1(0.948), SLH1(0.948), RPB3(0.948), TIF11

(0.948), YDL173W(0.948), YML053C(0.948), PEX4 (0.949), MIG1(0.949), CLU1(0.950), ECM32(0.950), FCY1(0.950), HSP32(0.950), MAL12(0.950), JLP2(0.950), DAT1(0.950), RMR1(0.950), KTR6(0.950), OST2(0.951), NOP12(0.951), IRC3(0.951), OPT2(0.952), YBL054W (0.952), PDX1(0.952), AMS1(0.952), YBR204C(0.953), SLM2(0.953), VPS64(0.953), PTH2(0.953), MRP1(0.953), TIF5(0.954), AAT2(0.954), CPR3(0.954), AVT6(0.954), CLF1(0.954), MDM38(0.954), COX12(0.954), ESS1 (0.954), RPG1(0.955), SNF11(0.955), ERV15(0.955), YPR078C(0.955), RHO3(0.956), SUE1(0.956), CLN2 (0.956), YFL040W(0.956), YLR040C(0.956), RLA1 (0.957), YMR272W-B(0.957), MND2(0.957), EHD3 (0.957), IMP4(0.957), PAH1(0.958), HMO1(0.958), RPL26A(0.958), PIR3(0.959), MNN5(0.959), FCY22 (0.959), SMD3(0.959), YER186C(0.959), QDR2(0.959), MHP1(0.960), CRH1(0.960), LSB3(0.960), RMD1(0.960), SDA1(0.960), AXL2(0.961), NOP16(0.961), YCL058W-A (0.962), ORC6(0.962), PRR2(0.963), STH1(0.963), CCA1 (0.963), FUS1(0.963), MRS6(0.963), YBP1(0.963), RPL12A(0.963), UTR4(0.964), MTF2(0.964), MAK31 (0.964), BOP2(0.964), UIP5(0.964), SSL1(0.965), INO4 (0.965), RPT3(0.965), YBR072C-A(0.966), YHR159W (0.966), ITR2(0.966), PUF3(0.967), ADD66(0.967), GCS1 (0.968), LYS2(0.968), MTR2(0.968), TRP1(0.968), HXT11 (0.968), ALG1(0.969), SPS18(0.969), YOR111W(0.969), STI1(0.969), SSD1(0.969), CRN1(0.969), CSN9(0.970), RSM22(0.970), YIL152W(0.970), TOF1(0.970), HOM2 (0.970), MOB1(0.971), RAD24(0.971), IRC25(0.971), RSM23(0.971), YLR049C(0.971), YBL055C(0.971), SPP41(0.972), YMR310C(0.972), YHC1(0.972), YNL040W(0.973), AIM41(0.973), APL5(0.973), ILV2 (0.974), YIR035C(0.974), REC8(0.974), MSS51(0.974), GAP1(0.975), EMP70(0.975), HAL1(0.975), CDC21 (0.975), VPS75(0.975), YER066W(0.975), MCM7(0.975), CHZ1(0.976), YKL121W(0.977), MMS2(0.977), BUL2 (0.977), SEC1(0.977), BEM2(0.977), YKR018C(0.978), NUP2(0.978), VPS73(0.978), YIL024C(0.978), YPL225W (0.979), FEN1(0.979), YSR3(0.979), CST9(0.979), YLR241W(0.979), MAK10(0.980), CUP2(0.980), CCP1 (0.980), ERV14(0.980), YJU3 (0.980), RAP1(0.980), IMP1 (0.980), COA1(0.981), TFA1(0.981), FAF1(0.981), ATP5 (0.981), ARG3(0.982), RVB1(0.982), RPA49(0.982), NSE4 (0.982), YKT6(0.982), RRN9(0.983), APM2(0.983), GAT3 (0.983), SPN1(0.983), CKB1(0.983), DTD1(0.983), TPO2 (0.983), PRP45(0.984), DEG1(0.984), PTC5(0.984), TSC10 (0.984), DPB11(0.984), YKR005C(0.985), RIM15(0.985), PNO1(0.985), COX15(0.985), VPS4(0.985), PKH2(0.986), MTR4(0.986), YLR053C(0.986), LEU4(0.986), YPK1 (0.987), PDX3(0.987), TIF2(0.988), YDL180W(0.988), FYV8(0.988), BUD13(0.988), YBR139W(0.988), TPK2 (0.988), SSH1(0.989), YGR102C(0.989), YDR348C (0.989), RPL28(0.990), QCR2(0.990), YAR1(0.990), SCP1 (0.990), TIP20(0.990), UBC7(0.990), SEC11(0.991), RPN11(0.993), TGL5(0.993), HSP60(0.993), RPL42B (0.994), PRS1(0.994), YKL018C-A(0.994), TFC6(0.994), RNH201(0.994), URA1(0.995), ALG9(0.995), MSG5 (0.995), AKR1(0.995), MNN11(0.996), OCA1(0.996), YGP1(0.997), PPX1(0.997), TSC3(0.997), PSF3(0.998), YAF9(0.998), YMR175W-A(0.998), LHP1(0.998), YMR252C(0.999), SLK19(0.999), YJR107W(0.999), PMC1(0.999), HCR1(0.999), SKG1(0.999), PCT1(0.999), LPE10(1.000), PGK1(1.000), HAS1(1.000), SEC23(1.000), GPI13(1.000), YDR476C(1.001), YLR073C(1.001), SUI3 (1.001), RCO1(1.001), LYS20(1.002), NUP170(1.002), EI1 (1.002), RAD27(1.002), YLL032C(1.002), GDB1(1.002), GON7(1.002), PRS4(1.002), GAL7(1.002), RAI1(1.003), MLC1(1.003), SWD3(1.003), REV1(1.003), FET3(1.003), DAL7(1.004), DAL80(1.004), COQ5(1.004), TRK2(1.005), PRP31(1.005), SYP1(1.005), RPL36A(1.005), OSH7 (1.005), RPL12B(1.005), UME6(1.006), LCB4(1.006), IZH2(1.006), MDH3(1.006), OGG1(1.006), RPL1A(1.007), YGL157W(1.007), HUB1(1.007), TGL4(1.007), CAF16 (1.007), NPP2(1.007), URE2(1.007), GMH1(1.007), AVT3 (1.007), FAA1(1.007), BET5(1.008), YPR091C(1.008), PET8(1.009), STB1(1.009), ERG13(1.009), UTP10(1.009), MMP1(1.010), YTH1(1.010), EMI2(1.010), MES1(1.010), PDS1(1.010), NPL3(1.010), PRD1(1.010), YGR235C (1.011), PHO8(1.011), PEX22(1.011), LAP4(1.011), LCB2 (1.011), YLR326W(1.011), EMP46(1.011), MRPS17 (1.011), AIM17(1.011), NUP57(1.011), YER134C(1.012), YCR076C(1.012), YBL104C(1.012), SSM4(1.012), YMR187C(1.012), YEF3(1.012), PIG1(1.012), ECM16 (1.012), SPO20(1.013), ILS1(1.013), MFT1(1.014), RRP46 (1.014), RPS23A(1.015), ECM40(1.015), STT4(1.015), SOK2(1.016), RPL9A(1.016), SIR1(1.017), SES1(1.017), CDC26(1.018), SSU1(1.018), SAS3(1.019), YKL187C (1.019), ARG8(1.019), RPL16B(1.019), LCB3(1.020), TVP18(1.020), APJ1(1.021), GDH1(1.021), IPT1(1.021), ATP7(1.021), YAR029W(1.021), PIS1(1.022), TRS23 (1.022), SEC72(1.022), CHA4(1.022), DMA2(1.023), RUP2(1.023), DCP2(1.024), KAP114(1.024), YTA12 (1.024), PHO87(1.024), TPS3(1.024), RPS10B(1.024), LIP2(1.025), PAF1(1.026), MEU1(1.026), ALK1(1.026), RIM11(1.026), SLA2(1.026), RSC6(1.027), CBC2(1.027), YBR016W(1.027), FIS1(1.027), RAS1(1.027), SFA1 (1.028), YOL057W(1.028), YOR292C(1.028), MCD4 (1.028), CSM1(1.028), MAK32(1.028), DAP2(1.028), EXG2(1.028), DID2(1.029), HXT15(1.029), DIE2(1.029), VAC8(1.030), YBR138C(1.030), NTH2(1.030), YCR099C (1.031), RTT107(1.031), MAF1(1.031), ERG9(1.031), PPN1(1.031), SRB4(1.032), CDC55(1.032), YDR248C (1.032), YDR003W-A(1.032), GLC8(1.033), PDR11 (1.033), SPB4(1.033), YSC83(1.034), YLR072W(1.034), MCH1(1.035), RPH1(1.035), DAD3(1.035), SPT3(1.036), YFR057W(1.036), IDI1(1.036), TDH3(1.036), OCA2 (1.036), PEX18(1.036), FUN30(1.037), RRP3(1.037), ABC1(1.037), IWR1(1.037), YJR088C(1.037), PTR2 (1.038), SEC26(1.039), AQY1(1.040), ECM21(1.040), BUD27(1.040), PFK26(1.041), YDR352W(1.041), CUP5 (1.041), ATG3(1.042), AGE2(1.042), RIX7(1.042), HSE1 (1.042), AGA1(1.043), GRX7(1.043), AGE1(1.043), TUB2 (1.043), YHR122W(1.043), RIB4(1.043), VRP1(1.043), LAS1(1.043), OCA4(1.044), YGR277C(1.044), BUB3 (1.044), LPD1(1.044), EMI5(1.044), CTF18(1.044), YOL073C(1.044), SIT1(1.045), LYS12(1.045), FTR1 (1.045), TUL1(1.045), EKI1(1.046), LEO1(1.046), GAL1 (1.046), VAC17(1.046), REV7(1.046), PMP2(1.046), TIM13(1.047), YMR158C-A(1.047), TLG2(1.047), YGR106C(1.047), YML079W(1.048), YFR045W(1.048), YBR056W(1.048), YLR065C(1.048), HSH49(1.048), MTF1(1.049), LAG1(1.049), ATE1(1.049), RFM1(1.049), RNH203(1.050), DBP8(1.050), TPS1(1.050), YGR205W (1.050), PIM1(1.050), RAD16(1.050), SPI1(1.051), SPP1 (1.051), CHS5(1.051), MNR1(1.051), PIL1(1.052), SMT3 (1.052), PEF1(1.052), SKO1(1.052), CDC45(1.052), SUC2 (1.052), RXT3(1.052), RPN9(1.053), SPO12(1.053), RPE1 (1.053), SEC15(1.053), HMI1(1.054), RRP4(1.054), ERG25(1.054), MUC1(1.055), TPT1(1.055), OPY2(1.055), OSH2(1.055), VNX1(1.055), PXA1(1.055), YSW1(1.057), SRP14(1.057), OST5(1.058), CDC4(1.058), RPL38(1.058), YDR520C(1.058), ARO2(1.059), DOM34(1.059), SWE1 (1.059), GTO1(1.059), RPL37B(1.060), RAD3(1.060), MEP2(1.060), PKH1(1.061), ARL1(1.061), ROX3(1.061),

SFT1(1.062), SIM1(1.062), CIA1(1.062), COX5B(1.062), CLN1(1.062), MNE1(1.062), BRE4(1.062), UBX5(1.063), DSL1(1.063), ACK1(1.063), YHR140W(1.063), ARG82(1.063), SCS22(1.063), ADH7(1.063), HSC82(1.063), ARO80(1.063), HED1(1.063), MAD1(1.064), TRP5(1.064), RPN3(1.065), SEN54(1.065), PTM1(1.065), ATG23(1.065), GIM4(1.065), YDR089W(1.066), MON2(1.066), PEX32(1.066), PUS6(1.066), YJL038C(1.066), SGN1(1.066), PRP39(1.066), YNR070W(1.067), SPO71(1.067), SAE3(1.067), MGR2(1.068), INP53(1.068), TUP1(1.068), SHP1(1.068), INO80(1.068), CDC23(1.068), GAB1(1.068), PTC1(1.069), SKI2(1.069), DNF3(1.069), YOR389W(1.070), AIM14(1.071), ATP16(1.071), VPS51(1.071), NSE3(1.071), UTP21(1.071), MDE1(1.072), ALY1(1.072), MNI2(1.072), BNS1(1.072), ILV1(1.073), TPO5(1.073), THI21(1.074), PEX2(1.074), YMR194C-B(1.074), SFI1(1.074), ESF1(1.074), YJL068C(1.075), GPI1(1.075), ISC10(1.075), RPL13A(1.076), YDR391C(1.076), TVP15(1.076), YNL108C(1.076), YDR051C(1.076), SRP101(1.076), SAS4(1.076), ARG4(1.077), PAN5(1.077), PTK1(1.077), THI6(1.077), YOR019W(1.077), GCN5(1.077), DID4(1.078), TRM11(1.078), ABZ2(1.079), YHR210C(1.079), RPL34B(1.079), POL31(1.079), RPS4B(1.080), COG4(1.080), RPS16B(1.080), LCB1(1.080), ARA2(1.080), VPH2(1.081), YBT1(1.081), HSM3(1.081), YBL036C(1.081), DAL2(1.081), VTC4(1.081), RPS21B(1.081), YOR131C(1.081), ADE13(1.081), YKL215C(1.081), LSM2(1.082), FAR10(1.082), MCH2(1.082), IMD3(1.082), USV1(1.082), YAR035C-A(1.082), RAM1(1.083), SNM1(1.083), PNG1(1.083), RFC3(1.084), ARP2(1.084), TOR2(1.084), ISC1(1.084), CTS1(1.085), YSH1(1.085), AIM4(1.085), BIT2(1.085), GVP36(1.086), SED1(1.086), SPG4(1.086), KGD1(1.086), NMT1(1.086), SSY1(1.086), LSC1(1.086), NRK1(1.086), YLR177W(1.086), SCD6(1.087), YDR210W(1.087), LRP1(1.087), URA2(1.087), PEX21(1.088), MCM5(1.088), SSE2(1.088), PYC2(1.088), GFD1(1.088), YNL247W(1.088), RAD17(1.089), BRE2(1.089), CDC48(1.089), IES5(1.089), RPL23A(1.089), PTR3(1.089), ATP20(1.089), PAU3(1.089), CPR8(1.090), ARO7(1.090), YRO2(1.090), HRB1(1.091), HSP42(1.091), RPS18B(1.091), FMP23(1.091), ADE6(1.091), DER1(1.092), PPE1(1.092), CUE3(1.092), ACF2(1.092), QNS1(1.092), IOC3(1.093), NAM9(1.093), YDL144C(1.094), ENB1(1.094), KTR3(1.095), PSD1(1.095), HOS1(1.096), FCY21(1.096), CAJ1(1.096), ERP4(1.096), LRC2(1.097), TFB5(1.098), PRM3(1.098), CPR7(1.098), MET17(1.098), SAH1(1.098), YGR149W(1.099), GAC1(1.099), TFC7(1.099), RHO5(1.099), TIF34(1.099), YPT1(1.099), MSS4(1.100), FLC2(1.100), PRE2(1.100), YCL068C(1.101), GAL80(1.101), SPG3(1.101), URB1(1.101), MGE1(1.102), STR2(1.102), RPL34A(1.102), UIP3(1.102), NPP1(1.102), FMP24(1.102), AIM23(1.102), BIO3(1.103), PRO2(1.103), TMN3(1.103), EST3(1.103), PHO5(1.104), YSP1(1.104), TUF1(1.104), ORM1(1.104), OLA1(1.105), NMA1(1.105), YMR209C(1.105), SEC27(1.105), SLA1(1.105), YCL012C(1.105), SLM1(1.106), NOP53(1.106), YLR162W-A(1.106), PAU13(1.106), ALA1(1.106), YDL133W(1.107), CDC37(1.107), HCA4(1.107), PRB1(1.107), GSY1(1.107), YIP3(1.108), TMA46(1.108), RPP1(1.109), PRP3(1.109), YBL107C(1.109), UBP14(1.110), VAM10(1.110), CBS1(1.110), YOR238W(1.110), OM14(1.110), SEC66(1.111), CST6(1.111), SSF2(1.111), FRS1(1.111), NCA2(1.112), HMX1(1.112), NOP13(1.112), RNR2(1.114), QDR3(1.114), OTU2(1.114), SPO13(1.114), HUL5(1.115), SED4(1.115), RRP42(1.115), CDC33(1.116), MLP1(1.116), GOR1(1.116), YDL119C(1.116), YJR039W(1.116), HNT2(1.116), SCM3(1.116), MET12(1.117), VPS33(1.117), MGR1(1.117), PCM1(1.117), YUH1(1.117), CDS1(1.117), SAP185(1.118), CRT10(1.118), SNF1(1.118), CMP2(1.118), APL6(1.118), IDH1(1.119), YDR428C(1.119), SEC21(1.119), APL4(1.119), PAP2(1.119), GPI17(1.119), SCH9(1.120), HOP1(1.120), MUK1(1.120), RPS25B(1.120), NOB1(1.120), STE23(1.121), YLR243W(1.122), GRE3(1.122), CCS1(1.122), VEL1(1.122), ENO2(1.123), COG6(1.123), RPL11B(1.123), HNT1(1.123), LEM3(1.123), GPI15(1.124), FSF1(1.124), SEC3(1.124), SOL2(1.124), PRS5(1.124), VPS71(1.124), ACC1(1.124), ADE8(1.124), GNA1(1.124), YNR024W(1.126), RSF2(1.126), MAL32(1.126), PAU21(1.126), SPS19(1.127), YIL002W-A(1.127), SPF1(1.127), CCT8(1.127), PRM2(1.128), PDH1(1.128), RBL2(1.128), PIF1(1.128), VBA1(1.128), AFG1(1.129), DIN7(1.129), IZH1(1.129), YPL105C(1.130), YCR051W(1.130), WWM1(1.130), SIP3(1.130), SYS1(1.131), HPC2(1.131), RPL40A(1.131), NCR1(1.131), YER078C(1.131), CAP1(1.131), GCN4(1.131), AIM38(1.131), PTC7(1.132), FUN14(1.132), COS8(1.132), MCH4(1.132), PRP24(1.132), CWC2(1.132), CLC1(1.132), SIR4(1.133), FUS3(1.133), YLR057W(1.133), ZRG17(1.133), YSA1(1.133), PTC3(1.134), UBP6(1.134), KAP122(1.134), EFT2(1.134), URA3(1.135), ALG2(1.135), POL5(1.135), RPL1B(1.136), LIP1(1.136), TMA20(1.137), NAS6(1.137), IRC5(1.137), KIN3(1.137), YPL033C(1.137), AVT4(1.137), YGR266W(1.137), CTI6(1.138), YNL050C(1.138), SDP1(1.139), ESF2(1.139), NFS1(1.140), YER078W-A(1.140), IZH4(1.140), CWC22(1.140), YGR110W(1.140), DYN2(1.140), SNF4(1.141), YMR178W(1.141), NSE5(1.142), RPL40B(1.142), TKL2(1.142), HIR1(1.142), RPS30A(1.142), HSP12(1.142), YDR539W(1.143), GCV1(1.144), NTG1(1.144), AZR1(1.144), SPO7(1.144), YNL022C(1.144), DIM1(1.145), VAM6(1.145), YNR061C(1.145), PDA1(1.145), YOR032W-A(1.145), SPC3(1.146), CSR1(1.146), COS9(1.147), YJR085C(1.147), PEX15(1.147), TGL2(1.147), SGD1(1.147), YPL278C(1.147), YIL108W(1.148), THP1(1.148), SCY1(1.149), YGR130C(1.149), UBC6(1.149), END3(1.149), UBP15(1.149), RPL35B(1.149), MSB2(1.149), YCT1(1.150), SOL3(1.150), YDL027C(1.151), KIP3(1.151), UTP11(1.151), SUB1(1.152), PRP19(1.152), DCW1(1.152), TAH18(1.152), YER010C(1.152), PIN1(1.152), GYP1(1.152), SCW10(1.152), CTK1(1.153), ARK1(1.153), FYV10(1.153), YCR016W(1.153), YDJ1(1.153), ARF1(1.153), BGL2(1.153), YHR100C(1.154), CBS2(1.154), REX3(1.154), TSA1(1.155), RNA14(1.155), RCE1(1.155), THR4(1.155), SIP18(1.156), PMS1(1.156), DSK2(1.156), CDC50(1.156), DPH5(1.156), HEM12(1.156), SER3(1.157), YML119W(1.157), ESC1(1.157), GAL11(1.158), PRE7(1.158), RPT5(1.158), ERG2(1.158), DSE1(1.158), SEC22(1.159), YFH7(1.159), HSF1(1.159), GOS1(1.160), WRS1(1.161), EXO70(1.161), TSA2(1.162), ALK2(1.162), COX6(1.162), KRI1(1.162), YGL015C(1.162), RPS17B(1.163), YDR367W(1.163), TOM20(1.163), RSP5(1.163), YBL086C(1.163), TRM44(1.163), YPR109W(1.164), PTP1(1.164), AVT7(1.164), CYR1(1.164), CIS1(1.164), FAL1(1.164), VPS28(1.165), AGA2(1.165), QRI1(1.165), ATS1(1.165), GIT1(1.166), THO1(1.166), FBP1(1.166), YJL016W(1.166), UGA3(1.166), YBR230W-A(1.167), CCE1(1.167), NDE1(1.167), SET5(1.168), HOT1(1.168), RPT1(1.168), CAR2(1.168), PRE4(1.169), ECM33(1.169), ECM11(1.169), RAD33(1.169), BUB2(1.169), SOP4(1.169), SPR1(1.170), MOG1(1.170), SPO11(1.171), YKR070W(1.171), YBR246W(1.171), YKL071W(1.172), AHP1(1.172), PRP42(1.172), GRC3(1.173), KEL3(1.173), YMR244W(1.174), YMR242W-A(1.174), HBN1(1.174), VAS1(1.174), RTT102(1.174),

ZUO1(1.175), YGR250C(1.175), FRQ1(1.175), YCL049C (1.175), MCR1(1.175), UBP11(1.175), TIF35(1.176), ATG26(1.176), YKL107W(1.177), HEM14(1.177), THR1 (1.178), LUG1(1.178), SPS100(1.178), VMA22(1.179), YEL020C(1.179), RPL2B(1.179), GAL10(1.180), FKS1 (1.180), YPL247C(1.180), YEL057C(1.180), RPS22A (1.181), TRK1(1.181), VTC2(1.181), SNU114(1.181), SWD1(1.181), UBC8(1.181), YPT52(1.181), XDJ1(1.182), YJR142W(1.182), COQ9(1.183), ERV25(1.184), YKL075C(1.184), FPR4(1.184), SEN2(1.184), GDT1 (1.184), NOP7(1.184), YOR251C(1.184), SRL1(1.184), YLL023C(1.185), IRA2(1.185), IES6(1.185), MLF3 (1.186), DIA1(1.186), MTG1(1.186), FPR1(1.186), NCE102(1.186), ERG4(1.187), SIF2(1.187), NUP53 (1.187), RPL14A(1.187), SEC18(1.187), SSB2(1.188), RAT1(1.188), YMR027W(1.188), GDI1(1.189), VAN1 (1.189), KAP123(1.189), ICL2(1.189), LPX1(1.189), RPP2A(1.190), SCD5(1.190), EXO84(1.190), CWC21 (1.191), TRE2(1.191), YGR153W(1.191), YCR061W (1.191), RAD14(1.192), CUL3(1.192), VPS53(1.192), GEA1(1.192), GET3(1.192), TAD2(1.193), POT1(1.193), MVP1(1.193), PUS4(1.194), SMC2(1.194), RFC5(1.194), TIF3(1.195), NTG2(1.195), HXT10(1.195), CDC60(1.195), ENT5(1.196), GAT4(1.196), PGU1(1.196), UFD4(1.197), RPL37A(1.198), PRE5(1.198), PDC6(1.198), GCV3 (1.198), EGD1(1.199), MSC7(1.200), KEM1(1.200), APN1 (1.200), APE2(1.200), YLR456W(1.200), MAK5(1.201), YPR172W(1.202), STE24(1.202), RPS9B(1.203), CRM1 (1.203), STP22(1.204), DIA2(1.205), ECO1(1.205), MCX1 (1.205), YKL065W-A(1.205), NTR2(1.205), HHO1(1.206), RRM3(1.206), PRE8(1.206), NYV1(1.206), RPC53(1.207), TMA23(1.208), REC104(1.208), ZTA1(1.209), TEC1 (1.209), TUB3(1.209), YJL123C(1.209), AST2(1.209), SNX4(1.210), ARC1(1.210), SOD1(1.210), SMA2(1.211), RGD1(1.211), PHM8(1.211), SEM1(1.211), GGA2(1.211), YAK1(1.211), RGA2(1.211), SCS3(1.212), YTA7(1.213), MDM12(1.213), AUR1(1.213), SKN7(1.213), MDG1 (1.213), RSM7(1.214), YOL038C-A(1.214), OSW2(1.214), TIR3(1.214), RSM28(1.214), NIF3(1.215), FRE6(1.215), MDM20(1.215), YNR071C(1.215), GDH2(1.215), VPS8 (1.216), MVD1(1.216), GCD2(1.216), TFP3(1.216), FMP33(1.216), NUG1(1.217), CPR6(1.219), SCP160 (1.219), SEC14(1.219), YNL181W(1.219), PRE6(1.220), YLR364W(1.220), HOG1(1.221), NUP49(1.221), RPL21B (1.221), RPL42A(1.221), GTT2(1.221), STR3(1.222), ARG5, 6(1.222), RPS24A(1.222), PPM1(1.222), AIM46 (1.222), ILM1(1.222), PEX10(1.222), PDS5(1.223), YDR042C(1.223), YDL218W(1.223), MGT1(1.223), NPC2(1.223), YLR194C(1.223), PDI1(1.223), XKS1 (1.223), SIW14(1.224), KOG1(1.224), PDR15(1.224), NGR1(1.225), SMX3(1.225), FIP1(1.225), UGA4(1.225), EDC1(1.225), YDL086W(1.225), GGA1(1.226), SMM1 (1.227), AIM39(1.227), UBC1(1.227), YGR203W(1.227), PRP4(1.227), YSF3(1.227), SNA3(1.228), SKI6(1.228), CDC12(1.228), VPS60(1.228), MSC1(1.229), SET1 (1.229), NMA111(1.229), SKI7(1.229), KRE5(1.229), FOL2(1.229), DAL3(1.230), SAK1(1.230), RVS161 (1.230), YBR141C(1.231), LHS1(1.231), YFL051C(1.231), YGR067C(1.231), NOT5(1.231), CKB2(1.231), ATG2 (1.232), YJR112W-A(1.232), RKM2(1.232), RPL36B (1.232), CNB1(1.232), PRP43(1.233), LCB5(1.233), PAC1 (1.233), ARP3(1.234), LRC1(1.234), RGR1(1.234), YDL157C(1.234), DPL1(1.234), GCY1(1.235), YER076C (1.235), TFB3(1.235), RPS8B(1.235), GAT2(1.235), GFD2 (1.235), MRP8(1.236), VAC14(1.236), YHR138C(1.237), PHO90(1.237), PSK2(1.238), ALT1(1.238), ERP5(1.238), LAS21(1.238), AIM9(1.239), SLZ1(1.240), SGM1(1.240), FMP27(1.241), HXT3(1.241), YGR273C(1.241), RAM2 (1.241), RET1(1.241), YIR007W(1.241), RPS2(1.242), MTQ2(1.242), RPS23B(1.242), COS12(1.242), RUB1 (1.242), RGP1(1.242), GYP7(1.243), YOL138C(1.243), PMT2(1.243), YMR130W(1.243), SPS4(1.244), RAD28 (1.244), YLR099W-A(1.245), YOR285W(1.245), MBR1 (1.245), MPH1(1.246), NUP159(1.246), SEC63(1.246), RPS16A(1.247), YPL206C(1.247), BCD1(1.247), HOT13 (1.248), IVY1(1.248), RNA15(1.248), YKR104W(1.248), STE4(1.249), PUP1(1.250), SFB2(1.251), YCK2(1.251), ODC1(1.251), FMP42(1.251), VPS24(1.251), YKL098W (1.252), YSY6(1.252), RTG2(1.252), LYS9(1.253), UTR1 (1.253), HRR25(1.253), YBR261C(1.254), RPS26A (1.254), KTR5(1.254), CHL1(1.255), MNN10(1.255), GLE2(1.255), CPD1(1.255), SNZ1(1.256), PAM17(1.256), HIR2(1.256), CDC28(1.257), YDR061W(1.257), ENA5 (1.257), APM3(1.258), YLR118C(1.258), AVT1(1.258), PEP12(1.258), PET18(1.258), MAM1(1.258), DOA1 (1.259), FPR2(1.259), PIB2(1.259), PRP21(1.260), TOP2 (1.261), YBL044W(1.261), OST6(1.261), AIM24(1.262), IRC18(1.262), OSW1(1.263), COT1(1.263), YOR387C (1.263), SKP1(1.263), STM1(1.263), YDL176W(1.263), YLR137W(1.263), ALE1(1.264), PBP1(1.264), YNL200C (1.264), YBL029C-A(1.265), SPE3(1.265), RRD2(1.265), CNN1(1.266), SPR6(1.266), PAN3(1.267), YRB1(1.268), YDL057W(1.268), YOR051C(1.268), POL4(1.268), ORC5 (1.269), IMP2(1.269), ATG19(1.269), ARO8(1.269), YJL163C(1.269), SWI5(1.270), LSP1(1.270), TMA19 (1.270), YET3(1.271), RAD26(1.271), MGA2(1.271), IME1(1.272), OXR1(1.272), GSF2(1.273), RPS18A (1.273), RUP1(1.273), YLR126C(1.273), KRE27(1.273), TVP23(1.273), INO1(1.273), ALG14(1.274), PUS5(1.274), VMA10(1.275), SPT16(1.275), YLL053C(1.276), CHC1 (1.276), MSH6(1.276), SDS24(1.277), PTC4(1.278), PSP2 (1.278), VBA2(1.278), TSR4(1.278), CPR4(1.278), DPP1 (1.279), TFG1(1.279), ARN2(1.279), YGL230C(1.279), NBP1(1.280), YKL077W(1.280), MOB2(1.280), DYN3 (1.280), UBC13(1.280), RFA3(1.281), SPG5(1.281), GYP5 (1.281), YPI1(1.281), YDR179W-A(1.281), CHA1(1.282), TOS4(1.282), ADH1(1.282), SPO1(1.282), JJJ2(1.283), ADK1(1.283), SOK1(1.284), GOT1(1.285), TIR4(1.285), ERP2(1.285), SEN1(1.285), PHO81(1.285), ARF2(1.285), YOR227W(1.285), TVP38(1.286), YDL089W(1.286), ZDS2(1.286), GCD6(1.286), SUI2(1.286), VAC7(1.287), TAH11(1.288), CTR9(1.288), YKL100C(1.289), NUP188 (1.289), GRE1(1.289), PHB2(1.289), BUD3(1.290), SMA1 (1.290), RPL20B(1.290), NSP1(1.291), PPZ2(1.291), STO1 (1.291), ETR1(1.291), SUL1(1.292), RPL6B(1.292), CPR5 (1.292), YAL018C(1.292), ELP6(1.292), ACP1(1.293), SHR3(1.293), KAP120(1.293), YBR137W(1.293), IME2 (1.293), SNF7(1.293), YCR023C(1.293), GIS2(1.294), YIP1(1.294), TFC3(1.294), CUE1(1.295), YLR283W (1.295), FUN12(1.296), BMH1(1.296), RIM1(1.297), YMC1(1.297), KIC1(1.297), NAR1(1.298), YBR184W (1.298), CAF4(1.298), CTK3(1.298), NUP157(1.299), PRY1(1.299), MFA1(1.300), POL2(1.300), YDL114W (1.300), STP3(1.301), IRC20(1.301), ZPS1(1.302), POP1 (1.303), DUN1(1.303), SLY1(1.303), UTP6(1.303), TAL1 (1.303), DIB1(1.303), PAC2(1.303), YNR029C(1.304), SPC72(1.305), RPC34(1.305), KTR7(1.305), KRR1(1.305), YBR062C(1.306), SSA4(1.306), VMA9(1.308), ATG22 (1.308), NRD1(1.309), INH1(1.309), REF2(1.312), TSC13 (1.312), UTP7(1.312), AIM15(1.313), ARC19(1.313), EHT1(1.313), YHL017W(1.313), NNF2(1.313), YPR027C (1.314), TGL1(1.314), PEX28(1.314), TEL1(1.315), PGM1 (1.315), PAN1(1.315), HRD3(1.315), RPL26B(1.316), SDT1(1.316), YER128W(1.317), PSY3(1.317), VPS52

(1.318), RPB4(1.318), AIM2(1.318), NUD1(1.318), RPS29B(1.320), PRO3(1.320), RPL32(1.321), PXA1(1.321), GID8(1.322), TRM3(1.322), SLX1(1.322), PEA2(1.322), UBR1(1.322), AIP1(1.322), RPS10A(1.323), CFD1(1.324), YOR114W(1.324), LEA1(1.324), MSN5(1.324), RPL6A(1.324), PTC2(1.324), YER071C(1.325), RAS2(1.325), ATG14(1.326), CDC11(1.326), RPS6B(1.326), URA6(1.326), RPN1(1.327), SFH5(1.329), YAP1801(1.329), FLR1(1.329), DDR48(1.329), YRA2(1.329), APN2(1.330), ELF1(1.330), YJL217W(1.331), YPR089W(1.331), GSP2(1.331), BUG1(1.331), PSE1(1.331), SUA5(1.332), GPM2(1.332), POS5(1.332), PRM5(1.334), TAF4(1.334), GIM5(1.336), BNR1(1.336), YPS7(1.337), HAL5(1.337), RPS27B(1.337), CAK1(1.337), PGA2(1.337), SSP2(1.338), PMR1(1.338), NUP85(1.339), LSB6(1.339), TMA17(1.340), TGL1(1.340), ASN2(1.340), SEI1(1.341), VMA7(1.341), MDR1(1.341), HBS1(1.341), PMT1(1.342), PHO2(1.342), YHR113W(1.342), SSO1(1.342), RET2(1.342), UBA1(1.342), ALD2(1.342), SEC28(1.343), SEH1(1.343), YMR144W(1.343), HOC1(1.343), PRT1(1.344), RPS19B(1.344), GCN2(1.345), SAP4(1.345), YLR179C(1.346), COQ6(1.346), LYS14(1.346), LSM12(1.347), YGL117W(1.347), RED1(1.348), VPS34(1.348), VTC3(1.348), BRF1(1.348), ARR2(1.350), VMA21(1.350), PSF1(1.351), SRL3(1.351), YDR379C-A(1.351), ALG12(1.352), RPS25A(1.352), SDS23(1.352), DGA1(1.352), YDR196C(1.353), LOC1(1.354), RPN2(1.355), ANB1(1.355), NAN1(1.355), STB2(1.355), CUE5(1.356), CDC8(1.356), SPH1(1.357), GID7(1.357), UBC4(1.357), RPS22B(1.358), ACT1(1.360), RPS8A(1.360), YNR068C(1.360), FRS2(1.360), TAF8(1.361), THI4(1.361), RBK1(1.362), SET3(1.362), YNL305C(1.362), TPP1(1.362), MSO1(1.363), NSA1(1.364), YMR210W(1.364), ERG24(1.364), YMR31(1.364), MAK11(1.364), URB2(1.364), FAD1(1.365), AGC1(1.366), OM45(1.366), APD1(1.367), GSH2(1.367), SPT14(1.367), YGR210C(1.368), RPS11A(1.368), SWH1(1.369), ANT1(1.369), SAP30(1.369), HRT3(1.369), NSG1(1.370), BAT2(1.370), SOM1(1.371), IPP1(1.372), HIS2(1.372), RSE1(1.372), RTT101(1.372), CRG1(1.373), YJR096W(1.374), IMH1(1.374), SPT7(1.374), MKT1(1.374), GTT3(1.375), PEX11(1.375), YDR374W-A(1.377), YPD1(1.377), DOS2(1.377), YEL023C(1.378), RPF1(1.378), BNA2(1.380), ATG27(1.380), RPL29(1.382), YPS6(1.382), RPL19B(1.382), YDR357C(1.382), ARO4(1.383), YBR096W(1.384), PEP8(1.384), RPL39(1.385), SCC4(1.386), HXT7(1.386), HSV2(1.386), APA2(1.386), TFC1(1.386), SEC53(1.386), PDR5(1.386), MUD2(1.387), RPL19A(1.387), TAF9(1.387), MXR1(1.388), RIX1(1.388), PKR1(1.389), CWC27(1.390), BFR1(1.390), YDR387C(1.390), UIP4(1.390), OST3(1.391), BUD6(1.392), GFA1(1.393), RPS8A(1.395), CRZ1(1.396), SLT2(1.396), SNC1(1.396), SEC5(1.397), PCL6(1.397), DAL5(1.398), MSB1(1.399), CSL4(1.399), COQ4(1.400), IAH1(1.400), YPL245W(1.400), PRI2(1.400), LOS1(1.400), SQS1(1.401), PBA1(1.401), YFR017C(1.402), HPA3(1.402), SCL1(1.403), YGR168C(1.404), SAP155(1.405), MON1(1.405), SGA1(1.405), MNI1(1.406), TFC8(1.407), FAB1(1.407), MED2(1.407), GCN3(1.408), PRE1(1.408), BBC1(1.409), GPA1(1.409), DIG2(1.409), IRS4(1.409), SXM1(1.410), SHU2(1.410), SRO7(1.411), GEF1(1.412), RPL24A(1.413), TMN2(1.413), RIB3(1.414), UBC9(1.414), MAL11(1.415), ARO10(1.415), LAC1(1.415), RCN1(1.416), MVB12(1.418), TBS1(1.418), CTL1(1.419), NTF2(1.419), BZZ1(1.420), HXT14(1.421), YGR125W(1.421), YNR062C(1.422), STE50(1.422), YLL056C(1.423), HIS3(1.423), CIN2(1.423), TCB3(1.423), NUM1(1.424), CPA1(1.425), PRP40(1.425), TRR1(1.425), TRP2(1.426), ADE16(1.427), EFT1(1.427), BET3(1.428), SUA7(1.430), RPS14A(1.430), FOL1(1.431), DPB4(1.431), VPS16(1.431), ANP1(1.431), YMR099C(1.432), VHS2(1.432), BMH2(1.432), ADH6(1.432), GSC2(1.433), DBR1(1.433), ADP1(1.433), CEG1(1.434), MBP1(1.434), FCP1(1.434), SRY1(1.434), YNL058C(1.435), AVO2(1.435), YMR196W(1.435), RPL35A(1.435), HIF1(1.435), YLR050C(1.436), YER187W(1.436), YOR186W(1.436), RAD57(1.437), ATH1(1.437), PEP7(1.437), YJL055W(1.438), YBR259W(1.439), UBX7(1.439), ILV6(1.439), SAM4(1.441), MRM1(1.441), PHO23(1.441), MYO4(1.443), BRE1(1.443), YFR032C(1.444), GAS4(1.444), MIP6(1.444), ERV46(1.444), YPR097W(1.444), PET10(1.445), HDA2(1.445), TRX2(1.445), MED4(1.446), SPO16(1.446), NSG2(1.446), GND2(1.447), PDB1(1.448), BDH1(1.448), NIT3(1.449), MUD1(1.449), ERG20(1.450), RPL18A(1.451), PAI3(1.452), TMA108(1.452), SAM50(1.452), SLY41(1.452), YDR461C-A(1.454), YMR265C(1.454), YJL132W(1.454), BLM10(1.454), SPO73(1.454), CWC15(1.455), ALO1(1.456), MAP1(1.456), YKR023W(1.456), PET130(1.456), YCS4(1.458), CWH41(1.458), ARP9(1.458), CHK1(1.459), PAM1(1.459), TAF10(1.459), ARA1(1.461), CGI121(1.461), YIL014C-A(1.461), CHS7(1.461), RPS21A(1.463), VMA13(1.463), NAT3(1.464), ARG2(1.464), DOG1(1.465), TMS1(1.465), PSF2(1.465), YHR126C(1.465), KAP104(1.466), DPS1(1.466), IRR1(1.466), YAL044W-A(1.466), RPL23B(1.467), YDR307W(1.467), RPL33A(1.468), NAB6(1.468), APA1(1.469), ALG6(1.469), MEX67(1.470), DAK1(1.471), ARC15(1.471), YOS1(1.472), GAD1(1.472), ECM22(1.473), CYS3(1.473), PBI2(1.474), YBR271W(1.474), GPI10(1.474), WBP1(1.477), ZRC1(1.477), FIG2(1.477), YOR262W(1.477), MSH3(1.478), IOC2(1.478), YGR201C(1.479), NAP1(1.479), KAE1(1.479), CHS1(1.480), GDE1(1.480), YTM1(1.480), YHR162W(1.480), TAD3(1.480), ALP1(1.481), TRM8(1.482), NMD2(1.482), YIM1(1.483), BCH1(1.483), RRP1(1.483), VCX1(1.483), UGA1(1.484), HOL1(1.484), GRX1(1.484), EMP24(1.484), YGR237C(1.485), FAP1(1.485), KTR2(1.486), PBP4(1.486), YER163C(1.486), RFS1(1.486), PTA1(1.487), MPD2(1.487), SGT2(1.487), IKI1(1.487), ECM29(1.488), REV3(1.489), TPD3(1.489), YDL124W(1.490), MUM2(1.491), YFR026C(1.491), PHS1(1.491), MLS1(1.493), POR1(1.494), PFD1(1.494), EGD2(1.494), GYP8(1.495), RPT2(1.495), TEX1(1.495), RPS5(1.495), TPK1(1.496), DOT5(1.497), LSB5(1.498), DMA1(1.498), BNA6(1.498), VAB2(1.499), AML1(1.500), SEC31(1.500), KIN1(1.501), STB4(1.502), GSP1(1.502), AAD4(1.502), MNN2(1.503), RPP1B(1.503), GUK1(1.506), MCK1(1.506), HSP31(1.506), SBP1(1.506), ZWF1(1.507), IST2(1.508), GPI16(1.508), CDC42(1.508), AHA1(1.509), UBP2(1.510), YNL115C(1.510), CCW14(1.510), YDL121C(1.510), MCA1(1.510), RPT4(1.511), ERP1(1.512), TMA7(1.513), WHI4(1.513), YDR131C(1.513), PDR1(1.514), TSR3(1.516), ATG11(1.516), DDP1(1.516), COQ2(1.516), RPP1A(1.517), PMP3(1.517), CRD1(1.517), PHO85(1.517), YGR017W(1.517), YIL055C(1.518), LAP3(1.518), YOR291W(1.519), GAS5(1.519), YKR043C(1.520), YIL083C(1.520), CHO2(1.521), ELP4(1.521), BIM1(1.522), CAM1(1.522), DAL82(1.523), UMP1(1.524), YBR241C(1.524), LTP1(1.524), PHO91(1.525), RPP0(1.526), YOR164C(1.526), TOM71(1.527), FAS2(1.528), FMP46(1.528), TMA22(1.528), YML131W(1.528), YCF1(1.530), OPI3(1.530), ROM1(1.530), IRC24(1.530), FYV6(1.531), ATG13(1.534), TRX3(1.534), ENP2(1.534), CEX1(1.534), VPS3(1.535), TRX1(1.536), DIT2(1.536), SEC4(1.536), GDH3(1.537), PRE9(1.537), UBP1(1.537), AYR1

(1.537), NIT2(1.537), PDR17(1.538), TUB1(1.539), KEG1 (1.539), CDC25(1.539), PIG2(1.539), NSE1(1.541), VPS25 (1.541), YLR414C(1.541), CWH43(1.541), COG2(1.545), RCY1(1.545), VPS68(1.546), RPL7A(1.548), TAF14 (1.549), SRB5(1.553), UPF3(1.553), YML096W(1.555), ARG81(1.555), NPR2(1.555), PSH1(1.556), TAF6(1.557), MCT1(1.557), SBH1(1.557), PBN1(1.558), VPS45(1.560), SRP68(1.560), SAY1(1.561), PEP1(1.562), CCT4(1.563), COQ10(1.565), RET3(1.566), SSE1(1.566), YSP3(1.567), ABZ1(1.567), PNS1(1.567), DPB3(1.568), YDL073W (1.568), ATM1(1.568), RBD2(1.568), YFR006W(1.569), DDI1(1.569), DCP1(1.570), SAS10(1.570), RMT2(1.571), FIG1(1.572), MUS81(1.573), UBI4(1.573), YBR285W (1.574), DLD1(1.576), RPS15(1.576), YPR170W-B(1.576), SRP1(1.577), PSK1(1.577), RAD4(1.578), PGD1(1.580), PMT4(1.581), ABF2(1.582), SEC24(1.584), URA10 (1.585), CWC23(1.585), RPS11B(1.586), TPM1(1.586), YLR290C(1.588), TRM9(1.588), YAP1(1.589), UGP1 (1.589), SPS2(1.590), PDR10(1.591), POM34(1.591), PNC1(1.591), STE11(1.593), GRH1(1.596), YMR018W (1.596), TRS33(1.596), HEF3(1.597), LAT1(1.597), BDS1 (1.597), HMF1(1.598), PRP6(1.600), FSH3(1.600), SRB2 (1.601), DUG1(1.601), ERD2(1.602), CDA2(1.602), RPS6A(1.602), HUT1(1.604), SHS1(1.604), IRA1(1.605), SSA3(1.606), ELP3(1.606), PRP46(1.606), CSM3(1.606), PEP4(1.607), YHC3(1.610), MDY2(1.610), RPL43A (1.613), HRQ1(1.613), YKL023W(1.613), DFM1(1.614), PCL8(1.614), SKG3(1.614), GPH1(1.615), NEJ1(1.616), URA4(1.617), GPX1(1.620), HOS2(1.622), YDR531W (1.623), PEP3(1.624), MAL31(1.625), YGR283C(1.626), HFD1(1.627), SPR28(1.627), SWP82(1.628), FUM1 (1.629), CDA1(1.629), HOM6(1.630), NHX1(1.631), SNF6 (1.632), ECI1(1.632), CDC10(1.632), MIS1(1.632), YIL165C(1.632), GTT1(1.636), PLP2(1.636), PFA4 (1.636), RPL30(1.637), PRE3(1.640), MTD1(1.640), MNT2(1.642), ECM30(1.643), YNL208W(1.645), YCR024C-B(1.645), PCA1(1.646), HCS1(1.648), DCC1 (1.650), FAR8(1.652), PPH22(1.654), DED81(1.656), GPM1(1.657), COF1(1.658), YGR042W(1.658), YPR148C (1.659), VPS55(1.659), JLP1(1.660), CAT2(1.661), GCN1 (1.664), YGL231C(1.664), GUS1(1.665), YGR111W (1.667), VMA4(1.671), YDR056C(1.671), SCS2(1.672), NQM1(1.675), UFE1(1.677), COG1(1.677), PAA1(1.677), IRC22(1.682), KTR1(1.682), TYW1(1.683), SSB1(1.683), SVP26(1.686), ESC8(1.687), YNL010W(1.687), TIF1 (1.689), EAF6(1.690), SHC1(1.690), KIN2(1.692), DCS2 (1.692), RPS1B(1.692), URA5(1.692), DSD1(1.693), YJL218W(1.694), NPT1(1.694), SRO77(1.695), FMN1 (1.695), CMD1(1.695), YTA6(1.697), RPL21A(1.699), ALG3(1.699), KRE2(1.703), PCL5(1.704), MDM34 (1.705), PFS2(1.708), SNF12(1.708), BNA1(1.709), AIM29 (1.710), SNU13(1.712), RNR4(1.712), MAP2(1.713), DCS1(1.716), RPN5(1.716), PDC2(1.722), DOP1(1.723), SPO74(1.725), PAP1(1.728), RPL24B(1.732), RPN8 (1.734), FPR3(1.734), ERS1(1.735), CPR1(1.736), FIT3 (1.740), HUG1(1.742), VPS5(1.742), PEX3(1.742), RPS29A(1.743), ERV29(1.743), CAF20(1.743), DOG2 (1.743), RPL4A(1.744), YCP4(1.745), PBY1(1.746), FUS2 (1.750), SNF2(1.752), SUI1(1.752), YMR262W(1.759), BUD8(1.761), TED1(1.763), TAH1(1.765), YCL048W-A (1.769), RPL41A(1.774), YDR374C(1.776), VMA8(1.777), YKR051W(1.777), YFL042C(1.778), ORM2(1.778), TAF12(1.778), APE3(1.781), YDR239C(1.782), ERV2 (1.784), SHR5(1.785), YHR192W(1.787), YRB30(1.791), PHO88(1.791), WHI2(1.792), LYS1(1.793), RHO1(1.795), VPS27(1.797), VMA6(1.797), PAB1(1.806), YJR015W (1.807), SIR2(1.809), FAR1(1.809), CPT1(1.814), ECM15 (1.815), ROK1(1.815), YFR018C(1.820), HYR1(1.821), POL1(1.821), CTS2(1.830), UBA4(1.832), SRP72(1.833), RTN2(1.834), HAP1(1.835), ARE2(1.836), RCK2(1.837), INM2(1.839), AFR1(1.840), YOS9(1.840), RTT103(1.842), RPS12(1.845), RNY1(1.847), PPA1(1.848), LEU3(1.849), ERG27(1.850), TMA29(1.851), UBX3(1.852), VPS15 (1.854), RPT6(1.855), LDB18(1.859), YPL088W(1.862), RPL5(1.863), RVS167(1.870), TIR2(1.871), PHA2(1.873), ERJ5(1.873), VPS30(1.876), IMD2(1.878), PES4(1.879), EMI1(1.897), YPR085C(1.901), YBR200W-A(1.903), FMP40(1.909), REH1(1.909), SGT1(1.911), CPS1(1.913), YOP1(1.917), TRR2(1.919), STS1(1.920), VPH1(1.931), SWA2(1.933), YGR026W(1.938), CDC53(1.938), FMP52 (1.941), YDR119W(1.945), RNQ1(1.953), SAG1(1.956), RPS20(1.974), TRM82(1.979), VPS1(1.981), YIP5(1.987), YPR1(1.988), ENT2(1.992), YPT31(1.997), PRX1(2.003), YHL039W(2.003), YHI9(2.022), BUD32(2.035), YLR361C-A(2.037), APL2(2.043), PTP3(2.046), YMR114C(2.049), LSC2(2.054), ATG10(2.056), SRP54 (2.065), ENT3(2.077), RPL3(2.080), TYR1(2.095), NAT1 (2.106), YNR021W(2.114), EBS1(2.126), HBT1(2.132), RPL15A(2.145), RPL41B(2.149), RPP2B(2.166), CBR1 (2.178), BNA4(2.233), PRC1(2.240), DIT1(2.244), RPS28A(2.260), ASP3-1(2.300), IDP1(2.304), SCW4 (2.321), VMA2(2.369), ALY2(2.382), and NAT5(2.449).

These results show that the yeast gene terminators exhibited an extremely wide and diverse range of expression intensities relative to the intensity of the PGK1 terminator, and that therefore exogenous genes can be expressed with the desired expression intensity by expressing one or two or more kinds of arbitrary genes in a yeast using a combination of one or two or more kinds of these terminators as necessary.

Example 6

Regulation of Excretory Expression Levels of Cellulase in a Yeast

In this example, different terminators were used to regulate the excretory expression levels of cellulase.

(Plasmid Preparation)

A TDH3 promoter sequence, a known *Rhizopus oryzae* secretory signal sequence, a Trichoderma endoglucanase 2 (TrEG2) gene and a terminator sequence were linked in that order to the SmaI site of Takara Bio pAUR112 to prepare a plasmid. NAT5 and RPL41B (for which increased GFP expression was confirmed in Example 5) and ICY2 (for which decreased GFP expression was confirmed in Example 5) were used as the terminators in this example, and PGK1 and a sequence from MFA2 were used as controls.

(Excretory Expression of Cellulase in a Yeast and Cellulose Decomposition Reaction)

Each of the plasmids prepared above was introduced into the BJ5464 yeast strain using a FROZEN-EZ YEAST TRANSFORMATION II KIT™ (Zymo Research). 3 each of the yeast clones obtained above were pre-cultured in SD-Ura medium (30° C., 24 hours), and then planted at a 20% seed rate in SD-Ura medium and sub-cultured (30° C., 24 hours). 10 µl of centrifugation supernatant was added to 90 µl of phosphoric acid-swollen cellulose (PSC) containing 50 m phosphate buffer (pH 5.0) and agitated, after which a decomposition reaction was performed for 3 hours at 40° C. After the reaction, 5 µl of centrifugation supernatant was taken and the amount of reducing sugar was measured by TZ assay (Journal of Biochemical and Biophysical Methods, 11 (1985), 109-115).

As in the measurement of GFP expression, the terminators of the NAT5 and RPL41B genes produced higher secretory levels than the terminator of the PGK1 gene as a control, while the terminator of the ICY2 gene produced a lower cellulase secretory level than the PGK1 terminator gene.

Example 7

Figure 3:
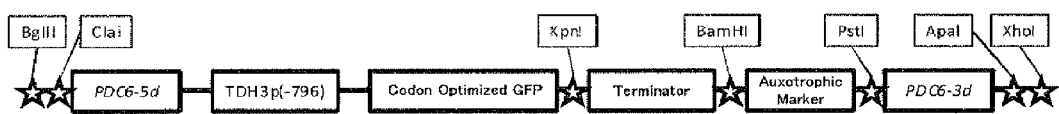
FIG. 3 shows an outline of an evaluation construct prepared in Example 7.

Based on the previous results, constructs were prepared for evaluating the top 44 terminators, including the standard SAG1t terminator. The evaluation constructs were configured as shown in FIG. 3, and specific genes were inserted at one location on the genome to prepare recombinant yeasts. The culture conditions were matched to $OD_{660}$=0.7, activity measurement was repeated 3 times with 10000 cells for each recombinant yeast, and the top 30 terminators were determined. The top 5 terminators were also determined under various culture conditions.

(1) Selection of Terminators for Evaluation

An attempt was made to prepare constructs for evaluating 44 terminators that exhibited higher activity than the standard SAG1t terminator (NAT5t, ALY2t, SCW4t, IDP1t, ASP3-1t, RPS28At, DIT1t, PRC1t, BNA4t, CBR1t, VMA2t, RPP2Bt, RPL41Bt, RPL15At, HBT1t, EBS1t, YNR021Wt, NAT1t, TYR1t, RPL3t, ENT3t, SRP54t, ATG10t, LSC2t, YMR114Ct, APL2t, YLR361C-At, BUD32t, PRX1t, YHL039Wt, YPT31t, ENT2t, YIP5t, YPR1t, TRM82t, VPS1t, RPS20t, RNQ1t, YDR119Wt, YGR026Wt, CDC53t, FMP52t, SWA2t and SAG1t in order from the one with the highest activity), and 40 were obtained as a result, excluding the four terminators YPR1t, VPS1t, RPS20t and SWA2t. The final total was 44 because four terminators (YHI9t, PPA1t, GUS1t and BUD6t) were originally judged to have lower activity than SAG1t, but actually exhibited higher activity than SAG1t in the course of screening.

(2) Preparation of Transformation Vectors

As shown in FIG. 3, evaluation constructs were obtained having the following configuration between the BglII site and the XhoI site of pSP73 (Promega). That is, each genome insertion construct comprised a 5' upstream sequence of PDC6 (-821 to -177 from initiation codon), a TDH3 promoter (-796 to -1), a yeast codon-optimized GFP gene, the respective terminator region, an auxotrophic marker and a 3' downstream sequence of PDC6 (+4 to +599 from termination codon) in that order. The auxotrophic marker was TRP1 or URA3. The construct shown in FIG. 3 is similar to a vector used in the reference literature (Yamanishi, M, Katahira S, Matsuyama T, TPS1 terminator increases mRNA and protein yield in *Saccharomyces cerevisiae* expression system, *Bioscience, Biotechnology and Biochemistry*, 75, 2234-2236 (2011)), except that the reporter gene is codon-optimized GFP (Yamanishi M, Matsuyama T, A modified Cre-lox genetic switch to dynamically control metabolic flow in transgenic *Saccharomyces cerevisiae*, *ACS Synthetic Biology*, 1, 172-180 (2012)). Each terminator region was cloned by ordinary methods using the KpnI site and BamHI site parts as a cassette.

(3) Preparation of Recombinant Yeast

Evaluation constructs corresponding to each of the terminators were introduced into the wild-type yeast W303-1a to prepare recombinant yeasts, which were then cultured under culture conditions conforming to $OD_{660}$=0.7, and the fluorescence intensity was measured by flow cytometry (FCM). Specifically, the wild-type yeast W303-1a was first cultured in YPD liquid medium, and then treated with a FROZEN-EZ YEAST TRANSFORMATION II KIT™ (Zymo Research) to prepare competent cells. The construct prepared in (2) was treated with the insertion site terminal restriction enzyme BglII or ClaI, and also with ApaI or XhoI to obtain fragments that were then added to the competent cells and diluted with PEG buffer. This was heated for 45 minutes to obtain a transformant. The transformant was cultured in tryptophan selection medium, and strains that maintained stable growth capacity were selected. These were then subjected to colony PCR to confirm proper introduction of the target gene.

(4) Ranking of Terminator Activity

Figure 4:
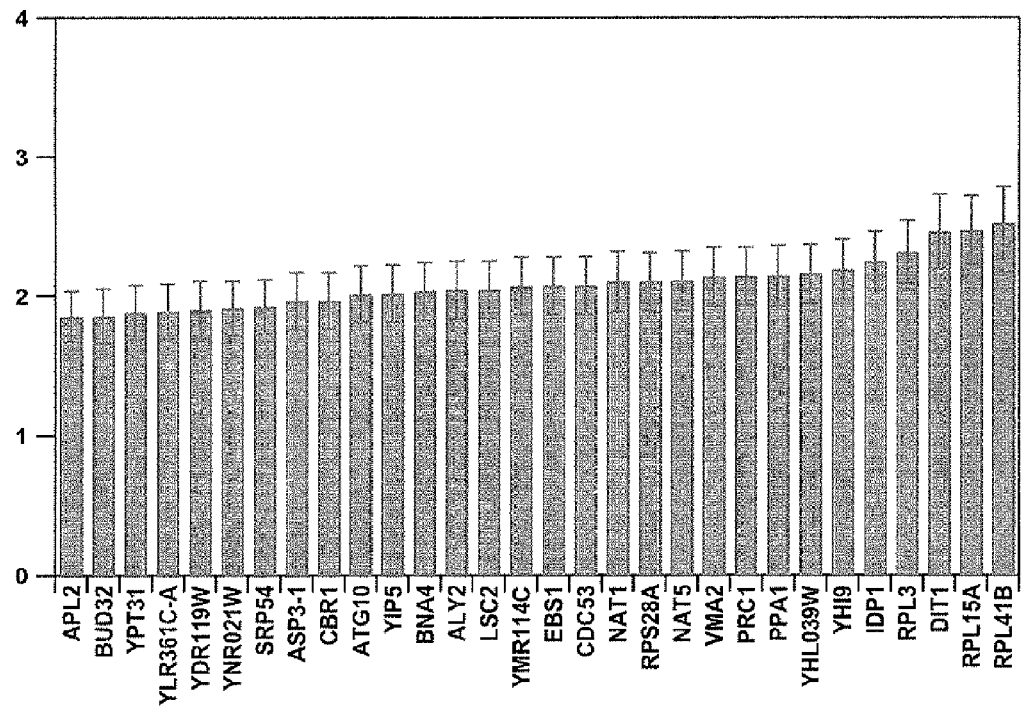
FIG. 4 shows the top 30 terminator regions selected in Example 7.

The respective strains of transformed yeast were pre-cultured in SD medium (2% glucose, 0.67% Yeast Nitrogen base w/o amino acids (Difco Laboratories, Inc.), 0.082% Complete Supplement Mixture (CSM)+40Ade (ForMedium Ltd.), inoculated in SD medium at about $OD_{660}$=0.1 and cultured to $OD_{660}$=0.7, and fluorescence intensity was measured. Using the fluorescence intensity emitted by the GFP fluorescent protein (reporter gene) as a marker of terminator activity, the GFP fluorescence intensity of 10000 cells emitting GFP fluorescence was measured for each sample using a flow cytometer (CELL LAB QUANTA™ SC MPL flow-cytometer, Beckman Coulter, Inc.). Excitation light with a wavelength of 488 nm was used together with a 510 nm/10 nm bandpass filter. The relative fluorescence intensity of each was determined given 1 as the fluorescence intensity of the PGK1t control strain. The experiment was repeated 3 times, and the average and standard deviation were calculated. All data were processed with IgorPro (ver. 6.1, WaveMetrics). The top 30 selected candidates are shown in FIGS. 4 and 5. As shown in FIGS. 4 and 5, there was some change in the order of activity, but relative expression intensity was at least 1.9.

Example 8

A terminator may have different activity under different culture conditions. Therefore, in this example 5 recombinant yeasts were prepared comprising the activity evaluation constructs for the top 5 terminators (RPL41B, RPL15A, DIT1, RPL3 and IDP1) introduced into a wild-type yeast (W303-1a), and terminator activity was measured under various culture conditions.

Figure 6:
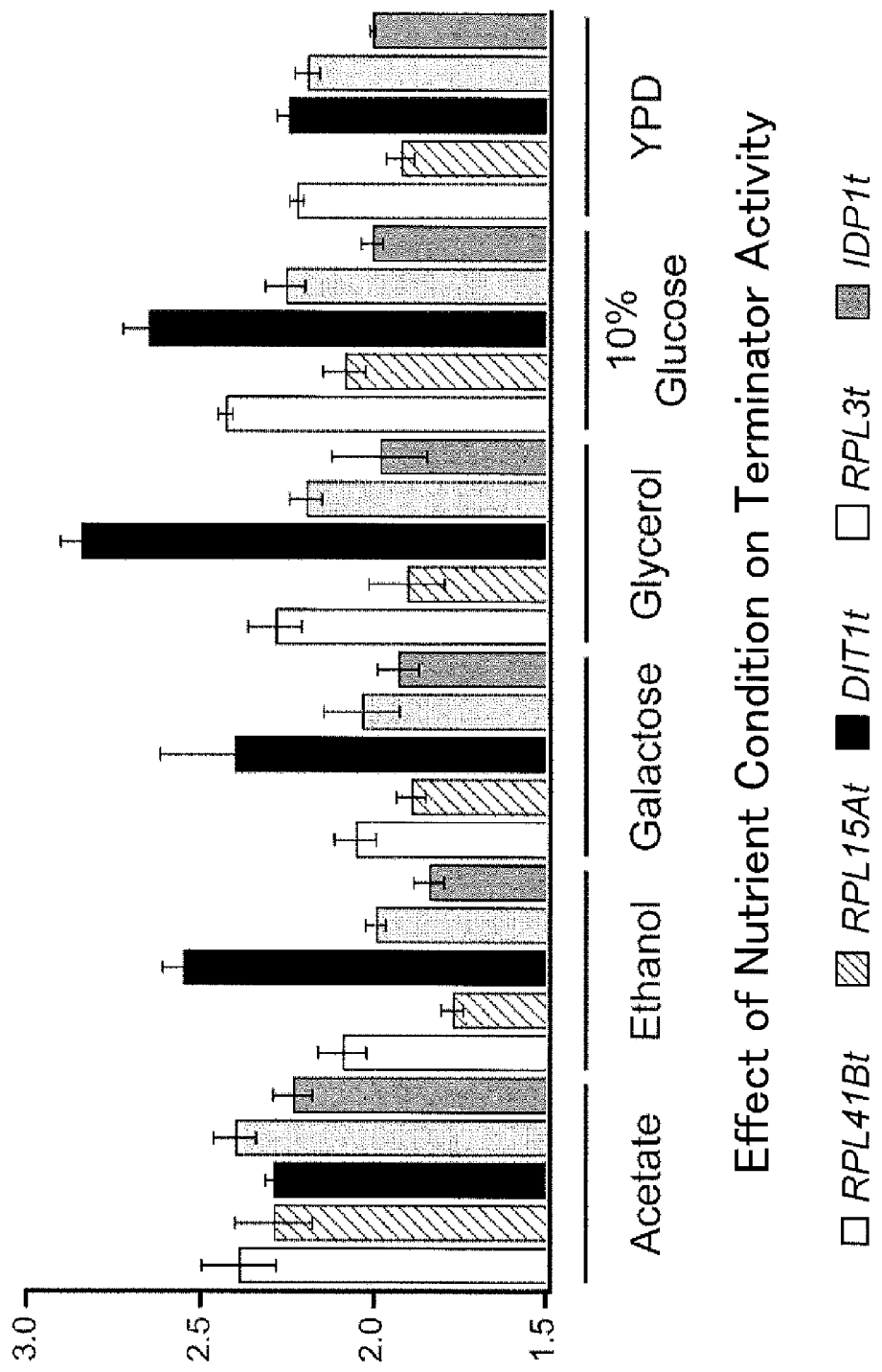
FIG. 6 shows the relationship between terminator activity and the type of carbon source using yeasts with the top 5 terminator regions introduced therein.

(1) Wild-type yeasts W303-1a having the top 5 terminators introduced therein and a W303-1a strain with PGK1t introduced as a control were pre-cultured in SD medium, seeded on SD medium at about $OD_{660}$=0.1, and cultured for 6 hours (about $OD_{660}$=0.7), after which the medium was replaced. After a further 6 hours of culture, fluorescence intensity was measured. To investigate the effect of the carbon source (nutrient conditions) in particular, the following media were used as replacement media. Basic medium (0.67% Yeast Nitrogen base w/o amino acids (Difco Laboratories, Inc.), 0.082% Complete Supplement Mixture (CSM)+40Ade (ForMedium Ltd.)) was used with 2% acetic acid, 2% ethanol, 2% galactose, 2% glycerol and 10% glucose added as carbon sources. YPAD 2% (2% glucose, 2% peptone, 1% yeast extract, 20 mg/L adenine) was used as a nutrient-rich medium. As in Example 7, the relative fluorescence intensity of each was determined given 1 as the GFP fluorescence intensity of the PGK1t control strain. The experiment was repeated 3 times, and the average value and standard deviation were calculated. The results are shown in FIG. 6. As shown in FIG. 6, changing the carbon source had very little effect on terminator activity. Moreover, DIT1t had the highest specific activity except in acetic acid medium, and RPL41B and RPL3 tended to be ranked next.

Figure 7:
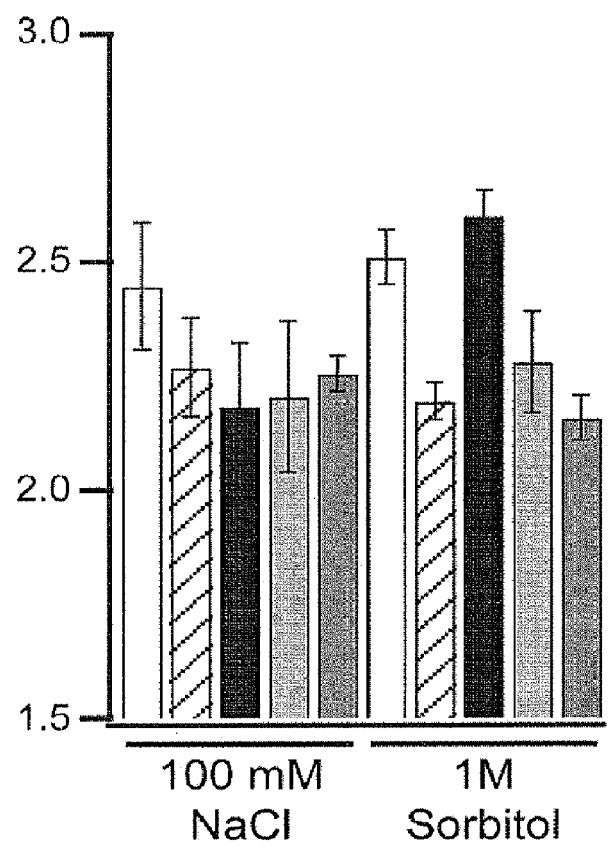
FIG. 7 shows the relationship between terminator activity and salt and osmotic stress using yeasts with the top 5 terminator regions introduced therein.

(2) Next, the same operations were performed as in (1) above except that SD+100 mM NaCl medium was used as the replacement medium for salt stress and SD+1M Sorbitol medium as the replacement medium for osmotic stress, and fluorescence intensity was measured. The results are shown in FIG. 7. As shown in FIG. 7, salt stress suppressed DIT1t activity somewhat. However, osmotic stress was shown to have virtually no effect.

Example 9

A terminator may have different activity in different wild-type yeasts. Therefore, in this example activity evaluation constructs for the top 5 terminators in FIGS. 4 and 5 were introduced into 5 kinds of wild-type yeast to prepare 25 recombinant yeasts, and terminator activity was measured.

(1) To evaluate terminator activity according to differences in the wild-type yeast used as the host, activity evaluation constructs for the top 5 terminators (RPL41B, RPL15A, DIT1, RPL3 and IDP1) were introduced into 5 different wild-type yeasts (A451, BY4741, TDO2, W303-1a and YPH499) to prepare 25 different recombinant yeasts, which were cultured until the stationary phase, and fluorescence activity was measured by flow cytometry (FCM) after 6, 12 and 24 hours.

(2) Constructs having a URA3 marker together with the top 5 terminator regions (RPL41B, RPL15A, DIT1, RPL3 and IDP1) and the standard PGK1 terminator region were prepared as in Example 7. Recombinant yeasts using 5 different wild-type yeasts as hosts were also prepared as in Example 7. The selection medium was uracil selection medium.

Figure 8:
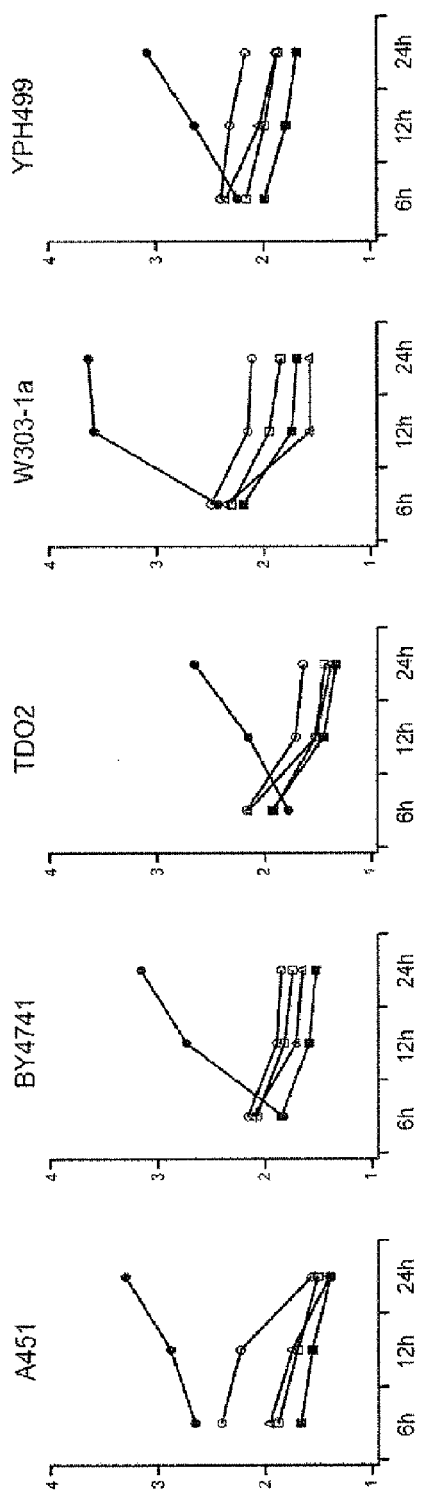
FIG. 8 shows the relationship between terminator activity and type of host (wild-type yeast) using yeasts with the top 5 terminator regions introduced therein.

(3) The respective strains of recombinant yeast were pre-cultured in SD medium (2% glucose, 0.67% Yeast Nitrogen base w/o amino acids (Difco Laboratories, Inc.), 0.082% Complete Supplement Mixture (CSM)+40Ade (For-Medium Ltd.), inoculated in SD medium at about $OD_{660}$=0.1 and cultured, and fluorescence intensity was measured after 6 hours (early logarithmic growth phase), 12 hours (middle logarithmic growth phase) and 24 hours (early stationary phase). The results are shown in FIG. 8. As shown in FIG. 8, the activity of the top 5 terminators was double that of the standard terminator regardless of the yeast strain, so it is appears that these terminators are not selective of budding yeast hosts. It was also shown that specific activity increases as DIT1t activity approaches the stationary phase.

It has thus been confirmed that expression levels in yeasts can be regulated by changing a terminator sequence.

Example 10

This example confirmed the effect of a reporter gene disposed upstream from the terminator region. Eight strains carrying eight different constructs (RPL41Bt, YIP5t, TYR1t, PGK1t, MFA2t, STD1t, FUR4t, GIC1t) having varying terminator intensities were obtained from a comprehensive evaluation, and recombinant strains were prepared by substituting the mKO2 gene for the GFP gene in each construct. Specifically, the GFP gene was altered by using SacI and KpnI to insert the mKO2 gene into the TDH3 promoter-GFP gene-terminator constructs used in the comprehensive evaluation.

PCR amplification was performed using the following primer set on a vector containing the construct, and the amplified DNA fragments were cloned by an In Fusion reaction (IN FUSION® Advantage PCR Cloning Kit, Clontech) into the eight strains used in the comprehensive evaluation to thereby obtain eight strains having the mKO2 gene substituted for the GFP gene.

5'primer:
(SEQ ID NO: 15890)
5'-CATAAACAAACAAAGAGCTCATGGTCTCCGTTATCAAACC-3'

3'primer:
(SEQ ID NO: 15891)
5'-GAAAAGGGGCCTGTGGTACCTTATGAATGGGCGACAGCATC-3'

Figure 9:
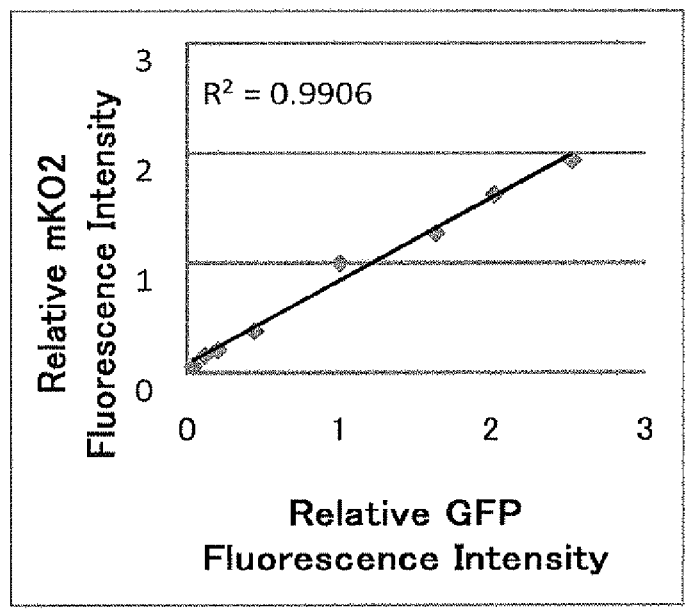
FIG. 9 shows the effect of reporter gene exchange on terminator region activity.
Figure 10:
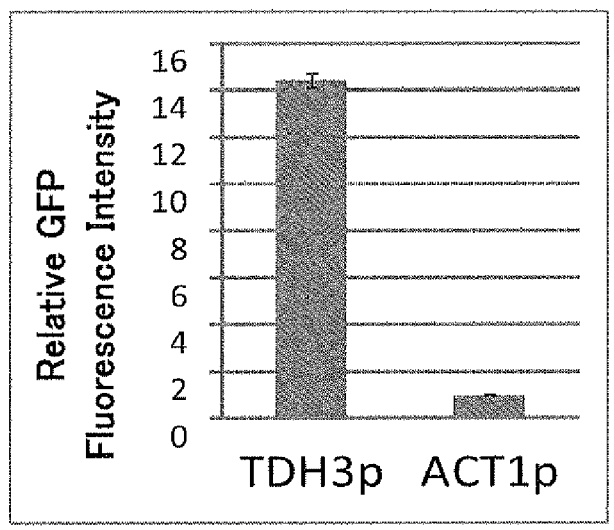
FIG. 10 shows the effect of promoter exchange on relative GFP fluorescence intensity.

The fluorescent intensity of each of the resulting eight strains of yeast was measured by flow cytometry in accordance with Example 5 except for a filter set (570/15) as a red fluorescence detection, and relative fluorescent intensity was evaluated in comparison with the fluorescent intensity of a transformed yeast that was identical apart from the PGK1 terminator region. The results are shown in FIG. 9. As shown in FIG. 9, the mKO2 gene exhibited a relative fluorescent intensity (r=0.99) roughly equivalent to that of the GFP gene. These results show that the expression level of a gene can be regulated regardless of the type of gene disposed upstream from the terminator region.

Example 11

This example confirmed the effect of a promoter disposed upstream from the terminator region. Terminator activity was evaluated using a high-expression TDH3 promoter in the comprehensive evaluation. With a strong promoter like the TDH3 promoter as used in this analysis, we might have overlooked or underestimated the subtle effects of the terminator regions because of overproduction of transcript and their functional cis-elements. To avoid this limitation, the terminator was evaluated with the ACT1 promoter, which is known as a low-expression promoter.

Constructs were prepared by replacing the TDH3 promoter sequences of fourteen different constructs (RPL41Bt, RPL15At, DIT1t, RPL3t, IDP1t, VMA2t, BNA4t, YIP5t, TUB1t, TYR1t, TPS1t, FMP52t, SCW4t, PGK1 t) obtained from the comprehensive evaluation and having varying terminator intensities with the ACT1 promoter. Specifically, constructs were prepared from the TDH3 promoter—GFP gene—terminator constructs used in the comprehensive evaluation by using the EcoRI and SacI restriction enzyme sites to substitute the ACT1 promoter.

PCR amplification was performed using the following primer set on a vector containing the construct, and the amplified DNA fragments were cloned by an In Fusion reaction (IN FUSION® Advantage PCR Cloning Kit, Clontech) into the fourteen strains used in the comprehensive evaluation to thereby obtain fourteen strains having the ACT1 promoter substituted for the TDH promoter.

5'primer:
(SEQ ID NO: 15892)
5'-TGTATCTGCACCTAGATCGAATTCACAAGCGCGCCTCTACCT
TGCAGAC-3'

3'primer:
(SEQ ID NO: 15893)
5'-CACCTTTAGAAGCCATGAGCTCTGTTAATTCAGTAAATTTTC
GATCTTG-3'

An intensity evaluation of the ACT1 promoter and TDH3 promoter was performed prior to the evaluation. Constructs were prepared comprising the GFP gene and PGK1 terminator disposed downstream from each promoter, and introduced into the PDC6 gene locus of the yeast W303-1a strain. Then, the GFP fluorescent intensities of the strains were compared by flow cytometry. As a result, as shown in FIG.

10, the GFP fluorescent intensity of the ACT1 promoter strain was roughly 14 times less than that of the TDH3 promoter strain.

Figure 11:
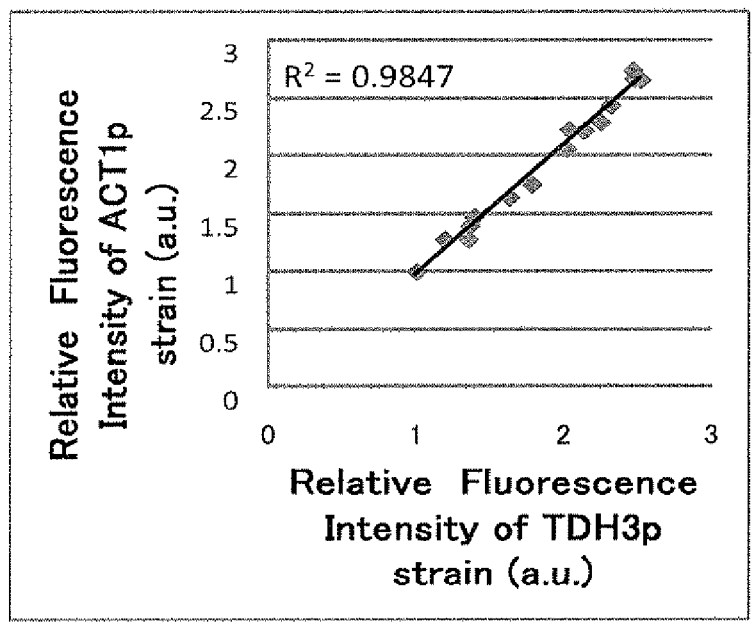
FIG. 11 shows the effect of promoter exchange on terminator region activity.

Then, the fluorescent intensity of each of the resulting fourteen strains of yeast was measured by flow cytometry in accordance with Example 5, and relative fluorescent intensity was evaluated in comparison with the fluorescent intensity of a transformed yeast that was identical apart from the PGK1 terminator region. The results are shown in FIG. 11. As shown in FIG. 11, the relative fluorescent intensities of yeasts carrying the GFP gene driven by the ACT1 promoter and under the control of fourteen different terminator regions correlated highly (r=0.98) with the relative fluorescent intensities of yeasts carrying the corresponding TDH3 promoter-driven GFP genes.

These results show that regulation of expression intensity by the terminator region is effective regardless of the type (expression intensity) of the promoter disposed upstream from the terminator region. They also show that the intrinsic expression regulation ability of the terminator region can be realized regardless of the type (expression intensity) of the promoter disposed upstream from the terminator region.

Example 12

This example investigated whether regulation of expression levels by differences in terminator sequence is possible in inducible promoter-driven systems. Strains were prepared having the GFP gene followed by the RPL15A and PGK1 terminator regions downstream from the GAL1 promoter, which is often used as an inducible promoter. Specifically, constructs were prepared by replacing the TDH3 promoter sequences of constructs (RPL15At, PGK1t) having two different terminator regions with the GAL1 promoter, which is known as an inducible promoter. Using a construct designed to allow galactose induction of GFP using the GAL1 promoter ("pGAL2pro-GFP; square", Matsuyama et al. (2010) *J. Biotech. Bioeng.* 111, 175-177), these were prepared by replacing the terminator region (CYC1t) of this construct with RPL15At and PGK1t, respectively.

PCR amplification was performed using the following primer sets together with fragments obtained by cleaving the construct described in the aforementioned literature with the restriction enzymes EcoNI and SalII, and the resulting amplified DNA fragments were cloned to a yeast harboring HIS3pro-GAL 1-GAL2 and GAL10pro GAL4 by an In-Fusion reaction.

```
Primers for RPL15At
5'primer:
                                    (SEQ ID NO: 15894)
5'-TGGATGAACTGTACAACTGAGGTACCTAAGCTGGTTGATG-3'

3'primer:
                                    (SEQ ID NO: 15895)
5'-GCTTCCTATATTATATATATAGTAATGTCGT-3'

Primers for PGK1t
5'primer:
                                    (SEQ ID NO: 15896)
5'-TGGATGAACTGTACAACTGAGGTACCGAATTGAATTGAAATC
GATAG-3'

3'primer:
                                    (SEQ ID NO: 15897)
5'-GCTTCCTATATTATATATATAGTAATGTCGT-3'
```

A galactose induction test was performed on the resulting yeasts, and the relative fluorescent intensity of each yeast four hours after galactose induction was evaluated in accordance with Example 5. The results are shown in FIG. 12.

Figure 12:
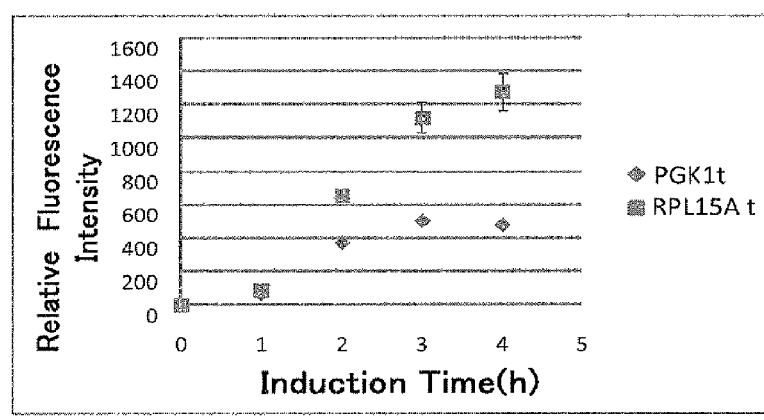
FIG. 12 shows the effect of promoter exchange between constitutive promoter and inducible promoter on region activity.

As shown in FIG. 12, GFP fluorescent intensity was at the leakage level immediately (0 hours) after induction, but had increased by roughly 1300 times after 4 hours. The GFP fluorescent intensity of the RPL15At strain was roughly 2.7 times that of the PGK1t strain after 4 hours, which is roughly the same as the value of 2.5 times found in the comprehensive evaluation. These results show that a terminator region obtained in the comprehensive evaluation regulated expression levels of a target protein even in a galactose induction test. Moreover, it was also shown that expression regulation by the terminator region is effective with either a constitutive promoter or inducible promoter, and is about the same regardless of the mode of operation of the promoter.

As shown above, the reliability of the comprehensive evaluation data was confirmed by substituting other sequences for the reporter protein located upstream from the terminator and the promoter upstream from the reporter protein. The reporter proteins of multiple strains used in the comprehensive evaluation were changed from GFP to mKO2, the low-expression ACT1 promoter and the inducible GAL1 promoter were substituted for the high-expression TDH3 promoter, and fluorescent intensity of the terminator strains was compared between systems. As a result, a strong correlation was seen between the test results from the comprehensive evaluation and the relative fluorescent intensities of the respective substituted strains. This suggests that the terminator intensity as measured in the comprehensive evaluation is attributable not to the effects of the surrounding sequences (in particular, the promoter, reporter protein gene sequence and other upstream sequences), but to the sequence of the terminator region itself. In other words, it was shown that the sequence of the terminator region affects the expression level of a protein located upstream from that sequence.

Contents of all of the references cited herein are incorporated by reference to this application.

SEQ ID NOS 1-10590, 15886-15897: primers.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09512436B2). An electronic copy of the "Sequence Listing" will also be available from the USPTO upon request and payment of the fee set forth in 37 CFR 1.19(b)(3).

What is claimed is:

1. A recombinant *Saccharomyces cerevisiae* yeast, comprising:
   a first promoter that functions in the recombinant *Saccharomyces cerevisiae* yeast,
   a first heterologous target gene controlled by the promoter, and
   a first regulator of gene expression disposed downstream from the first target gene, the first regulator of the gene expression comprising at least one terminator region of a yeast gene selected from the group consisting of:
   ORC4 set forth in SEQ ID NO: 10591,
   ICY2 set forth in SEQ ID NO: 10592,
   GIC1 set forth in SEQ ID NO: 10593,
   HLR1 set forth in SEQ ID NO: 10594,
   ECM13 set forth in SEQ ID NO: 10595,
   YLR108C set forth in SEQ ID NO: 10596,
   AQR1 set forth in SEQ ID NO: 10597,
   YHR213W-A set forth in SEQ ID NO: 10598,
   SUT1 set forth in SEQ ID NO: 10599, and
   PLB3 set forth in SEQ ID NO: 10600,
   wherein an expression intensity of the terminator region relative to that of the PGK1 terminator region is 0.1 or less when the recombinant *Saccharomyces cerevisiae* yeast is cultured in SD medium.

2. A method for producing an expression product of a target gene in *Saccharomyces cerevisiae*, the method comprising:
   culturing the recombinant *Saccharomyces cerevisiae* yeast according to claim 1 in SD medium, and
   expressing the first heterologous target gene.

3. A cassette for gene expression in *Saccharomyces cerevisiae*, the cassette comprising:
   a promoter that functions in *Saccharomyces cerevisiae*,
   a heterologous target gene controlled by the promoter; and
   a regulator of gene expression disposed downstream from the promoter, wherein the regulator of gene expression comprises a terminator region of a yeast gene selected from the group consisting of:
   ORC4 set forth in SEQ ID NO: 10591,
   ICY2 set forth in SEQ ID NO: 10592,
   GIC1 set forth in SEQ ID NO: 10593,
   HLR1 set forth in SEQ ID NO: 10594,
   ECM13 set forth in SEQ ID NO: 10595,
   YLR108C set forth in SEQ ID NO: 10596,
   AQR1 set forth in SEQ ID NO: 10597,
   YHR213W-A set forth in SEQ ID NO: 10598,
   SUT1 set forth in SEQ ID NO: 10599, and
   PLB3 set forth in SEQ ID NO: 10600,
   wherein an expression intensity of the terminator region relative to that of the PGK1 terminator region is 0.1 or less when a *Saccharomyces cerevisiae* transformed with the expression cassette is cultured in SD medium.

* * * * *